US011634395B2

(12) United States Patent
Miyahara et al.

(10) Patent No.: US 11,634,395 B2
(45) Date of Patent: Apr. 25, 2023

(54) SULFONAMIDE COMPOUND OR SALT THEREOF

(71) Applicant: Taiho Pharmaceutical Co., Ltd., Tokyo (JP)

(72) Inventors: Seiji Miyahara, Ibaraki (JP); Hiroyuki Ueno, Ibaraki (JP); Shoki Hara, Ibaraki (JP); Yoshio Ogino, Ibaraki (JP)

(73) Assignee: Taiho Pharmaceutial Co., Ltd., Tokyo (JP)

( * ) Notice: Subject to any disclaimer, the term of this patent is extended or adjusted under 35 U.S.C. 154(b) by 0 days.

(21) Appl. No.: 17/000,807

(22) Filed: Aug. 24, 2020

(65) Prior Publication Data

US 2020/0399235 A1  Dec. 24, 2020

Related U.S. Application Data

(60) Division of application No. 16/751,555, filed on Jan. 24, 2020, now Pat. No. 10,889,555, which is a continuation of application No. 16/305,691, filed as application No. PCT/JP2017/020166 on May 30, 2017, now abandoned.

(30) Foreign Application Priority Data

May 31, 2016 (JP) .............................. JP2016-109609

(51) Int. Cl.
C07D 271/07 (2006.01)
A61P 35/00 (2006.01)
C07D 413/12 (2006.01)
C07D 413/14 (2006.01)
C07D 417/12 (2006.01)
C07D 491/107 (2006.01)

(52) U.S. Cl.
CPC ............ *C07D 271/07* (2013.01); *A61P 35/00* (2018.01); *C07D 413/12* (2013.01); *C07D 413/14* (2013.01); *C07D 417/12* (2013.01); *C07D 491/107* (2013.01)

(58) Field of Classification Search
CPC ............................... C07D 271/07; A61P 35/00
See application file for complete search history.

(56) References Cited

U.S. PATENT DOCUMENTS

| | | | |
|---|---|---|---|
| 8,022,225 | B2 | 9/2011 | Ono et al. |
| 10,889,555 | B2 * | 1/2021 | Miyahara ................ A61P 35/00 |
| 2006/0110383 | A1 | 5/2006 | Honjo et al. |
| 2009/0118222 | A1 | 5/2009 | Nomura et al. |
| 2010/0041655 | A1 | 2/2010 | Ono et al. |
| 2011/0218248 | A1 | 9/2011 | Jordine et al. |
| 2013/0005678 | A1 | 1/2013 | Sandvold et al. |
| 2019/0010158 | A1 | 1/2019 | Ishida |
| 2019/0350932 | A1 | 11/2019 | Miura et al. |
| 2020/0157066 | A1 | 5/2020 | Miyahara et al. |
| 2020/0361883 | A1 | 11/2020 | Nakamura et al. |
| 2020/0399235 | A1 | 12/2020 | Miyahara et al. |
| 2020/0405697 | A1 | 12/2020 | Ueno et al. |

FOREIGN PATENT DOCUMENTS

| | | |
|---|---|---|
| EP | 3466934 A1 | 4/2019 |
| RU | 2543621 C2 | 3/2015 |
| WO | 99/21859 A1 | 5/1999 |
| WO | 00/29375 A1 | 5/2000 |
| WO | 01/10454 A2 | 2/2001 |
| WO | 01/83450 A2 | 11/2001 |
| WO | 02/018390 A1 | 3/2002 |
| WO | 2004/014300 A2 | 2/2004 |
| WO | 2006/080509 A1 | 8/2006 |
| WO | 2007/083089 A1 | 7/2007 |
| WO | 2007/089018 A1 | 8/2007 |
| WO | 2009/023059 A2 | 2/2009 |
| WO | 2017/111074 A1 | 6/2017 |
| WO | 2017/150725 A1 | 9/2017 |
| WO | 2017/209155 A1 | 12/2017 |

OTHER PUBLICATIONS

International Search Report issued in related International Patent Application No. PCT/JP2017/020166 dated Jul. 25, 2017.
Syed et al., "Synthesis, QSAR and anti-HIV activity of new 5-benzylthio-1,3,4-oxadiazoles derived from alpha-amino acids," Journal of Enzyme Inhibition and Medicinal Chemistry, 26: 668-680 (2011).
Zareef et al., "Carbonic anhydrase inhibitors. Inhibition of human tumor-associated isozymes IX and cytosolic isozymes I and II with some 1,3,4-oxadiazole-thiols," Journal of Enzyme Inhibition and Medicinal Chemistry, 21: 351-359 (2006).
Ahmad et al., "Identification of Non-nucleoside Human Ribonucleotide Reductase Modulators," Journal of Medicinal Chemistry, 58: 9498-9509 (2015).
Jordan et al., "Ribonucleotide Reductases," Annual Review of Biochemistry, 67: 71-98 (1998).
Elford et al., "Ribonucleotide Reductase and Cell Proliferation," The Journal of Biological Chemistry, 245: 5228-5233 (1970).
Nilsson et al., "Metabolic enzyme expression highlights a key role for MTHFD2 and the mitochondrial folate pathway in cancer," Nature Communications, 5: 3128 (2014).
Liu et al., "Ribonucleotide reductase small subunit M2 serves as a prognostic biomarker and predicts poor survival of colorectal cancers," Clinical Science, 124: 567-578 (2013).

(Continued)

*Primary Examiner* — Golam M Shameem
(74) *Attorney, Agent, or Firm* — Morgan, Lewis & Bockius LLP

(57) ABSTRACT

The present invention provides a novel sulfonamide compound having a ribonucleotide reductase inhibitory activity or a salt thereof, and a pharmaceutical composition containing the same as an active ingredient.
A compound represented by Formula (I) [wherein, $X^1$ represents an oxygen atom or the like; $X^2$ represents an oxygen atom; $X^3$ represents —NH—; $X^4$ represents a hydrogen atom or the like; $R^1$ represents —C($R^{11}$)($R^{12}$)— or the like; $R^{11}$ and $R^{12}$ are the same or different and each represents a hydrogen atom or the like; $R^2$ represents an optionally substituted $C^6$-$C^{14}$ aromatic hydrocarbon group or the like; $R^3$ represents an optionally substituted $C^6$-$C^{14}$ aromatic hydrocarbon group or the like; $R^4$ represents a hydrogen atom or the like] or a salt thereof.

40 Claims, 2 Drawing Sheets

(56) References Cited

OTHER PUBLICATIONS

Shao et al., "Targeting ribonucleotide reductase for cancer therapy," Expert Opinion on Therapeutic Targets, 17: 1423-1437 (2013).
Finch et al., "Triapine (3-Aminopyridine-2-carboxaldehyde-thiosemicarbazone): A Potent Inhibitor of Ribonucleotide Reductase Activity with Broad Spectrum Antitumor Activity," Biochemical Pharmacology, 59: 983-991 (2000).
Zhu et al., "Inhibitory mechanisms of heterocyclic carboxaldehyde thiosemicabazones for two forms of human ribonucleotide reductase," Biochemical Pharmacology, 78: 1178-1185 (2009).
Yen et al., "Characterization of a Hydroxyurea-resistant Human KB Cell Line with Supersensitivity to 6-Thioguanine," Cancer Research, 54: 3686-3691 (1994).
Kalinowski et al., "The Evolution of Iron Chelators for the Treatment of Iron Overload Disease and Cancer," Pharmacological Reviews, 57: 547-583 (2005).
Kunos et al., "Management of 3-aminopyridine-2-carboxaldehyde thiosemicarbazone-induced methemoglobinemia," Future Oncology, 8: 145-150 (2012).
Office Action issued in related Indian Patent Application No. 201817049173 dated Sep. 25, 2019.
Syed et al., STN International HCAPLUS database (Columbus, Ohio) Accession No. 2011: 1168579.
Cowen et al., STN International HCAPLUS database (Columbus, Ohio) Accession No. 2007: 816399.
Office Action issued in related Chinese Patent Application No. 201780045742.8 dated Aug. 26, 2021 (see partial English translation).
Faqing et al., "Medicinal Chemistry," 67 (2012) (see CN OA translation).
International Search Report issued in related International Patent Application No. PCT/JP2020/021108 dated Jul. 14, 2020.
International Search Report issued in related International Patent Application No. PCT/IB2018/059430 dated Feb. 5, 2019.
International Search Report issued in related International Patent Application No. PCT/JP2018/043697 dated Feb. 5, 2019.
Sigmond et al., "The synergistic interaction of gemcitabine and cytosine arabinoside with the ribonucleotide reductase inhibitor triapine is schedule dependent," Biochemical Pharmacology, 73,1548-1557 (2007).
Pardoll et al., "The blockade of immune checkpoints in cancer immunotherapy," Nature Reviews Cancer, 12 (4) 252-264 (2016).
Topalian et al., "Safety, Activity, and Immune Correlates of Anti-PD-1 Antibody in Cancer," The New England Journal of Medicine, 366 (26): 2443-2454 (2012).
Kuznetsova, "Qualitative X-ray analysis: Guidelines," Federal Agency for Education State Educational Institution of Higher Professional Education, Irkutsk State University, Department of General Physics (2005).
Small Medical Encyclopedia, Moscow, Medicine, 5: 90-96 (1996).
Office Action issued in related Russian Patent Application No. 2020121153 dated Feb. 11, 2022.
Yuchi Kato "Regimen Management in cancer pharmacotherapy," Japanese Journal of Drug Informatics, 11 (4) 217-222(2010).
28 Leukemia Chemistry Regimen, Internetarchive waybackmachine https://www.saiseikai-hp.chuo.fukuoka.jp/cancer/pdf/rejimen/28.pdf (retrieved Nov. 12, 2021).
Murren et al., "Phase I and Pharmacokinetic Study of Triapine, a Potent Ribonucleotide Reductase Inhibitor, Administered Daily for Five Days in Patients with Advanced Solid Tumors," Clinical Cancer Research, 9: 4092-4100 (2003).
Goss et al., "Gene expression signature based screening identifies ribonucleotide reductase as a candidate therapeutic target in Ewing sarcoma," Oncotarget, 7 (39): 63003-63019 (2016).
International Search Report issued in corresponding International Patent Application No. PCT/JP2021/033854 dated Nov. 30, 2021.
International Search Report issued in corresponding International Patent Application No. PCT/JP2021/033855 dated Nov. 30, 2021.
Office Action issued in related Russian Patent Application No. 2021139254 dated Sep. 21, 2022.
Belikov, Pharmaceutical Chemistry, Moscow, "MEDpress-inform," 27-29 (2007).
Dyson, Chemistry of Synthetic Drugs, "MIR" Moscow (1964).

* cited by examiner

[Figure 1]
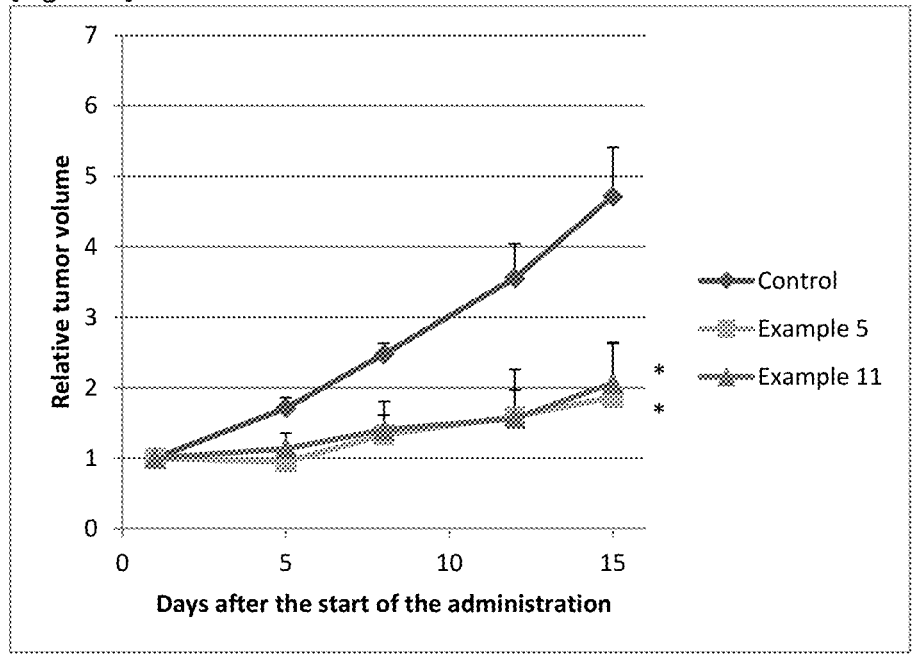
[Figure 2]
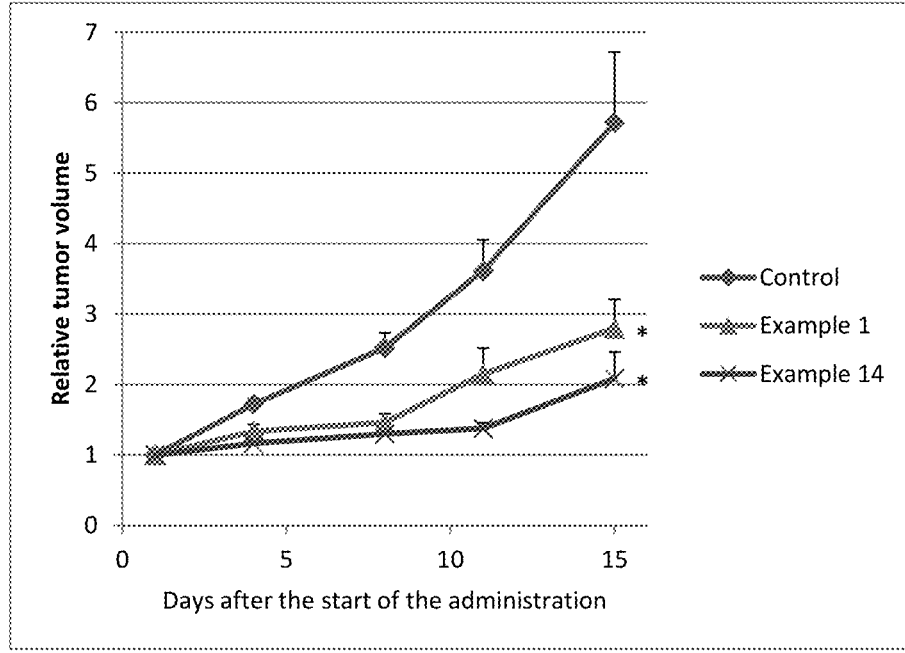

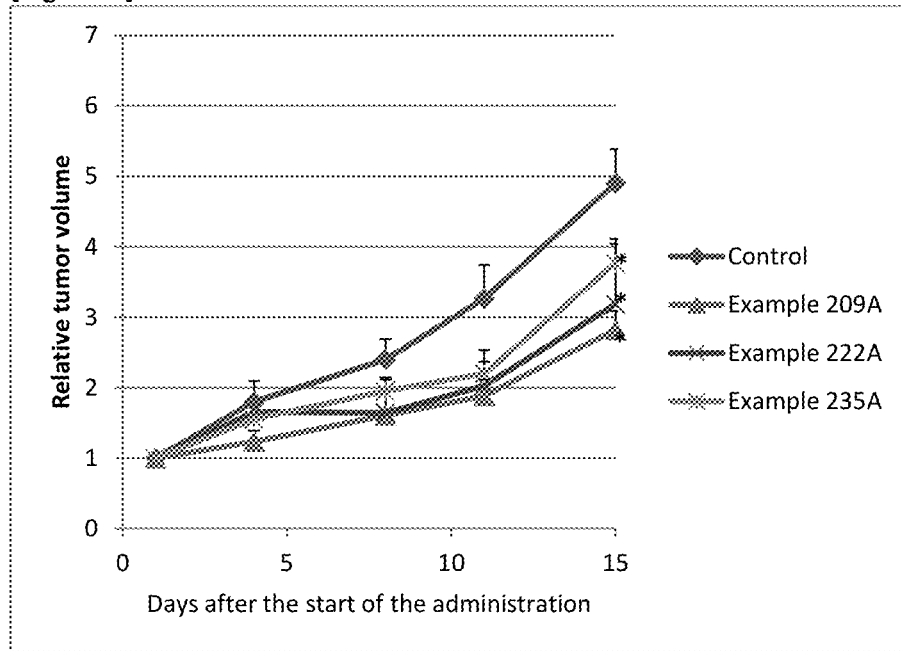
[Figure 3]
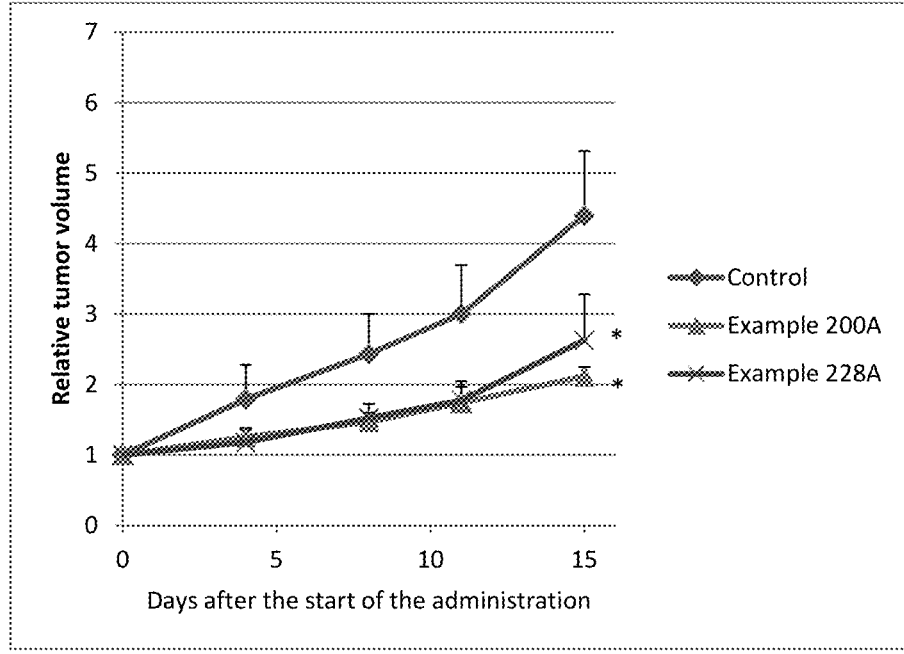
[Figure 4]

SULFONAMIDE COMPOUND OR SALT THEREOF

TECHNICAL FIELD

The present invention relates to a novel sulfonamide compound having a ribonucleotide reductase inhibitory activity or a salt thereof, and a pharmaceutical composition containing the same as an active ingredient.

BACKGROUND

Ribonucleotide reductase (hereinafter also referred to as RNR) is composed of a hetero-oligomer of a large subunit M1 and a small subunit M2, and expression of both is required for enzyme activity. RNR recognizes ribonucleoside 5'-diphosphate (hereinafter also referred to as NDP) as a substrate and catalyzes a reduction reaction to 2'-deoxyribonucleoside 5'-diphosphate (hereinafter also referred to as dNDP). Since RNR is a rate-limiting enzyme in the de novo dNTP synthesis pathway, RNR plays an essential role in DNA synthesis and repair (Non-Patent Document 1).

The enzymatic activity of RNR is closely related to cell proliferation, and there is a report that the enzymatic activity is particularly high in cancer (Non-Patent Document 2). Indeed, in various types of solid tumors and blood cancers, numerous correlations have been reported with overexpression of M2, a subunit of RNR, and their prognosis (Non-Patent Documents 3 and 4). In addition, cell growth inhibition by inhibiting RNR and anti-tumor effect in vivo have been reported in cell lines derived from several cancer types and in nonclinical models (Non-Patent Documents 5 and 6), thus it is strongly suggested that RNR is one of important target molecules for cancer treatment.

Conventionally, hydroxyurea (hereinafter also referred to as HU) and 3-aminopyridine-2-carboxaldehyde thiosemicarbazone (hereinafter also referred to as 3-AP) are known as compounds having an RNR inhibitory activity. These compounds differ in structure from the sulfonamide compounds of the present invention. Although HU has been used clinically for over 30 years, its RNR inhibitory activity is very weak and its effect is limited (Non-Patent Document 7). In addition, tolerance to the use of HU is also considered a problem (Non-Patent Document 8). Meanwhile, 3-AP has a structure having the capability to chelate to metal ions, and it has been known that 3-AP chelates mainly to iron ions, thereby inhibiting RNR (Non-Patent Document 9). However, 3-AP has been suggested as having an off-target effect to various other iron-ion-requiring proteins, and it has been known that side effects such as hypoxia, dyspnea, methemoglobinemia and the like are caused in clinical cases (Non-Patent Document 10).

Therefore, it has been strongly desired to develop an RNR inhibitor which has a better RNR inhibitory activity and a structure which does not chelate with metal ions and is useful for diseases associated with RNR, such as tumors.

Meanwhile, as a compound having a sulfonamide structure, Non-Patent Document 11 discloses a compound (4a-e) having the following formula:

[chemical formula 1]

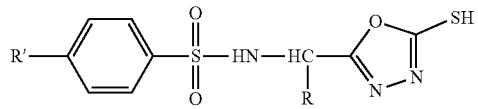

(wherein, R represents $CH_2Ph$, and R' represents Me). However, the compound (4a-e) is a production intermediate for obtaining the 5-benzylthio-1,3,4-oxadiazole derivatives as an objective compound having an anti-HIV activity. Non-Patent Document 11 does not disclose a physiological activity of the compound (4a-e), and does not suggest an RNR inhibition activity and antitumor effects of the compound (4a-e).

PRIOR ART DOCUMENT

Non-Patent Document

[Non-Patent Document 1] Annu. Rev. Biochem. 67, 71-98. (1998)
[Non-Patent Document 2] J. Biol. Chem. 245, 5228-5233. (1970)
[Non-Patent Document 3] Nat. Commun. 5, 3128 doi: 10.1038/ncomms 4128 (2014)
[Non-Patent Document 4] Clin. Sci. 124, 567-578. (2013)
[Non-Patent Document 5] Expert. Opin. Ther. Targets 17, 1423-1437 (2013)
[Non-Patent Document 6] Biochem. Pharmacol. 59, 983-991 (2000)
[Non-Patent Document 7] Biochem. Pharmacol. 78, 1178-1185 (2009)
[Non-Patent Document 8] Cancer Res. 54, 3686-3691 (1994)
[Non-Patent Document 9] Pharmacol. Rev. 57, 547-583 (2005)
[Non-Patent Document 10] Future Oncol. 8, 145-150 (2012)
[Non-Patent Document 11] J. Enzym. Inhib. Med. Chem. 26, 5, 668-680 (2011)

SUMMARY OF THE INVENTION

Problems to be Solved by the Invention

An object of the present invention is to provide a novel compound which selectively and strongly inhibits RNR and is useful as an antitumor agent and a therapeutic agent for other diseases involving RNR.

Means to be Solved by the Invention

As a result of extensive studies to solve the above-mentioned problems, the inventors of the present invention have found that a group of compounds having a sulfonamide structure represented by the following formula (I) has excellent RNR inhibitory activity, and is useful as an antitumor agent etc., and completed the present invention.

The present invention provides the following: [1] to [33].

[1]

A compound represented by the following formula (I):

[chemical formula 2]

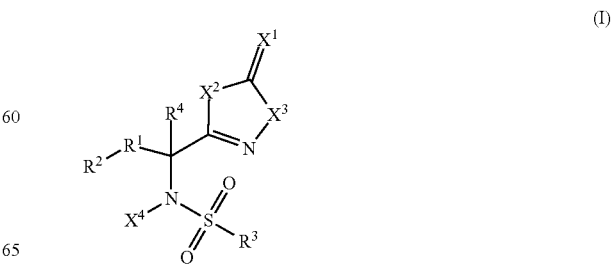

(I)

[In the formula, $X^1$ represents an oxygen atom or a sulfur atom;

$X^2$ represents an oxygen atom or —NH—;

$X^3$ represents —NH— or an oxygen atom;

$X^4$ represents a hydrogen atom or a C1-C6 alkyl group;

$R^1$ represents —C($R^{11}$)($R^{12}$)— or —C(=CH$_2$)—;

$R^{11}$ and $R^{12}$ are the same or different and represent a hydrogen atom, a halogen atom, or a hydroxy group, or a C1-C6 alkyl group, alternatively may be taken together with carbon atoms to which $R^{11}$ and $R^{12}$ are attached to form a saturated hydrocarbon ring having 3 to 8 carbon atoms;

$R^2$ represents a C6-C14 aromatic hydrocarbon group or a 9 or 10 membered fully unsaturated heterocyclic group, wherein $R^2$ may have substituents, and when $R^2$ has two substituents on the carbon atoms which are adjacent each other on the aromatic hydrocarbon ring, the substituents may be fused together with carbon atoms to which the substituents are attached to form a saturated or partially unsaturated 4-8 membered hydrocarbon ring or heterocyclic ring, either of which may have substituents, $R^3$ represents a C6-C14 aromatic hydrocarbon group or a 5-10 membered fully unsaturated heterocyclic group, wherein $R^3$ may have substituents, and when $R^3$ has two substituents on carbon atoms which are adjacent each other on the aromatic hydrocarbon ring, the substituents may be fused together with carbon atoms to which the substituents are attached to form a saturated or partially unsaturated 4-8 membered hydrocarbon ring or heterocyclic ring, either of which may have substituents; and $R^4$ represents a hydrogen atom or a C1-C6 alkyl group;

(with the proviso that $X^1$ is an oxygen atom when $X^2$ represents an oxygen atom, $X^3$ represents —NH—, $X^4$ represents a hydrogen atom, $R^1$ represents —CH$_2$—, $R_2$ represents a phenyl group, $R^3$ represents 4-methylphenyl group, and $R^4$ represents a hydrogen atom)]

or a salt thereof.

[2]

The compound or a salt thereof according to [1], wherein in formula (I):

$R^{11}$ represents a halogen atom, a hydroxy group, or a C1-C6 alkyl group;

$R^{12}$ represents a hydrogen atom, a halogen atom, a hydroxy group, or a C1-C6 alkyl group; or $R^{11}$ and $R^{12}$ may be taken together with carbon atoms to which $R^{11}$ and $R^{12}$ are attached to form a saturated hydrocarbon ring having 3 to 8 carbon atoms.

[3]

The compound or a salt thereof according to [1] or [2], wherein in formula (I), $X^1$ represents an oxygen atom.

[4]

The compound or a salt thereof according to any one of [1]-[3], wherein in formula (I), $X^2$ represents an oxygen atom.

[5]

The compound or a salt thereof according to any one of [1]-[4], wherein in formula (I), $X^3$ represents —NH—.

[6]

The compound or a salt thereof according to any one of [1]-[5], wherein in formula (I), $X^4$ represents a hydrogen atom.

[7]

The compound or a salt thereof according to any one of [1]-[6], wherein in formula (I), $R^1$ represents —C($R^{11}$)($R^{12}$)— (in which $R^{11}$ represents a C1-C6 alkyl group, and $R^{12}$ represents a hydrogen atom).

[8]

The compound or a salt thereof according to any one of [1]-[7], wherein in formula (I):

$R^2$ represents a C6-C14 aromatic hydrocarbon group or a 9-10 membered fully unsaturated heterocyclic group, wherein $R^2$ may be substituted with $R^{21}$, and when $R^2$ has two substituents on the carbon atoms which are adjacent each other on the aromatic hydrocarbon ring, the substituents may be fused together with carbon atoms to which the substituents are attached to form a saturated or partially unsaturated 4-8 membered hydrocarbon ring or heterocyclic ring, either of which may be substituted with Rz;

$R^{21}$ represents: a halogen atom; an amino carbonyl group; a cyano group; a C1-C6 alkyl group optionally substituted with Rx; a C3-C6 cycloalkyl group optionally substituted with Rx; a C2-C6 alkynyl group optionally substituted with Rx; a C6-C14 aromatic hydrocarbon group optionally substituted with Ry; or a 5-10 membered unsaturated heterocyclic group optionally substituted with Rz;

Rx represents a halogen atom or a C6-C14 aromatic hydrocarbon group;

Ry represents a halogen atom or a C1-C6 alkoxy group;

Rz represents a halogen atom, a C1-C6 alkyl group, a halogeno C1-C6 alkyl group, a C3-C6 cycloalkyl group, a C1-C6 alkoxy group, a C6-C14 aromatic hydrocarbon group, a nitrogen-containing saturated heterocyclic group, or a nitrogen-containing saturated heterocyclic carbonyl group.

[9]

The compound or a salt thereof according to any one of [1]-[8], wherein in formula (I):

$R^3$ represents a C6-C14 aromatic hydrocarbon group or a 5-10 membered fully unsaturated heterocyclic group, wherein $R^3$ may be substituted with $R^{31}$, and when $R^3$ has two substituents on the carbon atoms which are adjacent each other on the aromatic hydrocarbon ring, the substituent may be fused together with carbon atoms to which the substituents are attached to form a saturated or partially unsaturated 4-8 membered hydrocarbon ring or heterocyclic ring, either of which may be substituted with Rc;

$R^{31}$ represents: a halogen atom; a cyano group; a nitro group; a carboxyl group; a thioamide group; a C1-C6 alkyl group optionally substituted with Ra; an amino group optionally substituted with Ra; a C3-C6 cycloalkyl group optionally substituted with Rb; a C1-C6 alkoxy group optionally substituted with Rb; a C2-C7 alkoxycarbonyl group; a C1-C14 acyl group optionally substituted with Rb; a C6-C14 aromatic hydrocarbon group optionally substituted with Rb; a 5-10 membered unsaturated heterocyclic group optionally substituted with Rc; an amino carbonyl group optionally substituted with Rd and Re; or —S(=O)$_2$Rf;

Ra represents a halogen atom, a hydroxy group, a C1-C14 acyl group, a C1-C14 acyloxy group, a C2-C6 alkynyl group, or a C1-C6 alkoxy C1-C6 alkoxy group;

Rb represents a halogen atom, an amino group, or a C1-C6 alkoxy group; Rc represents: a halogen atom; a hydroxy group; an amino group; an oxo group; a C1-C6 alkyl group optionally substituted with a hydroxy group; a halogeno C1-C6 alkyl groups; a C1-C14 acyl groups; a C1-C14 acylamino group; a C1-C14 acyloxy group; or a C7-C13 aralkyloxy group;

Rd and Re are the same or different and represent: a hydrogen atom; a hydroxy group; a C7-C13 aralkyloxy group; or C1-C6 alkyl group optionally substituted with a hydroxyl group; alternatively taken together with nitrogen atom which is adjacent to Rd and Re to form a saturated or unsaturated 4-10 membered heterocyclic ring group optionally substituted with an amino group, a spiro heterocyclic ring group, or a bridged heterocyclic ring group; and Rf represents an amino group, a C1-C6 alkyl group, or a 4-10 membered saturated heterocyclic group.

[10]

The compound or a salt thereof according to any one of [1]-[9], wherein in formula (I):

$R^2$ represents a C6-C14 aromatic hydrocarbon group or a bicyclic 9-10 membered fully unsaturated heterocyclic ring group having 1-3 heteroatoms selected from the group consisting of a nitrogen atom, a sulfur atom, and an oxygen atom, wherein $R^2$ may be substituted with $R^{21}$, and when $R^2$ has two substituents on the carbon atoms which are adjacent each other on the aromatic hydrocarbon ring, the substituents may be fused together with carbon atoms to which the substituents are attached to form a saturated or partially unsaturated monocyclic hydrocarbon ring having 4-8 carbon atoms (optionally substituted with a C1-C6 alkyl group) or a saturated or partially unsaturated monocyclic 4-8 membered heterocyclic ring having 1-3 heteroatoms selected from a nitrogen atom, a sulfur atom and an oxygen atom (optionally substituted with a C1-C6 alkyl group);

$R^{21}$ represents a halogen atom, an amino carbonyl group, a cyano group, a C1-C6 alkyl group (optionally substituted with halogen atoms), a C3-C6 cycloalkyl group, a C2-C6 alkynyl group (optionally substituted with C6-C14 aromatic hydrocarbons groups), a C6-C14 aromatic hydrocarbon group (optionally substituted with group selected from a halogen atom and a C1-C6 alkoxy group), or an unsaturated monocyclic or bicyclic 5-10 membered heterocyclic group having 1-3 hetero atoms selected from the group consisting of a nitrogen atom, a sulfur atom, and an oxygen atom (optionally substituted with a group selected from the group consisting of a halogen atom, a C1-C6 alkyl group, a halogeno C1-C6 alkyl group, a C3-C6 cycloalkyl group, a C1-C6 alkoxy group, a C6-C14 aromatic hydrocarbon group, a nitrogen-containing saturated heterocyclic group, and nitrogen-containing saturated heterocyclic carbonyl group).

[11]

The compound or a salt thereof according to any one of [1]-[10], wherein in formula (I):

$R^2$ represents a C6-C14 aromatic hydrocarbon group, wherein $R^2$ may be substituted with $R^{21}$, and when $R^2$ has two substituents on the carbon atoms which are adjacent each other on the aromatic hydrocarbon ring, the substituents may be fused together with carbon atoms to which the substituents are attached to form a saturated or partially unsaturated monocyclic hydrocarbon ring having 4-8 carbon atoms (optionally substituted with a C1-C6 alkyl group);

$R^{21}$ represents a halogen atom, a cyano group, a C1-C6 alkyl group (optionally substituted with a halogen atom), a C3-C6 cycloalkyl group, a phenyl group (optionally substituted with a group selected from the group consisting of a halogen atom and a C1-C6 alkoxy group), or an unsaturated monocyclic or bicyclic 5-10 membered heterocyclic group having 1-3 hetero atoms selected from the group consisting of a nitrogen atom, a sulfur atom, and an oxygen atom (optionally substituted with a group selected from the group consisting of a halogen atom, a C1-C6 alkyl group, a halogeno C1-C6 alkyl group, a C3-C6 cycloalkyl group, a C1-C6 alkoxy group, a morpholino group, a piperidinyl group and a morpholinocarbonyl group).

[12]

The compound or a salt thereof according to any one of [1]-[11], wherein in formula (I):

$R^2$ represents a C6-C10 aromatic hydrocarbon group, wherein $R^2$ may be substituted with $R^{21}$, and when $R^2$ has two substituents on the carbon atoms which are adjacent each other on the aromatic hydrocarbon ring, the substituents may be fused together with carbon atoms to which the substituents are attached to form a saturated or partially unsaturated monocyclic hydrocarbon ring having 5 or 6 carbon atoms (optionally substituted with a C1-C6 alkyl group);

$R^{21}$ represents a halogen atom, a C1-C6 alkyl group, or a monocyclic 5 or 6 membered unsaturated heterocyclic group having 1-3 nitrogen atom(s) (optionally substituted with a C1-C6 alkyl group).

[13]

The compound or a salt thereof according to any one of [1]-[12], wherein in formula (I):

$R^3$ represents a C6-C14 aromatic hydrocarbon group, or a monocyclic or bicyclic 5-10 membered fully unsaturated heterocyclic group having 1-3 hetero atoms selected from a nitrogen atom, a sulfur atom and an oxygen atom, wherein $R^3$ may be substituted with $R^{31}$, and when $R^3$ has two substituents on the carbon atoms which are adjacent each other on the aromatic hydrocarbon ring, the substituents may be fused together with carbon atoms to which the substituents are attached to form a saturated or partially unsaturated monocyclic hydrocarbon ring having 4-8 carbon atoms (optionally substituted with a group selected from the group consisting of a halogen atom; a hydroxy group; an amino group; an oxo group; a C1-C6 alkyl group optionally substituted with a hydroxy group; a halogeno C1-C6 alkyl group; a C1-C14 acyl group; a C1-C14 acylamino group; a C1-C14 acyloxy group; and a C7-C13 aralkyloxy group), or a saturated or partially unsaturated monocyclic 4-8 membered heterocyclic ring having 1-4 heteroatoms selected from a nitrogen atom, a sulfur atom and an oxygen atom (optionally substituted with a group selected from the group consisting of a halogen atom, a hydroxy group, an amino group, an oxo group, a C1-C6 alkyl group optionally substituted with a hydroxy group; a halogeno C1-C6 alkyl group; a C1-C14 acyl group; a C1-C14 acylamino group; a C1-C14 acyloxy group and a C7-C13 aralkyloxy group);

$R^{31}$ represents a halogen atom, a cyano group, a nitro group, a carboxyl group, a thioamide group, a C1-C6 alkyl group (optionally substituted with a group selected from the group consisting of a halogen atom, a hydroxy group, a C1-C14 acyl group, C1-C14 acyloxy group, a C2-C6 alkynyl group, and a C1-C6 alkoxy C1-C6 alkoxy group), an amino group (optionally substituted with a C1-C14 acyl group), a C3-C6 cycloalkyl group (optionally substituted with an amino group), a C1-C6 alkoxy group (optionally substituted with a halogen atom), a C2-C7 alkoxycarbonyl group, a C1-C14 acyl group (optionally substituted with a halogen atom), a C6-C14 aromatic hydrocarbon group (optionally substituted with a group selected from the group consisting of a halogen atom, an amino group and a C1-C6 alkoxy group), a monocyclic or bicyclic 5-10 membered unsaturated heterocyclic group having 1-4 heteroatoms selected from a nitrogen atom, a sulfur atom and an oxygen atom (optionally substituted a group selected from with the group consisting of a halogen atom, an oxo group and a C1-C6 alkyl group), an amino carbonyl group optionally substituted with Rd and Re (wherein Rd and Re are the same or different, and present a hydrogen atom, a hydroxy group, a C7-C13 aralkyloxy group, or a C1-C6 alkyl group optionally substituted with a hydroxy group, alternatively taken together with the adjacent nitrogen atom to form: a saturated or unsaturated monocyclic or bicyclic 4-10 membered heterocyclic group, optionally substituted with an amino group, having 1-3 hetero atoms selected from a nitrogen atom, a sulfur atom, and an oxygen atom; a spiro heterocyclic group; or a bridged heterocyclic group), or —S(=O)$_2$Rf (wherein Rf represents an amino group, a C1-C6 alkyl group, or a 4-10 membered saturated heterocyclic group).

[14]

The compound or a salt thereof according to any one of [1]-[13], wherein in formula (I):

$R^3$ represents a C6-C10 aromatic hydrocarbon group or a fully unsaturated monocyclic or bicyclic 5-10 membered heterocyclic group having 1-3 heteroatoms selected from a nitrogen atom, a sulfur atom and an oxygen atom, wherein $R^3$ may be substituted with $R^{31}$, when $R^3$ has two substituents on the carbon atoms which are adjacent each other on the aromatic hydrocarbon ring, $R^3$ may be fused together with carbon atoms to which the substituents are attached to form a saturated or partially unsaturated monocyclic hydrocarbon having 4-8 carbon atoms (optionally substituted with groups selected from the group consisting of a halogen atom, a hydroxy group, an amino group, an oxo group, a C1-C6 alkyl group (which is optionally substituted with a hydroxy group), a halogeno C1-C6 alkyl group, a C1-C14 acyl group, a C1-C14 acylamino group, and a C1-C14 acyloxy group), or a saturated or partially unsaturated monocyclic 4-8 membered heterocyclic ring having 1-3 heteroatoms selected from the group consisting of a nitrogen atom, a sulfur atom and an oxygen atom (optionally substituted with a group selected from the group consisting of: a halogen atom; a hydroxy group; an amino group; an oxo group; and a C1-C6 alkyl group optionally substituted with a hydroxy group; a halogeno C1-C6 alkyl group; a C1-C14 acyl group; a C1-C14 acylamino group; and a C1-C14 acyloxy group);

$R^{31}$ represents a halogen atom, a cyano group, a nitro group, a carboxyl group, a thioamide group, a C1-C6 alkyl group (optionally substituted with a group selected from the group consisting of a halogen atom, a hydroxy group, a C1-C14 acyl group, a C1-C14 acyloxy group, a C2-C6 alkynyl group, and a C1-C6 alkoxy C1-C6 alkoxy group), an amino group, a C3-C6 cycloalkyl group (optionally substituted with an amino group), a C1-C6 alkoxy group (optionally substituted with a halogen atom), a C2-C7 alkoxycarbonyl group, a C1-C14 acyl group (optionally substituted with a halogen atom), a C6-C10 aromatic hydrocarbon group (optionally substituted with a halogen atom), an unsaturated monocyclic or bicyclic 5-10 membered heterocyclic group having 1 to 4 hetero atoms selected from a nitrogen atom, a sulfur atom and an oxygen atom (optionally substituted with a group consisting of a C1-C6 alkyl group and an oxo group), a —CONH$_2$ group, a (mono- or di-C1-C6 alkyl)aminocarbonyl group, a hydroxyamino carbonyl group, (C7-C13 aralkyloxy)oxyaminocarbonyl group, an aminosulfonyl group, a C1-C6 alkylsulfonyl group, or a piperidinosulfonyl group.

[15]

The compound or a salt thereof according to any one of [1]-[14], wherein in formula (I):

$R^3$ represents a C6-C10 aromatic hydrocarbon group (wherein the C6-C10 aromatic hydrocarbon group may be substituted with $R^{31}$, and when a C6-C10 aromatic hydrocarbon group has two substituents on the carbon atoms which are adjacent each other on the aromatic hydrocarbon ring, the substituents may be fused together with carbon atoms to which the substituents are attached to form a saturated or partially unsaturated monocyclic 4-6 membered heterocyclic ring having 1-3 heteroatoms selected from a nitrogen atom, a sulfur atom and an oxygen atoms (optionally substituted with a group selected from the group consisting of a hydroxy group, an amino group, an oxo group, a C1-C6 alkyl group, a halogeno C1-C6 alkyl group; a C1-C14 acyl amino group and a C1-C14 acyloxy group)), alternatively presents a fully unsaturated monocyclic 5 or 6 membered heterocyclic ring having 1-3 heteroatoms selected from a nitrogen atom, a sulfur atom and an oxygen atom (optionally substituted with a group selected from the group consisting of: a halogen atom; a C1-C6 alkyl group optionally substituted with a hydroxy group; a C1-C6 alkoxy group; a C2-C7 alkoxycarbonyl group; a —CONH$_2$ group; a (mono- or di-C1-C6 alkyl)aminocarbonyl group; a pyrrolidin-1-ylcarbonyl group; a morpholin-4-ylcarbonyl group; a 2-oxa-7-azaspiro[3.5]nonanyl group; a 3-oxa-8-azabicyclo[3.2.1]octanyl group; and an 8-oxa-3-azabicyclo[3.2.1]octanyl group), $R^{31}$ represents a halogen atom, an amino group, a C1-C6 alkyl group (optionally substituted with a group selected from the group consisting of a halogen atom and a hydroxy group), a C1-C6 alkoxy group (optionally substituted with a halogen atom), an unsaturated monocyclic 5 or 6 membered heterocyclic group having 1 to 4 hetero atoms selected from a nitrogen atom, a sulfur atom and an oxygen atom, a —CONH$_2$ group, a (mono or di-C1-C6 alkyl) aminocarbonyl group, or a hydroxyamino carbonyl group.

[16]

The compound or a salt thereof according to any one of [1]-[15], wherein in formula (I):

$X^1$ represents an oxygen atom,
$X^2$ represents an oxygen atom,
$X^3$ represents —NH—,
$X^4$ represents a hydrogen atom,
$R^1$ represents —C($R^{11}$)($R^{12}$)— (wherein $R^{11}$ represents a C1-C6 alkyl group, and $R^{12}$ represents a hydrogen atom), and $R^2$ represents a C6-C10 aromatic hydrocarbon group, wherein $R^2$ may be substituted with $R^{21}$, and when $R^2$ has two substituents on the carbon atoms which are adjacent each other on the aromatic hydrocarbon ring, the substituents may be fused together with carbon atoms to which the substituents are attached to form a saturated or partially unsaturated monocyclic hydrocarbon ring having 5 or 6 carbon atoms (optionally substituted with a C1-C6 alkyl group); and $R^{21}$ represents a halogen atom, a C1-C6 alkyl group, or a monocyclic 5 or 6 membered unsaturated heterocyclic group having 1-3 nitrogen atom(s) (optionally substituted with a C1-C6 alkyl group);

$R^3$ represents a C6-C10 aromatic hydrocarbon group (wherein the C6-C10 aromatic hydrocarbon group may be substituted with $R^{31}$, and when a C6-C10 aromatic hydrocarbon group has two substituents on the carbon atoms which are adjacent each other on the aromatic hydrocarbon ring, the substitutes may be fused together with carbon atoms to which the substituents are attached to form a saturated or partially unsaturated monocyclic 4-6 membered heterocyclic ring having 1-3 heteroatoms selected from a nitrogen atom, a sulfur atom and an oxygen atom (optionally substituted with a group selected from the group consisting of a hydroxy group, an amino group, an oxo group, a C1-C6 alkyl group, a halogeno C1-C6 alkyl group, a C1-C14 acyl amino group, and a C1-C14 acyloxy group)), alternatively presents a fully unsaturated monocyclic 5 or 6 membered heterocyclic ring having 1-3 heteroatoms selected from a nitrogen atom, a sulfur atom and an oxygen atom (optionally substituted with a group selected from the group consisting of a halogen atom, a C1-C6 alkyl group optionally substituted with a hydroxy group, a C1-C6 alkoxy group, a C2-C7 alkoxycarbonyl group, a —$CONH_2$ group, a (mono- or di-C1-C6 alkyl)aminocarbonyl group, a pyrrolidin-1-ylcarbonyl group, a morpholin-4-ylcarbonyl group, a 2-oxa-7-azaspiro[3.5]nonanyl group, a 3-oxa-8-azabicyclo[3.2.1]octanyl group and an 8-oxa-3-azabicyclo[3.2.1]octanyl group), $R^{31}$ represents a halogen atom, an amino group, a C1-C6 alkyl group (optionally substituted with a group selected from the group consisting of a halogen atom and a hydroxy group), a C1-C6 alkoxy group (optionally substituted with a halogen atom), a monocyclic 5 or 6 membered unsaturated heterocyclic group having 1 to 4 hetero atoms selected from a nitrogen atom, a sulfur atom and an oxygen atom, a —$CONH_2$ group, a (mono or di-C1-C6 alkyl) aminocarbonyl group, or a hydroxyamino carbonyl group.

$R^4$ represents a hydrogen atom.

[17]

The compound or a salt thereof according to any one of [1]-[16], wherein in formula (I):

$X^1$ represents an oxygen atom, $X^2$ represents an oxygen atom, $X^3$ represents —NH—, $X^4$ represents a hydrogen atom, $R^1$ represents —$C(R^{11})(R^{12})$— (wherein $R^{11}$ represents a methyl group, and $R^{12}$ represents a hydrogen atom), and $R^2$ represents a phenyl group, or a naphthyl group, wherein $R^2$ may be substituted with $R^{21}$, and when $R^2$ has two substituents on the carbon atoms which are adjacent each other on the aromatic hydrocarbon ring, the substituents may be fused together with carbon atoms to which the substituents are attached, to form a saturated or partially unsaturated monocyclic hydrocarbon ring having 5 or 6 carbon atoms (optionally substituted with a C1-C6 alkyl group); and $R^{21}$ represents a halogen atom or a C1-C6 alkyl group;

$R^3$ represents a phenyl group (wherein the phenyl group may be substituted with $R^{31}$, and when a phenyl group has two substituents on the carbon atoms which are adjacent each other on a benzene ring, the substitutes may be fused together with carbon atoms to which the substituents are attached to form a saturated or partially unsaturated monocyclic 6 membered heterocyclic ring having 1 or 2 oxygen atom(s) (optionally substituted with a group selected from the group consisting of a hydroxy group and a C1-C6 alkyl group)), or a pyridyl group (optionally substituted with a —$CONH_2$ group, a (mono- or di-C1-C6 alkyl)aminocarbonyl group, or a pyrrolidin-1-ylcarbonyl group);

$R^{31}$ represents a halogen atom, an amino group, a C1-C6 alkyl group or a —$CONH_2$ group;

$R^4$ represent a hydrogen atom.

[18]

The compound or a salt thereof according to any one of claims 1-17, wherein the compound is selected from the following compounds (1)-(19):

(1) 5-bromo-2-(N-((1S,2R)-2-(6-fluoro-2,3-dimethylphenyl)-1-(5-oxo-4,5-dihydro-1,3,4-oxadiazol-2-yl)propyl) sulfamoyl)benzamide;

(2) 5-chloro-2-(N-((1S,2R)-2-(2,3-dimethylphenyl)-1-(5-oxo-4,5-dihydro-1,3,4-oxadiazol-2-yl)propyl)sulfamoyl) benzamide;

(3) 5-bromo-2-(N-((1S,2R)-2-(2,3-dimethylphenyl)-1-(5-oxo-4,5-dihydro-1,3,4-oxadiazol-2-yl)propyl)sulfamoyl) benzamide;

(4) 5-chloro-2-(N-((1S,2R)-2-(6-fluoro-2,3-dimethylphenyl)-1-(5-oxo-4,5-dihydro-1,3,4-oxadiazol-2-yl)propyl) sulfamoyl)benzamide (5) 5-chloro-2-(N-((1S,2R)-2-(2-fluoronaphthalen-1-yl)-1-(5-oxo-4,5-dihydro-1,3,4-oxadiazol-2-yl)propyl)sulfamoyl)benzamide;

(6) 5-chloro-2-(N-((1S,2R)-2-(3-ethyl-6-fluoro-2-methylphenyl)-1-(5-oxo-4,5-dihydro-1,3,4-oxadiazol-2-yl) propyl)sulfamoyl)benzamide;

(7) 5-chloro-2-(N-((1S,2R)-2-(3-chloro-6-fluoro-2-methylphenyl)-1-(5-oxo-4,5-dihydro-1,3,4-oxadiazol-2-yl) propyl)sulfamoyl)benzamide;

(8) 5-bromo-2-(N-((1S,2R)-2-(3-chloro-6-fluoro-2-methylphenyl)-1-(5-oxo-4,5-dihydro-1,3,4-oxadiazol-2-yl) propyl)sulfamoyl)benzamide;

(9) 2-(N-((1S,2R)-2-(3-bromo-6-fluoro-2-methylphenyl)-1-(5-oxo-4,5-dihydro-1,3,4-oxadiazol-2-yl)propyl)sulfamoyl)-5-chloro-benzamide;

(10) 5-chloro-N-((1S,2R)-2-(6-fluoro-2,3-dimethylphenyl)-1-(5-oxo-4,5-dihydro-1,3,4-oxadiazol-2-yl)propyl)-6-(pyrrolidine-1-carbonyl)pyridine-2-sulfonamide;

(11) 5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide;

(12) 5-chloro-N-((1S,2R)-2-(3-chloro-6-fluoro-2-methylphenyl)-1-(5-oxo-4,5-dihydro-1,3,4-oxadiazol-2-yl) propyl)-4-hydroxy-4-methyl-chroman-8-sulfonamide;

(13) N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methylchroman-8-sulfonamide;

(14) 5-Chloro-N-((1S,2R)-2-(3-chloro-6-fluoro-2-methylphenyl)-1-(5-oxo-4,5-dihydro-1,3,4-oxadiazol-2-yl) propyl)-4-hydroxy-4-methyl-d3-chroman-8-sulfonamide;

(15) 5-chloro-N-((1S,2R)-2-(6-fluoro-2,3-dimethylphenyl)-1-(5-oxo-4,5-dihydro-1,3,4 oxadiazol-2-yl)propyl)-4-hydroxychroman-8-sulfonamide;

(16) 3-Chloro-6-(N-((1S,2R)-2-(6-fluoro-2,3-dimethylphenyl)-1-(5-oxo-4,5-dihydro-1,3,4-oxadiazol-2-yl)propyl) sulfamoyl)-N,N-dimethylpicolinamide;

(17) 4-Amino-2-methoxy-N-((1S,2R)-2-(8-methylnaphthalen-1-yl)-1-(5-oxo-4,5-dihydro-1,3,4-oxadiazol-2-yl)propyl)benzenesulfonamide;

(18) 4-Amino-N-((1S,2R)-2-(2,3-dihydro-1H-inden-4-yl)-1-(5-oxo-4,5-dihydro-1,3,4-oxadiazol-2-yl)propyl)-2-methoxybenzenesulfonamide; or

(19) 5-chloro-2-((1S,2R)-methyl-d3-2-(6-fluoro-2,3-dimethylphenyl)-1-(5-oxo-4,5-dihydro-1,3,4-oxadiazol-2-yl) propyl)sulfamoyl)benzamide.

[19]

A ribonucleotide reductase inhibitor comprising the compound or a salt thereof according to any one of [1]-[16] as an active ingredient.

[20]

A medicament comprising the compound or a salt thereof according to any one of [1]-[18].

[21]

A pharmaceutical composition comprising the compound or a salt thereof according to any one of [1]-[18] and a pharmaceutically acceptable carrier.

[22]

An anti-tumor agent comprising the compound or a salt thereof according to any one of [1]-[18] as an active ingredient.

[23]

An anti-tumor agent for oral administration comprising the compound or a salt thereof according to any one of [1]-[18] as an active ingredient.

[24]
Use of the compound or a salt thereof according to any one of [1]-[18] for manufacturing a ribonucleotide reductase inhibitor.
[25]
Use of the compound or a salt thereof according to any one of [1]-[18] for manufacturing a pharmaceutical composition.
[26]
Use of the compound or a salt thereof according to any one of [1]-[18] for manufacturing an anti-tumor agent.
[27]
Use of the compound or a salt thereof according to any one of [1]-[18] for manufacturing anantitumor agent for oral administration.
[28]
The compound or a salt thereof according to any one of [1]-[18] for use for inhibiting ribonucleotide reductase.
[29]
The compound or a salt thereof according to any one of [1]-[18] for use as a medicament.
[30]
The compound or a salt thereof according to any one of [1]-[18] for use for preventing and/or treating tumors.
[31]
The compound or a salt thereof according to any one of [1]-[18] for use for preventing and/or treating tumors by oral administration.
[32]
A method of inhibiting ribonucleotide reductase comprising administering an effective amount of the compound or a salt thereof according to any one of [1]-[18] to a subject in need thereof.
[33]
A method of preventing and/or treating tumors comprising administering an effective amount of the compound or a salt thereof according to any one of [1]-[18] to a subject in need thereof.

Effect of the Invention

According to the present invention, the novel sulfonamide compounds represented by the above formula (I) or salts thereof useful as RNR inhibitors are provided.

The compounds of the present invention or a salt thereof have an excellent RNR-inhibiting activity, and show a growth inhibitory effect for cancer cell lines. Accordingly, the compounds of the present invention or a salt thereof are useful as an anti-tumor agent and a therapeutic agent for other diseases where RNR are involved.

BRIEF DESCRIPTION OF THE DRAWINGS

FIG. 1 It is a diagram illustrating daily variation of relative tumor volume (hereinafter also referred to as "RTV") with the compound according to the present invention.

FIG. 2 It is a diagram showing daily variation of RTV with the compound according to the present invention.

FIG. 3 It is a diagram showing daily variation of RTV with the compound according to the present invention.

FIG. 4 It is a diagram showing daily variation of RTV with the compound according to the present invention.

DETAILED DESCRIPTION OF THE INVENTION

The compounds of the present invention represented by formula (I) are compounds having a sulfonamide structure, and are novel compounds which are not described in the prior art literature described hereinafter.

"CA-CB" as used herein refers to a group having a carbon number of A-B in the present specification. For example, "C1-C6 alkyl group" represents an alkyl group having 1 to 6 carbon atoms. The term "A-B members" indicates that the number of atoms constituting the ring (ring members) is A-B. For example, "5-10 membered unsaturated heterocyclic group" means an unsaturated heterocyclic group whose ring member is 5-10.

"Substituent" as used herein refers to a halogen atom, a hydroxy group, an amino group, an oxo group, a cyano group, a nitro group, a carboxyl group, an aminocarbonyl group, a thioamide group, a C1-C6 alkyl group, a C2-C6 alkynyl group, a C3-C6 cycloalkyl group, a C1-C6 alkoxy group, a C1-C6 alkoxy C1-C6 alkoxy group, a halogeno C1-C6 alkyl group, a halogeno C1-C6 alkoxy group, a C6-C14 aromatic hydrocarbon group, an unsaturated heterocyclic group, a saturated heterocyclic group, a nitrogen-containing saturated heterocyclic group, a nitrogen-containing saturated heterocyclic carbonyl group, a C1-C14 acyl group, a C1-C14 acylamino group, a C2-C7 alkoxycarbonyl group, a C1-C14 acyloxy group, C7-C13 aralkyloxy group and the like.

"Halogen atom" as used herein refers to a fluorine atom, a chlorine atom, a bromine atom, and an iodine atom.

"C1-C6 alkyl group" as used herein refers to a straight or branched saturated hydrocarbon group having 1 to 6 carbon atoms, such as a methyl group, an ethyl group, an n-propyl group, an isopropyl group, an n-butyl group, an isobutyl group, a tert-butyl group, an n-pentyl group, an isopentyl group, a hexyl group and the like.

"C2-C6 alkynyl group" as used herein refers to an unsaturated straight-chain or branched hydrocarbon group having 2 to 6 carbon atoms and at least one triple bond, e.g., ethynyl, 1- or 2-propynyl group, 1-, 2- or 3-butynyl group, 1-methyl-2-propynyl group and the like.

"C3-C6 cycloalkyl group" as used herein refers to a saturated cyclic hydrocarbon group having 3 to 6 carbon atoms, for example, a cyclopropyl group, a cyclobutyl group, a cyclopentyl group, a cyclohexyl group and the like.

"C1-C6 alkoxy group" as used herein refers to an oxy group to which a straight-chain or branched saturated hydrocarbon group having 1 to 6 carbon atoms is bonded, for example, a methoxy group, an ethoxy group, a propoxy group, an isopropoxy group, an n-butoxy group, an isobutoxy group, a tert-butoxy group, a pentyloxy group, an isopentyloxy group, a hexyloxy group and the like.

"C1-C6 alkoxy C1-C6 alkoxy group" as used herein refers to a C1-C6 alkoxy group in which one of the hydrogen atom of the C1-C6 alkoxy group is substituted with a C1-C6 alkoxy group, for example, a methoxymethoxy group, a methoxyethoxy group, a methoxy propoxy group, an ethoxymethoxy group, an ethoxyethoxy group, a propoxy methoxy group and the like.

"halogeno C1-C6 alkyl group" as used herein refers to a C1-C6 alkyl group in which one or more hydrogen atoms are substituted with a halogen atom, for example, a fluoromethyl group, a difluoromethyl group, a trifluoromethyl group, a trichloromethyl group, a fluoroethyl group, 1,1,1-trifluoroethyl group, a mono fluoro-n-propyl group, a perfluoro-n-propyl group, a perfluoro isopropyl group and the like.

"C6-C14 aromatic hydrocarbon group" as used herein refers to a monocyclic or polycyclic aromatic hydrocarbon group having 6 to 14 carbon atoms, for example, a phenyl group, a naphthyl group, an anthracenyl group, a phenanthryl group, a fluorenyl group and the like.

"Unsaturated heterocyclic group" as used herein refers to a monocyclic or polycyclic unsaturated heterocyclic group having at least one hetero atom selected from a nitrogen atom, a sulfur atom and an oxygen atom (preferably 1 to 4, more preferably 1 to 3). The unsaturated heterocyclic group includes a fully unsaturated heterocyclic group (a fully unsaturated heterocyclic group) and a partially unsaturated heterocyclic group (a partially unsaturated heterocyclic group).

A fully unsaturated heterocyclic group includes, for example, a pyrrolyl group, an imidazolyl group, a pyrazolyl group, a triazolyl group, a tetrazolyl, a furanyl (a furyl group), an oxazolyl group, an isoxazolyl group, an oxadiazolyl group, a thiophenyl group (a thienyl group), a thiazolyl group, an isothiazolyl group, a thiadiazolyl group, a pyridinyl group (a pyridyl group), a pyrimidinyl group (pyrimidyl group), a pyrazinyl group (a pyrazyl group), a pyridazinyl group, an indolyl group, an isoindolyl group, an indazolyl group (a benzpyrazol group), a benzimidazolyl group, a benzotriazolyl group, an azaindolyl group, a pyrrolopyridinyl group, an imidazopyridinyl group, a pyrazolopyridinyl group, a triazolopyridinyl group, a pyrrolopyrimidinyl group, an imidazopyrimidinyl group, a pyrazolopyrimidinyl group, a benzofuranyl group, a benzoxazolyl group, a benzothiophenyl group (a benzothienyl group), a benzothiazolyl group, a benzothiadiazolyl group, a benzofuranyl group (a benzofuryl group), a quinolyl group, an isoquinolyl group, a quinazolinyl group, a quinoxalyl group and the like.

A partially unsaturated heterocyclic group includes, for example, a dihydropyranyl group, a dihydro triazolyl group, a dihydrofuranyl group, a dihydrooxadiazolyl group, a dihydroquinolyl group, a dihydroquinazolinyl group, an indolinyl group, a tetrahydroisoquinolyl group, a methylenedioxyphenyl group, an ethylenedioxy phenyl group, a dihydrobenzofuranyl group, a dihydro-benzoxazolyl group, a dihydropyridooxazinyl group and the like.

"Saturated heterocyclic group" as used herein refers to a single or polycyclic fully saturated heterocyclic group having at least one hetero atom selected from a nitrogen atom, a sulfur atom and an oxygen atom (preferably 1 to 4, more preferably 1 to 3), and includes, for example, an azetidinyl group, a pyrrolidinyl group, a piperidinyl group, a piperazinyl group, a hexamethyleneimino group, a morpholino group, a thiomorpholino group, a homopiperazinyl group, a tetrahydrofuranyl group, a tetrahydropyranyl group, a tetrahydrothiophenyl group, a thiazolidinyl group, an oxazolidinyl group and the like.

"Nitrogen-containing saturated heterocyclic group" as used herein refers to a saturated heterocyclic group having one or more nitrogen atoms, which optionally includes a hetero atom other than nitrogen atom, and includes, for example, a morpholino group.

"Nitrogen-containing saturated heterocyclic carbonyl group" as used herein refers to a carbonyl group to which a nitrogen-containing saturated heterocyclic group is bonded, and includes, for example, a morpholinocarbonyl group.

"C1-C14 acyl group", as used herein refers to a carbonyl group to which a hydrogen atom, a C1-C6 alkyl group, a C6-C14 aromatic hydrocarbon group or an unsaturated heterocyclic group is bonded, and includes, for example: a formyl group; a (C1-C6 alkyl) carbonyl group such as an acetyl group, a propanoyl group, a butanoyl group; a (C3-C6 cycloalkyl) carbonyl group such as a cyclopropanoyl group, a cyclobutanoyl group; or a (C6-C13) arylcarbonyl group such as a benzoyl group, a naphthyl carbonyl group, a fluorenylcarbonyl group.

"C1-C14 acylamino group" as used herein refers to an amino group in which one or two hydrogen atoms are substituted with a C1-C14 acyl group, and includes, for example, an acetylamino group, a propanoylamino group, a butanoylamino group, a cyclopropanoyl amino group.

"C2-C7 alkoxycarbonyl group", as used herein refers to a carbonyl group to which a C1-C6 alkoxy group is bonded, and includes, for example, a methoxycarbonyl group, an ethoxycarbonyl group, an n-propoxycarbonyl group, an iso-propoxycarbonyl group, an n-butoxycarbonyl group, a tert-butoxycarbonyl group and the like.

"C1-C14 acyloxy group" as used herein refers to, for example, a formyloxy group; a (C1-C6 alkyl)carbonyloxy group such as a methyl carbonyloxy group, an ethyl carbonyloxy group, an n-propyl carbonyloxy group, an isopropylcarbonyloxy group, an n-butylcarbonyloxy group, an iso-butylcarbonyloxy group, a tert-butylcarbonyloxy group, an n-pentylcarbonyloxy group, an iso-pentylcarbonyloxy group, a hexylcarbonyloxy group and the like; a (C3-C6 cycloalkyl)carbonyloxy group such as a cyclopropanoyloxy group, a cyclobutanoyloxy group and the like; a (C6-C13 aryl)carbonyloxy group such as a phenylcarbonyloxy group, naphthylcarbonyloxy group, a fluorenylcarbonyloxy group and the like.

"C7-C13 aralkyloxy group" as used herein refers to an alkylloxy group in which one hydrogen atom is substituted with an aryl group, and includes, for example, a benzyloxy group, a phenethyloxy group, a naphthylmethyloxy group, a fluorenylmethyloxy group and the like.

"Saturated or partially unsaturated hydrocarbon ring" as used herein refers to a monocyclic or polycyclic saturated or partially unsaturated hydrocarbon ring, and includes, for example, a cyclopropane ring, a cyclobutane ring, a cyclopentane ring, a cyclohexane ring, a cycloheptane ring, a cyclooctane ring, a cyclobutene ring, a cyclopentene ring, a cyclohexene ring, a cycloheptene ring, a cyclooctadiene ring and the like.

"Saturated or partially unsaturated heterocyclic ring" as used herein refers to a monocyclic or polycyclic saturated or partially unsaturated heterocyclic a ring having a hetero atom selected from a nitrogen atoms a sulfur atom and an oxygen atom, and includes, for example, an oxirane ring, an azetidine ring, a pyrrolidine ring, an imidazolidine ring, a piperidine ring, a piperazine ring, a morpholine ring, a tetrahydrofuran ring, a tetrahydropyran ring, a dioxane ring, a tetrahydrothiophene ring, a dihydropyran ring, a dihydrofuran ring and the like.

"Spiro heterocyclic group" as used herein refers to a saturated or unsaturated spiro heterocyclic group having a spiro carbon atom and a hetero atom selected from a nitrogen atom, a sulfur atom and an oxygen atom, and includes, for example, a 2-oxa-6-azaspiro[3.4]octanyl group, a 2-oxa-7-azaspiro[3.5]nonanyl group and the like.

"Bridged heterocyclic group" as used herein refers to a bridged heterocyclic group having more than one ring, which have two bridgehead carbons and a hetero atom selected from a nitrogen atom, a sulfur atom and an oxygen atom, and includes, for example, a 3-oxa-8-azabicyclo [3.2.1]octanyl group, an 8-oxa-3-azabicyclo[3.2.1]octanyl group and the like.

In the compounds represented by the formula (I) of the present specification, $X^1$ is an oxygen atom or a sulfur atom. $X^1$ is preferably an oxygen atom.

In the compounds represented by the formula (I) of the present specification, $X^2$ is an oxygen atom or —NH—. $X^2$ is preferably an oxygen atom.

In the compounds represented by the formula (I) of the present specification, $X^3$ is —NH— or an oxygen atom. $X^3$ is preferably —NH—.

In the compounds of the formula (I), $X^4$ is a hydrogen atom or a C1-C6 alkyl group.

"C1-C6 alkyl group" represented by $X^4$ is preferably a C1-C3 alkyl group, more preferably a methyl group.

$X^4$ is preferably a hydrogen atom or a methyl group, more preferably a hydrogen atom.

In the compounds of the formula (I), $R^1$ is, —C($R^{11}$)($R^{12}$)— or —C(=CH$_2$)—.

In —C($R^{11}$)($R^{12}$)—, $R^{11}$ and $R^{12}$ are the same or different, and are a hydrogen atom, a halogen atom, a hydroxy group, or a C1-C6 alkyl group, alternatively taken together with the carbon atoms to which they attach to form a saturated hydrocarbon ring having 3 to 8 carbon atoms.

"Halogen atom" represented by $R^{11}$ and $R^{12}$ is preferably a fluorine atom, a chlorine atom, a bromine atom, more preferably a fluorine atom.

"C1-C6 alkyl group" indicated in $R^{11}$ and $R^{12}$ is preferably a C1-C3 alkyl group, more preferably a methyl group or an ethyl group, more preferably a methyl group.

"Saturated hydrocarbon ring having 3 to 8 carbon atoms", which is formed by combining $R^{11}$ and $R^{12}$ together with the carbon atoms to which they attached, is preferably a monocyclic saturated hydrocarbon ring of 3 to 6 carbon atoms, and more preferably a cyclopropane ring.

Preferably, $R^{11}$ is a halogen atom, a hydroxy group, or a C1-C6 alkyl group, and $R^{12}$ is a hydrogen atom, a halogen atom, a hydroxy group, or a C1-C6 alkyl group, alternatively $R^{11}$ and $R^{12}$ are taken together with the carbon atoms to which they are attached to form a saturated hydrocarbon ring having 3 to 8 carbon atoms. More preferably, $R^{11}$ is a C1-C6 alkyl group, and $R^{12}$ is a hydrogen atom, and more preferably $R^{11}$ is a methyl group, and $R^{12}$ is a hydrogen atom.

$R^1$ is preferably —C($R^{11}$)($R^{12}$)—, $R^{11}$ is a halogen atom, a hydroxy group, or a C1-C6 alkyl group, and $R^{12}$ is a hydrogen atom, a halogen atom, hydroxy group, or a C1-C6 alkyl group, alternatively $R^{11}$ and $R^{12}$ are taken together with the carbon atoms to which they are attached to form a saturated hydrocarbon ring having 3 to 8 carbon atoms. More preferably, —C($R^{11}$)($R^{12}$)—, and, $R^{11}$ is a C1-C6 alkyl group, $R^{12}$ is a hydrogen atom. Even more preferably, it is —CH(CH$_3$)—.

In the compounds of the formula (I), $R^2$ is a C6-C14 aromatic hydrocarbon group or a 9-10 membered fully unsaturated heterocyclic group.

"C6-C14 aromatic hydrocarbon group" represented by $R^2$ is preferably a C6-C10 aromatic hydrocarbon group, more preferably a phenyl group or a naphthyl group, even more preferably a phenyl group.

Furthermore, "fully unsaturated heterocyclic group having 9-10 membered" represented by $R^2$ is preferably a bicyclic 9-10 membered fully unsaturated heterocyclic group having 1-3 heteroatoms selected from a nitrogen atom, a sulfur atom and an oxygen atom, more preferably a bicyclic 9-10 membered fully unsaturated heterocyclic group having 1-2 hetero atoms selected from a nitrogen atom and a sulfur atom, even more preferably a benzothiophenyl group, a benzothiazolyl group, a quinolyl group.

In the compounds of the formula (I), $R^2$ may be unsubstituted or may have a substituent. Further, when $R^2$ has two substituents on the carbon atoms adjacent each other on the aromatic hydrocarbon ring, $R^2$ may form a 4 to 8-membered saturated or partially unsaturated hydrocarbon ring or a heterocyclic ring having substituent(s), wherein the substitutes are fused to form a ring together with the carbon atom to which they are attached.

When $R^2$ has a substituent, the substituted position of the substituent is not particularly limited, but, for example, preferably 2, 3, 5, or 6-position when $R^2$ is a phenyl group. Furthermore, the number of substituent is not particularly limited, but preferably zero, i.e. it is unsubstituted or 1-4, and more preferably 1-4 or 1-3. When the number of substituents is two or more, the types of the substituent may be the same or different.

In the compounds of formula (I), preferably, $R^2$ may be substituted with the "substituent", more preferably, $R^2$ may be substituted with $R^{21}$. Also, preferably, when $R^2$ has two substituents on the carbon atoms adjacent each other on the aromatic hydrocarbon ring, the substituents may be fused together with the carbon atom to which they are attached to form a saturated or partially unsaturated 4-8 membered hydrocarbon ring or heterocyclic ring optionally substituted with Rz.

$R^{21}$, which can be substituted at $R^2$, is a halogen atom, an aminocarbonyl group, a cyano group, a C1-C6 alkyl group which may be substituted with Rx, a C3-C6 cycloalkyl group which may be substituted with Rx, a C2-C6 alkynyl group which may be substituted with Rx, a C6-C14 aromatic hydrocarbon group which may be substituted with Ry, or an unsaturated 5-10 membered heterocyclic ring which may be substituted with Rz.

The position at which $R^{21}$ is a substituted is not particularly limited, but, for example, preferably 2, 3, 5, or 6-position when $R^2$ is a phenyl group. Furthermore, the number of the substituent $R^{21}$ is not particularly limited, but preferably zero, i.e. it is unsubstituted, or 1-4, more preferably 1-4 or 1-3. When the number of the substituent $R^{21}$ is two or more, the types of the substituent may be the same or different.

"Halogen atom" indicated in $R^{21}$ is preferably a fluorine atom, a chlorine atom, or a bromine atom.

"C1-C6 alkyl group" in the "C1-C6 alkyl group which may be substituted with Rx" indicated in $R^{21}$ is preferably a C1-C3 alkyl group, more preferably a methyl group or an ethyl group.

The substituent Rx in the "C1-C6 alkyl group which may be substituted with Rx" indicated in $R^{21}$ is a halogen atom or a C6-C14 aromatic hydrocarbon group. The substituent Rx is preferably a halogen atom, more preferably a fluorine atom. The number of Rx which is substituted at C1-C6 alkyl group is not particularly limited, but preferably zero, i.e., unsubstituted, or 1-3. When the number of substituent Rx is 2 or more, the types of the substituent may be the same or different.

"C3-C6 cycloalkyl group" in the "C3-C6 cycloalkyl group which may be substituted with Rx" indicated in $R^{21}$ is preferably a cyclopropyl group.

Rx in the "C3-C6 cycloalkyl group which may be substituted with Rx" indicated in $R^{21}$ is a halogen atom as mentioned above, or a C6-C14 aromatic hydrocarbon group, preferably a halogen atom, more preferably a fluorine atom. The number of Rx substituted at the C3-C6 cycloalkyl group is not particularly limited, but preferably zero, i.e. it is unsubstituted, or 1, more preferably 0. When the number of substituents Rx is 2 or more, the types of the substituent may be the same or different.

"C2-C6 alkynyl group" in the "C2-C6 alkynyl group which may be substituted with Rx" indicated in $R^{21}$ is preferably a C2-C4 alkynyl group, more preferably an ethynyl group.

The substituent Rx in the "C2-C6 alkynyl group may be substituted with Rx" indicated in $R^{21}$ is a halogen atom as mentioned above, or a C6-C14 aromatic hydrocarbon group, preferably a C6-C14 aromatic hydrocarbon group, more preferably a C6-C10 aromatic hydrocarbon group, more preferably a phenyl group.

The number of Rx substituted at the C2-C6 alkynyl group is not particularly limited, but preferably zero, i.e. it is unsubstituted, or 1, more preferably 1. When the number of the substituents Rx is 2 or more, the types of the substituent may be the same or different.

"C6-C14 aromatic hydrocarbon group" in the "C6-C14 aromatic hydrocarbon group which may be substituted with Ry" indicated in $R^{21}$ is preferably a C6-C10 aromatic hydrocarbon group, more preferably a phenyl group.

The substituent Ry in the "C6-C14 aromatic hydrocarbon group which may be substituted with Ry" indicated in $R^{21}$ is a halogen atom or a C1-C6 alkoxy group.

A halogen atom indicated in Ry is preferably a fluorine atom or chlorine atom. Also, a C1-C6 alkoxy group indicated in Ry is preferably a C1-C3 alkoxy group, more preferably a methoxy group.

The substituent Ry in the "C6-C14 aromatic hydrocarbon group which may be substituted with Ry" indicated in $R^{21}$ is preferably a fluorine atom, a chlorine atom, or a C1-C3 alkoxy group, more preferably a fluorine atom, a chlorine atom or a methoxy group. The number of Ry substituted in the C6-C14 aromatic hydrocarbon group is not particularly limited, but preferably zero, i.e. unsubstituted, or it is 1 or 2. When the number of the substituents Ry is 2 or more, the types of substituent may be the same or different.

"5 to 10-membered unsaturated heterocyclic group" in the "5 to 10-membered unsaturated heterocyclic group optionally substituted with Rz" indicated in $R^{21}$ is preferably a fully or partially unsaturated monocyclic or bicyclic 5-10 membered heterocyclic group having 1-3 hetero atoms selected from a nitrogen atom, a sulfur atom and an oxygen atom, more preferably a monocyclic or bicyclic 5 to 10-membered unsaturated heterocyclic group having 1 to 3 hetero atoms selected from a nitrogen atom, a sulfur atom or an oxygen atom, more preferably a monocyclic 5-6 membered unsaturated heterocyclic group having 1-3 nitrogen atoms or an oxygen atom. Preferably, it is a pyrrolyl group, an imidazolyl group, a pyrazolyl group, a pyridyl group, a pyrimidyl group, an oxazolyl group, a dihydropyridooxazinyl group, more preferably, a pyrazolyl group, a pyridyl group, a pyrimidyl group, an oxazolyl group, a dihydropyridooxazinyl group, more preferably a pyrazolyl group.

The substituent Rz in the "5 to 10-membered unsaturated heterocyclic group optionally substituted with Rz" indicated in $R^{21}$ is a halogen atom, a C1-C6 alkyl group, a halogeno C1-C6 alkyl group, a C3-C6 cycloalkyl group, a C1-C6 alkoxy group, a C6-C14 aromatic hydrocarbon group, a nitrogen-containing saturated heterocyclic group, or a nitrogen-containing saturated heterocyclic carbonyl group.

"Halogen atom" indicated in Rz is preferably a fluorine atom or a chlorine atom.

"C1-C6 alkyl group" indicated in Rz is preferably a C1-C3 alkyl group, more preferably a methyl group, or an ethyl group.

"Halogeno C1-C6 alkyl group" indicated in Rz is preferably a halogeno C1-C3 alkyl group, more preferably a difluoromethyl group or a trifluoromethyl group.

"C3-C6 cycloalkyl group" indicated in Rz is preferably a cyclopropyl group or a cyclobutyl group.

"C1-C6 alkoxy group" indicated in Rz is preferably a C1-C3 alkoxy group, more preferably a methoxy group.

"C6-C14 aromatic hydrocarbon group" indicated in Rz is preferably a phenyl group.

"Nitrogen-containing saturated heterocyclic group" represented by Rz is preferably a morpholino group or a piperidinyl group.

"Nitrogen-containing saturated heterocyclic carbonyl group" indicated in Rz is preferably a morpholinocarbonyl group.

The substituent Rz in the "5 to 10-membered unsaturated heterocyclic group optionally substituted with Rz" is preferably a halogen atom, a C1-C6 alkyl group, a halogeno C1-C6 alkyl group, a C3-C6 cycloalkyl group, a C1-C6 alkoxy group, a phenyl group, a morpholino group, a piperidinyl group, or a morpholinocarbonyl group, more preferably a C1-C6 alkyl group, more preferably a methyl group. The number of Rz which is substituted at the 5 to 10-membered unsaturated heterocyclic group is not particularly limited, but preferably zero, i.e. unsubstituted, or preferably 1 or 2. When the number of the substituent Rz is 2 or more, the type of the substituent may be the same or different.

$R^{21}$, which can be substituted at $R^2$, is preferably, a halogen atom, an aminocarbonyl group, a cyano group, a C1-C6 alkyl group (optionally substituted with a halogen atom), a C3-C6 cycloalkyl group, a C2-C6 alkynyl group (optionally substituted with a C6-C14 aromatic hydrocarbon group) a C6-C14 aromatic hydrocarbon group (optionally substituted with a group selected from a halogen atom and a C1-C6 alkoxy group), or a monocyclic or bicyclic 5 to 10-membered unsaturated heterocyclic group having 1 to 3 hetero atoms selected from a nitrogen atom, a sulfur atom and an oxygen atom (optionally substituted with a group selected from a halogen atom, a C1-C6 alkyl group, a halogeno C1-C6 alkyl group, a C3-C6 cycloalkyl group, a C1-C6 alkoxy group, a C6-C14 aromatic hydrocarbon group, a nitrogen-containing saturated heterocyclic group, and a nitrogen-containing saturated heterocyclic carbonyl group).

More preferably, a halogen atom, a cyano group, a C1-C6 alkyl group (optionally substituted with a halogen atom), a C3-C6 cycloalkyl group, a phenyl group (optionally substituted with a group selected from the group consisting of a halogen atom or a C1-C6 alkoxy group), or monocyclic or bicyclic 5 to 10-membered unsaturated heterocyclic group having 1 to 3 hetero atom(s) selected from a nitrogen atom, a sulfur atom and an oxygen atom (optionally substituted with a group selected from a halogen atom, a C1-C6 alkyl group, a halogeno C1-C6 alkyl group, a C3-C6 cycloalkyl group, a C1-C6 alkoxy group, a morpholino group, a piperidinyl group and a morpholinocarbonyl group).

More preferably, a halogen atom, a C1-C6 alkyl group, or a monocyclic 5 or 6-membered unsaturated heterocyclic group having 1 to 3 of a nitrogen atom(s) (optionally substituted with a C1-C6 alkyl group).

More preferably, a halogen atom or a C1-C6 alkyl group.

In the compounds of the formula (I), when the number of the substituents at $R^2$ is 2 or more, and there are two substituents at the carbons which are adjacent each other on the aromatic hydrocarbon ring, "4 to 8-membered saturated or partially unsaturated hydrocarbon ring or heterocyclic ring which may have substituent(s)", which is formed by combining the substituents and the carbon atom to which they are attached, is a ring, for example a ring fused to a benzene ring." Saturated or partially unsaturated 4 to 8-membered hydrocarbon ring or heterocyclic ring" in the "4-8 membered saturated or partially unsaturated hydrocarbon ring or heterocyclic ring, which may have substituent(s)" is preferably a monocyclic saturated or partially unsaturated hydrocarbon ring, or a monocyclic 4 to 8-membered saturated or partially unsaturated heterocyclic ring having 1 to 3 hetero atoms selected from a nitrogen atom, a sulfur atom and an oxygen atoms, more preferably, a saturated or partially unsaturated hydrocarbon ring having 4 to 8 carbon atoms, more preferably, a monocyclic saturated or partially unsaturated hydrocarbon ring having 4 to 6 carbon atoms, or a monocyclic 4-6 membered saturated or partially unsaturated heterocyclic ring having 1 to 3 heteroatoms selected from nitrogen atom, a sulfur atom, and an oxygen atom, and even more preferably, a monocyclic saturated or partially unsaturated hydrocarbon ring having 5 or 6 carbon atoms, more preferably a saturated hydrocarbon ring having 5 carbon atoms.

The substituent Rz in the "4 to 8-membered saturated or partially unsaturated hydrocarbon ring or heterocyclic ring optionally substituted with Rz" is, as mentioned above, a halogen atom, a C1-C6 alkyl group, a halogeno C1-C6 alkyl group, a C3-C6 cycloalkyl group, a C1-C6 alkoxy group, a C6-C14 aromatic hydrocarbon group, a nitrogen-containing saturated heterocyclic group, or a nitrogen-containing saturated heterocyclic carbonyl group, preferably a C1-C6 alkyl group, and more preferably, a C1-C3 alkyl group, and even more preferably, a methyl group. The number of Rz which substitutes at a saturated or partially unsaturated hydrocarbon ring or heterocyclic ring is not particularly limited, but preferably zero, i.e., unsubstituted, or it is one, more preferably it is zero, i.e., unsubstituted. When the number of the substituents Rz is 2 or more, the type of substituent may be the same or different.

"Saturated or partially unsaturated 4-8 membered hydrocarbon ring or heterocyclic ring optionally substituted with Rz" is preferably a monocyclic saturated or partially unsaturated hydrocarbon ring having 4 to 8 carbon atoms, which is optionally substituted with Rz, or a monocyclic 4-8 membered saturated or partially unsaturated heterocyclic ring having 1 to 3 hetero atoms selected from a nitrogen atom, a sulfur atom, and an oxygen atom, more preferably a monocyclic saturated or partially unsaturated hydrocarbon ring having 4 to 8 carbon atoms (which may be substituted with a C1-C6 alkyl group) or a monocyclic saturated or partially unsaturated 4-8 membered heterocyclic ring having 1-3 heteroatoms selected from a nitrogen atom, a sulfur atom and an oxygen atom (optionally substituted with a C1-C6 alkyl group), more preferably a saturated or partially unsaturated monocyclic hydrocarbon ring having 4 to 8 carbon atoms (optionally substituted with a C1-C6 alkyl group), more preferably a monocyclic saturated or partially unsaturated hydrocarbon ring having 5 or 6 carbon atoms (optionally substituted with a C1-C6 alkyl group).

In the compounds represented by formula (I), a fused ring, which is formed when the compound has two substituents on the carbon atoms adjacent each other on the aromatic hydrocarbon ring of $R^2$, is for example, a dihydro-indene ring, a tetrahydronaphthalene ring, a dihydrobenzofuran ring.

In the compounds represented by formula (I), $R^2$ is preferably a C6-C14 aromatic hydrocarbon group or a bicyclic fully unsaturated 9-10 membered heterocyclic group having 1 to 3 heteroatoms selected from a nitrogen atom, a sulfur atom and an oxygen atoms, and $R^2$ may be substituted with $R^{21}$, and when $R^2$ has two substituents on the carbon atom adjacent each other on the aromatic hydrocarbon ring, $R^2$ may be a monocyclic saturated or partially unsaturated hydrocarbon ring having 4 to 8 carbon atoms (optionally substituted with a C1-C6 alkyl group) wherein the substituents are fused together with the carbon atom to which each of the substituent is bonded, or a monocyclic 4-8 membered saturated or partially unsaturated heterocyclic ring having 1 to 3 hetero atoms selected from a nitrogen atom, a sulfur atom and an oxygen atoms (optionally substituted with a C1-C6 alkyl group); and $R^{21}$ is a halogen atom, an aminocarbonyl group, a cyano group, a C1-C6 alkyl group (optionally substituted with a halogen atom), a C3-C6 cycloalkyl group, a C2-C6 alkynyl group (optionally substituted with a C6-C14 aromatic hydrocarbon group), a C6-C14 aromatic hydrocarbon group (optionally substituted with a group selected from the group consisting of a halogen atom and a C1-C6 alkoxy group), or a monocyclic or bicyclic 5-10 membered unsaturated heterocyclic ring having 1 to 3 hetero atoms selected from a nitrogen atom, a sulfur atom, and an oxygen atom (optionally substituted with a group selected from the group consisting of a halogen atom, a C1-C6 alkyl group, a halogeno C1-C6 alkyl group, a C3-C6 cycloalkyl group, a C1-C6 alkoxy group, a C6-C14 aromatic hydrocarbon group, a nitrogen-containing saturated heterocyclic group, and a nitrogen-containing saturated heterocyclic carbonyl group).

In the compounds represented by formula (I), $R^2$ is more preferably a C6-C14 aromatic hydrocarbon group, wherein $R^2$ may be substituted with $R^{21}$, and when $R^2$ has two substituents on the carbon atom adjacent each other on the aromatic hydrocarbon ring, $R^2$ may form a monocyclic saturated or partially unsaturated hydrocarbon ring having 4 to 8 carbon atoms (optionally substituted with a C1-C6 alkyl group) wherein the substituents are fused together with the carbon atom to which each of the substituent is bonded;

$R^{21}$ is a halogen atom, a cyano group, a C1-C6 alkyl group (optionally substituted with a halogen atom), a C3-C6 cycloalkyl group, a phenyl group (optionally substituted with a group selected from the group consisting of a halogen atom a C1-C6 alkoxy group), or a monocyclic or bicyclic 5-10 membered unsaturated heterocyclic ring having 1 to 3 hetero atoms selected from a nitrogen atom, a sulfur atom and an oxygen atom (optionally substituted with a group selected from the group consisting of a halogen atom, a C1-C6 alkyl group, a halogeno C1-C6 alkyl group, a C3-C6 cycloalkyl group, a C1-C6 alkoxy group, a morpholino group, a piperidinyl group and a morpholinocarbonyl group).

Also, in the compounds represented by formula (I), $R^2$ is more preferably a C6-C10 aromatic hydrocarbon group, wherein $R^2$ may be substituted with $R^{21}$, and when $R^2$ has two substituents on the carbon atom adjacent each other on the aromatic hydrocarbon ring, $R^2$ may form a monocyclic saturated or partially unsaturated hydrocarbon ring having 5 or 6 carbon atoms (optionally substituted with a C1-C6 alkyl group) wherein the substituents are fused together with the carbon atom to which each of the substituents is bonded; and $R^{21}$ is a halogen atom, a C1-C6 alkyl group, or a monocyclic 5 or 6-membered unsaturated heterocyclic ring having 1-3 nitrogen atom(s) (optionally substituted with a C1-C6 alkyl group).

Also, in the compounds represented by formula (I), $R^2$ is especially preferably a phenyl group or a naphthyl group (optionally substituted with a group selected from the group consisting of a halogen atom and a C1-C6 alkyl group); an indanyl group (2,3-dihydro-1H-indenyl group); or a tetrahydronaphthyl group.

In the compounds represented by formula (I), $R^3$ is a C6-C14 aromatic hydrocarbon group or a 5 to 10-membered fully unsaturated heterocyclic group.

"C6-C14 aromatic hydrocarbon group" indicated in $R^3$ is preferably a C6-C10 aromatic hydrocarbon group, more preferably a phenyl group, or a naphthyl group, particularly preferably a phenyl group.

"5 to 10-membered fully unsaturated heterocyclic group" indicated in $R^3$ is a monocyclic or bicyclic 5 to 10-membered fully unsaturated heterocyclic group having 1-3 hetero atoms selected from a nitrogen atom, a sulfur atom and an oxygen atom, more preferably, a monocyclic or bicyclic 5 to 7-membered fully unsaturated heterocyclic group having 1-3 heteroatoms selected from a nitrogen atom, a sulfur atom and an oxygen atom, particularly preferably a monocyclic 5 to 6-membered fully unsaturated heterocyclic ring having 1-3 heteroatoms selected from a nitrogen atom, a sulfur atom and an oxygen atoms. Preferably, an imidazolyl group, a pyridyl group, a thiophenyl group, an indolyl group, an indazolyl group, a benzopyranyl group, a benzotriazolyl group, a benzothiadiazolyl group, an isoxazolyl group, a quinolyl group, more preferably an imidazolyl group, a pyridyl group, a thiophenyl group, an indolyl group, an indazolyl group, a benzopyranyl group, a benzotriazolyl group, a benzothiadiazolyl group, a quinolyl group, more preferably a pyridyl group, a thiophenyl group, an indolyl group, an indazolyl group, a benzopyranyl group, a benzotriazolyl group, a quinolyl group, more preferably a pyridyl group.

In the compounds represented by formula (I), $R^3$ may be unsubstituted or may have a substituent. Also, when $R^3$ has two substituents on the carbon atoms adjacent each other on the aromatic hydrocarbon ring, $R^3$ may form a 4 to 8-membered saturated or partially unsaturated hydrocarbon ring or heterocyclic ring, which may be substituted, wherein the substituents are fused together with the carbon atom to which each of the substituents is bonded; and When $R^3$ has a substituent, the position of the substituent is not particularly limited. Although the number of the substituent is not limited, it is particularly preferably 0, i.e. unsubstituted. Alternatively, the number of the substituent is 1 to 4, more preferably 1 to 3. When the number of substituent is two or more, the types of the substituent may be the same or different.

In the compounds represented by formula (I), preferably $R^3$ may be substituted with the "substituent", more preferably $R^3$ may be substituted with $R^{31}$. Also, preferably, when $R^3$ has two substituents on the carbon atoms adjacent each other on the aromatic hydrocarbon ring, $R^3$ may form a 4 to 8-membered saturated or partially unsaturated hydrocarbon ring or heterocyclic ring, which may be substituted with Rc, wherein the substituents are fused together with the carbon atom to which each of the substituents is bonded.

$R^{31}$, which can be substituted at $R^3$, is a halogen atom, a cyano group, a nitro group, a carboxyl group, a thioamide group, a C1-C6 alkyl group which may be substituted with Ra, an amino group which may be substituted with Ra, a C3-C6 cycloalkyl group which may be substituted with Rb, a C1-C6 alkoxy group which may be substituted with Rb, a C2-C7 alkoxycarbonyl group, a C1-C14 acyl group which may be substituted with Rb, a C6-C14 aromatic hydrocarbon ring which may be substituted with Rb, an 5 to 10-membered unsaturated heterocyclic ring which may be substituted with Rc, an aminocarbonyl group which may be substituted with Rd and Re, or —S(=O)$_2$Rf.

Although the number of the substituent is not limited, it is particularly preferably 0, i.e. unsubstituted. Alternatively, the number of the substituent is 1 to 4, more preferably 1 to 3. When the number of substituent is two or more, the types of the substituent may be the same or different.

"Halogen atom" indicated in $R^{31}$ is preferably a fluorine atom, a chlorine atom, or a bromine atom, more preferably a chlorine atom, or a bromine atom.

"C1-C6 alkyl group" of "a C1-C6 alkyl group which may be substituted with Ra" indicated in $R^{31}$ is preferably a C1-C3 alkyl group, more preferably a methyl group.

The substituent Ra of "a C1-C6 alkyl group which may be substituted with Ra" indicated in $R^{31}$ is a halogen atom, a hydroxy group, a C1-C14 acyl group, a C1-C14 acyloxy group, a C2-C6 alkynyl group, or a C1-C6 alkoxy C1-C6 alkoxy group.

"Halogen atom" indicated in Ra is preferably a fluorine atom.

"C1-C14 acyl group" indicated in Ra is preferably an acetyl group.

"C1-C14 acyloxy group" indicated in Ra is preferably an acetyloxy group.

"C2-C6 alkynyl group" indicated in Ra is preferably an ethynyl group, 1-propynyl group.

"C1-C6 alkoxy C1-C6 alkoxy group" indicated in Ra is preferably a methoxymethoxy group.

The substituent Ra of "a C1-C6 alkyl group may be substituted with Ra" indicated in $R^{31}$ is preferably a halogen atom, a hydroxy group, a C1-C6 acyloxy group, a C2-C6 alkynyl group, or a C1-C6 alkoxy C1-C6 alkoxy group, more preferably a halogen atom, or a hydroxy group. Although the number of Ra which is substituted at the C1-C6 alkyl is not particularly limited, preferably zero, i.e. unsubstituted, or one or more. When the number of the substituents Ra is 2 or more, the types of the substituent may be the same or different.

Ra of "an amino group optionally substituted with Ra" indicated in $R^{31}$ is a halogen atom, a hydroxy group, a C1-C14 acyl group, a C1-C14 acyloxy group, a C2-C6 alkynyl group, or a C1-C6 alkoxy C1-C6 alkoxy group, preferably a C1-C14 acyl group, more preferably an acetyl group.

The number of Ra substituted at the amino group is not particularly limited, preferably zero, i.e. unsubstituted, or is 1, more preferably 0.

"C3-C6 cycloalkyl group" in the "C3-C6 cycloalkyl group optionally substituted with Rb" indicated in $R^{31}$ is preferably a cyclopropyl group.

Rb in the "C3-C6 cycloalkyl group optionally substituted with Rb" indicated in $R^{31}$ is a halogen atom, an amino group, or a C1-C6 alkoxy group.

"Halogen atom" indicated in Rb is preferably a fluorine atom.

"C1-C6 alkoxy group" indicated in Rb is preferably a C1-C3 alkoxy group, more preferably a methoxy group.

Rb in the "C3-C6 cycloalkyl group optionally substituted with Rb" indicated in $R^{31}$ is preferably an amino group. The number of Rb substituting at the C3-C6 cycloalkyl group is not particularly limited, preferably zero, i.e. unsubstituted, or is 1, more preferably 0. When the number of substituents Rb is two or more, the types of the substituent may be the same or different.

"C1-C6 alkoxy group" in the "C1-C6 alkoxy group optionally substituted with Rb" indicated in $R^{31}$ is preferably a C1-C3 alkoxy group, more preferably a methoxy group.

Rb in the "C1-C6 alkoxy group optionally substituted with Rb" indicated in $R^{31}$ is, as mentioned above, a halogen atom, an amino group, or a C1-C6 alkoxy group, preferably a halogen atom, more preferably a fluorine atom. Although number of Rb substituent to a C1-C6 alkoxy group is not limited, it is zero, i.e. unsubstituted, or one or two. When the number of substituent Rb is two or more, the types of the substituent may be the same or different.

"C2-C7 alkoxycarbonyl group" indicated in $R^{31}$ is preferably a C2-C4 alkoxycarbonyl group, more preferably a methoxycarbonyl group.

"C1-C14 acyl group" in the "C1-C14 acyl group optionally substituted with Rb" indicated in $R^{31}$ is preferably an acetyl group.

Rb in the "C1-C14 acyl group optionally substituted with Rb" indicated in $R^{31}$ is, as mentioned above, a halogen atom, an amino group, or a C1-C6 alkoxy group, preferably a halogen atom, more preferably a fluorine atom. Although number of Rb substituent at a C1-C14 acyl group is not limited, it may be zero, i.e. unsubstituted, or one to three. When the number of substituents Rb is two or more, the types of the substituent may be the same or different.

"Thioamide group" indicated in $R^{31}$ is preferably —C(=S)—NH$_2$.

"C6-C14 aromatic hydrocarbon group" in the "C6-C14 aromatic hydrocarbon group optionally substituted with Rb" indicated in $R^{31}$ is preferably a C6-C10 aromatic hydrocarbon group, and more preferably a phenyl group.

The substituent Rb in the "C6-C14 aromatic hydrocarbon group optionally substituted with Rb" indicated in $R^{31}$ is, as mentioned above, a halogen atom, an amino group, or a C1-C6 alkoxy group, and preferably a halogen atom or a C1-C3 alkoxy group, and more preferably a halogen atom, and more preferably a fluorine atom. Although the number of Rb substituting at a C6-C14 aromatic hydrocarbon group is not particularly limited, it is preferably zero, i.e. unsubstituted, or it is one. When the number of the substituents Rb is 2 or more, the type of groups may be the same or different.

"5 to 10-membered unsaturated heterocyclic group" in the "5 to 10-membered unsaturated heterocyclic group optionally substituted with Rc" indicated in $R^{31}$ is preferably a monocyclic or bicyclic 5-10 membered fully or partially unsaturated heterocyclic group having 1 to 4 hetero atoms selected from a nitrogen atom, a sulfur atom and an oxygen atom, more preferably a monocyclic 5 to 6-membered unsaturated heterocyclic group having 1 to 4 hetero atoms selected from a nitrogen atom, a sulfur atom and an oxygen atom. Preferably it is a pyrrolyl group, an imidazolyl group, a pyrazolyl group, a tetrazolyl group, an isoxazolyl group, an oxadiazolyl group, a dihydro oxadiazolyl group, preferably a pyrazolyl group, a 1,3,4-oxadiazolyl group, a 2,3-dihydro-1,3,4-oxazolyl group.

The substituent Rc in the "5-10 membered unsaturated heterocyclic group optionally substituted with one or more of Rc" indicated in $R^{31}$ is a halogen atom, a hydroxy group, an amino group, an oxo group, a C1-C6 alkyl group optionally substituted with a hydroxy group, a halogeno C1-C6 alkyl group, a C1-C14 acyl, or a C1-C14 acylamino group, a C1-C14 acyloxy group, or a C7-C13 aralkyloxy group.

"Halogen atom" indicated in Rc is preferably a fluorine atom.

"C1-C6 alkyl groups optionally substituted with a hydroxy group" indicated in Rc is preferably a C1-C3 alkyl group optionally substituted with a hydroxy group, and more preferably a methyl group or a hydroxyethyl group.

"Halogeno C1-C6 alkyl group" represented by Rc is preferably a halogeno C1-C3 alkyl group, more preferably a trifluoromethyl group, a difluoroethyl group.

"C1-C14 acyl group" indicated in Rc is preferably an acetyl group or a cyclopropanoyl group.

"C1-C14 acylamino group" indicated in Rc is preferably an acetylamino group.

"C1-C14 acyloxy group" indicated in Rc is preferably an acetyloxy group.

"C7-C13 aralkyloxy group" indicated in Rc is preferably a benzyloxy group.

Rc in the "5 to 10-membered unsaturated heterocyclic group optionally substituted with Rc" indicated in $R^{31}$ is preferably a halogen atom, a C1-C6 alkyl group, or an oxo group, more preferably a C1-C6 alkyl group or an oxo group, more preferably a C1-C6 alkyl group. Although the number of Rc substituting at 5 to 10-membered unsaturated heterocyclic group is not particularly limited, it is preferably zero, i.e. unsubstituted, or preferably it is one or more than 2, more preferably it is zero. When the number of the substituents Rc is 2 or more, the type of groups may be the same or different.

"An amino carbonyl group optionally substituted with Rd and Re" indicated in $R^{31}$ is specifically represented by the following group (II).

[Formula 3]

(II)

Rd and Re are the same or different and represent: a hydrogen atom; a hydroxy group; a C7-C13 aralkyloxy group; or C1-C6 alkyl group optionally substituted with hydroxyl groups; alternatively taken together with a nitrogen atom which is adjacent to Rd and Re to form a saturated or unsaturated 4 to 10-membered heterocyclic ring group optionally substituted with an amino group, a spiro heterocyclic ring group, or a bridged heterocyclic ring group.

"C7-C13 aralkyloxy group" indicated in Rd or Re is preferably a benzyloxy group.

"C1-C6 alkyl group optionally substituted with hydroxy groups" indicated in Rd or Re is preferably a C1-C3 alkyl group optionally substituted with a hydroxy group, more preferably a methyl group, or a hydroxyethyl group.

"A saturated heterocyclic group" in the "4 to 10-membered saturated heterocyclic group optionally substituted with an amino group" in Rd or Re is preferably a monocyclic or bicyclic 4 to 10-membered saturated heterocyclic group having 1 to 3 heteroatoms selected from a nitrogen atom, a sulfur atom, and an oxygen atom, preferably a 5 to 6-membered monocyclic saturated heterocyclic group having 1 to 3 heteroatoms selected from a nitrogen atom, a sulfur atom, and an oxygen atom, more preferably an azetidinyl group, a pyrrolidinyl group, a piperidino group, a piperazinyl group, a morpholino group.

"An unsaturated heterocyclic group" in the "4 to 10-membered saturated or unsaturated heterocyclic group optionally substituted with an amino group", which is formed together with Rd or Re and the adjacent nitrogen atoms, is preferably a monocyclic or bicyclic or 5 to 10-membered unsaturated heterocyclic group having 1 to 3 hetero atoms selected from a nitrogen atom, a sulfur atom, an oxygen atom, more preferably a monocyclic 5 to 6-membered unsaturated heterocyclic group having 1 to 3 hetero atoms selected from a nitrogen atom, a sulfur atom, an oxygen atom, particularly preferably a pyrrolyl group.

"Spiroheterocyclic group" formed together with Rd or Re and the adjacent nitrogen atom is preferably a monosupiro heterocyclic group, more preferably an oxoazaspirononanyl-carbamoyl group, or an azasupirooctanylcarbamoyl group.

"Bridged heterocyclic group" formed together with Rd or Re and the adjacent nitrogen atom indicated is preferably a bicyclic bridged heterocyclic group, more preferably an oxoazabicyclooctanylcarbamoyl group.

The substituents Rd and Re in the "aminocarbonyl group optionally substituted with Rd and Re" indicated in $R^{31}$ are preferably the same or different, and present a hydroxy group or a C1-C6 alkyl group, alternatively taken together with the adjacent nitrogen atom to form a monocyclic 5 to 6-membered saturated heterocyclic group, which may be substituted with an amino group, having 1 to 3 heteroatoms selected from a nitrogen atom, a sulfur atom and an oxygen atom, a monosupiro heterocyclic group or a bicyclic bridged heterocyclic group.

"An amino carbonyl group optionally substituted with Rd and Re" indicated in $R^{31}$ is preferably a —$CONH_2$ group, (a mono or di-C1-C6 alkyl)aminocarbonyl group, a hydroxyamino group, a (C7-C13 aralkyl)oxyaminocarbonyl group, or a cyclicaminocarbonyl group, more preferably a —$CONH_2$ group, (a mono or di-C1-C3 alkyl)aminocarbonyl group, a hydroxyaminocarbonyl group, a benzyloxycarbonylgroup, a pyrrolidin-1-ylcarbonyl group, a piperidin-1-ylcarbonyl group, a piperazin-1-ylcarbonyl group, a morpholin-4-ylcarbonyl group, an azetidin-1-ylcarbonyl group, an oxo azabicyclooctanylcarbonyl group, an oxo azaspiro nonanylcarbonyl group, an azaspirooctanylcarbonyl group, more preferably a —$CONH_2$ group, a dimethylaminocarbonyl group, or a pyrrolidin-1-ylcarbonyl group.

Rf of "—$S(=O)_2Rf$" indicated in $R^{31}$ is an amino group, a C1-C6 alkyl group, or a 4 to 10-membered saturated heterocyclic group.

C1-C6 alkyl group indicated in Rf is preferably a C1-C3 alkyl group, more preferably a methyl group.

A 4 to 10-membered saturated heterocyclic group indicated in Rf is preferably a monocyclic or bicyclic 4 to 10-membered saturated heterocyclic group having 1 to 3 heteroatoms selected from a nitrogen atom, a sulfur atom and an oxygen atom, more preferably a monocyclic 5 to 6-membered saturated heterocyclic group having 1 to 3 heteroatoms selected from a nitrogen atom, a sulfur atom, and an oxygen atom, more preferably a pyrrolidinyl group, a piperidino group, or a piperazinyl group.

"—$S(=O)_2Rf$" indicated in $R^{31}$ is preferably an aminosulfonyl group, a methylsulfonyl group, or a piperidinosulfonyl group.

$R^{31}$ which may be substituted with $R^3$ is preferably a halogen atom, a cyano group, a nitro group, a carboxyl group, a thioamide group, a C1-C6 alkyl group (which may be substituted with a group selected from the group consisting of a halogen atom, a hydroxy group, a C1-C14 acyl group, a C1-C14 acyloxy group, a C2-C6 alkynyl and a C1-C6 alkoxy C1-C6 alkoxy group), an amino group (which may be substituted with a C1-C14 acyl group), a C3-C6 cycloalkyl group (which may be substituted with an amino group), a C1-C6 alkoxy group (which may be substituted with halogen atoms), a C2-C7 alkoxycarbonyl group, a C1-C14 acyl group (which may be substituted with halogen atoms), a C6-C14 aromatic hydrocarbon group (which may be substituted with a group selected from the group consisting of a halogen atom, an amino group and a C1-C6 alkoxy group), monocyclic or bicyclic 5 to 10 membered unsaturated heterocyclic ring having 1 to 4 hetero atoms selected from a nitrogen atom, a sulfur atom and an oxygen atom (which may be substituted with a group consisting of a halogen atom, an oxo group, and a C1-C6 alkyl group), an aminocarbonyl group optionally substituted with Rd and Re (wherein, Rd and Re are the same or different, and present a hydrogen atom, a hydroxy group, a C7-C13 aralkyloxy group, or a C1-C6 alkyl group which may be substituted with a hydroxyl group, alternatively they are taken together with the adjacent nitrogen atom to form a monocyclic or bicyclic 4-10 membered saturated or unsaturated heterocyclic group having 1 to 3 hetero atoms selected from a nitrogen atom, a sulfur atom and an oxygen atom, a spiro heterocyclic group, or a bridged heterocyclic group), or —$S(=O)_2Rf$ (wherein Rf is an amino group, a C1-C6 alkyl group, or a 4-10 membered saturated heterocyclic group).

More preferably, it is a halogen atom, a cyano group, a nitro group, a carboxyl group, a thioamide group, a C1-C6 alkyl group (which may be substituted with a group selected from the group consisting of a halogen atom, a hydroxy group, a C1-C14 acyloxy group, a C2-C6 alkynyl group and a C1-C6 alkoxy C1-C6 alkoxy group), an amino group, a C3-C6 cycloalkyl group (which may be substituted with an amino group), a C1-C6 alkoxy group (which may be substituted with a halogen atom), a C2-C7 alkoxycarbonyl group, a C1-C14 acyl group (which may be substituted with a halogen atom), C6-C10 aromatic hydrocarbon group (which may be substituted with a halogen atom), a monocyclic or bicyclic 5 to 10-membered unsaturated heterocyclic group having 1 to 4 hetero atoms selected from a nitrogen atom, a sulfur atom and an oxygen atom (which may be substituted with a group selected from the group consisting of a C1-C6 alkyl group and an oxo group), a —$CONH_2$ group, a (mono- or di-C1-C6 alkyl)aminocarbonyl group, a hydroxyaminocarbonyl group, a (C7-C13 aralkyl)oxyaminocarbonyl group, a cyclic aminocarbonyl group, an aminosulfonyl group, a C1-C6 alkylsulfonyl group, or a piperidinosulfonyl a group.

More preferably, it is a halogen atom, an amino group, a C1-C6 alkyl group (which may be substituted with a group selected from the group consisting of a halogen atom and a hydroxy group) a C1-C6 alkoxy group (which may be substituted with halogen atoms), a monocyclic 5 or 6-membered unsaturated heterocyclic group having 1 to 4 hetero atoms selected from a nitrogen atom, a sulfur atom and an oxygen atom, a —$CONH_2$ group, a (mono or di C1-C6 alkyl) aminocarbonyl group, or a hydroxyamino group.

More preferably, it is a halogen atom, an amino group, a C1-C6 alkoxy group, or a —$CONH_2$ group.

When the compound of the formula (I) has two or more substituents on $R^3$ and two substituents on the carbon atoms adjacent each other on the aromatic hydrocarbon ring of $R^3$, the "4 to 8-membered saturated or partially unsaturated hydrocarbon ring or heterocyclic ring which may be substituted", which is formed with the carbon atoms to which they are attached, is the ring, such as a ring fused to a benzene ring. "4 to 8-membered saturated or partially unsaturated hydrocarbon ring or heterocyclic ring" in the "4 to 8-membered saturated or partially unsaturated hydrocarbon ring or heterocyclic ring which may be substituted" is preferably a monocyclic saturated or partially unsaturated hydrocarbon ring having 4 to 8 carbon atoms, or 4 to 8-membered saturated or partially unsaturated hetero ring having 1 to 4 hetero atoms selected from the group consisting of a nitrogen atom, a sulfur atom and an oxygen atom, more preferably, a monocyclic 4 to 6-membered saturated or partially unsaturated heterocyclic ring having 1 to 3 hetero atoms selected from the group consisting of a nitrogen atom, a sulfur atom and an oxygen atom, more preferably a monocyclic 6-membered saturated or partially unsaturated heterocyclic ring having one or two oxygen atom(s).

Substituent Rc in the "4 to 8-membered saturated or partially unsaturated hydrocarbon ring or heterocyclic ring which is optionally substituted with Rc" is a halogen atom, a hydroxy group, an amino group, an oxo group, a C1-C6 alkyl group which is optionally substituted with a hydroxy group, a halogeno C1-C6 alkyl group, a C1-C14 acyl group, a C1-C14 acylamino group, a C1-C14 acyloxy group, or a C7-C13 aralkyloxy group, preferably a hydroxy group, an amino group, an oxo group, or a C1-C6 alkyl group which is optionally substituted with a hydroxy group, a halogeno C1-C6 alkyl group, a C1-C14 acyl group, a C1-C14 acyloxy group, more preferably a hydroxy group, or a C1-C6 alkyl group. The number of Rc which substitutes at a saturated or partially unsaturated hydrocarbon ring or heterocyclic ring is not particularly limited, but is preferably 1 to 3. When the number of substituent Rc is 2 or more, the type of groups may be the same or different.

"4 to 8-membered saturated or partially unsaturated hydrocarbon ring or heterocyclic ring which is optionally substituted with Rc" is preferably a monocyclic saturated or partially unsaturated hydrocarbon ring (which is optionally substituted with a group selected from the group consisting of a halogen atom, a hydroxy group, an amino group, an oxo group, a C1-C6 alkyl group optionally substituted with a hydroxy group, a halogeno C1-C6 alkyl group, a C1-C14 acyl group, a C1-C14 acylamino group, a C1-C14 acyloxy group and a C7-C13 aralkyloxy group), a monocyclic 4 to 8-membered saturated or partially unsaturated heterocyclic ring having 1 to 4 hetero atoms selected from a nitrogen atom, a sulfur atom, and an oxygen atom from sulfur atom and an oxygen atom (which is optionally substituted with a group selected from the group consisting of a halogen atom, a hydroxy group, an amino group, an oxo group, a C1-C6 alkyl group optionally substituted with a hydroxy group, a halogeno C1-C6 alkyl group, a C1-C14 acyl group, a C1-C14 acylamino group, a C1-C14 acyloxy group and a C7-C13 aralkyloxy group).

More preferably, a monocyclic saturated or partially unsaturated hydrocarbon ring having 4 to 8 carbon atoms (which is optionally substituted with a group selected from the group consisting of a halogen atom, a hydroxy group, an amino group, an oxo group, and a C1-C6 alkyl group optionally substituted with a hydroxy group, a halogeno C1-C6 alkyl group a C1-C14 acyl group, a C1-C14 acylamino group, and a C1-C14 acyloxy group), or a monocyclic 4 to 8-membered saturated or partially unsaturated heterocyclic ring having 1 to 3 hetero atoms selected from a nitrogen atom, a sulfur atom and an oxygen atom (which is optionally substituted with a group selected from the group consisting of a halogen atom, a hydroxy group, an amino group, an oxo group, a C1-C6 alkyl group optionally substituted with a hydroxy group, a halogeno C1-C6 alkyl group, a C1-C14 acyl group, a C1-C14 acylamino group, and a C1-C14 acyloxy group).

More preferably, a monocyclic 4 to 6-membered heterocyclic ring having 1 to 3 heteroatoms selected from a nitrogen atom, a sulfur atom and an oxygen atom, (which is optionally substituted with a group selected from the group consisting of a hydroxy group, an amino group, an oxo group, a C1-C6 alkyl group, a halogeno C1-C6 alkyl group, a C1-C14 acylamino group and a C1-C14 acyloxy group).

More preferably, a monocyclic 6-membered saturated or partially unsaturated heterocyclic ring having 1 or two oxygen atom(s) (which is optionally substituted with a group selected from the group consisting of a hydroxyl group and a C1-C6 alkyl group).

In the compounds represented by the formula (I), a fused ring which is formed when there are two substituents on the carbon atoms adjacent each other on the aromatic hydrocarbon ring of $R^3$, is for example, a chroman ring, a dihydrobenzoxazine ring, a dihydroindene ring, an indoline ring, a tetrahydroquinoxaline ring, a dihydrobenzodioxane ring, a tetrahydronaphthalene ring, a tetrahydroquinoline ring, a tetrahydroisoquinoline ring, a dihydrobenzothiophene ring, an isoindoline ring, a dihydroisobenzofuran ring, a dihydrobenzoimidazole ring, and the like.

In the compounds represented by the formula (I), $R^3$ is preferably a C6-C14 aromatic hydrocarbon group, or a monocyclic or bicyclic 5 to 10-membered fully unsaturated heterocyclic group having 1 to 3 heteroatom(s) selected from a nitrogen atom, a sulfur atom and an oxygen atom, wherein $R^3$ may be substituted with $R^{31}$, or when $R^3$ has two substituents on the carbon atoms which are adjacent each other on the aromatic hydrocarbon ring, the substituents may be fused together with carbon atoms to which the substituents are attached to form a monocyclic saturated or partially unsaturated hydrocarbon ring having 4 to 8 carbon atoms (which is optionally substituted with a group consisting of the group selected from a halogen atom, a hydroxy group, an amino group, an oxo group, a C1-C6 alkyl group optionally substituted with a hydroxy group, a halogeno C1-C6 alkyl group, a C1-C14 acyl group, a C1-C14 acylamino group, a C1-C14 acyloxy group, and a C7-C13 aralkyloxy group), or, a monocyclic 4 to 8-membered saturated or partially unsaturated heterocyclic ring having 1 to 4 hetero atoms selected from a nitrogen atom, a sulfur atom or an oxygen atom (optionally substituted with a group selected from the group consisting of a halogen atom, a hydroxy group, an amino group, an oxo group, a C1-C6 alkyl group optionally substituted with a hydroxy group, a halogeno C1-C6 alkyl groups, a C1-C14 acyl group, a C1-C14 acylamino group, a C1-C14 acyloxy group, a C7-C13 aralkyloxy group);

$R^{31}$ is a halogen atom, a cyano group, a nitro group, a carboxyl group, a thioamide group, a C1-C6 alkyl group (optionally substituted with a group selected from the group consisting of a halogen atom, a hydroxy group, a C1-C14 acyl group, a C1-C14 acyloxy group, a C2-C6 alkynyl group and a C1-C6 alkoxy C1-C6 alkoxy group), an amino group (optionally substituted with a C1-C14 acyl group), a C3-C6 cycloalkyl group (optionally substituted with an amino group), a C1-C6 alkoxy group (optionally substituted with halogen atoms), a C2-C7 alkoxycarbonyl group, a C1-C14 acyl group (optionally substituted with a halogen atom), a C6-C14 aromatic hydrocarbon group (optionally substituted with a group selected from the group consisting of a halogen atom, an amino group and a C1-C6 alkoxy group), a monocyclic or bicyclic 5 to 10-membered unsaturated heterocyclic group having 1 to 4 heteroatoms selected from a nitrogen atom, a sulfur atom and an oxygen atom (optionally substituted with a group selected from the group consisting of a halogen atom, an oxo group, and a C1-C6 alkyl group), an amino carbonyl group optionally substituted with Rd and Re (wherein Rd and Re are the same or different, and are a hydrogen atom, hydroxy group, a C7-C13 aralkyloxy group, a C1-C6 alkyl group which is optionally substituted with a hydroxyl group, alternatively taken together with the adjacent nitrogen atom to form a monocyclic or bicyclic 4 to 10-membered saturated or unsaturated heterocyclic group having 1 to 3 heteroatoms selected from a nitrogen, a sulfur and an oxygen atom, which may be substituted with an amino group, a spiro heterocyclic group, or a bridged heterocyclic group), or —S(=O)$_2$Rf (wherein Rf is an amino group, a C1-C6 alkyl group, or a 4 to 10-membered saturated heterocyclic group).

In the compounds represented by the formula (I), $R^3$ is more preferably a C6-C10 aromatic hydrocarbon group, or a monocyclic or bicyclic 5 to 10-membered fully unsaturated heterocyclic group having 1 to 3 hetero atoms selected from a nitrogen atom, a sulfur atom and an oxygen atom, wherein $R^3$ is optionally substituted with $R^{31}$, and when it has two substituents on the carbon atoms which are adjacent each other on the aromatic hydrocarbon ring, the substituents may be fused together with carbon atoms to which the substituents are attached to form a monocyclic saturated or partially unsaturated hydrocarbon ring having 4 to 8 carbon atoms (which is optionally substituted with a group consisting of the group selected from a halogen atom, a hydroxy group, an amino group, an oxo group, a C1-C6 alkyl group optionally substituted with a hydroxy group, a halogeno C1-C6 alkyl group, a C1-C14 acyl group, a C1-C14 acylamino group, and a C1-C14 acyloxy group), or a monocyclic 4 to 8-membered saturated or partially unsaturated heterocyclic ring having 1 to 3 hetero atoms selected from a nitrogen atom, a sulfur atom and an oxygen atom (optionally substituted with a group selected from the group consisting of a halogen atom, a hydroxy group, an amino group, an oxo group, a C1-C6 alkyl group optionally substituted with a hydroxy group; a halogeno C1-C6 alkyl groups; a C1-C14 acyl group; a C1-C14 acylamino group; a C1-C14 acyloxy group);

$R^{31}$ is a halogen atom, a cyano group, a nitro group, a carboxyl group, thioamide group, a C1-C6 alkyl group (optionally substituted with a group selected from the group consisting of a halogen atom, a hydroxy group, a C1-C14 acyloxy group, a C2-C6 alkynyl group and a C1-C6 alkoxy C1-C6 alkoxy group), an amino group, a C3-C6 cycloalkyl group (optionally substituted with an amino group), a C1-C6 alkoxy group (optionally substituted with a halogen atom), a C2-C7 alkoxycarbonyl group, a C1-C14 acyl group (optionally substituted with a halogen atom), C6-C10 aromatic hydrocarbon group (which may be substituted with a halogen atom), a monocyclic or bicyclic 5 to 10-membered unsaturated heterocyclic group having 1 to 4 hetero atoms selected from a nitrogen atom, a sulfur atom, and an oxygen atom (optionally substituted with a group selected from the group consisting of a C1-C6 alkyl group or an oxo group), —CONH$_2$ group, (mono- or di-C1-C6 alkyl) aminocarbonyl group, a hydroxyamino group, (C7-C13 aralkyl) oxy aminocarbonyl group, a cyclic amino carbonyl group, an aminosulfonyl group, a C1-C6 alkylsulfonyl group, or a piperidinosulfonyl group.

In the compounds represented by the formula (I), $R^3$ is more preferably a C6-C10 aromatic hydrocarbon group (wherein the C6-C10 aromatic hydrocarbon group is optionally substituted with $R^{31}$, and when a C6-C10 aromatic hydrocarbon group has two substituents on the carbon atoms which are adjacent each other on the aromatic hydrocarbon ring, the substituents may be fused together with carbon atoms to which the substituents are attached to form a monocyclic 4 to 6-membered saturated or partially unsaturated hetero ring having 1 to 3 hetero atoms (which is optionally substituted with a group consisting of a hydroxy group, an amino group, an oxo group, a C1-C6 alkyl group, a halogeno C1-C6 alkyl group, a C1-C14 acylamino group, and a C1-C14 acyloxy group), or a monocyclic 5 to 6-membered fully unsaturated heterocyclic group having 1 to 3 hetero atoms selected from a nitrogen atom, a sulfur atom and an oxygen atom (which is optionally substituted with a group selected from the group consisting of a halogen atom, a C1-C6 alkyl group optionally substituted with a hydroxyl group, a C1-C6 alkoxy group, a C2-C7 alkoxycarbonyl group, a —CONH$_2$ group (mono- or di-C1-C6 alkyl) aminocarbonyl group, a pyrrolidin-1-ylcarbonyl group, a morpholin-4-ylcarbonyl group, a 2-oxa-7-azaspiro[3.5]nonanyl group, a 3-oxa-8-azabicyclo[3.2.1]octanyl group, and an 8-oxa-3-azabicyclo[3.2.1]octanyl group);

$R^{31}$ is a halogen atom, an amino group, a C1-C6 alkyl group (which is optionally substituted with a group selected from the group consisting of a halogen atom and a hydroxy group), a C1-C6 alkoxy group (which is optionally substituted with a halogen atom), a 5 or 6-membered unsaturated heterocyclic group having 1 to 4 hetero atoms selected from a nitrogen atom, a sulfur atom and an oxygen atom, a —CONH$_2$ group, a (mono or di-C1-C6 alkyl) aminocarbonyl group, or a hydroxyamino group.

Also, in the compounds represented by formula (I), $R^3$ is particularly preferably a phenyl group (wherein the phenyl group may be substituted with $R^{31}$, and when a phenyl group has two substituents on the carbon atoms which are adjacent each other on a benzene ring, the substituents may be fused together with carbon atoms to which the substituents are attached to form a monocyclic 6-membered saturated or partially unsaturated hetero ring having one or two oxygen atoms (which is optionally substituted with a group selected from the group consisting of a hydroxy group and a C1-C6 alkyl group)), or a pyridyl group (optionally substituted with a —CONH$_2$ group, a (mono or di C1-C6 alkyl) aminocarbonyl group, or a pyrrolidin-1-yl carbonyl group);

$R^{31}$ is a halogen atom, an amino group, a C1-C6 alkoxy group, or a —CONH$_2$ group.

In the compounds represented by the formula (I), $R^4$ is a hydrogen atom, or a C1-C6 alkyl group.

"C1-C6 alkyl group" indicated in $R^4$ is preferably a C1-C3 alkyl group, more preferably a methyl group.

$R^4$ is preferably a hydrogen atom, or a methyl group, more preferably a hydrogen atom.

In the compounds of formula (I) of present invention, preferred compounds include the following.

In formula (I), $X^1$ represents an oxygen atom or a sulfur atom;
$X^2$ represents an oxygen atom;
$X^3$ represents —NH—;
$X^4$ represents a hydrogen atom or a methyl group;
$R^1$ represents —C($R^{11}$)($R^{12}$) (wherein $R^{11}$ and $R^{12}$ are the same or different, and a hydrogen atom or C1-C6 alkyl group);
$R^2$ represents a C6-C14 aromatic hydrocarbon group, wherein $R^2$ may be substituted with $R^{21}$, and when $R^2$ has two substituents on the carbon atoms which are adjacent each other on the aromatic hydrocarbon ring, the substituents may be fused together with carbon atoms to which the substituents are attached to form a monocyclic saturated or partially unsaturated hydrocarbon ring having 4 to 8 carbons (which is optionally substituted with a C1-C6 alkyl group);
$R^{21}$ is a halogen atom, a cyano group, C1-C6 alkyl group (which is optionally substituted with a halogen atom), a C3-C6 cycloalkyl group, a phenyl group (which is optionally substituted with a group selected from the group consisting of a halogen atom and a C1-C6 alkoxy group), or a monocyclic or bicyclic 5 to 10-membered unsaturated heterocyclic group having 1 to 3 hetero atoms selected from a nitrogen atom, a sulfur atom and an oxygen atom (which is optionally substituted with a group selected from the group consisting of a halogen atom, a C1-C6 alkyl group, a halogeno C1-C6 alkyl group, a C3-C6 cycloalkyl group, a C1-C6 alkoxy group, a morpholino group, a piperidinyl group and a morpholinocarbonyl group);
$R^3$ is a C6-C10 aromatic hydrocarbon group, or a monocyclic or bicyclic 5 to 10-membered fully unsaturated heterocyclic group having 1 to 3 hetero atoms selected from a nitrogen atom, a sulfur atom and an oxygen atom, wherein $R^3$ is optionally substituted with $R^{31}$, and when $R^3$ has two substituents on the carbon atoms which are adjacent each other on the aromatic hydrocarbon ring, the substituents may be fused together with carbon atoms to which the substituents are attached to form a monocyclic saturated or partially unsaturated hydrocarbon ring having 4 to 8 carbon atoms (which is optionally substituted with a group consisting of the group selected from a halogen atom, a hydroxy group, an amino group, an oxo group, a C1-C6 alkyl group optionally substituted with a hydroxy group, a halogeno C1-C6 alkyl group, a C1-C14 acyl group, a C1-C14 acylamino group, and a C1-C14 acyloxy group), or a monocyclic 4 to 8-membered saturated or partially unsaturated heterocyclic ring having 1 to 3 hetero atoms selected from a nitrogen atom, a sulfur atom and an oxygen atom (optionally substituted with a group selected from the group consisting of a halogen atom, a hydroxy group, an amino group, an oxo group, a C1-C6 alkyl group optionally substituted with a hydroxy group; a halogeno C1-C6 alkyl group; a C1-C14 acyl group; a C1-C14 acylamino group; and C1-C14 acyloxy group);

$R^{31}$ is a halogen atom, a cyano group, a nitro group, a carboxyl group, a thioamide group, a C1-C6 alkyl group (optionally substituted with a group selected from the group consisting of a halogen atom, a hydroxy group, a C1-C14 acyloxy group, a C2-C6 alkynyl group and a C1-C6 alkoxy C1-C6 alkoxy group), an amino group, a C3-C6 cycloalkyl group (optionally substituted with an amino group), a C1-C6 alkoxy group (optionally substituted with a halogen atom), a C2-C7 alkoxycarbonyl group, a C1-C14 acyl group (optionally substituted with a halogen atom), a C6-C10 aromatic hydrocarbon ring (optionally substituted with a halogen atom), a monocyclic or bicyclic 5 to 10-membered unsaturated heterocyclic group having 1 to 4 hetero atoms selected from a nitrogen atom, a sulfur atom, and an oxygen atom (optionally substituted with a group selected from the group consisting of a C1-C6 alkyl group and an oxo group), —$CONH_2$ group, a (mono- or di-C1-C6 alkyl)aminocarbonyl group, a hydroxyaminocarbonyl group, a (C7-C13 aralkyloxy)oxyaminocarbonyl group, a cyclic aminocarbonyl group, an aminosulfonyl group, a C1-C6 alkylsulfonyl group, or a piperidinosulfonyl group; and $R^4$ represents a hydrogen atom;

or a salt thereof.

Furthermore, in the compounds of formula (I) of the present invention, more preferable compounds include the following.

In formula (I), $X^1$ represents an oxygen atom;

$X^2$ represents an oxygen atom;

$X^3$ represents —NH—;

$X^4$ represents a hydrogen atom;

$R^1$ represents —C($R^{11}$)($R^{12}$) (wherein $R^{11}$ represents a C1-C6 alkyl group, and $R^{12}$ represents a hydrogen atom);

$R^2$ represents a C6-C10 aromatic hydrocarbon group, wherein $R^2$ may be substituted with $R^{21}$, and when $R^2$ has two substituents on the carbon atoms which are adjacent each other on the aromatic hydrocarbon ring, the substituents may be fused together with carbon atoms to which the substituents are attached to form a monocyclic saturated or partially unsaturated hydrocarbon ring having 5 or 6 carbons (which is optionally substituted with a C1-C6 alkyl group);

$R^{21}$ is a halogen atom, a C1-C6 alkyl group or a monocyclic 5 to 6-membered unsaturated heterocyclic group having 1 to 3 nitrogen atom(s) (which is optionally substituted with a C1-C6 alkyl group);

$R^3$ is a C6-C10 aromatic hydrocarbon group (wherein the C6-C10 aromatic hydrocarbon group is optionally substituted with $R^{31}$, and when a C6-C10 aromatic hydrocarbon group has two substituents on the carbon atoms which are adjacent each other on the aromatic hydrocarbon ring, the substituents may be fused together with carbon atoms to which the substituents are attached to form a monocyclic 4 to 6-membered saturated or partially unsaturated heterocyclic ring having 1 to 3 hetero atoms selected from a nitrogen atom, a sulfur atom and an oxygen atom (optionally substituted with a group selected from the group consisting of a hydroxy group, an amino group, an oxo group, a C1-C6 alkyl group, a halogeno C1-C6 alkyl group, a C1-C14 acyl group, a C1-C14 acylamino group, and C1-C14 acyloxy group) or a monocyclic 5 to 6-membered fully unsaturated heterocyclic group having 1 to 3 hetero atoms selected from a nitrogen atom, a sulfur atom and an oxygen atom (which is optionally substituted with a group selected from the group consisting of a halogen atom, a C1-C6 alkyl group optionally substituted with a hydroxyl group, a C1-C6 alkoxy group, a C2-C7 alkoxycarbonyl group, a —$CONH_2$ group, (mono- or di-C1-C6 alkyl) aminocarbonyl group, a pyrrolidin-1-ylcarbonyl group, a morpholin-4-ylcarbonyl group, a 2-oxa-7-azaspiro[3.5]nonanyl group, a 3-oxa-8-azabicyclo[3.2.1]octanyl group, and an 8-oxa-3-azabicyclo[3.2.1]octanyl group);

$R^{31}$ is a halogen atom, an amino group, a C1-C6 alkyl group (optionally substituted with a group selected from the group consisting of a halogen atom and a hydroxy group), a C1-C6 alkoxy group (optionally substituted with a halogen atom), a monocyclic 5 to 6-membered unsaturated heterocyclic group having 1 to 4 hetero atoms selected from a nitrogen atom, a sulfur atom, and an oxygen atom, a —$CONH_2$ group, (mono- or di-C1-C6 alkyl)aminocarbonyl group, a hydroxyaminocarbonyl group; and $R^4$ represents a hydrogen atom;

or a salt thereof.

In the compounds of formula (I) of the present invention, more preferable compounds include the following.

In formula (I), $X^1$ represents an oxygen atom;

$X^2$ represents an oxygen atom;

$X^3$ represents —NH—;

$X^4$ represents a hydrogen atom;

$R^1$ represents —C($R^{11}$)($R^{12}$) (wherein $R^{11}$ represents a methyl group, and $R^{12}$ represents a hydrogen atom);

$R^2$ represents a phenyl group or a naphthyl group, wherein $R^2$ may be substituted with $R^{21}$, and when $R^2$ has two substituents on the carbon atoms which are adjacent each other on the aromatic hydrocarbon ring, the substituents may be fused together with carbon atoms to which the substituents are attached to form a monocyclic saturated or partially unsaturated hydrocarbon ring having 5 or 6 carbons (which is optionally substituted with a C1-C6 alkyl group);

$R^{21}$ is a halogen atom or a C1-C6 alkyl group;

$R^3$ is a phenyl group (wherein the phenyl group is optionally substituted with $R^{31}$, and when a phenyl group has two substituents on the carbon atoms which are adjacent each other on a benzene ring, the substituents may be fused together with carbon atoms to which the substituents are attached to form a monocyclic 6-membered saturated or partially unsaturated heterocyclic ring having 1 or 2 oxygen atom(s) (optionally substituted with a group selected from the group consisting of a hydroxyl group and a C1-C6 alkyl group), or a pyridyl group (optionally substituted with a —$CONH_2$ group, a (mono- or di-C1-C6 alkyl) aminocarbonyl group, a pyrrolidin-1-ylcarbonyl group)

$R^{31}$ is a halogen atom, an amino group, a C1-C6 alkoxy group, a —$CONH_2$ group; and $R^4$ represents a hydrogen atom;

or a salt thereof.

Particularly preferable compounds of the present invention include the following.

(1) 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide;

(2) 5-chloro-2-(N-((1S,2R)-2-(2,3-dimethylphenyl)-1-(5-oxo-4,5-dihydro-1,3,4-oxadiazol-2-yl)propyl)sulfamoyl)benzamide;

(3) 5-bromo-2-(N-((1S,2R)-2-(2,3-dimethylphenyl)-1-(5-oxo-4,5-dihydro-1,3,4-oxadiazol-2-yl)propyl)sulfamoyl)benzamide;

(4) 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide;

(5) 5-chloro-2-(N-((1S,2R)-2-(2-fluoronaphtalen-1-yl)-1-(5-oxo-4,5-dihydro-1,3,4-oxadiazol-2-yl)propyl)sulfamoyl)benzamide;

(6) 5-chloro-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide;

(7) 5-chloro-2-(N-((1S,2R)-2-(3-chloro-6-fluoro-2-methylphenyl)-1-(5-oxo-4,5-dihydro-1,3,4-oxadiazol-2-yl)propyl)sulfamoyl)benzamide;

(8) 5-bromo-2-(N-((1S,2R)-2-(3-chloro-6-fluoro-2-methylphenyl)-1-(5-oxo-4,5-dihydro-1,3,4-oxadiazol-2-yl)propyl)sulfamoyl)benzamide;

(9) 2-(N-((1S,2R)-2-(3-bromo-6-fluoro-2-methylphenyl)-1-(5-oxo-4,5-dihydro-1,3,4-oxadiazol-2-yl)propyl)sulfamoyl)-5-chloro-benzamide;

(10) 5-chloro-N-((1S,2R)-2-(6-fluoro-2,3-dimethylphenyl)-1-(5-oxo-4,5-dihydro-1,3,4-oxadiazol-2-yl)propyl)-6-(pyrrolidine-1-carbonyl)pyridine-2-sulfonamide;

(11) 5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide;

(12) 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-chroman-8-sulfonamide;

(13) N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methyl-chroman-8-sulfonamide;

(14) 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-d3-chroman-8-sulfonamide;

(15) 5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide;

(16) 3-chloro-6-(N-((1S,2R)-2-(6-fluoro-2,3-dimethylphenyl)-1-(5-oxo-4,5-dihydro-1,3,4-oxadiazol-2-yl)propyl)sulfamoyl)-N,N-dimethylpicolinamide;

(17) 4-amino-2-methoxy-N-((1S,2R)-2-(8-methylnaphthalen-1-yl)-1-(5-oxo-4,5-dihydro-1,3,4-oxadiazol-2-yl)propyl)benzenesulfonamide;

(18) 4-amino-N-((1S,2R)-2-(2,3-dihydro-1H-inden-4-yl)-1-(5-oxo-4,5-dihydro-1,3,4-oxadiazo-2-yl)propyl)-2-methoxybenzenesulfonamide; and

(19) 5-chloro-2-((1S,2R)-methyl-d3-2-(6-fluoro-2,3-dimethylphenyl)-1-(5-oxo-4,5-dihydro-1,3,4-oxadiazol-2-yl)propyl)sulfamoyl)benzamide.

A method of preparing the compound according to the present invention is described by giving examples. The compounds of the formula (I) of the present invention, for example, can be prepared by the following production method. However, the present invention is not limited to this method.

[Formula 4]

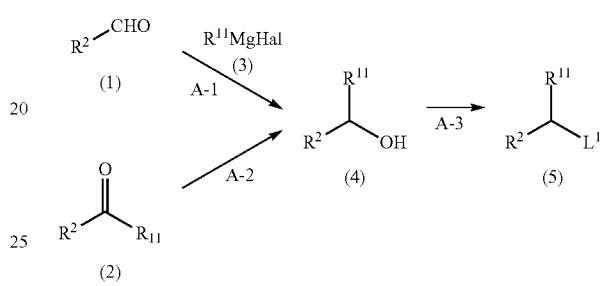

[wherein, $L^1$ represents a leaving group. The symbols have the same meanings as defined above.]

[A-1]

In this process, a compound represented by general formula (4) can be prepared by reacting a compound represented by general formula (1) with an organometallic reagent (3) such as Grignard reagent represented by $R^{11}MgHal$.

Hal represents a halogen atom.

The amount of Grignard reagent (3) 0.8 to 20 equivalents relative to compound (1), preferably 1.0 to 10 equivalents. The reaction temperature is −80° C. to 100° C., preferably −78° C. to 50° C. The reaction time is 0.1 to 24 hours, preferably 0.1 to 3 hours.

In this step, a compound represented by general formula (4), wherein $R^{11}$ is H, can be prepared by reacting the compound represented by formula (1) with a well-known reducing agent instead of Grignard reagent (3).

The reducing agents to be used include, for example, sodium borohydride, lithium borohydride, lithium aluminum hydride, diethoxy aluminum lithium hydride, triethoxy lithium aluminum hydride, tri-t-butoxy aluminum lithium hydride, aluminum magnesium hydride, aluminum hydride magnesium chloride, sodium aluminum hydride, sodium triethoxyaluminum hydride, bis(2-methoxyethoxy) aluminum sodium hydride, diisobutylaluminum hydride (hereinafter DIBAL-H) and the like, and preferably sodium borohydride.

The reaction solvent to be used is not particularly limited as long as it does not affect the reaction, for example, ethers (diethyl ether, tetrahydrofuran, 1,4-dioxane, 1,2-dimethoxyethane, and the like), alcohols (methanol, ethanol, and the like), and water, and preferably methanol.

The amount of reducing agent used is 0.8 to 10 equivalents relative to the compound (1), preferably 1 to 5 equivalents.

The reaction temperature is from 0° C. to the boiling point temperature of the solvent, preferably 0 to 40° C. The reaction time is from 0.05 to 24 hours, preferably 0.2 to 2 hours. Thus, the compound represented by general formula (4) obtained in the above manner can be subjected to the next step with or without isolation and purification by a well-known separation and purification means described below

[A-2]

In this step, a compound represented by general formula (4) can be prepared by reacting a compound represented by general formula (2) with well-known reducing agents, The reducing agents to be used include sodium borohydride.

The reaction solvents to be used are not particularly limited as long as they do not affect the reaction, and, for example, ethers (diethyl ether, tetrahydrofuran, 1,4-dioxane, 1,2-dimethoxyethane, etc.), alcohols (methanol, ethanol, 2-propanol, tert-butanol, ethylene glycol, etc.), water and the like, preferably methanol or ethanol.

The amount of reducing agent is 0.8 to 10 equivalents relative to the compound (2), preferably 1 to 5 equivalents.

The reaction temperature is between 0° C. and the boiling point temperature of the solvent, preferably 0 to 40° C. The reaction time is from 0.05 to 24 hours, preferably 0.2 to 2 hours. Thus, the obtained compound represented by general formula (4) can be subjected to the next step with or without isolation and purification by well-known separation and purification means described below.

[A-3]

In this process, a compound represented by general formula (5) can be prepared by reacting a compound represented by general formula (4) with a halogenating agent or sulfonyl halide hydrocarbons.

Leaving groups represented by $L^1$ are, for example, a halogen atom such as a chlorine atom, a bromine atom or an iodine atom, a methylsulfonyloxy group, a trifluoromethylsulfonyloxy group, an organic sulfonyloxy group such as a p-tolylsulfonyloxy group.

The reaction solvents to be used are not particularly limited as long as they do not affect the reaction, for example, ethers (diethyl ether, tetrahydrofuran, 1,4-dioxane, 1,2-dimethoxyethane, etc.), halogenated hydrocarbons (dichloromethane, chloroform, 1,2-dichloroethane, carbon tetrachloride, etc.), aromatic hydrocarbons (benzene, toluene, xylene, pyridine, etc.), and preferably ethers.

The halogenating agents to be used are, for example, thionyl chloride, oxalyl chloride, phosphorus pentachloride, phosphorus trichloride, thionyl bromide, phosphorus tribromide and the like. Preferably, it is thionyl chloride or phosphorus tribromide. The sulfonyl halide hydrocarbons are, for example, methanesulfonyl chloride, ethanesulfonyl chloride, p-toluenesulfonyl chloride or phenylsulfonyl chloride and the like.

The reaction solvents to be used are not particularly limited as long as they do not affect the reaction, and, for example, ethers (diethyl ether, tetrahydrofuran, 1,4-dioxane, 1,2-dimethoxyethane, etc.), halogenated hydrocarbons (dichloromethane, chloroform, 1,2-dichloroethane, carbon tetrachloride), aromatic hydrocarbons (benzene, toluene, xylene, etc.), and preferably dichloromethane.

The amount of the halogenating agent or sulfonyl halide hydrocarbons is 0.3 equivalents to 20 equivalents relative to the compound (4), preferably 0.3 to 4 equivalents.

The reaction temperature is −20° C. to 100° C., preferably from 0° C. to 100° C. The reaction time is generally 0.01 to 200 hours, preferably 0.5 hour to 24 hours. Thus, the obtained compound represented by general formula (5) can be subjected to the next step with or without isolation and purification by well-known separation and purification means described below.

[Formula 5]

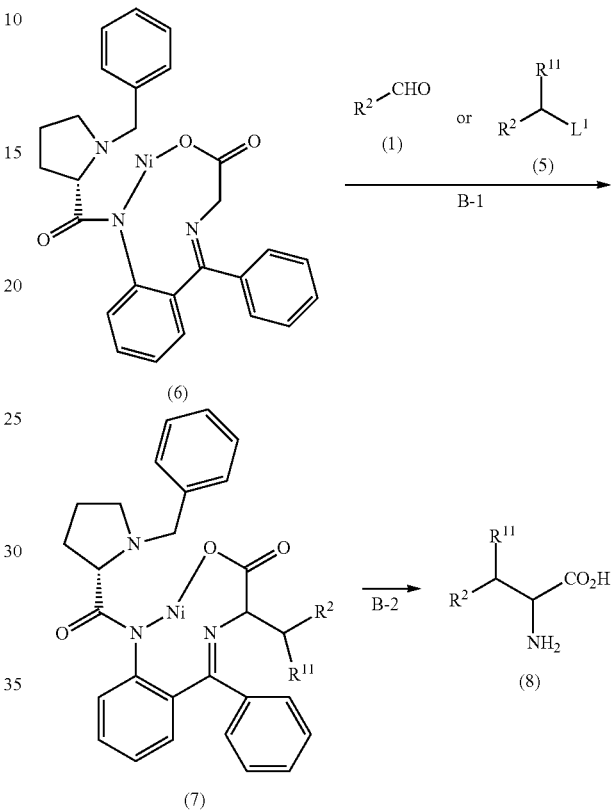

[Symbols in the formula are as defined above.]

[B-1]

In this process, a nickel complex represented by general formula (7) is prepared by reacting a compound represented by general formula (1) or (5) with a readily available compound represented by formula (6).

The reaction solvents to be used are not particularly limited as long as they do not affect the reaction, and for example, organic solvents or mixtures thereof such as ethers (diethyl ether, tetrahydrofuran, 1,4-dioxane, 1,2-dimethoxyethane, etc.), halogenated hydrocarbons (dichloromethane, chloroform, 1,2-dichloroethane, carbon tetrachloride), aromatic hydrocarbons (benzene, toluene, xylene, etc.), aliphatic hydrocarbons (hexane, pentane, cyclohexane, etc.), nitriles (acetonitrile, propionitrile etc.), amides (N,N-dimethylformamide (hereinafter, also referred to as DMF), N,N-dimethylacetamide, N-methylpyrrolidinone, and preferably DMF.

The bases to be used are, for example: organic amines such as triethylamine, tripropylamine, diisopropylethylamine, N-methylmorpholine, pyridine, lutidine, or collidine; alkali metal salts such as sodium carbonate, potassium carbonate, cesium carbonate, sodium phosphate, potassium phosphate, sodium hydroxide, potassium hydroxide; alkali metal alkoxides such as sodium methoxide, sodium ethoxide, sodium tert-butoxide, potassium tert-butoxide; a strong base lithium amide such as lithium diisopropylamide; a strong base hexamethyldisilazane such as lithium hexamethyl disilazane, sodium hexamethyldisilazane, potassium hexamethyldisilazane; and preferably sodium hydroxide, potassium hydroxide, potassium tert-butoxide and the like.

The amount of the base to be used is usually 0.1 to 100 equivalents relative to compound (6), preferably 1 to 20 equivalents.

The amount of compound (1) or (5) is 0.5 to 10 equivalents relative to compound (6), preferably 1 to 5 equivalents.

The reaction temperature is −80 to 50° C., preferably −60 to 40° C. The reaction time is 0.2 to 24 hours, preferably 0.5 to 6 hours. The pressure used in the above preparing method may not be particularly limited, and examples thereof include, about 0.1 to 10 atm. A nickel complex represented by general formula (7) which is obtained in this method can be subjected to the next step with or without isolation and purification by well-known separation and purification means described below.

[B-2]

In this step, an amino acid represented by general formula (8) can be prepared by reacting the nickel complex or a salt thereof with an acid represented by general formula (7).

The acids to be used are not particularly limited but include publicly known acids. The acids may be an inorganic acid or an organic acid. The inorganic acids include such as hydrochloric acid, nitric acid, sulfuric acid, and perchloric acid. The organic acids include such as acetic acid, trifluoroacetic acid, methanesulfonic acid, trifluoromethanesulfonic acid, oxalic acid, propionic acid, butyric acid, valeric acid, and the like. Preferably, the acid is hydrochloric acid, sulfuric acid, trifluoroacetic acid, or methanesulfonic acid, more preferably, it is hydrochloric acid, or methanesulfonic acid.

The amount of the acid is not particularly limited, and usually 0.1 to 50 equivalents relative to the nickel complex represented by general formula (7), and preferably 0.3 to 10 equivalents.

The solvent to be used is preferably alcohol, more preferable to methanol or ethanol.

The reaction temperature is usually 0° C. to 100° C., and preferably 40 to 80° C. The reaction time is usually 0.1 to 72 hours, and preferably 0.1 to 10 hours. The pressure used in the above preparing method is not particularly limited, and examples thereof include, 0.1 to 10 atm. The amino acid represented by general formula (8) obtained in the present method can be subjected to the next process with or without a separation and purification means by well-known separation and purification means described below or transformation between protection and deprotection.

[Formula 6]

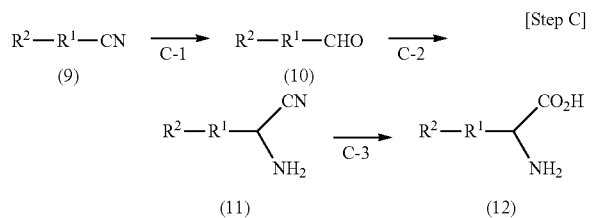

(9) (10) (11) (12) [Step C]

[Symbols in the formula are as defined above.]

[C-1]

In this step, a compound represented by general formula (10) can be prepared by reacting a compound represented by general formula (9) with a well-known reducing agent.

The reducing agent is tri(ethoxy) aluminum lithium hydride, tri(sec-butyl)boron lithium hydride, or DIBAL-H, and the like, and preferably DIBAL-H.

The amount of the reducing agent is usually 1 to 10 equivalents relative to the compound (9), preferably 2.0 to 10 equivalents.

The solvent to be used is ether type solvents (tetrahydrofuran, 1,4-dioxane, etc.), aprotic polar solvents (N,N-dimethylformamide, dimethyl sulfoxide, acetonitrile, etc.), halogen solvents (dichloromethane, chloroform, etc.), aromatic hydrocarbon solvents (toluene, xylene, etc.) or a mixed solvent thereof and the like, and preferably dichloromethane.

The reaction temperature is −100° C. to 50° C., preferably −100 to 10° C. The reaction time is 0.1 to 24 hours, preferably 0.2 to 5 hours.

The pressure used in the above preparing method may not be particularly limited, and examples thereof include, from about 0.1 to 10 atm.

The compound represented by general formula (10) which is the obtained in this method can be subjected to the next step with or without isolation and purification by well-known separation and purification means described below.

The compound represented by general formula (9) can be prepared by the methods described in the reference (international publication No. WO2011/071,565), or, if necessary, combining the methods described in the reference examples and examples.

[C-2]

In this step, a compound represented by general formula (11) is prepared by reacting with a compound represented by general formula (10) with a cyanide agent and ammonia. The cyanide agent to be used is, for example, hydrogen cyanide, metal cyanides, cyanohydrin compounds, acyl cyanides, halogenated cyanides and the like. The metal cyanides are, for example, alkali metal cyanides such as sodium cyanides, potassium cyanides; alkaline earth metal cyanides such as calcium cyanide; transition metal cyanides such as copper cyanide. Preferably, it is potassium cyanide.

The ammonia used in the present step can be ammonia gas, liquid ammonia or an aqueous ammonia solution, and an aqueous ammonia solution is desirable in terms of that it does not require complicated reaction apparatus.

The solvent to be used is not particularly limited as long as it does not affect the reaction, and it includes ethers (tetrahydrofuran, 1,4-dioxane, etc.), aprotic polar solvents (N,N-dimethylformamide, dimethyl sulfoxides, acetonitrile, etc.), halogen solvents (dichloromethane, chloroform, etc.), aromatic hydrocarbon solvents such as toluene, alcohol solvents (methanol, ethanol, etc.), water, and a mixed solvent thereof, and preferably water and a mixed solvent of methanol.

The amount of cyanide agent to be used is generally 1 to 10 equivalents relative to compound (10), preferably 2.0 to 5.0 equivalents. The amount of ammonia used in the reaction is preferably 1.5 to 10 equivalents relative to the compound (10), and more preferably 1.8 to 2.5 equivalents. Ammonium chloride is added as needed. Its amount is usually 0.2 to 2.0 equivalents relative to the compound of (10), preferably 0.1 to 0.5 equivalent.

The reaction temperature is −100° C. to 100° C., preferably 0 to 60° C. The reaction time is 0.1 to 24 hours, preferably 0.2 to 5 hours. The pressure used in the above preparing method may not be particularly limited, and examples thereof include, from about 0.1 to 10 atm. The compound represented by general formula (11) can be subjected to the next step with or without isolation and purification by well-known separation and purification means as described below.

[C-3]

In this process, the compound represented by general formula (12) is prepared in the same manner as [B-2] described above using the compound represented by general formula (11). The compound represented by general formula (12) can be subjected to the next step with or without isolation and purification by well-known separation and purification means as described below. Hereinafter, post process for the compounds represented by general formulae (8) and (12) are described as an example.

Furthermore, in the present process, $R^1$ and $R^2$ can be converted to the structures corresponding to protection/deprotection groups or the present invention.

[Formula 7]

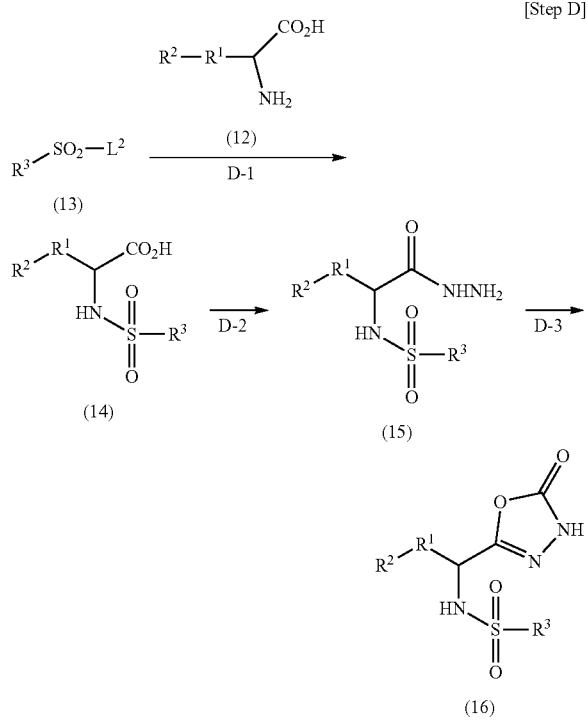

[In the formula, $L^2$ represents a leaving group. The symbols have the same meanings as defined above.]

[D-1]

In this step, a carboxylic acid represented by general formula (14) can be prepared by reacting an amino acid represented by general formula (12) with a sulfonic acid halide represented by general formula (13) in the presence of a base.

The base to be used is alkali metal salts such as sodium carbonate, potassium carbonate, cesium carbonate, sodium phosphate, potassium phosphate, sodium hydroxide, or organic amines such as trimethylamine or potassium hydroxide, triethylamine, tripropylamine, diisopropylethylamine, N-methylmorpholine, pyridine, lutidine, and collidine are exemplified, and preferably triethylamine.

The reaction solvent to be used is not particularly limited as long as it does not affect the reaction, and it is organic solvents or water, etc. such as ethers (diethyl ether, tetrahydrofuran, 1,4-dioxane, 1,2-dimethoxyethane, etc.), halogenated hydrocarbons (dichloromethane, chloroform, 1,2-dichloroethane, carbon tetrachloride), aromatic hydrocarbons (benzene, toluene, xylene, etc.), aliphatic hydrocarbons (hexane, pentane, cyclohexane, etc.), nitriles (acetonitrile, propionitrile etc.), amides (DMF, N,N-dimethylacetamide, N-methylpyrrolidinone and the like. These solvents may be used in a mixture at an appropriate ratio.

The number of equivalents of base and an amine is from 0.5 to 10 equivalents, respectively, preferably 1.0 to 5.0 equivalents.

The amount of the sulfonic acid halide is appropriately set by the compounds represented by general formula (12), but is not limited to, and, usually, is 1.0 to 5.0 equivalents relative to the compound represented by general formula (12), more preferably 1.0 to 2.5 equivalents.

The reaction temperature is appropriately by the compounds represented by general formula (12), but is not limited to, and, for example, a −20 to 70° C., preferably 0 to 40° C. The reaction time is generally 0.1 to 24 hours, preferably 0.2 to 6.0 hours. The compound represented by general formula (14) can be subjected to the next step with or without isolation and purification by well-known separation and purification means as described below.

The compound represented by general formula (13) can be prepared by the methods described in the reference (Tetrahedoron Lett. 51, 418-421 (2010)), or, if necessary, combining the methods described in the reference examples and examples.

[D-2]

In this step, a compound represented by general formula (15) can be prepared by reacting a carboxylic acid represented by general formula (14) with a condensing agent and hydrazine. Alternatively, it can be prepared by reacting hydrazine derivative having an appropriate protecting group with the carboxylic acid represented by general formula (14) in the same manner, and then carrying out the reaction for eliminating the protecting group.

The condensing agent is, for example 1,1'-carbonyldiimidazole (hereinafter, CDI), dicyclohexylcarbodiimide, 1-ethyl-3-(3-dimethylaminopropyl)carbodiimide hydrochloride and the like, preferably CDI.

The solvent to be used is not particularly limited as long as it does not affect the reaction, for example, organic solvents such as ethers (diethyl ether, tetrahydrofuran, 1,4-dioxane, 1,2-dimethoxyethane, etc.), halogenated hydrocarbons (dichloromethane, chloroform, 1,2-dichloroethane, carbon tetrachloride), aromatic hydrocarbons (benzene, toluene, xylene, etc.), aliphatic hydrocarbons (hexane, pentane, cyclohexane, etc.), nitriles (acetonitrile, propionitrile etc.), and amides (DMF, N,N-dimethylacetamide, N-methylpyrrolidinone, and they can be used alone or in combination.

The amount of the condensing agent with respect to the compound represented by Formula (14) is generally 1 to 50 equivalents, preferably about 1 to 5. The amount of hydrazine relative to the compound represented by general formula (14) is generally 1 to 100 equivalents, preferably 1-5 equivalents. The base is organic bases such as triethylamine, pyridine, 4-dimethylaminopyridine, diazabicycloundecene and the like.

The reaction temperature is −20 to 80° C., preferably 0 to 40° C. The reaction time is usually from 0.05 to 24 hours, more preferably 0.05 to 6 hours. The compound represented by general formula (15) can be subjected to the next step with or without isolation and purification by well-known separation and purification means as described below.

[D-3]

In this step, a compound represented by general formula (16) of the present invention can be prepared by cyclization of the compound represented by general formula (15) with the acylating agent.

The acylating agent is, for example isobutyl chloroformate, CDI, phosgene, triphosgene and the like, preferably CDI. The base is, organic bases such as triethylamine, N,N-diisopropylethylamine, pyridine, 4-dimethylaminopyridine, and like diazabicycloundecene and the like.

The amount of the acylating agent with respect to the compound represented by Formula (15) is typically preferably 1 to 50 equivalents, and more preferably 1 to 5 equivalents.

The solvent to be used is not particularly limited as long as it does not affect the reaction, for example, organic solvents such as ethers (diethyl ether, tetrahydrofuran, 1,4-dioxane, 1,2-dimethoxyethane, etc.), halogenated hydrocarbons (dichloromethane, chloroform, 1,2-dichloroethane, carbon tetrachloride), aromatic hydrocarbons (benzene, toluene, xylene, etc.), aliphatic hydrocarbons (hexane, pentane, cyclohexane, etc.), nitriles (acetonitrile, propionitrile etc.), amides (DMF, N,N-dimethylacetamide, N-methylpyrrolidinone, etc.) and the like, and they may be used singly or as a mixture.

The reaction temperature is −20 to 80° C., preferably 0 to 50° C. The reaction time is generally 0.5 to 24 hours, preferably 0.5 to 8 hours. The compound represented by general formula (16) can be subjected to the next step with or without isolation and purification by well-known separation and purification means as described below.

The compound represented by general formula (16) of the present invention can be synthesized by 1) protecting the amino group of the amino acid of the compound represented by above general formula (12) with a well-known suitable protecting group, 2) converting the carboxylic acid moiety to the oxadiazolone ring in the same method as [D-2], 3) deprotecting the protective group in a well-known method, 4) sulfonamidation in the same manner as [D-1].

[Formula 8]

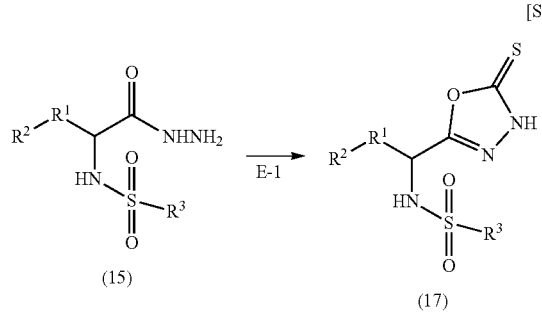

[Step E]

(15) → (17)

[In the formula, the symbols have the same meanings as defined above.]

[E-1]

In this step, a compound represented by general formula (17) of the present invention can be prepared by reacting the compound represented by general formula (15) with carbon disulfide.

The base used in this reaction is, for example, alkali metal salts such as sodium hydroxide, potassium hydroxide, organic amines such as triethylamine, alkali metal alkoxides, such as sodium methoxide, sodium ethoxide, sodium tert-butoxide, potassium tert-butoxide, metal amides such as lithium diisopropylamide, and preferably potassium hydroxide.

The amount of the base to be used is, with respect to the compound represented by Formula (15), generally 1 to 20 equivalents, preferably 1 to 5 equivalents. The amount of carbon disulfide is, with respect to the compound represented by Formula (15), generally 1 to 20 equivalents, preferably 1 to 5 equivalents.

The solvent to be used is not particularly limited as long as it does not affect the reaction, for example, organic solvents, water such as alcohols (methanol, ethanol, propanol), ethers (diethyl ether, tetrahydrofuran, 1,4-dioxane, 1,2-dimethoxyethane), halogenated hydrocarbons (dichloromethane, chloroform, 1,2-dichloroethane, carbon tetrachloride), aromatic hydrocarbons (benzene, toluene, xylene, etc.), aliphatic hydrocarbons (hexane, pentane, cyclohexane), amides (DMF, N,N-dimethylacetamide, N-methylpyrrolidinone, and the like, and they can be used singly or as a mixture.

The reaction temperature is 0 to 150° C., preferably between 20 to 100° C. The reaction time is generally from 0.5 to 24 hours, preferably 1.0 to 12 hours. The compound represented by general formula (17) of the present invention can be isolated and purified by well-known separation and purification means.

[Formula 9]

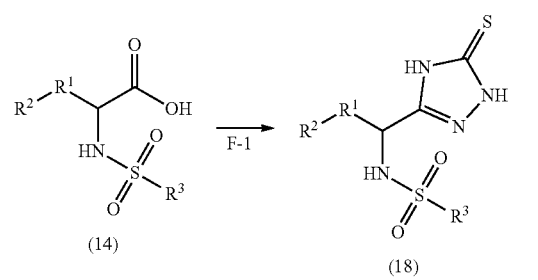

[Step F]

(14) → (18)

[In the formula, the symbols have the same meanings as defined above.]

[F-1]

In this step, a compound of general formula (18) can be prepared by condensation and simultaneously cyclization of the compound represented by general formula (14) and thiosemicarbazide.

The condensing agent is, for example CDI, dicyclohexylcarbodiimide, 1-ethyl-3-(3-dimethylaminopropyl)carbodiimide hydrochloride and the like, preferably 1-ethyl-3-(3-dimethylaminopropyl)carbodiimide hydrochloride.

The solvent to be used is not particularly limited as long as it does not affect the reaction, for example, organic solvents such as ethers (diethyl ether, tetrahydrofuran, 1,4-dioxane, 1,2-dimethoxyethane, etc.), halogenated hydrocarbons (dichloromethane, chloroform, 1,2-dichloroethane, carbon tetrachloride), aromatic hydrocarbons (benzene, toluene, xylene, etc.), aliphatic hydrocarbons (hexane, pentane, cyclohexane, etc.), nitriles (acetonitrile, propionitrile etc.), amides (DMF, N,N-dimethylacetamide, N-methylpyrrolidinone and the like. They may be used singly or as a mixture.

The amount of the condensing agent is, with respect to the compound represented by general formula (14), 1.0 to 50 equivalents, preferably 1 to 5 equivalents. The amount of thiosemicarbazide is, with respect to the compound represented by general formula (14), generally 1 to 100 equivalents, preferably 1.0 to 5.0 equivalents. The base is organic bases such as triethylamine, N,N-diisopropylethylamine, pyridine, 4-dimethylaminopyridine, diazabicycloundecene and the like.

The reaction temperature is −20 to 180° C., preferably 0 to 100° C. The reaction time is usually 0.05 to 24 hours, preferably 0.05 to 6 hours. The compound represented by formula (18) of the present invention can be isolated and purified by well-known separation and purification means as described below.

[Formula 10]

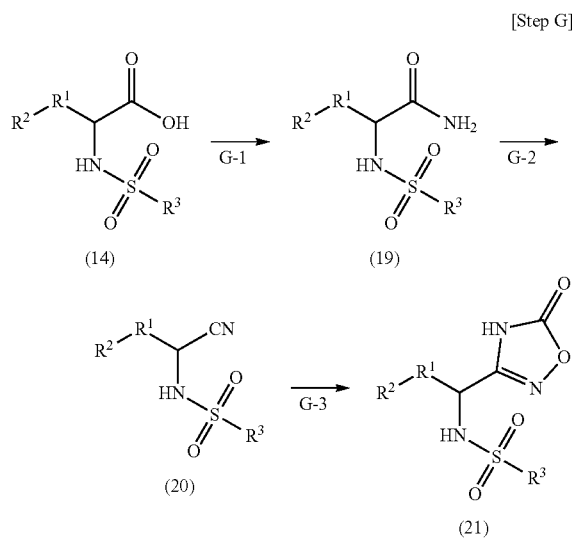

[In the formula, the symbols have the same meanings as defined above.]

[G-1]

In this step, a compound represented by general formula (19) can be prepared by reacting the carboxylic acid represented by general formula (14) with a condensation agent and ammonia.

The condensing agent is, for example, 1,1'-carbonyldiimidazole (hereinafter, CDI), dicyclohexylcarbodiimide, 1-ethyl-3-(3-dimethylaminopropyl)carbodiimide hydrochloride and the like, preferably CDI.

The solvent to be used is not particularly limited as long as it does not affect the reaction, for example, organic solvents such as ethers (diethyl ether, tetrahydrofuran, 1,4-dioxane, 1,2-dimethoxyethane, etc.), halogenated hydrocarbons (dichloromethane, chloroform, 1,2-dichloroethane, carbon tetrachloride), aromatic hydrocarbons (benzene, toluene, xylene, etc.), aliphatic hydrocarbons (hexane, pentane, cyclohexane, etc.), nitriles (acetonitrile, propionitrile etc.), amides (DMF, N,N-dimethylacetamide, N-methylpyrrolidinone and the like. They may be used singly or as a mixture.

The amount of the condensing agent with respect to the compound represented by general formula (14) is generally 1 to 50 equivalents, preferably 1 to 5 equivalents. Ammonia is used as an aqueous solution or hydrochloric acid salt, and its amount relative to the compound represented by general formula (14) is generally 1 to 100 equivalents, preferably 1.0 to 5.0 equivalents. The bases include, for example, organic bases such as triethylamine, pyridine, 4-dimethylaminopyridine, diazabicycloundecene and the like.

The reaction temperature is −20 to 80° C., preferably 0 to 40° C. The reaction time is usually from 0.05 to 24 hours, preferably 0.05 to 6 hours. The compound represented by general formula (19) can be subjected to the next step with or without isolation and purification by well-known separation and purification means as described below.

[G-2]

In this step, a nitrile represented by general formula (20) can be prepared from the amide compound represented by general formula (19).

Dehydrating agents include, for example, oxalyl chloride, thionyl chloride, cyanuric chloride and the like, preferably cyanuric chloride.

The solvent to be used is not particularly limited as long as it does not affect the reaction, for example, organic solvents such as ethers (diethyl ether, tetrahydrofuran, 1,4-dioxane, 1,2-dimethoxyethane, etc.), halogenated hydrocarbons (dichloromethane, chloroform, 1,2-dichloroethane, carbon tetrachloride), aromatic hydrocarbons (benzene, toluene, xylene, etc.), aliphatic hydrocarbons (hexane, pentane, cyclohexane, etc.), nitriles (acetonitrile, propionitrile etc.), amides (DMF, N,N-dimethylacetamide, N-methylpyrrolidinone and the like. They may be used singly or as a mixture.

The amount of dehydrating agent with respect to the compound represented by general formula (19) is usually 1 to 50 equivalents.

The reaction temperature is −20 to 80° C., preferably between 0 to 40° C. The reaction time is usually from 0.05 to 24 hours, preferably from 0.05 to 3 hours. The compound represented by general formula (20) can be subjected to the next step with or without isolation and purification by well-known separation and purification means as described below.

[G-3]

In this step, an amidoxime compound is obtained from the nitrile compound represented by general formula (20) by adding hydroxylamine, and then it reacts with an acylating agent followed by cyclization reaction with application of heat to produce a compound represented by general formula (21).

The amount of the hydroxylamine to be used for preparing amidoxime is generally 1 to 50 equivalents in reaction to the compound represented by general formula (20).

The solvent to be used is not particularly limited as long as it does not affect the reaction, for example, organic solvent such as ethers (diethyl ether, tetrahydrofuran, 1,4-dioxane, 1,2-dimethoxyethane, etc.), halogenated hydrocarbons (dichloromethane, chloroform, 1,2-dichloroethane, carbon tetrachloride), aromatic hydrocarbons (benzene, toluene, xylene, etc.), aliphatic hydrocarbons (hexane, pentane, cyclohexane, etc.), nitriles (acetonitrile, propionitrile etc.), amides (DMF, N,N-dimethylacetamide, N-methylpyrrolidinone and the like). They may be used singly or as a mixture.

The reaction temperature is −20 to 100° C., preferably 0 to 60° C. The reaction time is generally from 0.05 to 3 days, preferably 0.05 to 12 hours. The obtained amidoxime compound represented by general formula (20) can be subjected to the next step with or without isolation and purification by well-known separation and purification means as described below.

The acylating agent used for amide oxime is, for example, chloroformate, 2-ethylhexyl, CDI, phosgene, triphosgene and the like, preferably chloroformate 2-ethylhexyl. The base to be used includes organic bases such as triethylamine, N,N-diisopropylethylamine, pyridine, 4-dimethylaminopyridine, diazabicycloundecene and the like.

The amount of the acylating agent is usually 1 to 50 equivalents relative to the amide oxime compound, and more preferably about 1 to 3 equivalents.

The solvent to be used is not particularly limited as long as it does not affect the reaction, for example, organic solvents such as ethers (diethyl ether, tetrahydrofuran, 1,4-dioxane, 1,2-dimethoxyethane, etc.), halogenated hydrocarbons (dichloromethane, chloroform, 1,2-dichloroethane, carbon tetrachloride), aromatic hydrocarbons (benzene, toluene, xylene, etc.), aliphatic hydrocarbons (hexane, pentane, cyclohexane, etc.), nitriles (acetonitrile, propionitrile etc.), amides (DMF, N,N-dimethylacetamide, N-methylpyrrolidinone, etc.) and the like), and they can be used singly or as a mixture, and they can be switched to other solvents during the reaction.

The reaction temperature with the acylating agent is to −20, 80° C., preferably 0 to 40° C. The reaction time is generally 0.5 to 24 hours, preferably 0.5 to 3 hours. The reaction temperature used for cyclization reaction of the obtained acylated compound is 0 to 150° C., preferably 0 to 120° C. The reaction time is generally from 0.5 to 24 hours, preferably 0.5 to 12 hours. The obtained compound represented by general formula (21) can be subjected to the next step with or without isolation and purification by well-known separation and purification means as described below.

The compound represented by formula (I) of the present invention and intermediates thereof can be isolated and purified by well-known separation and purification means such as recrystallization, crystallization, distillation, or column chromatography. The compound of the present invention and synthetic intermediates are usually possible to form a pharmacologically acceptable salt thereof in a well-known manner, and also can be converted to each other.

When optical isomers, stereoisomers, tautomers, or rotary isomers are present in the compound of the present invention, the compound of the present invention encompasses these isomers or the mixture thereof. For example, when an optical isomer in the compound of the present invention is present, unless otherwise stated, racemate and an optical isomer resolved from a racemate are also encompassed in the compound of the present invention. These isomers can be obtained by a well-known synthetic method, separation means (concentration, solvent extraction, column chromatography, recrystallization and the like) respectively with a single compound. In the compound of the present invention, for example, when $X^1$=oxygen atom, $X^2$=oxygen atom, $X^3$=NH, there are tautomers as shown below, any of the isomers are also included in the present invention.

[Formula 11]

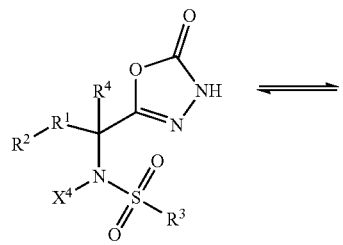

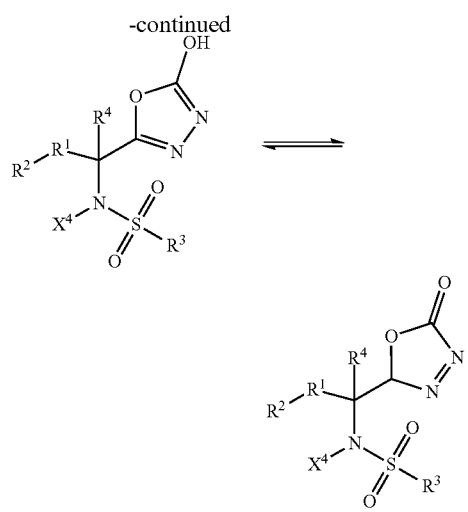

The compound of the present invention or a salt thereof may be amorphous (amorphous) or a crystalline form, and the crystalline form may be a single crystalline form or polymorphic mixture, which are encompassed by the compound of the present invention or a salt thereof. The crystals can be prepared by applying a well-known crystallization method.

Furthermore, the compound of the present invention or a salt thereof can be a solvate (e.g., hydrate etc.) or a non-solvate, both of which are encompassed in the compound of the present invention or a salt thereof. The compounds labeled with isotopes (e.g., deuterium, $^3H$, $^{14}C$, $^{35}S$, $^{125}I$, etc.) and the like are also encompassed by the compound of the present invention or a salt thereof.

Although the prodrugs of the compound of the present invention or a salt thereof are also included in the present invention, the prodrugs refer to the compounds which convert into the compound of the present invention or a salt thereof by a reaction with an enzyme or gastric acid under the physiological condition in the living body, i.e., the compounds which convert into the compound of the present invention or a salt thereof by enzymatic oxidation, reduced, or hydrolysis and the like or the compounds which convert into the compound of the present invention or a salt thereof by gastric acid. Furthermore, a prodrug of the compound of the present invention or a salt thereof may be the compounds which convert into the compound of the present invention or a salt thereof under physiological conditions as described in Hirokawa Shoten 1990 annual "Development of Pharmaceuticals" Volume 7 Molecular Design pages 163-198.

A salt of the compound of the present invention means a salt that is pharmaceutically acceptable.

The compound of the present invention or a salt thereof has an inhibitory activity against RNR. The compound of the present invention or a salt thereof is useful as a medicament for prevention or treatment of RNR-related diseases without causing side effects based on the off-target effects of the iron ions requiring protein due to its excellent RNR inhibitory activity and its structure that does not chelate to metal ions. The "RNR-related disease" includes diseases whose incidence can be decreased or whose symptom is in remission or alleviated and/or completely cured by deleting or suppressing and/or inhibiting functions of RNR. Such diseases are, for example, malignant tumors. Malignant tumors of interest is not particularly limited, head and neck cancer, gastrointestinal cancer (esophageal cancer, gastric cancer, duodenal cancer, liver cancer, biliary tract cancer (gallbladder•bile duct cancer, etc.), pancreatic cancer, colorectal cancer (colon cancer, rectal cancer etc.), etc.), lung cancer (non-small cell lung cancer, small cell lung cancer, mesothelioma, etc.), breast cancer, genital cancer (ovarian cancer, uterine cancer (cervical cancer, endometrial cancer, etc.), etc.), urinary cancer (kidney cancer, bladder cancer, prostate cancer, testicular tumor, etc.), hematopoietic tumors (leukemia, malignant lymphoma, multiple myeloma, etc.), bone and soft tissue tumors, skin cancer, brain tumor and the like.

"RNR" herein includes a human or non-human RNR, preferably a human RNR.

Accordingly, the present invention provides an RNR inhibitor including the compound of the present invention or a salt thereof as an active ingredient. Furthermore, the present invention relates to the use of the compound of the present invention or a salt thereof for the manufacture of the RNR inhibitors. The present invention also provides the use of the compound of the present invention or a salt thereof as RNR inhibitors. Furthermore, the present invention provides the compound of the present invention or a salt thereof for use as RNR inhibitors.

In yet another embodiment, the present invention provides a medicament containing the compound of the present invention or a salt thereof as an active ingredient. Furthermore, the present invention relates to use of the compound of the present invention or a salt thereof for the manufacture of a medicament. Further, the present invention provides the use as medicaments of the compound of the present invention or a salt thereof. Further, the present invention provides the compound of the present invention or a salt thereof for use as a medicament.

In yet another embodiment, the present invention provides a pharmaceutical composition comprising the compound of the present invention or a salt thereof and a pharmaceutically acceptable carrier.

In a preferred embodiment, the medicament or pharmaceutical composition is a therapeutic agent for the RNR-related diseases, in a more preferred embodiment, the medicament or pharmaceutical composition is an antitumor agent.

In yet another embodiment, the present invention comprises administering an effective amount of the compound of the present invention or a salt thereof to a subject to provide an RNR activity suppression method. Further, the present invention comprises administering an effective amount of the compound of the present invention or a salt thereof to a subject to provide a method of treating RNR-related diseases. In a preferred embodiment, a method of treating RNR-related diseases is a method of treating tumors. In the treatment method, the subjects include human or non-human animal in need of the method.

When using the compound of the present invention or a salt thereof as a pharmaceutical, it is optionally formulated with a pharmaceutically acceptable carrier, and various dosage forms can be adopted depending on the prevention or therapeutic purposes, and as the dosage forms include, for example, oral agents, injections, suppositories, ointments, and any of such patches. Since the compound of the present invention or a salt thereof has an excellent oral absorbability, oral agents are preferable. These dosage forms can be prepared by preparation methods commonly known by a person with ordinary skill in the art.

With respect to pharmaceutically acceptable carriers, conventional various organic or inorganic carrier substances are used as pharmaceutical materials, and it is formulated as: excipients, binders, disintegrating agents, lubricants, coloring agents for solid preparations; and solvents, solubilizing agents, suspending agents, isotonizing agents, buffers, soothing agent for liquid preparations and the like. Further, if necessary, pharmaceutical additives can also be used, which include such as preservative agents, antioxidants, coloring agents, sweetening agents, flavoring agents, stabilizing agents.

With respect to the pharmaceutically acceptable carriers and the pharmaceutical additives, in general, they include, for example, as the excipient, lactose, sucrose, sodium chloride, glucose, starch, calcium carbonate, kaolin, microcrystalline cellulose, silicic acid and the like; as are binders, water, ethanol, propanol, simple syrup, a glucose solution, a starch solution, a gelatin solution, carboxymethyl cellulose, hydroxypropyl cellulose, hydroxypropyl starch, methyl cellulose, ethyl cellulose, shellac, calcium phosphate, polyvinylpyrrolidone, and the like; as disintegrants, dry starch, sodium alginate, agar powder, sodium hydrogen carbonate, calcium carbonate, sodium lauryl sulfate, stearic acid monoglyceride, lactose and the like; as lubricants, purified talc stearate, borax, polyethylene glycol and the like; as colorant, titanium oxide, iron oxide and the like; as flavoring agents, sucrose, orange peel, citric acid, tartaric acid and the like.

When preparing an oral solid preparation, it can be prepared by adding an excipient to the compound of the present invention, and if necessary, further adding binders, disintegrants, lubricants, colorants, or flavoring agents and the like, followed by formulating into tablets, coated tablets, granules, powders, capsules and the like.

When preparing injectable forms, it can be prepared by adding pH control agents, buffers, stabilizers, isotonic agents, local anesthetic agents and the like to the compound of the present invention, followed by formulating into subcutaneous, intramuscular and intravenous injections with a conventional manner.

The amount of the compound of the present invention to be formulated in each dosage unit forms described above can be, in general, per dosage unit form, 0.05 to 1000 mg for the oral dosage, about 0.01 to 500 mg for injection, 1 to 1000 mg for suppositories with the proviso that they may be altered depending on the symptoms of the patients to be applied or its dosage forms.

Further, the daily dose of a drug with the dosage form is, with respect to the compound of the present invention, 0.05 to 5000 mg per day for adult (body weight 50 kg), preferably 0.1 to 2000 mg, and preferably the aforementioned amount is administered once or 2 to 3 times a day with the proviso that they may be altered depending on symptoms of the patients, weight, age, or gender and the like.

EXAMPLES

The present invention is described below in more detail with examples and test examples, but the present invention is not intended to be limited to these examples.

Various reagents used in the examples were commercially available products, unless otherwise stated. Biotage Ltd. SNAP-ULTRA (registered trademark) Silica prepacked column was used for a silica gel column chromatography, or Biotage made SNAP KP-C18-HS (registered trademark) Silica prepacked column was used for a reverse phase silica gel column chromatography. HPLC purified by preparative reverse phase column chromatography was performed under the following conditions. Injection volume and gradient was carried out appropriately.

Column: YMC-Actus Triart C18, 30×50 mm, 5 μm
UV detection: 254 nm
Column flow rate: 40 mL/min
Mobile phase: water/acetonitrile (0.1% formic acid)
Injection amount: 1.0 mL
Gradient: water/acetonitrile (10% to 90%)

AL400 (400 MHz; JEOL (JEOL)) and Mercury400 (400 MHz; Agilent Technologies) were used for NMR spectra, and tetramethylsilane was used as an internal standard when tetramethylsilane was included in the heavy solvent, otherwise it was measured using NMR solvent as an internal standard, showing all δ value in ppm. Furthermore, LCMS spectra were measured under the following conditions using a Waters made ACQUITY SQD (quadrupole).

Column: Waters made ACQUITY UPLC (registered trademark) BEH C18, 2.1×50 mm, 1.7 μm
MS detection: ESI negative
UV detection: 254 and 280 nm
Column flow rate: 0.5 mL/min
Mobile phase: water/acetonitrile (0.1% formic acid)
Injection amount: 1 μL

| Gradient (table 1) | | |
|---|---|---|
| Time (min) | Water | Acetonitrile |
| 0 | 95 | 5 |
| 0.1 | 95 | 5 |
| 2.1 | 5 | 95 |
| 3.0 | STOP | |

The meanings of the abbreviations are shown below.
s: singlet
d: doublet
t: triplet
q: quartet
dd: double doublet
dt: double triplet
td: triple doublet
tt: triple triplet
ddd: double double doublet
ddt: double double triplet
dtd: double triple doublet
tdd: triple-double doublet
m: multiplet
br: broad
brs: broad singlet
DMSO-d$_6$: deuterated dimethyl sulfoxide
CDCl$_3$: heavy chloroform
CD$_3$OD: heavy methanol
CDI: 1,1'-carboxymethyl sulfonyl diimidazole
DAST: N,N-diethylaminosulfur trifluoride
DIBAL-H: diisobutylaluminum hydride
DMF: dimethylformamide
DMSO: dimethylsulfoxide
THF: Tetrahydrofuran
WSC=EDCI=1-ethyl-3-(3-dimethylaminopropyl)carbodiimide
HOBt=1-hydroxybenzotriazole Reference Example A1
2-(1-bromoethyl)-1-fluoro-3,4-dimethylbenzene

[Formula 12]

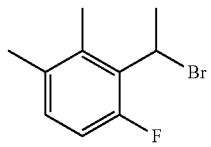

Step 1

1-(6-fluoro-2,3-dimethylphenyl)ethanol

After dropping a diethyl ether solution of methylmagnesium bromide (3.0 M, 70 mL) to a THF solution of 6-fluoro-2,3-dimethyl-benzaldehyde (22.0 g) (300 mL) at 0° C., the reaction mixture was stirred at room temperature for 1 hour. Under ice-bath condition, a saturated aqueous ammonium chloride solution (150 mL) was added dropwise, and ethyl acetate (200 mL) was added, and the resultant was separated into different layers. The organic layer was successively washed with HCl (1M, 200 mL), water (200 mL) and saline (200 mL), and then dried over anhydrous magnesium sulfate, and concentrated under reduced pressure to obtain 1-(6-fluoro-2,3 dimethylphenyl)ethanol (23.7 g).

(Step 2)

Phosphorus tribromide (26.5 mL) was added dropwise at 0° C. to a chloroform solution (120 mL) of 1-(6-fluoro-2,3-dimethylphenyl)ethanol (23.7 g) obtained in the above Step 1, and the reaction solution was stirred for 30 minutes at 0° C. The reaction mixture was added to an ice-cold saturated aqueous sodium bicarbonate (1 L). After chloroform (500 mL) was added to the mixture, the resultant was separated into different layers, and the organic layer was successively washed with water (200 mL) and saline (200 mL). The organic layer was dried over anhydrous magnesium sulfate to give the title compound (29.5 g) by concentrating under reduced pressure.

Reference Example A2 to A41

Aldehyde and methylmagnesium bromide were reacted together as starting materials in the same manner as in Reference Example A1, Step 1 and Step 2, and then the resultant was reacted with phosphorus tribromide to obtain the compounds of Reference Examples A2 to A41. However, the compounds of Reference Examples A40 and A41 were obtained in the same procedure using ethylmagnesium bromide and methyl iodide-d3-magnesium respectively instead of methylmagnesium bromide.

TABLE 1-1
| Reference Example | Starting Material | Synthesized Compound |
|---|---|---|
| A2 |  | 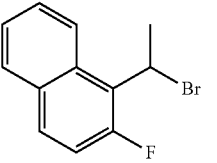 |
| A3 | 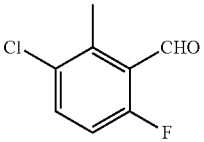 | 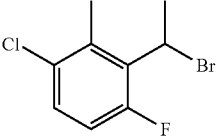 |
| A4 | 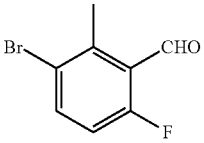 | 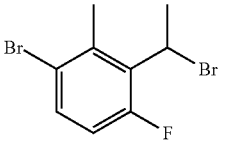 |
| A5 | 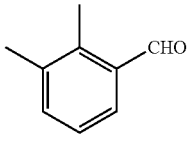 | 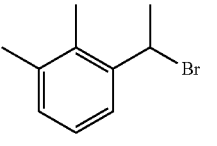 |
| A6 | 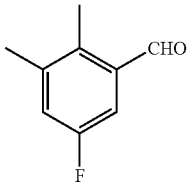 | 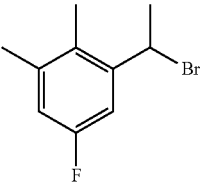 |
| A7 | 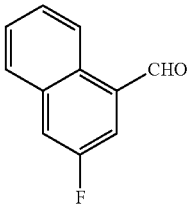 [SMILES: O=Cc1cc(F)cc2ccccc12] | 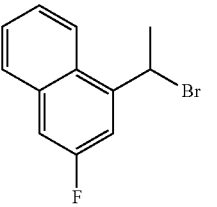 |
| A8 | 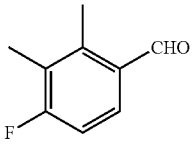 | 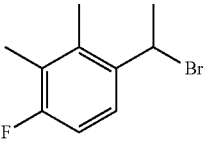 |
| A9 | 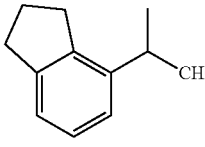 | 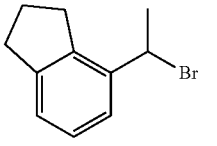 |
| A10 | 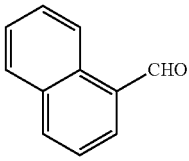 [SMILES: O=Cc1cccc2ccccc12] | 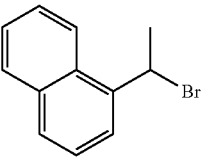 |
TABLE 1-1-continued
| Reference Example | Starting Material | Synthesized Compound |
|---|---|---|
| A11 | 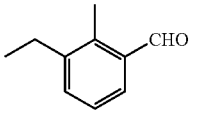 | 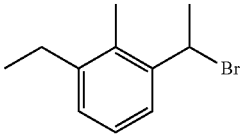 |
| A12 | 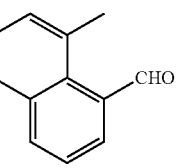 | 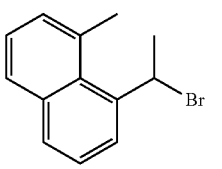 |
| A13 | 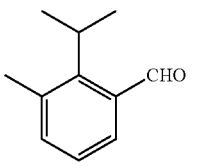 | 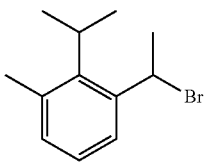 |
| A14 | 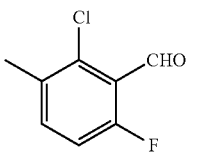 | 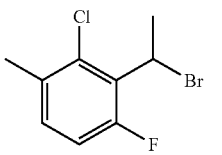 |
| A15 |  | 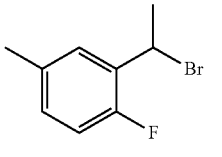 |
TABLE 1-2
| Reference Example | Starting Material | Synthesized Compound |
|---|---|---|
| A16 | 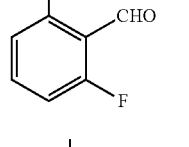 | 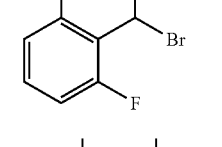 |
| A17 | 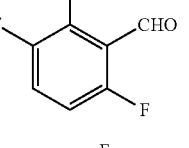 | 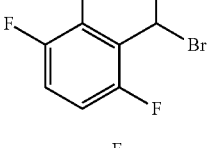 |
| A18 | 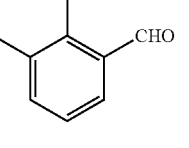 | 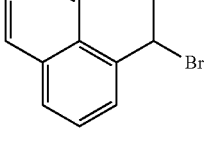 |

TABLE 1-2-continued

| Reference Example | Starting Material | Synthesized Compound |
|---|---|---|
| A19 | tetrahydronaphthalene-CHO | tetrahydronaphthalene-CH(Br)CH₃ |
| A20 | fluorene-CHO | fluorene-CH(Br)CH₃ |
| A21 | fluorene-CHO (isomer) | fluorene-CH(Br)CH₃ (isomer) |
| A22 | F-naphthalene-CH(CH₃)-CHO | F-naphthalene-CH(CH₃)-Br |
| A23 | F-naphthalene-CH(CH₃)-CHO | F-naphthalene-CH(CH₃)-Br |
| A24 | dimethyl-tetrahydronaphthalene-CH(CH₃)-CHO | dimethyl-tetrahydronaphthalene-CH(CH₃)-Br |
| A25 | benzothiophene-CHO | benzothiophene-CH(Br)CH₃ |
| A26 | methyl-biphenyl-CHO | methyl-biphenyl-CH(Br)CH₃ |
| A27 | 2,3-dihydrobenzofuran-CHO | 2,3-dihydrobenzofuran-CH(Br)CH₃ |

TABLE 1-2-continued

| Reference Example | Starting Material | Synthesized Compound |
|---|---|---|
| A28 | 2,3-dihydrobenzofuran-CHO | 2,3-dihydrobenzofuran-CH(Br)CH₃ |
| A29 | methyl-naphthalene-CHO | methyl-naphthalene-CH(Br)CH₃ |

TABLE 1-3

| Reference Example | Starting Material | Synthesized Compound |
|---|---|---|
| A30 | F,methyl-benzene-CHO | F,methyl-benzene-CH(Br)CH₃ |
| A31 | benzothiophene-CHO | benzothiophene-CH(Br)CH₃ |
| A32 | F,F-benzene-CHO | F,F-benzene-CH(Br)CH₃ |
| A33 | methyl-2,3-dihydrobenzofuran-CHO | methyl-2,3-dihydrobenzofuran-CH(Br)CH₃ |
| A34 | methyl-benzene-CHO | methyl-benzene-CH(Br)CH₃ |
| A35 | F,F,methyl-benzene-CHO | F,F,methyl-benzene-CH(Br)CH₃ |
| A36 | F,methyl-benzene-CHO | F,methyl-benzene-CH(Br)CH₃ |

TABLE 1-3-continued

| Reference Example | Starting Material | Synthesized Compound |
|---|---|---|
| A37 | benzothiazole-CHO | benzothiazole-CH(CH3)Br |
| A38 | quinoline-8-CHO | quinoline-8-CH(CH3)Br |
| A39 | 2-ethyl-6-methylbenzaldehyde | 2-ethyl-6-methyl-α-bromoethylbenzene |
| A40 | 2,3-dimethyl-6-fluorobenzaldehyde (ethyl) | corresponding bromoethyl |
| A41 | 2,3-dimethyl-6-fluorobenzaldehyde | corresponding CD3-bromo compound |

Reference Example B1
2-(1-bromoethyl)-4-ethyl-1-fluoro-3-methylbenzene

[Formula 13]

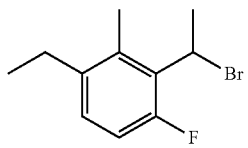

Step 1

2-bromo-3-ethyl-6-fluorobenzaldehyde

To a THF solution (150 mL) of 2-bromo-1-ethyl-4-fluorobenzene (14.4 g), a THF solution of lithium diisopropylamide (1.5 M, 54 mL) was added dropwise at −78° C. After stirring the reaction solution for 30 minutes, DMF (6.5 mL) was added and the mixture was further stirred for 20 minutes. Water (50 mL) and hydrochloric acid (6 M, 50 mL) were successively added dropwise to the reaction solution, and the mixture was extracted twice with hexane (100 mL). The combined organic layer was washed with saturated saline (50 mL) twice, dried over anhydrous sodium sulfate, and concentrated under reduced pressure, and 2-bromo-3-ethyl-6-fluorobenzaldehyde (14.5 g) was obtained.

Step 2

3-ethyl-6-fluoro-2-methylbenzaldehyde

To a 1,4-dioxane solution (200 mL) of 2-bromo-3-ethyl-6-fluorobenzaldehyde obtained from Step 1 above (14.5 g), water (90 mL), tripotassium phosphate (32.0 g), methylboronic acid (6.4 g) and [bis (diphenylphosphino) ferrocene] palladium (II) dichloride dichloromethane additive (1.75 g) were added, and the reaction solution was heated under reflux at 110° C. for 2 hours. The reaction solution was allowed to cool to room temperature, and the mixture was further stirred for 2 hours after hexane (90 mL) was added. The reaction solution was filtered through CELITE, and the filtrate was separated after the residue was washed with hexane. The organic layer was washed twice with saturated saline (100 mL), and after being dried over anhydrous sodium sulfate, it was concentrated under reduced pressure. The residue was purified by silica gel column chromatography (eluent: hexane/ethyl acetate), and 3-ethyl-6-fluoro-2-methylbenzaldehyde (8.4 g) was obtained.

(Step 3)

According to the methods of Reference Example A1 Steps 1 and 2, using 3-ethyl-6-fluoro-2-methylbenzaldehyde (8.4 g) obtained in the above Step 2, the same operation was carried out to obtain the title compound.

Reference Examples B2 to B6

According to the methods of Reference Example B1 Steps 1 and 2 and Reference Example A1 Steps 1 and 2, the following compounds of Reference Examples B2 to B5 were synthesized. Also, according to the methods of Reference Example B1 Step 1, and Reference Example A1 Steps 1 and 2, the compound of Reference Example B6 was synthesized.

TABLE 2

| Reference Example | Starting Material | Synthesized Compound |
|---|---|---|
| B2 | methyl-bromo-difluorobenzene | methyl-bromoethyl-difluoro-methylbenzene |
| B3 | cyclopropyl-bromo-fluorobenzene | cyclopropyl-bromoethyl-fluoro-methylbenzene |
| B4 | F3C-bromo-fluorobenzene | F3C-bromoethyl-fluoro-methylbenzene |

TABLE 2-continued

| Reference Example | Starting Material | Synthesized Compound |
|---|---|---|
| B5 | 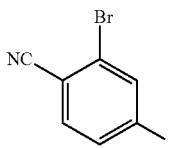 | 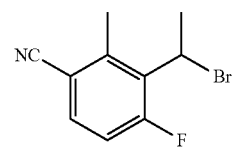 |
| B6 | 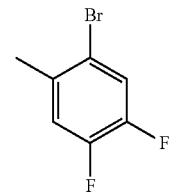 | 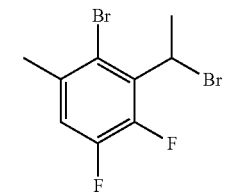 |

Reference Example C1
7-(1-chloroethyl)-1-methyl-2,3-dihydro-1H-indene

[Formula 14]

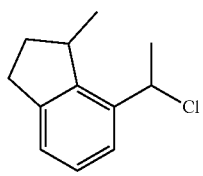

Sodium borohydride (261 mg) was added to a methanol solution (5.0 mL) of 1-(3-methyl-2,3-dihydro-1H-inden-4-yl)ethanone (1.0 g), and the mixture was stirred at room temperature for 30 minutes. The reaction solution was added to water (10 mL) and then extracted twice with ethyl acetate (20 mL). The combined organic layer was washed with saturated saline (20 mL), dried over anhydrous sodium sulfate, and concentrated under reduced pressure. The obtained residue was dissolved in dichloromethane (5.0 mL), thionyl chloride (2.0 mL) was added at room temperature, and the reaction solution was stirred at 50° C. for 30 minutes. Water was added to the reaction solution, and the mixture was extracted twice with ethyl acetate (20 mL). The combined organic layer was washed with saturated saline (20 mL), dried over anhydrous sodium sulfate, and concentrated under reduced pressure to give the title compound (1.1 g).

Reference Examples C2 to C4

According to the method of Reference Example C1, the following compounds of Reference Examples C2 to C4 were synthesized.

TABLE 3

| Reference Example | Starting Material | Synthesized Compound |
|---|---|---|
| C2 | 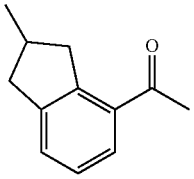 | 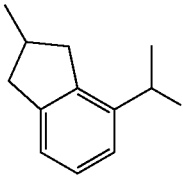 |
| C3 | 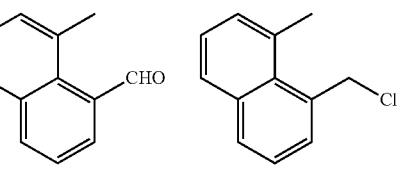 | 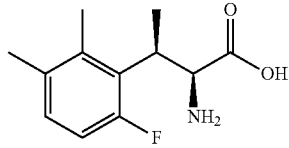 [SMILES: Cc1ccc(F)c([C@@H](C)[C@@H](N)C(=O)O)c1C] |
| C4 | 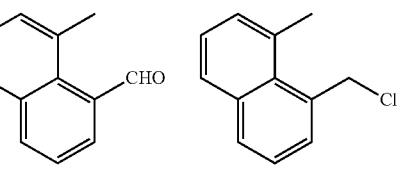 | 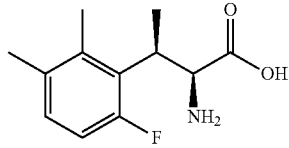 [SMILES: Cc1ccc(F)c([C@@H](C)[C@@H](N)C(=O)O)c1C] |

Reference Example D1 (2S,3R)-2-amino-3-(6-fluoro-2,3-dimethylphenyl)butanoic acid

[Formula 15]

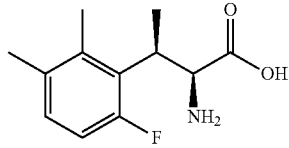 [SMILES: Cc1ccc(F)c([C@@H](C)[C@@H](N)C(=O)O)c1C]

A DMF solution (50 mL) of 2-(1-bromoethyl)-1-fluoro-3,4-dimethylbenzene (14.0 g) obtained in Reference Example A1 was added dropwise to a DMF solution (50 mL) of (S)-2-[o-[(N-benzylprolyl)amino]phenyl]-benzylideneamino-acetate (2-)-N,N,N-nickel (II) (14.5 g), and potassium hydroxide (16.3 g), and the mixture was stirred at the same temperature for 1 hour. A saturated ammonium chloride solution (50 mL) and ethyl acetate (50 mL) were added to the reaction solution, the layers were separated, and the aqueous layer was extracted twice with ethyl acetate (50 mL). The combined organic layers were washed successively with water (50 mL) and saturated saline (50 mL), dried over anhydrous sodium sulfate, and concentrated under reduced pressure. The residue was purified by silica gel column chromatography (eluent: ethyl acetate/hexane). The obtained compound was dissolved in methanol (120 mL), hydrochloric acid (3 M, 90 mL) was added, and the mixture was stirred at 80° C. for 45 minutes. Methanol was distilled off under reduced pressure, and chloroform (50 mL) and water (50 mL) were added to the residue. The aqueous layer was washed with chloroform (50 m L) and concentrated under reduced pressure. The residue was purified by reverse phase silica gel column chromatography (methanol/water) to give the title compound (2.0 g). $^1$H NMR (CD$_3$OD) δ: 7.03 (dd, J=8.2, 5.7 Hz, 1H), 6.79 (dd, J=11.7, 8.4 Hz, 1H), 3.74-3.87 (m, 2H), 2.29 (s, 3H), 2.25 (s, 3H), 1.40 (dd, J=6.8, 2.4 Hz, 3H)

Reference Examples D2 to D58

After the alkylating agent obtained in Reference Examples A2 to A41, Reference Examples B1 to B6, and Reference Examples C1 to C4 and (S)-2-[o-[(N-benzylprolyl)amino]phenyl]-benzylideneamino-acetate (2-)-N,N,N-nickel (II) were reacted, the compounds of Reference Examples D2 to D58 shown below were prepared by acid hydrolysis. However, for the compound of Reference Example D56, 6-fluoro-2,3-dimethylbenzaldehyde was used as a starting material, and the compounds of Reference Examples D57 and 58 were prepared by the same method by using (R)-2-[o-[(N-benzylprolyl)amino]phenyl]-benzylideneamino-acetate (2-)-N,N,N-nickel (II) instead of (S)-2-[o-[(N-benzylprolyl)amino]phenyl]-benzylideneamino-acetate (2-)-N,N,N-nickel (II).

TABLE 4-1

| Reference Example | Starting Material (Reference example number or structural formula) | Synthesized Compound |
|---|---|---|
| D2 | A1 | |
| D3 | A2 | |
| D4 | A3 | |
| D5 | A4 | |
| D6 | A5 | |
| D7 | A6 | |
| D8 | A7 | |
| D9 | A8 | |
| D10 | A9 | |
| D11 | A10 | |
| D12 | A11 | |
| D13 | A12 | |

TABLE 4-2

| Reference Example | Starting Material (Reference example number or structural formula) | Synthesized Compound |
|---|---|---|
| D14 | A13 | |

TABLE 4-2-continued

| Reference Example | Starting Material (Reference example number or structural formula) | Synthesized Compound |
|---|---|---|
| D15 | A14 | 3-(2-chloro-6-fluoro-3-methylphenyl)-2-amino-butanoic acid structure |
| D16 | A15 | 3-(2-fluoro-5-methylphenyl)-2-aminobutanoic acid structure |
| D17 | A16 | 3-(2-fluoro-6-methylphenyl)-2-aminobutanoic acid structure |
| D18 | A16 | 3-(2-fluoro-6-methylphenyl)-2-aminobutanoic acid (other diastereomer) structure |
| D19 | A17 | 3-(3,6-difluoro-2-methylphenyl)-2-aminobutanoic acid structure |
| D20 | A18 | 3-(8-fluoronaphthalen-1-yl)-2-aminobutanoic acid structure |
| D21 | A19 | 3-(5,6,7,8-tetrahydronaphthalen-1-yl)-2-aminobutanoic acid structure |
| D22 | A20 | 3-(9H-fluoren-4-yl)-2-aminobutanoic acid structure |
| D23 | A21 | 3-(9H-fluoren-4-yl)-2-aminobutanoic acid structure |

TABLE 4-2-continued

| Reference Example | Starting Material (Reference example number or structural formula) | Synthesized Compound |
|---|---|---|
| D24 | A22 | 3-(6-fluoronaphthalen-1-yl)-2-aminobutanoic acid structure |
| D25 | A23 | 3-(5-fluoronaphthalen-1-yl)-2-aminobutanoic acid structure |

TABLE 4-3

| Reference Example | Starting Material (Reference example number or structural formula) | Synthesized Compound |
|---|---|---|
| D26 | A24 | 3-(5,5-dimethyl-5,6,7,8-tetrahydronaphthalen-1-yl)-2-aminobutanoic acid structure |
| D27 | A25 | 3-(benzothiophen-4-yl)-2-aminobutanoic acid structure |
| D28 | A26 | 3-(2-methylbiphenyl-3-yl)-2-aminobutanoic acid structure |
| D29 | A27 | 3-(2,3-dihydrobenzofuran-4-yl)-2-aminobutanoic acid structure |
| D30 | A28 | 3-(2,3-dihydrobenzofuran-7-yl)-2-aminobutanoic acid structure |
| D31 | A29 | 3-(2-methylnaphthalen-1-yl)-2-aminobutanoic acid structure |

TABLE 4-3-continued

| Reference Example | Starting Material (Reference example number or structural formula) | Synthesized Compound |
|---|---|---|
| D32 | A30 | 3-fluoro-2-methylphenyl alanine derivative |
| D33 | A31 | benzothiophen-3-yl alanine derivative |
| D34 | A32 | 2,3-difluorophenyl alanine derivative |
| D35 | A33 | 3-methyl-2,3-dihydrobenzofuran-4-yl alanine derivative |
| D36 | A33 | 3-methyl-2,3-dihydrobenzofuran-4-yl alanine derivative (diastereomer) |
| D37 | A34 | 2-methylphenyl alanine derivative |

TABLE 4-4

| Reference Example | Starting Material (Reference example number or structural formula) | Synthesized Compound |
|---|---|---|
| D38 | A35 | 2-fluoro-6-methylphenyl alanine derivative |
| D39 | A36 | 2-fluoro-3-methylphenyl alanine derivative |

TABLE 4-4-continued

| Reference Example | Starting Material (Reference example number or structural formula) | Synthesized Compound |
|---|---|---|
| D40 | A37 | benzothiazol-4-yl alanine derivative |
| D41 | A38 | quinolin-8-yl alanine derivative |
| D42 | A39 | 2-ethyl-3-methylphenyl alanine derivative |
| D43 | A40 | 2,3-dimethyl-6-fluorophenyl α-ethyl alanine derivative |
| D44 | A41 | 2,3-dimethyl-6-fluorophenyl α-CD3 alanine derivative |
| D45 | B1 | 3-ethyl-2-methyl-6-fluorophenyl alanine derivative |
| D46 | B2 | 2,3-dimethyl-5,6-difluorophenyl alanine derivative |
| D47 | B3 | 3-cyclopropyl-2-methyl-6-fluorophenyl alanine derivative |
| D48 | B4 | 3-trifluoromethyl-2-methyl-6-fluorophenyl alanine derivative |

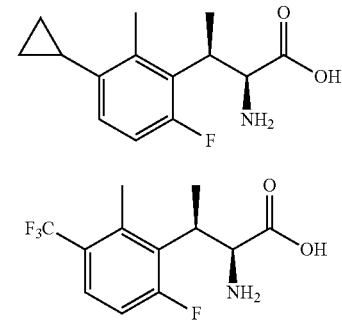

TABLE 4-4-continued

| Reference Example | Starting Material (Reference example number or structural formula) | Synthesized Compound |
|---|---|---|
| D49 | B5 | (structure) |
| D50 | B6 | (structure) |
| D51 | C1 | (structure) |

TABLE 4-5

| Reference Example | Starting Material (Reference example number or structural formula) | Synthesized Compound |
|---|---|---|
| D52 | C1 | (structure) |
| D53 | C2 | (structure) |
| D54 | C3 | (structure) |
| D55 | C4 | (structure) |
| D56 | (structure) | (structure) |
| D57 | A1 | (structure) |
| D58 | A1 | (structure) |

Reference Example D59 2-Amino-3-(6-fluoro-2,3-dimethylphenyl)-3-methylbutanoic acid monohydrochloride

[Formula 16]

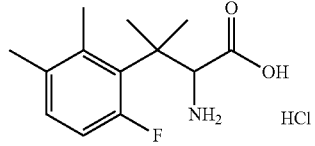

Step 1

2-(6-fluoro-2,3-dimethylphenyl)-2-methylpropanal 2-(6-fluoro-2,3-dimethylphenyl)-2-methylpropanenitrile (700 mg) was dissolved in dichloromethane (35 mL) and cooled to −78° C. A toluene solution (1.0 M, 10 mL) of diisobutylaluminum hydride was added, and the reaction solution was stirred for 1 hour at the same temperature. Methanol (5.0 mL) and CELITE (20 g) were sequentially added, and the mixture was stirred at room temperature for 1 hour. The reaction solution was filtered through CELITE, washed with hexane/ethyl acetate=1/1 (30 mL), and the filtrate was concentrated under reduced pressure. The residue was purified by silica gel column chromatography (eluent: Hexane/ethyl acetate) to obtain 2-(6-fluoro-2,3-dimethylphenyl)-2-methylpropanal (400 mg).

Step 2

2-amino-3-(6-fluoro-2,3-dimethylphenyl)-3-methylbutanonitrile 2-(6-fluoro-2,3-dimethylphenyl)-2-methylpropanal (400 mg) obtained in the above Step 1 was dissolved in methanol (7.0 mL) and water (10 ml), 28% aqueous ammonia (280 µL), potassium cyanide (130 mg), and ammonium chloride (110 mg) were added, and the reaction solution was stirred for 12 hours at 70° C. A saturated aqueous sodium hydrogen carbonate solution (5.0 mL) was added to the reaction solution, and the mixture was extracted with ethyl acetate (20 mL). The organic layer was washed with saturated saline (20 mL), dried over anhydrous sodium sulfate, and concentrated under reduced pressure. The residue was purified by silica gel column chromatography (eluent: hexane/ethyl acetate) to obtain 2-amino-3-(6-fluoro-2,3-dimethylphenyl)-3-methylbutanonitrile (380 mg).

Step 3

2-amino-3-(6-fluoro-2,3-dimethylphenyl)-3-methylbutanonitrile (380 mg) obtained from the above Step 2 was dissolved in hydrochloric acid (12M, 5.0 mL), and the reaction solution was stirred for 12 hours at 100° C. The reaction solution was cooled to room temperature and was concentrated under reduced pressure to obtain the title compound (300 mg).

Reference Example D60 2-Amino-2-(1-(6-fluoro-2,3-dimethylphenyl)cyclopropyl)acetic acid monohydrochloride

[Formula 17]

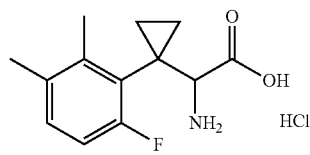

The title compound was synthesized according to the method of Reference Example D59, using 1-(6-fluoro-2,3-dimethylphenyl)cyclopropanecarbonitrile instead of 2-(6-fluoro-2,3-dimethylphenyl)-2-methylpropanenitrile.

Reference Example D61
2-Amino-3-(6-fluoro-2,3-dimethylphenyl)-3-butenoic acid monohydrochloride

[Formula 18]

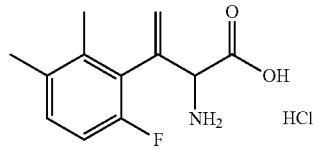

Step 1

2-(6-fluoro-2,3-dimethyl)-2-hydroxy-propanenitrile

In dichloromethane (20 mL) solution of 1-(6-fluoro-2,3-dimethylphenyl)ethanone (1.3 g), zinc iodide (480 mg) and trimethylsilyl cyanide (2.0 mL) were added, and the reaction mixture was stirred for 12 hours at room temperature. An aqueous solution of sodium hydroxide (2 M, 10 mL) was added to the reaction solution, and the mixture was extracted with ethyl acetate/hexane=1/1 (20 mL). The organic layer was washed with hydrochloric acid (2 M, 20 mL) and saturated saline (20 mL) in this order, dried over anhydrous sodium sulfate, and concentrated under reduced pressure. The residue was purified by silica gel column chromatography (eluent: hexane/ethyl acetate) to obtain 2-(6-fluoro-2,3-dimethyl)-2-hydroxy-propanenitrile (1.4 g).

Step 2

2-fluoro-2-(6-fluoro-2,3-dimethylphenyl)propanenitrile

To dichloromethane solution (5.0 mL) of 2-(6-fluoro-2,3-dimethyl)-2-hydroxy-propanenitrile (170 mg) obtained from the above Step 1, DAST (150 µL) was added, and the reaction solution was stirred at room temperature for 12 hours. A saturated aqueous sodium hydrogen carbonate solution (10 mL) was added to the reaction solution, and the mixture was extracted with ethyl acetate/hexane=1/1 (20 mL). The organic layer was washed with saturated saline (10 mL), dried over anhydrous sodium sulfate, and concentrated under reduced pressure. The residue was purified by silica gel column chromatography (eluent: hexane/ethyl acetate) to obtain 2-fluoro-2-(6-fluoro-2,3-dimethylphenyl)propanenitrile (100 mg).

Step 3

2-amino-3-fluoro-3-(6-fluoro-2,3-dimethylphenyl)-butanenitrile

From 2-fluoro-2-(6-fluoro-2,3-dimethylphenyl)propanenitrile obtained in the above Step 2, according to the method of Reference Example D59 Steps 1-2, 2-amino-3-fluoro-3-(6-fluoro-2,3-dimethylphenyl)-butanenitrile was obtained.

Step 4

2-amino-3-(6-fluoro-2,3-dimethylphenyl)-3-butenoic acid monohydrochloride

2-Amino-3-fluoro-3-(6-fluoro-2,3-dimethylphenyl)-butanenitrile (460 mg) obtained in the above Step 3 was dissolved in hydrochloric acid (12 M, 3.0 mL), and the mixture was stirred for 12 hours at 100° C. The mixture was cooled to room temperature and concentrated under reduced pressure to obtain the title compound.

Reference Example E1 5-chloro-8-(chlorosulfonyl)-4-methyl-d 3-chroman-4-yl acetate

[Formula 19]

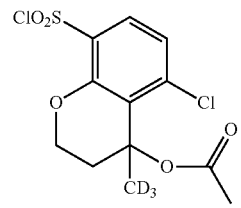

Step 1

8-bromo-5-chloro-4-methylchroman-4-ol

THF (50 mL) was added to a diethyl ethyl ether solution (1.0 M, 63 mL) of methyl iodide-d3-magnesium, and a THF solution (50 mL) of 8-bromo-5-chlorochroman-4-one (7.5 g) was added dropwise at room temperature. The reaction solution was stirred for 10 minutes at the same temperature, in an ice bath, hydrochloric acid (1M, 50 mL) was slowly added dropwise, and ethyl acetate (50 mL) was added to separate layers. The aqueous layer was extracted with ethyl acetate (50 mL), and the combined organic layer was washed with saturated saline (50 mL), dried over anhydrous sodium sulfate, and concentrated under reduced pressure. The residue was purified by silica gel column chromatography (eluent: hexane/ethyl acetate) to obtain 8-bromo-5-chloro-4-methylchroman-4-ol (7.7 g).

Step 2

8-bromo-5-chloro-4-methyl-d3-chroman-4-ylacetate

To an anhydrous acetic acid solution (100 mL) of 8-bromo-5-chloro-4-methylchroman-4-ol (7.7 g) obtained in the above Step 1, an acetonitrile solution (12 mL) of scandium trifluoromethanesulfonate (III) (340 mg) was added dropwise at −40° C., and the reaction solution was stirred for 30 minutes at the same temperature. A saturated aqueous sodium hydrogen carbonate solution (100 mL) and ethyl acetate (100 mL) were sequentially added to the reaction solution, and the layers were separated. The aqueous layer was extracted with ethyl acetate (100 mL), and the combined organic layers were washed twice with a saturated aqueous sodium hydrogen carbonate solution (100 mL) and once with saturated saline (100 mL). The organic layer was dried over anhydrous sodium sulfate and concentrated under reduced pressure. The residue was purified by silica gel column chromatography (eluent: hexane/ethyl acetate) to obtain 8-bromo-5-chloro-4-methyl-d3-chroman-4-ylacetate (8.9 g).

Step 3

8-(benzylthio)-5-chloro-4-methyl-d3-chroman-4-yl acetate

To a 1,4-dioxane solution (70 mL) of 8-bromo-5-chloro-4-methyl-d3-chroman-4-yl acetate (6.7 g) obtained in the above Step 2, 4,5-bis(diphenylphosphino)-9,9-dimethylxanthene (600 mg), tris(dibenzylideneacetone) dipalladium (0) (480 mg), N,N-diisopropylethylamine (7.2 mL) and benzylmercaptan (2.8 ml) were added, and the reaction solution was stirred for 2 hours at 90° C. The reaction solution was allowed to cool to room temperature and filtered through CELITE. After washing the residue with hexane (50 mL), water (50 mL) was added to the filtrate for layering. The organic layer was washed with saturated saline (50 mL), dried over anhydrous sodium sulfate, and concentrated under reduced pressure. The reaction solution was concentrated under reduced pressure, and the residue was purified by silica gel column chromatography (eluent: hexane/ethyl acetate) to obtain 8-(Benzylthio)-5-chloro-4-methyl-d3-chroman-4-yl acetate (6.3 g).

Step 4

To an acetonitrile solution (100 mL) of 8-(benzylthio)-5-chloro-4-methyl-d3-chroman-4-yl acetate (6.3 g) obtained in the above Step 3, water (3 mL), acetic acid (4.3 mL) and 1,3-dichloro-5,5-dimethylhydantoin (7.2 g) were each added, and the reaction solution was stirred for 30 minutes at the same temperature. A saturated aqueous sodium hydrogen carbonate solution (70 mL) and ethyl acetate (70 mL) were added to the reaction solution, and the layers were separated. The aqueous layer was extracted with ethyl acetate (70 mL). The combined organic layer was washed with saturated saline (70 mL), dried over anhydrous sodium sulfate, and concentrated under reduced pressure. The residue was purified by silica gel column chromatography (eluent: hexane/ethyl acetate) to obtain the title compound (5.3 g).

Reference Example E5 5-chloro-8-(chlorosulfonyl)-4-(trifluoromethyl)chroman-4-yl acetate

[Formula 20]

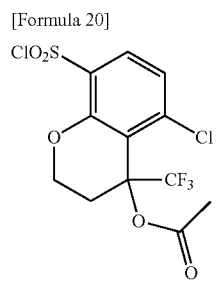

Step 1

8-bromo-5-chloro-4-(trifluoromethyl)chroman-4-ol

To a THF solution (4 mL) of 8-bromo-5-chloro-chromanon-4-one (398.2 mg), cesium fluoride (340.2 mg) and trifluoromethyltrimethylsilane (0.68 mL) were added at room temperature, and the reaction solution was stirred for 4 hours. An ammonium chloride aqueous solution (5 mL) was added to the reaction solution, and the mixture was extracted with ethyl acetate/hexane=1/1 (15 mL). The organic layer was washed with saturated saline (10 mL), dried over anhydrous sodium sulfate, and concentrated under reduced pressure. The residue was purified by column chromatography (eluent: hexane/ethyl acetate) to obtain 8-bromo-5-chloro-4-(trifluoromethyl)chromanone-4-ol (139.2 mg).

Step 2

From 8-bromo-5-chloro-4-(trifluoromethyl)chroman-4-ol obtained from the above Step 1, the title compound was obtained according to the method of Reference Example E1 Step 2-4.

Reference Example E6 8-(chlorosulfonyl)-4-(trifluoromethyl)chroman-4-yl acetate By using 8-bromo-chroman-4-one as a starting material, the title compound was obtained, according to the method of Reference Example E5 Steps 1 and 2.

Reference Examples E2 to E4 and E7 to E34

According to the method of Reference Example E1 Steps 1-4, the compounds of Reference Examples E2 to E4 were synthesized. According to the method of Reference Examples E1 Step 3 and 4, the compounds of Reference Examples E7 to E32 were synthesized. According to the method of Reference Example E1 Step 2-4, the compounds of Reference Example E33 and E34 were synthesized. The compounds of Reference Examples E2 to E4 and E7 to E34, and the starting materials are listed in the following table.

TABLE 5-1

| Reference Example | Starting Material | Synthesized Compound |
|---|---|---|
| E2 | 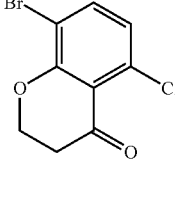 | 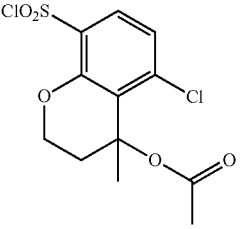 [SMILES: CC(=O)OC1(C)CCOc2c(S(=O)(=O)Cl)ccc(Cl)c21] |
| E3 | 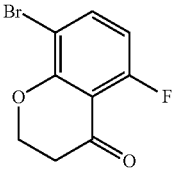 | 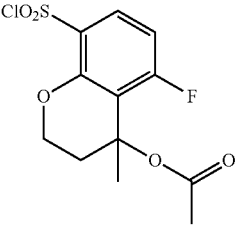 [SMILES: CC(=O)OC1(C)CCOc2c(S(=O)(=O)Cl)ccc(F)c21] |
| E4 | 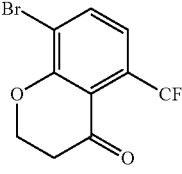 | 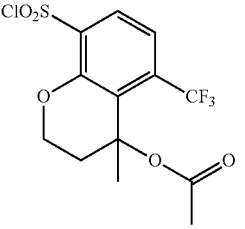 [SMILES: CC(=O)OC1(C)CCOc2c(S(=O)(=O)Cl)ccc(C(F)(F)F)c21] |
| E7 | 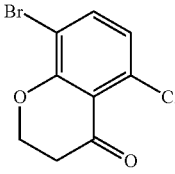 | 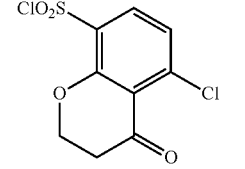 [SMILES: O=C1CCOc2c(S(=O)(=O)Cl)ccc(Cl)c21] |
| E8 | 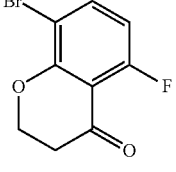 | 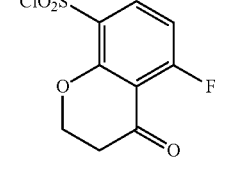 |
| E9 | 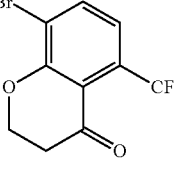 | 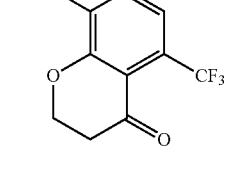 |
| E10 | 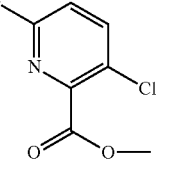 | 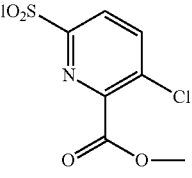 |
| E11 | 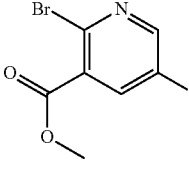 | 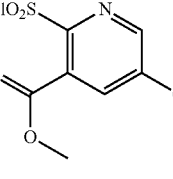 |
| E12 | 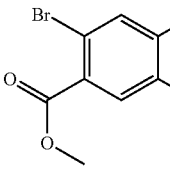 | 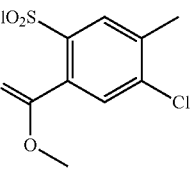 |
| E13 | 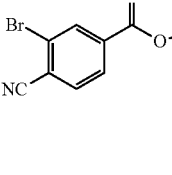 | 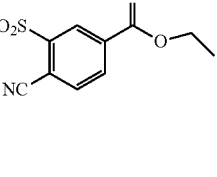 |
| E14 | 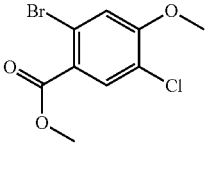 | 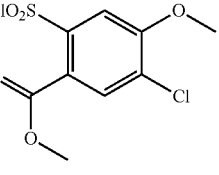 |
| E15 | 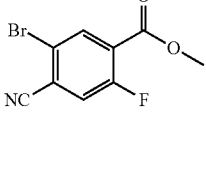 | 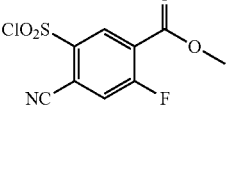 |

TABLE 5-2

| Reference Example | Starting Material | Synthesized Compound |
|---|---|---|
| E16 | Methyl 5-bromo-4-cyano-2-chlorobenzoate (Br, NC, Cl, CO₂Me) | Methyl 5-chlorosulfonyl-4-cyano-2-chlorobenzoate (ClO₂S, NC, Cl, CO₂Me) |
| E17 | Methyl 7-bromo-2,3-dihydro-1,4-benzodioxine-6-carboxylate | Methyl 7-chlorosulfonyl-2,3-dihydro-1,4-benzodioxine-6-carboxylate |
| E18 | 6-Bromo-3-chloro-2-cyanopyridine | 6-Chlorosulfonyl-3-chloro-2-cyanopyridine |
| E19 | 1-(2-bromo-5-chlorophenyl)ethanone | 1-(2-chlorosulfonyl-5-chlorophenyl)ethanone |
| E20 | 2-bromo-5-cyclopropylbenzonitrile | 2-chlorosulfonyl-5-cyclopropylbenzonitrile |
| E21 | 2-bromo-5-ethylbenzonitrile | 2-chlorosulfonyl-5-ethylbenzonitrile |
| E22 | 5-bromo-6-cyano-2-chloropyridine | 5-chlorosulfonyl-6-cyano-2-chloropyridine |
| E23 | 8-bromo-2,2-dimethylchroman-4-one | 8-chlorosulfonyl-2,2-dimethylchroman-4-one |
| E24 | tert-butyl 7-bromo-3,4-dihydroisoquinoline-2(1H)-carboxylate | tert-butyl 7-chlorosulfonyl-3,4-dihydroisoquinoline-2(1H)-carboxylate |

TABLE 5-2-continued

| Reference Example | Starting Material | Synthesized Compound |
|---|---|---|
| E25 | 8-bromo-5-chloro-3,4-dihydronaphthalen-1(2H)-one | 8-(chlorosulfonyl)-5-chloro-3,4-dihydronaphthalen-1(2H)-one |
| E26 | 1-(3-bromo-6-chloro-2-methoxyphenyl)ethan-1-one | 1-(3-(chlorosulfonyl)-6-chloro-2-methoxyphenyl)ethan-1-one |
| E27 | 2-bromo-5-chloro-3-methoxypyridine | 2-(chlorosulfonyl)-5-chloro-3-methoxypyridine |
| E28 | methyl 2-bromo-5-chloro-4-fluorobenzoate | methyl 2-(chlorosulfonyl)-5-chloro-4-fluorobenzoate |
| E29 | methyl 2-bromo-5-chloro-3-fluorobenzoate | methyl 2-(chlorosulfonyl)-5-chloro-3-fluorobenzoate |

TABLE 5-3

| Reference Example | Starting Material | Synthesized Compound |
|---|---|---|
| E30 | 8-bromo-5,7-difluorochroman-4-one | 8-(chlorosulfonyl)-5,7-difluorochroman-4-one |
| E31 | methyl 2-bromo-4,5-dimethoxybenzoate | methyl 2-(chlorosulfonyl)-4,5-dimethoxybenzoate |
| E32 | 5-bromo-2-chloro-4-cyanopyridine | 5-(chlorosulfonyl)-2-chloro-4-cyanopyridine |
| E33 | 1-(3-bromo-2,6-dichlorophenyl)ethan-1-ol | 1-(3-(chlorosulfonyl)-2,6-dichlorophenyl)ethyl acetate |
| E34 | 1-(6-bromo-3-chloropyridin-2-yl)ethan-1-ol | 1-(6-(chlorosulfonyl)-3-chloropyridin-2-yl)ethyl acetate |

Reference Example E35 5-Chloro-6-(pyrrolidine-1-carbonyl)pyridine-2-sulfonyl chloride

[Formula 21]

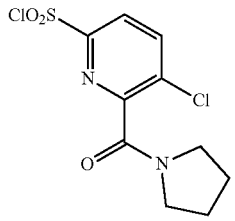

Step 1 methyl 6-(benzylthio)-3-chloropicolinate

According to the method of Reference Example E1 Step 3, methyl 6-(benzylthio)-3-chloropicolinate was obtained from methyl 6-bromo-3-chloropicolinate.

Step 2

6-(benzylthio)-3-chloropicolinic acid

Methyl 6-(benzylthio)-3-chloropicolinate (1.0 g) obtained in the above Step 1 was dissolved in THF (5.0 mL) and water (1.0 ml), lithium hydroxide (165 mg) was added, and the reaction solution was stirred at room temperature for 16 hours. The reaction solution was added to hydrochloric acid (1 M, 10 mL) and extracted twice with ethyl acetate (20 mL). The organic layer was washed with saturated saline (10 mL), dried over anhydrous sodium sulfate, and concentrated under reduced pressure to obtain 6-(benzylthio)-3-chloropicolinic acid (920 mg).

Step 3

(6-(benzylthio)-3-chloropyridin-2-yl)(pyrrolidin-1-yl)methanone 6-(benzylthio)-3-chloro-picolinic acid (100 mg) obtained in the above Step 2 was dissolved in DMF (2.5 mL), CDI (the 116 mg) was added, the reaction solution was stirred at room temperature for 10 minutes, and then triethylamine (150 µL) and pyrrolidine (60 µL) were added, and the reaction solution was stirred for 12 hours at 50° C. The reaction solution was added to water (20 mL) and extracted with ethyl acetate (20 mL). The organic layer was washed with saturated saline (20 mL), dried over anhydrous sodium sulfate, and concentrated under reduced pressure. The residue was purified by silica gel column chromatography (eluent: hexane/ethyl acetate) to obtain (6-(benzylthio)-3-chloropyridin-2-yl)(pyrrolidin-1-yl)methanone (105 mg).

Step 4

The title compound was obtained from (6-(benzylthio)-3-chloropyridin-2-yl)(pyrrolidin-1-yl)methanone obtained in the above Step 3 according to the method of Reference Example E1 Step 4.

Reference Examples E36 to E43

According to the method of Reference Examples E35 Step 3 and E1 Step 4, the compounds of Reference Examples E36 to E43 shown below were synthesized from 6-(benzylthio)-3-chloropicolinic acid obtained from Reference Example E35 Step 2

TABLE 5-4

| Reference Example | Synthesized Compound |
|---|---|
| E36 | (structure) |
| E37 | (structure) |
| E38 | (structure) |
| E39 | (structure) |
| E40 | (structure) |

TABLE 5-4-continued

| Reference Example | Synthesized Compound |
|---|---|
| E41 | ClO₂S-pyridine-Cl with C(=O)-N-pyrrolidine-NH-C(=O)O-tBu |
| E42 | ClO₂S-pyridine-Cl with C(=O)-N-(2-oxa-7-azaspiro[3.5])nonane |
| E43 | ClO₂S-pyridine-Cl with C(=O)-N-(2-azaspiro[3.3])heptane |

Reference Example E44 1-(6-chloro-3-(chlorosulfonyl)-2-methoxyphenyl)ethyl acetate

[Formula 22]

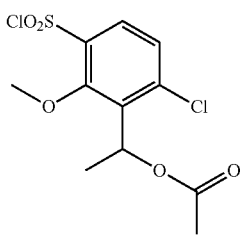

Step 1

3-bromo-6-chloro-2-methoxybenzaldehyde

According to the method of Reference Example B1 Step 1, 3-bromo-6-chloro-2-methoxybenzaldehyde was obtained from 1-bromo-4-chloro-2-methoxybenzene.

Step 2

1-(3-bromo-6-chloro-2-methoxyphenyl)ethanol

From 3-bromo-6-chloro-2-methoxybenzaldehyde obtained in the above Step 1, 1-(3-bromo-6-chloro-2-methoxyphenyl)ethanol was obtained according to the method of Reference Example A1 Step 1.

Step 3

1-(3-bromo-6-chloro-2-methoxyphenyl)ethyl acetate 1-(3-bromo-6-chloro-2-methoxyphenyl)ethanol (1.9 g) obtained in the above Step 2 was dissolved in dichloromethane (20 mL), triethylamine (2.0 mL), N,N-dimethyl-4-aminopyridine (100 mg), and acetic acid anhydride (1.2 mL) were successively added, and the reaction solution was stirred for 30 minutes at room temperature. The reaction solution was concentrated under reduced pressure, and the residue was purified by silica gel column chromatography (eluent: hexane/ethyl acetate) to obtain 1-(3-bromo-6-chloro-2-methoxyphenyl)ethyl acetate)(2.2 g).

Step 4

From the 1-(3-bromo-6-chloro-2-methoxyphenyl)ethyl acetate obtained in the above Step 3, the title compound was obtained according to the method of Reference Examples E1 Steps 3 and 4.

Reference Example E45 1-(5-Chloro-2-(chlorosulfonyl)-3-methoxypyridin-4-yl)ethyl acetate

[Formula 23]

According to each of the methods of Reference Example B1 Step 1, Reference Example A1 Step 1, Reference Example E44 Step 3 and Reference Example E1 Steps 3 and 4, the title compound was obtained using 2-bromo-5-chloro-3-methoxypyridine instead of 1-bromo-4-chloro-2-methoxybenzene.

Reference Example E46 2-(6-chloro-3-(chlorosulfonyl)-2-methoxyphenyl)propan-2-yl acetate

[Formula 24]

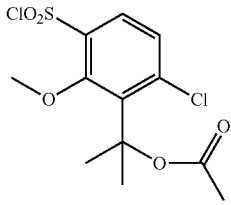

Step 1

1-(3-bromo-6-chloro-2-methoxyphenyl)ethanone

To a dichloromethane solution (30 mL) of 1-(3-bromo-6-chloro-2-methoxyphenyl)ethanol (2.8 g) obtained by Reference Example E44 Step 2, 1,1,1-triacetoxy-1,1-dihydro-1,2-benziodoxol-3-(1H)-one (5.4 g) was added, and the reaction solution was stirred for 20 minutes at room temperature. The reaction solution was added dropwise to a mixed solution of a saturated sodium hydrogen carbonate aqueous solution/a sodium hydrogen sulfite solution=1/1 (50 mL) in an ice bath, and the layers were separated. The organic layer was washed with saturated saline (20 mL), dried over anhydrous sodium sulfate, and concentrated under reduced pressure. The residue is purified by silica gel column chromatography (eluent: hexane/ethyl acetate) to obtain 1-(3-bromo-6-chloro-2-methoxyphenyl)ethanone (2.7 g).

Step 2

2-(3-bromo-6-chloro-2-methoxyphenyl)propan-2-yl acetate

From 1-(3-bromo-6-chloro-2-methoxyphenyl)ethanone obtained in the above Step 1, 2-(3-bromo-6-chloro-2-methoxyphenyl)propan-2-yl acetate was obtained according to the method of Reference Example E1 Steps 1 and 2.

Step 3

From the 2-(3-bromo-6-chloro-2-methoxyphenyl)propan-2-yl acetate (500 mg) obtained in the above Step 2, the title compound was obtained according to the method of Reference Examples E1 steps 3 and 4.

Reference Example E47 4-Chloro-2-(2,2-difluoroethoxy)benzene-1-sulfonyl chloride

[Formula 25]

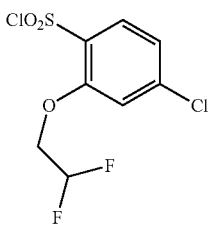

Step 1

1-bromo-4-chloro-2-(2,2-difluoroethoxy)benzene

To a DMF solution (5 mL) of 2-bromo-5-chlorophenol (244 mg), potassium carbonate (325 mg) and 2,2-difluoroethyl 4-methylbenzenesulfonate (320 mg) were added, and the reaction solution was stirred for 3 hours at 95° C. The reaction solution was added to an aqueous sodium hydroxide solution (1 M, 20 mL) and extracted with toluene/ethyl acetate=1/1 (20 mL). The organic layer was washed with saturated saline (20 mL), dried over anhydrous sodium sulfate, and concentrated under reduced pressure. The residue was purified by silica gel column chromatography (eluent: hexane/ethyl acetate) to obtain 1-bromo-4-chloro-2-(2,2-difluoroethoxy)benzene (315 mg).

Step 2

The title compound was synthesized from 1-bromo-4-chloro-2-(2,2-difluoroethoxy)benzene obtained in the above Step 1 according to the method of Reference Examples E1 Steps 3 and 4.

Reference Examples E48 and E49

According to the methods of Reference Example E47 Step 1 and Reference Example E1 Steps 3 and 4, the compounds of Reference Examples E48 and 49 shown below were synthesized. However, regarding Reference Example 48, sodium chlorodifluoroacetate was used instead of 2,2-difluoroethyl 4-methylbenzenesulfonate.

TABLE 5-5

| Reference Example | Starting Material | Synthesized Compound |
|---|---|---|
| E48 | ![Br, HO, Cl phenol] | ![ClO2S, O-CHF2, Cl benzene] |

TABLE 5-5-continued

| Reference Example | Starting Material | Synthesized Compound |
|---|---|---|
| E49 | ![E49 SM](Br, OH, methyl ester) | ![E49 Product](ClO2S, OCH2CHF2, methyl ester) |

Reference Example E50
4-chloro-2-(isoxazol-5-yl)benzene-1-sulfonyl chloride

[Formula 26]

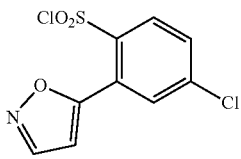

Step 1

5-(2-bromo-5-chlorophenyl)isoxazole

An N,N-dimethylformamide dimethyl acetal solution (6.0 mL) of 1-(2-bromo-5-chlorophenyl)ethanone (400 mg) was stirred for 16 hours at 140° C. After cooling to room temperature, the reaction mixture was concentrated under reduced pressure, and the resulting residue was purified by silica gel column chromatography (eluent: hexane/ethyl acetate). The obtained compound was dissolved in methanol (4.0 mL), hydroxylamine hydrochloride (175 mg) was added, and the reaction solution was stirred at room temperature for 16 hours. The reaction solution was added to an aqueous sodium bicarbonate solution (20 mL) and extracted with ethyl acetate (20 mL). The organic layer was washed with saturated saline (20 mL), dried over anhydrous sodium sulfate, and concentrated under reduced pressure. The residue was purified by silica gel column chromatography to purify (eluent: hexane/ethyl acetate) to obtain 5-(2-bromo-5-chlorophenyl)isoxazole (430 mg).

Step 2

From 5-(2-bromo-5-chlorophenyl)isoxazole obtained in the above Step 1, the title compound was obtained according to the method of Reference Example E1 Steps 3,4.

Reference Example E51 tert-butyl benzyloxy(5-chloro-2-(chlorosulfonyl)benzoyl)carbamate

[Formula 27]

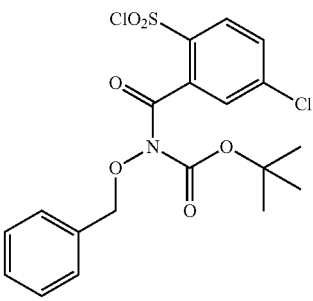

Step 1

N-(benzyloxy)-2-(benzylthio)-5-chlorobenzamide

According to the method of Reference Example E1 Step 3, N-(benzyloxy)-2-(benzylthio)-5-chlorobenzamide was synthesized from N-(benzyloxy)-2-bromo-5-chlorobenzamide.

Step 2 tert-butyl benzyloxy (2-(benzylthio)-5-chloro-benzoyl)carbamate

To a dichloromethane (10 mL) solution of N-(benzyloxy)-2-(benzylthio)-5-chlorobenzamide (433 mg) obtained from Reference Example 1, N,N-dimethyl-4-aminopyridine (280 mg) and di-tert-butyl dicarbonate (740 mg) were added, and the reaction solution was stirred for 16 hours at 55° C. The reaction solution was concentrated under reduced pressure, and the resulting residue was purified by silica gel column chromatography (eluent: hexane/ethyl acetate) to obtain tert-butylbenzyloxy (2-(benzylthio)-5-chlorobenzoyl)carbamate (549 mg).

Step 3

From the tert-butylbenzyloxy (2-(benzylthio)-5-chlorobenzoyl)carbamate obtained in the above Step 2, the title compound was obtained according to the method of Reference Example E1 Step 4.

Reference Example E52 tert-butyl (5-chloro-2-(chlorosulfonyl)benzoyl)(methyl)carbamate

[Formula 28]

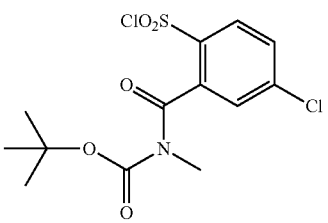

Step 1

2-bromo-5-chloro-N-methylbenzamide

From 2-bromo-5-chlorobenzoic acid and methylamine, 2-bromo-5-chloro-N-methylbenzamide was obtained according to the method of Reference Example E35 Step 3.

Step 2 tert-butyl (2-bromo-5-chlorobenzoyl)(methyl)carbamate (2-bromo-5-chlorobenzoyl)(methyl)carbamate was obtained from 2-bromo-5-chloro-N-methylbenzamide obtained in the above step 1 according to the method of Reference Example E51 Step 2.

Step 3

From the tert-butyl (2-bromo-5-chlorobenzoyl)(methyl) carbamate obtained in the above Step 2, the title compound was obtained according to the method of Reference Examples E1 steps 3 and 4.

Reference Example E53 methyl 5-chloro-2-(chlorosulfonyl)-4-nitrobenzoate

[Formula 29]

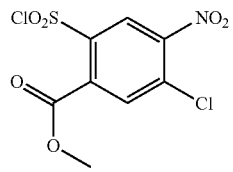

Step 1 methyl 2-bromo-5-chloro-4-nitrobenzoate

To a 2-methyl-2-propanol solution (5 mL) of 1-bromo-4-chloro-2-methyl-5-nitrobenzene (1.0 g), water (5 mL), anisole (2.5 mL), and potassium permanganate (1.6 g) were added, and the reaction solution was stirred at 100° C. for 20 hours. The reaction solution was cooled to room temperature, filtered through CELITE, and washed with water (10 mL) and ethyl acetate (10 mL). The combined filtrates were added to hydrochloric acid (1 M, 20 mL), and the layers were separated. The aqueous layer was extracted three times with ethyl acetate (20 mL). The combined organic layer was washed with saturated saline (20 mL), dried over anhydrous sodium sulfate, and concentrated under reduced pressure. The obtained residue was dissolved in methanol (5.0 mL), dichloromethane (10 mL) and a hexane solution of trimethylsilyldiazomethane (0.6 M, 6.0 mL) were added, and the reaction solution was stirred at room temperature for 20 minutes. The reaction solution was concentrated under reduced pressure, and the residue was purified by silica gel column chromatography (eluent: hexane/ethyl acetate) to obtain methyl 2-bromo-5-chloro-4-nitrobenzoate (529 mg).

Step 2

From the methyl 2-bromo-5-chloro-4-nitrobenzoate obtained in the above Step 1, the title compound was obtained according to the method of Reference Example E1 Steps 3 and 4.

Reference Example E54 4-chloro-2-(5-oxo-4,5-dihydro-1,3,4-oxadiazol-2-yl)benzene-1-sulfonyl chloride

[Formula 30]

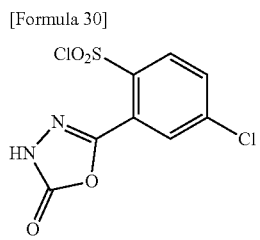

Step 1

5-(2-bromo-5-chlorophenyl)-1,3,4-oxadiazol-2(3H)-one

CDI (310 mg) was added to a THF (6.0 mL) suspension of 2-bromo-5-chlorobenzoic acid (300 mg), and the reaction solution was stirred at room temperature for 20 minutes. The reaction solution was ice-cooled, hydrazine•monohydrate (160 μL) was added, and the reaction solution was stirred at the same temperature for 20 minutes. The reaction solution was added to water (15 mL) and extracted with ethyl acetate (15 mL). The organic layer was washed with saturated saline (20 mL), dried over anhydrous sodium sulfate, and concentrated under reduced pressure. The obtained residue was dissolved in 1,4-dioxane (6.0 mL), CDI (310 mg) was added, and the reaction solution was stirred at 45° C. for 2 hours. The reaction solution was added to water (15 mL) and extracted with ethyl acetate (15 mL). The organic layer was washed with saturated saline (20 mL), dried over anhydrous sodium sulfate, and concentrated under reduced pressure. The resulting residue was purified by silica gel column chromatography (eluent: hexane/ethyl acetate) to obtain 5-(2-bromo-5-chlorophenyl)-1,3,4-oxadiazol-2(3H)-one (300 mg).

Step 2

From the 5-(2-bromo-5-chlorophenyl)-1,3,4-oxadiazol-2(3H)-one obtained in the above Step 1, the title compound is obtained in accordance with the method of Steps 3 and 4 of Reference Example E1.

Reference Example E55 tert-butyl N-tert-butoxycarbonyl-N-(1-(5-chloro-2-chlorosulfonyl-phenyl)cyclopropyl]carbamate

[Formula 31]

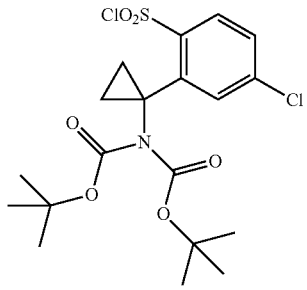

Step 1

1-(2-benzylsulfanyl-5-chlorophenyl)cyclopropanamine

To a THF (10 mL) suspension of 2-(benzylthio)-5-chlorobenzonitrile (1.0 g) and titanium tetraisopropoxide (1.3 mL), a diethyl ether solution (3.0 M, 3.0 mL) of methylmagnesium bromide was added dropwise at −78° C., and the reaction solution was stirred at the same temperature for 10 minutes. To the reaction solution, boron trifluoride diethyl ether complex (1.1 mL) was added, and the mixture was further stirred at room temperature for 1 hour, and then water (5 mL) and an aqueous sodium hydroxide solution (1 M, 5 mL) were added to separate layers, the aqueous layer was extracted with diethyl ether (20 mL). The combined organic layers were washed with saturated saline (20 mL), dried over anhydrous magnesium sulfate, and concentrated under reduced pressure. The residue was purified by silica gel column chromatography (eluent: hexane/ethyl acetate) to obtain 1-(2-benzylsulfanyl-5-chloro-phenyl)cyclopropanamine (490 mg).

Step 2 tert-butyl N-[1-(2-benzylsulfanyl-5-chloro-phenyl)-cyclopropyl]-N-tert-butoxycarbonyl-carbamate To a 1,2-dichloroethane solution (10 mL) of 1-(2-benzylsulfanyl-5-chloro-phenyl)cyclopropanamine (490 mg) obtained in the above Step 1, N,N-dimethyl-4-aminopyridine (210 mg) and di-tert-butyl dicarbonate (1.8 g) were added, and the reaction solution was stirred at 50° C. for 16 hours. The reaction solution was added to hydrochloric acid (1 M, 10 mL) and extracted with ethyl acetate (15 mL). The organic layer was washed with saturated saline (20 mL), dried over anhydrous magnesium sulfate, and concentrated under reduced pressure. The residue was purified by silica gel column chromatography (eluent: hexane) to obtain tert-butyl N-[1-(2-benzylsulfanyl-5-chloro-phenyl)cyclopropyl]-N-tert-butoxycarbonyl-carbamate (502 mg).

Step 3

From tert-butyl N-[1-(2-benzylsulfanyl-5-chloro-phenyl)cyclopropyl]-N-tert-butoxycarbonyl-carbamate obtained in the above Step 2, the title compound is obtained in accordance with the method of Reference Example E1 step 4.

Reference Example E56 methyl 6-(bis(tert-butoxycarbonyl)amino)-3-chlorosulfonyl-2-methoxybenzoate

[Formula 32]

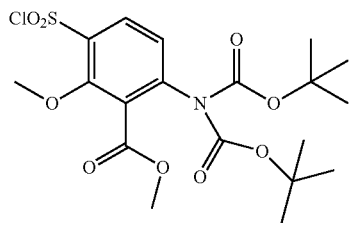

Step 1 methyl 6-(bis(tert-butoxycarbonyl)amino)-3-bromo-2-methoxybenzoate

From methyl 6-amino-3-bromo-2-methoxybenzoate, methyl 6-(bis(tert-butoxycarbonyl)amino)-3-bromo-2-methoxybenzoate was obtained according to the method of Reference Example E55 Step 2.

Step 2

The title compound was obtained from methyl 6-(bis(tert-butoxycarbonyl)amino)-3-bromo-2-methoxybenzoate obtained in the above step 1 according to the method of Reference Examples E1 Steps 3 and 4.

Reference Example E57 5-Chloro-4,4-difluorochroman-8-sulfonyl chloride

[Formula 33]

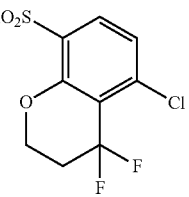

Step 1

8-(benzylthio)-5-chlorochroman-4-one

From 8-bromo-5-chlorochroman-4-one, 8-(benzylthio)-5-chlorochroman-4-one was obtained according to the method of Reference Example E1 Step 3.

Step 2

8-(benzylthio)-5-chloro-4,4-difluorochroman

From 8-(benzylthio)-5-chlorochroman-4-one (125 mg) obtained in the above Step 1, 8-(benzylthio)-5-chloro-4,4- difluorochroman was obtained according to the method of Reference Example D61 Step 2.

Step 3

From the 8-(benzylthio)-5-chloro-4,4-difluorochroman obtained in the above Step 2, the title compound was obtained according to the method of Reference Example E1 Step 4.

Reference Example E58 tert-Butyl 5-chloro-8-(chlorosulfonyl)-2H-benzo[b][1,4]oxazin-4(3H)-carboxylate

[Formula 34]

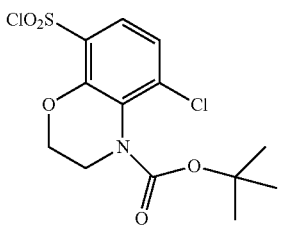

Step 1

8-bromo-5-chloro-3,4-dihydro-2H-benzoxazine 1,2-dibromoethane (500 μL) and potassium carbonate (3.0 g) were added to a DMF solution (6 mL) of 2-amino-6-bromo-3-chlorophenol (1.3 g), and the reaction solution was stirred for 12 hours at 100° C. The reaction solution was allowed to cool to room temperature, a saturated aqueous ammonium chloride solution (10 mL) and ethyl acetate (10 mL) were added to the reaction solution, the layers were separated, and the aqueous layer was extracted with ethyl acetate (20 mL). The combined organic layer was washed with saturated saline (10 mL), dried over anhydrous sodium sulfate, and concentrated under reduced pressure. The residue was purified by silica gel column chromatography (eluent: hexane/ethyl acetate) to obtain 8-bromo-5-chloro-3,4-dihydro-2H-benzoxazine (400 mg).

Step 2 tert-butyl 8-bromo-5-chloro-2H-benzo[b][1,4]oxazin-4(3H)-carboxylate

To dioxane solution (5 mL) of 8-bromo-5-chloro-3,4-dihydro-2H-1,4-benzoxazine (223 mg), 4-dimethylaminopyridine (44 mg), triethylamine (0.25 mL) and di-tert-butyl dicarbamate (458 mg) were added at room temperature, and the reaction solution was stirred for 2 hours. The reaction solution was concentrated under reduced pressure, and the residue was purified by column chromatography (eluent: hexane/ethyl acetate) to obtain tert-butyl 8-bromo-5-chloro-2H-benzo [b][1,4]oxazin-4(3H)-carboxylate (140 mg).

Step 3

From tert-butyl 8-bromo-5-chloro-2H-benzo[b][1,4]oxazin-4(3H)-carboxylate obtained in the above Step 2, the title compound is obtained according to the method of Steps 3 and 4 of Reference Example E1.

Reference Example E59 tert-butyl 8-(chlorosulfonyl)-2H-benzo[b][1,4]oxazin-4(3H)-carboxylate

[Formula 35]

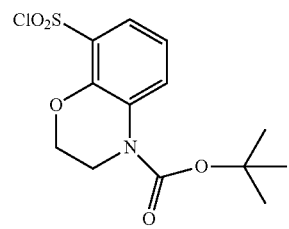

Step 1 tert-butyl 8-bromo-2H-benzo[b][1,4]oxazin-4(3H)-carboxylate

From 8-bromo-3,4-dihydro-2H-benzo[b][1,4]oxazine, tert-butyl 8-bromo-2H-benzo[b][1,4]oxazin-4(3H)-carboxylate was obtained according to the method of Reference Example E58 Step 2.

Step 2

From tert-butyl 8-bromo-2H-benzo[b][1,4]oxazin-4(3H)-carboxylate obtained in the above Step 1, the title compound was obtained, in accordance with Reference Example E1 Steps 3 and 4.

Reference Example E60 tert-butyl 4-(chlorosulfonyl)-1H-indole-1-carboxylate

[Formula 36]

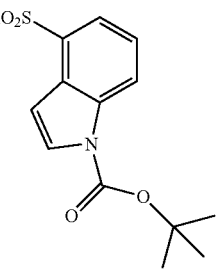

From the commercially available tert-butyl 4-bromo-1H-indole-1-carboxylate (Ark Pharm, Inc.), the title compound was obtained according to the method of Reference Example E1 steps 3 and 4.

Reference Example E61 5-chloro-4-ethyl-3,4-dihydro-2H-benzo[b][1,4]oxazin-8-sulfonyl chloride

[Formula 37]

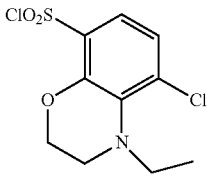

Step 1

8-bromo-5-chloro-4-ethyl-2,3-dihydro-1,4-benzoxazine

To a DMSO solution (2.0 mL) of 8-bromo-5-chloro-3,4-dihydro-2H-benzoxazine (380 mg) obtained in Reference Example E58 Step 1, potassium hydroxide (120 mg) and ethyl iodide (100 μL) were added, and the reaction solution was stirred at 100° C. for 2 hours. The reaction solution was allowed to cool to room temperature, a saturated aqueous solution of ammonium chloride (10 mL) and ethyl acetate (10 mL) were added to separate layers, and the aqueous layer was extracted with ethyl acetate (10 mL). The combined organic layer was washed with saturated saline (10 mL), dried over anhydrous sodium sulfate, and concentrated under reduced pressure. The reaction solution was concentrated under reduced pressure, and the residue was purified by silica gel column chromatography (eluent: hexane/ethyl acetate) to obtain 8-bromo-5-chloro-4-ethyl-2,3-dihydro-1,4-benzoxazine (105 mg).

Step 2

From the 8-bromo-5-chloro-4-ethyl-2,3-dihydro-1,4-benzoxazine obtained in the above Step 1, the title compound was obtained according to the method of Reference Examples E1 Steps 3 and 4.

Reference Example E62 4-(cyclopropanecarbonyl)-3,4-dihydro-2H-benzo[b][1,4]oxazin-8-sulfonyl chloride

[Formula 38]

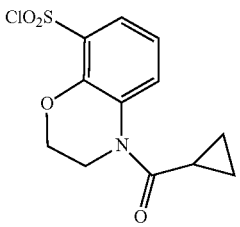

Step 1

(8-bromo-2H-benzo[b][1,4]oxazin-4(3H)-yl)(cyclopropyl)methanone

Sodium hydride (18 mg) was added to a THF solution (2.0 mL) of 8-bromo-3,4-dihydro-2H-benzoxazine (62 mg) at 0° C., and the reaction solution was stirred for 30 minutes. Cyclopropanecarbonyl chloride (170 μL) was added to the reaction solution, and the mixture was further stirred at room temperature for 2 hours. A saturated ammonium chloride aqueous solution (10 mL) and ethyl acetate (10 mL) were sequentially added to the reaction solution to separate layers, and the aqueous layer was extracted with ethyl acetate (10 mL). The combined organic layer was washed with saturated saline (10 mL), dried over anhydrous sodium sulfate, and concentrated under reduced pressure. The resulting residue was purified by silica gel column chromatography (eluent: hexane/ethyl acetate) to give (8-bromo-2H-benzo[b][1,4]oxazin-4(3H)-yl)(cyclopropyl)methanone (87 mg).

Step 2

From (8-bromo-2H-benzo[b][1,4]oxazin-4(3H)-yl)(cyclopropyl)methanone obtained in the above Step 1 according to the method of Steps 3 and 4 of Reference Example E1, the title compound was obtained.

Reference Example E63 5-chloro-4-(2,2-difluoroethyl)-3-oxo-3,4-dihydro-2H-benzo[b][1,4]oxazin-8-sulfonyl chloride

[Formula 39]

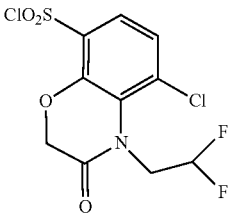

Step 1

8-bromo-5-chloro-2H-benzo[b][1,4]oxazin-3(4H)-one 2-amino-6-bromo-3-chlorophenol (140 mg) was dissolved in THF (2.0 mL), chloroacetyl chloride (100 μL) and sodium hydrogencarbonate (240 mg) were added and the reaction solution was stirred at room temperature for 3 hours. Potassium carbonate (440 mg) was added to the reaction solution, and the mixture was further stirred at 80° C. for 5 hours. The reaction solution was allowed to cool to room temperature, and a saturated aqueous solution of ammonium chloride (10 mL) and ethyl acetate (10 mL) were added to separate layers, and the aqueous layer was extracted with ethyl acetate (20 mL). The combined organic layer was washed with saturated saline (10 mL), dried over anhydrous sodium sulfate, and concentrated under reduced pressure to give 8-bromo-5-chloro-2H-benzo[b][1,4]oxazin-3(4H)-one (160 mg).

Step 2

8-bromo-5-chloro-4-(2,2-difluoroethyl)-2H-benzo[b][1,4]oxazin-3(4H)-one

To a DMF (2.5 mL) solution of 8-bromo-5-chloro-2H-benzo[b][1,4]oxazin-3(4H)-one (69 mg) obtained in the above Step 1, potassium carbonate (420 mg) and 2,2-difluoroethyl paratoluene sulfonate (500 mg) were sequentially added, and the reaction solution was stirred at 100° C. for 3 hours. The reaction solution was allowed to cool to room temperature, and a saturated aqueous solution of ammonium chloride (10 mL) and ethyl acetate (10 mL) were added to separate layers, and the aqueous layer was extracted with ethyl acetate (10 mL). The combined organic layer was washed with saturated saline (10 mL), dried over anhydrous sodium sulfate, and concentrated under reduced pressure. The obtained residue was purified by silica gel column chromatography (eluent: hexane/ethyl acetate) to give 8-bromo-5-chloro-4-(2,2-difluoroethyl)-2H-benzo[b][1,4]oxazin-3(4H)-one (85 mg).

Step 3

8-(benzylthio)-5-chloro-4-(2,2-difluoroethyl)-2H-benzo[b][1,4]oxazin-3(4H)-one

From 8-bromo-5-chloro-4-(2,2-difluoroethyl)-2H-benzo[b][1,4]oxazin-3(4H)-one obtained in the above Step 2, 8-(benzylthio)-5-chloro-4-(2,2-difluoroethyl)-2H-benzo[b][1,4]oxazin-3 (4H)-one was obtained according to the method of Reference Example E1 Step 3.

Step 4

From the 8-(benzylthio)-5-chloro-4-(2,2-difluoroethyl)-2H-benzo[b][1,4]oxazin-3(4H)-one, the title compound was obtained in the above Step 3, according to the method of Reference Example E1 Step 4.

Reference Example E64 and E65

From 8-bromo-5-chloro-2H-benzo[b][1,4]oxazin-3(4H)-one obtained from Reference Example E63 Step 1, the following compounds of reference examples E64 and E65 are synthesized according to method of Reference Example E63 Step 2, and Reference Example E1 Steps 3 and 4.

Reference Example E66 5-chloro-4-(2,2-difluoroethyl)-3,4-dihydro-2H-benzo[b][1,4]oxazine-8-sulfonyl chloride

[Formula 40]

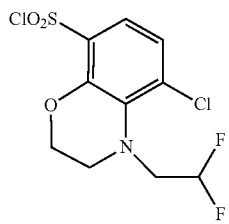

Step 1

8-(benzylthio)-5-chloro-4-(2,2-difluoroethyl)-3,4-dihydro-2H-benzo[b][1,4]oxazine To a THF solution (5 mL) of 8-(benzylthio)-5-chloro-4-(2,2-difluoroethyl)-2H-benzo[b][1,4]oxazin-3(4H)-one (270 mg) obtained from Reference Example 63 Step 3, dimethylsulfide borane (1.0 mL) was added, and the reaction solution was stirred at 70° C. for 4 hours. The reaction solution was allowed to cool to room temperature, methanol (5 mL), ethyl acetate (10 mL), and water (10 mL) were added in order to separate layers, and the aqueous layer was extracted with ethyl acetate (10 mL). The combined organic layer was washed with saturated saline (10 mL), dried over anhydrous sodium sulfate, and concentrated under reduced pressure. The residue was purified by silica gel column chromatography (eluent: hexane/ethyl acetate) to obtain 8-(benzylthio)-5-chloro-4-(2,2-difluoroethyl)-3,4-dihydro-2H-benzo[b][1,4]oxazine (154 mg).

TABLE 5-6

| Reference Example | Alkylating agent | Synthesized Compound |
|---|---|---|
| E64 | MeI | (structure) |
| E65 | I~~O~~Bn | (structure) |

Step 2

From the 8-(benzylthio)-5-chloro-4-(2,2-difluoroethyl)-3,4-dihydro-2H-benzo[b][1,4]oxazine obtained in the above Step 1, the title compound was obtained according to the method of Reference Example E1 Step 4.

Reference Example E67 2-cyano-5-(morpholine-4-carbonyl)benzene-1-sulfonyl chloride

[Formula 41]

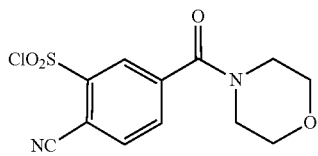

Step 1 ethyl 3-(benzylthio)-4-cyanobenzoate

Ethyl 3-(benzylthio)-4-cyanobenzoate was obtained from ethyl 3-bromo-4-cyanobenzoate according to the method of Reference Example E1 Step 3.

Step 2

6-(benzylthio)-4-cyano-benzoic acid

An aqueous sodium hydroxide solution (3 M, 4.0 mL) was added to a THF (4.0 mL) solution of ethyl 3-(benzylthio)-4-cyanobenzoate (344 mg) obtained in the above Step 1, and the reaction solution was stirred at room temperature for 16 hours. The reaction solution was added to hydrochloric acid (1 M, 15 mL) and extracted twice with ethyl acetate (20 mL). The combined organic layer was washed with saturated saline (10 mL), dried over anhydrous sodium sulfate, and concentrated under reduced pressure to obtain 6-(benzylthio)-4-cyanobenzoic acid (210 mg).

Step 3

2-(benzylthio)-4-(morpholine-4-carbonyl)benzonitrile

Using 6-(benzylthio)-4-cyano-benzoic acid obtained from the above Step 2 and morpholine, 2-(benzylthio)-4-(morpholine-4-carbonyl)benzonitrile was obtained according to Reference Example E35 Step 3.

Step 4

From the 2-(benzylthio)-4-(morpholine-4-carbonyl)benzonitrile obtained in the above Step 3, the title compound was obtained according to the method of Reference Example E1 Step 4.

Reference Example E68 2-cyano-5-(dimethylcarbamoyl)benzene-1-sulfonyl chloride

[Formula 42]

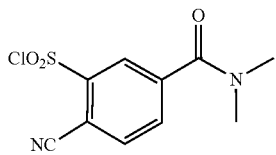

Step 1

2-(benzylthio)-4-cyano-N,N-dimethylbenzamide

According to the method of Reference Example E35 Step 3, from 6-(benzylthio)-4-cyanobenzoic acid obtained in Reference Example E67 Step 2 and dimethylamine, 2-(benzylthio)-4-cyano-N,N-dimethylbenzamide was obtained.

Step 2

From the 2-(benzylthio)-4-cyano-N,N-dimethylbenzamide obtained in the above Step 1, the title compound was obtained according to the method of Reference Example E1 Step 4.

Reference Example E69 4-chloro-2-cyano-5-(dimethylcarbamoyl)benzene-1-sulfonyl chloride

[Formula 43]

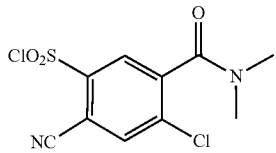

The title compound was synthesized from methyl 5-bromo-2-chloro-4-cyanobenzoate according to each of the methods of Reference Example E1 Step 3, Reference Example E67 Step 2, Reference Example E35 Step 3 and Reference Example E1 Step 4.

Reference Example E70 tert-butyl (5-chloro-8-(chlorosulfonyl)chroman-4-yl)carbamate

[Formula 44]

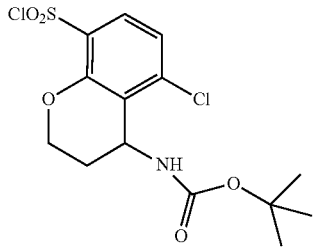

Step 1

8-benzyl-sulfanyl-5-chlorochroman-4-one

From 8-bromo-5-chlorochroman-4-one, 8-benzylsulfanyl-5-chlorochroman-4-one was obtained according to the method of Reference Example E1 Step 3.

Step 2

8-benzyl-sulfanyl-5-chlorochroman-4-amine 8-benzylsulfanyl-5-chlorochroman-4-one (460 mg) obtained in the above Step 1 was dissolved in methanol (3.0 mL), ammonium chloride (1.2 g) was added, and the reaction solution was stirred at room temperature for 2 hours. Sodium cyanoborohydride (670 mg) was added to the reaction solution, and the mixture was further stirred at 80° C. for 14 hours. A saturated aqueous sodium hydrogen carbonate solution (10 mL), an aqueous sodium hydroxide solution (5 M, 10 mL) and chloroform (20 mL) were added successively to the reaction solution to separate layers, and the aqueous layer was extracted twice with chloroform (20 mL). The combined organic layer was washed with saturated saline (10 mL), dried over anhydrous sodium sulfate, and concentrated under reduced pressure. The residue was purified by silica gel column chromatography (ethyl acetate) to obtain 8-benzylsulfanyl-5-chlorochroman-4-amine (216 mg).

Step 3 tert-butyl (8-(benzylthio)-5-chlorochroman-4-yl)carbamate

From 8-benzylsulfanyl-5-chloro-chroman-4-amine (216 mg) obtained in the above Step 2, tert-butyl (8-(benzylthio)-5-chlorochroman-4-yl)carbamate was obtained according to Reference Example E58 Step 2.

Step 4

From the tert-butyl (8-(benzylthio)-5-chlorochroman-4-yl)carbamate obtained in the above Step 3, the title compound was obtained according to the method of Reference Example E1 Step 4.

Reference Example E71
4-acetamido-5-chlorochroman-8-sulfonyl chloride

[Formula 45]

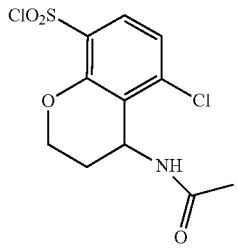

Step 1

N-(8-bromo-5-chlorochromanon-4-yl)acetamide

8-Bromo-5-chlorochromanon-4-amine (250 mg) was dissolved in DMF (2.0 mL) and THF (7.0 mL), N,N-dimethyl-4-aminopyridine (45 mg), triethylamine (400 µL) and acetic anhydride (200 µL) were sequentially added, and the mixture was stirred at room temperature for 2 hours. Water (10 mL) was added to the reaction solution, and the mixture was extracted with ethyl acetate (10 mL). The organic layer was washed with saturated saline (20 mL), dried over anhydrous sodium sulfate, and concentrated under reduced pressure. The residue was purified by silica gel column chromatography (eluent: hexane/ethyl acetate) to obtain N-(8-bromo-5-chlorochromanon-4-yl)acetamide (260 mg).

Step 2

From the N-(8-bromo-5-chlorochromanon-4-yl)acetamide obtained in the above Step 1, the title compound was obtained according to the method of Reference Examples E1 steps 3 and 4.

Reference Example E72 1-(3-chloro-6-(chlorosulfonyl)pyridin-2-yl)-2,2,2-trifluoroethylacetate

[Formula 46]

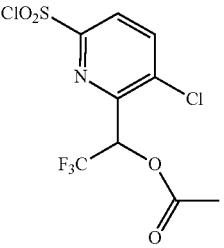

Step 1

1-(6-bromo-3-chloropyridin-2-yl)-2,2,2-trifluoroethanol

Cesium fluoride (700 mg) and (trifluoromethyl)trimethylsilane (700 µL) were added to a THF (10 mL) solution of 6-bromo-3-chloropicolinaldehyde (770 mg), and the reaction solution was stirred at room temperature for 4 hours. A saturated aqueous sodium hydrogen carbonate solution (10 mL) was added to the reaction solution, and the mixture was extracted with ethyl acetate (20 mL). The organic layer was washed with saturated saline (10 mL), dried over anhydrous sodium sulfate, and concentrated under reduced pressure. The residue was purified by silica gel column chromatography (eluent: hexane/ethyl acetate) to obtain 1-(6-bromo-3-chloropyridin-2-yl)-2,2,2-trifluoroethanol (600 mg).

Step 2

From 1-(6-bromo-3-chloropyridin-2-yl)-2,2,2-trifluoroethanol obtained in the above Step 1, according to the method of Reference Examples E44 Step 3 and E1 Steps 3 to 4, the title compound was obtained.

Reference Example E73 methyl 5-bromo-2-(chlorosulfonyl)nicotinate

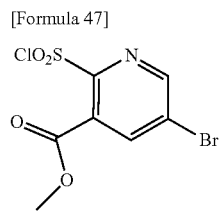

[Formula 47]

Step 1 methyl 2-(benzylthio)-5-bromo-nicotinate

Sodium hydride (285 mg) was added to a THF (5.0 mL) solution of benzyl mercaptan (700 μL) at 0° C., and the reaction solution was stirred at room temperature for 15 min. A THF (3.0 mL) solution of methyl 2,5-dibromonicotinate (1.59 g) was added dropwise to the reaction solution, and the mixture was stirred at 0° C. for 20 minutes. The reaction solution was added to water (10 mL) and extracted with ethyl acetate (20 mL). The organic layer was washed with saturated saline (10 mL), dried over anhydrous sodium sulfate, and concentrated under reduced pressure. The residue was purified by silica gel column chromatography (eluent: hexane/ethyl acetate) to obtain methyl 2-(benzylthio)-5-bromonicotinate (1.5 g).

Step 2

From the methyl 2-(benzylthio)-5-bromonicotinate obtained in the above Step 1, the title compound was obtained according to the method of Reference Example E1 Step 4.

Reference Example F1 5-((1S,2R)-1-Amino-2-(6-fluoro-2,3-dimethylphenyl)propyl)-1,3,4-oxadiazol-2(3H)-one monohydrochloride

[Formula 48]

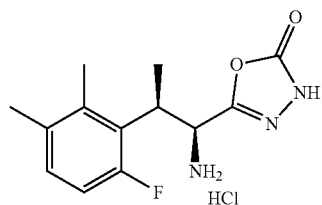

Step 1

(2S,3R)-2-((tert-butoxycarbonyl)amino)-3-(6-fluoro-2,3-dimethylphenyl)butanoic acid Water (9 mL), 1,4-dioxane (9 mL) and triethylamine (955 μL) were sequentially added to (2S,3R)-2-amino-3-(6-fluoro-2,3-dimethylphenyl)butanoic acid (515 mg) obtained in Reference Example D1, and the mixture was cooled to 0° C. Di-tert-butyl dicarbonate (650 mg) was added to the reaction solution at the same temperature, and the mixture was stirred for 45 minutes. The reaction solution was added to hydrochloric acid (1 M, 20 mL) and extracted with ethyl acetate (20 mL). The organic layer was washed with saturated saline (20 mL), dried over anhydrous magnesium sulfate, and concentrated under reduced pressure. The residue is purified by silica gel column chromatography (eluent: hexane/ethyl acetate/2% acetic acid) to obtain (2S,3R)-2-((tert-butoxycarbonyl)amino)-3-(6-fluoro-2,3-dimethylphenyl)butanoic acid (745 mg).

Step 2 tert-butyl ((1S,2R)-2-(6-fluoro-2,3-dimethylphenyl)-1-(5-oxo-4,5-dihydro-1,3,4-oxadiazol-2-yl)propyl)carbamate To a THF solution (14.0 mL) of (2S,3R)-2-(tert-butoxycarbonylamino)-3-(6-fluoro-2,3-dimethylphenyl)butanoic acid (440 mg) obtained in the above Step 1, CDI (302 mg) was added, and the reaction solution was stirred at room temperature for 20 minutes. The reaction solution was cooled to 0° C., hydrazine·monohydrate (200 μL) was added, and the mixture was stirred at the same temperature for 30 minutes. The reaction solution was added to water (20 mL) and extracted with ethyl acetate (20 mL). The organic layer was washed with saturated saline (20 mL), dried over anhydrous sodium sulfate, and concentrated under reduced pressure. CDI (560 mg) was added to a 1,4-dioxane (14 mL) solution of the obtained residue, and the reaction solution was stirred at room temperature for 30 minutes. The reaction solution was added to water (20 mL) and extracted with ethyl acetate (20 mL). The organic layer was washed with saturated saline (20 mL), dried over anhydrous sodium sulfate, and concentrated under reduced pressure. The obtained residue was purified by silica gel column chromatography by purification (eluent: hexane/ethyl acetate) to obtain tert-butyl ((1S,2R)-2-(6-fluoro-2,3-dimethylphenyl)-1-(5-oxo-4,5-dihydro-1,3,4-oxadiazol-2-yl)propyl)carbamate (356 mg).

Step 3 tert-butyl ((1S,2R)-2-(6-fluoro-2,3-dimethylphenyl)-1-(5-oxo-4,5-dihydro-1,3,4-oxadiazol-2-yl)propyl)carbamate (550 mg) obtained in the above Step 2 was dissolved in hydrochloric acid-1,4-dioxane (4 M, 5.0 mL), and the reaction solution was stirred at room temperature for 1.5 hours. The reaction solution was concentrated under reduced pressure to obtain the title compound.

Reference Examples F2 to F10

According to the method of Reference Example F1 Steps 1 to 3, the following compounds of Reference Examples F2 to F10 were synthesized.

TABLE 6

| Reference Example | Starting Material (Reference example number or structural formula) | Synthesized Compound |
|---|---|---|
| F2 | Reference Example D6 | 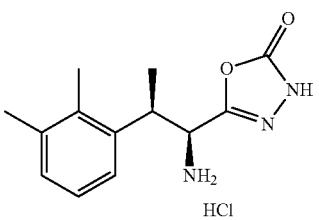 [SMILES: Cc1cccc([C@@H](C)[C@H](N)c2n[nH]c(=O)o2)c1C ; Cl] HCl |
| F3 | Reference Example D3 | 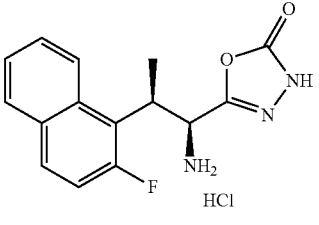 [SMILES: C[C@H](c1c(F)ccc2ccccc12)[C@H](N)c1n[nH]c(=O)o1 ; Cl] HCl |
| F4 | Reference Example D13 | 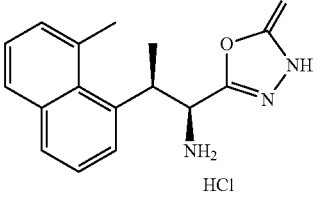 HCl |
| F5 | Reference Example D10 | 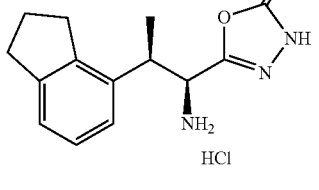 HCl |
| F6 | Reference Example D41 | 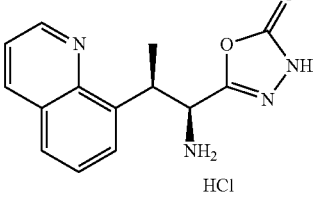 HCl |
| F7 | Reference Example D4 | 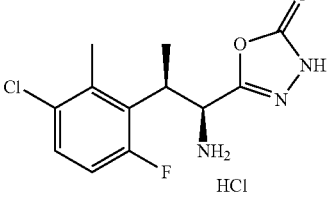 HCl |

TABLE 6-continued

| Reference Example | Starting Material (Reference example number or structural formula) | Synthesized Compound |
|---|---|---|
| F8 | Reference Example D5 | 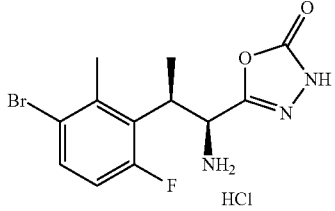 [SMILES: Cc1c(Cl)ccc(F)c1[C@@H](C)[C@H](N)c1n[nH]c(=O)o1 ; Cl] HCl |
| F9 | Reference Example D45 | 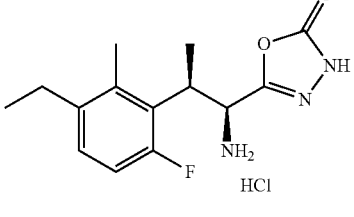 HCl |
| F10 | Reference Example D61 | 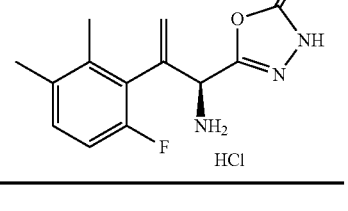 HCl |

Example 1

5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide

Step 1

To a 1,4-dioxane (5.0 mL) solution and water (5.0 mL) of (2S,3R)-2-amino-3-(6-fluoro-2,3-dimethylphenyl)butanoic acid (300 mg) obtained in Reference Example D1, triethylamine (570 μL) was added and then cooled to 0° C. 4-Bromo-2-cyanobenzene-1-sulfonyl chloride (362 mg) was added to the reaction solution, and the mixture was stirred at the same temperature for 45 minutes. The reaction solution was added to hydrochloric acid (1 M, 15 mL) and extracted with ethyl acetate (15 mL). The organic layer was washed with saturated saline (20 mL), dried over anhydrous magnesium sulfate, and concentrated under reduced pressure. The residue was purified by silica gel column chromatography (eluent: hexane/ethyl acetate/2% acetic acid) to obtain (2S,3R)-2-(4-bromo-2-cyanophenylsulfonamido)-3-(6-fluoro-2,3-dimethylphenyl)butanoic acid (465 mg).

Step 2

To a THF (5.0 mL) solution of (2S,3R)-2-(4-bromo-2-cyanophenylsulfonamido)-3-(6-fluoro-2,3-dimethylphenyl)butanoic acid (465 mg) obtained in the above Step 1, CDI (210 mg) was added, and the reaction solution was stirred at room temperature for 20 minutes. The reaction solution was cooled to 0° C., hydrazine•monohydrate (200 μL) was added, and the mixture was stirred at the same temperature for 20 minutes. The reaction solution was added to water (20 mL) and extracted with ethyl acetate (20 mL). The organic layer was washed with saturated saline (20 mL), dried over anhydrous sodium sulfate, and concentrated under reduced pressure.

CDI (211 mg) was added to a 1,4-dioxane (4.0 mL) solution of the obtained residue, and the reaction solution was stirred at 45° C. for 1 hour. The reaction solution was added to water (20 mL) and extracted with ethyl acetate (20 mL). The organic layer was washed with saturated saline (20 mL), dried over anhydrous sodium sulfate, and concentrated under reduced pressure. The obtained residue was purified by silica gel column chromatography (eluent: hexane/ethyl acetate) to obtain 4-bromo-2-cyano-N-((1S,2R)-2-(6-fluoro-2,3-dimethylphenyl)-1-(5-oxo-4,5-dihydro-1,3,4-oxadiazol-2-yl)propyl)benzenesulfonamide (386 mg).

Step 3

To a DMSO (5.0 mL) solution of 4-bromo-2-cyano-N-((1S,2R)-2-(6-fluoro-2,3-dimethylphenyl)-1-(5-oxo-4,5-dihydro-1,3,4-oxadiazol-2-yl)propyl)benzenesulfonamide (386 mg) obtained in the above Step 2, hydrogen peroxide water (1.0 mL) and potassium carbonate (420 mg) were added sequentially in an ice bath, and the reaction solution was stirred at 60° C. for 2.5 hours. The reaction solution was slowly added to hydrochloric acid (1 M, 15 mL) in an ice bath and then extracted with ethyl acetate (15 mL). The organic layer was washed with saturated saline (20 mL), dried over anhydrous sodium sulfate, and concentrated under reduced pressure. The residue was purified by silica gel column chromatography (eluent: hexane/ethyl acetate) to give the title compound.

Examples 2 to 128

Compounds of Examples 2 to 43 were synthesized according to the method of Example 1 Steps 1 to 3. Compounds of Examples 44 to 128 were synthesized according to the method of Example 1 Step 1 and 2. The necessary raw materials are listed in the following table.

TABLE 7-1

| Example | Starting Material | ArSO2Cl | Name of the Synthesized Compound |
|---|---|---|---|
| 2 | Reference Example D10 | E22 | 6-chloro-3-(N-((1S,2R)-2-(2,3-dihydro-1H-inden-4-yl)-1-(5-oxo-4,5-dihydro-1,3,4-oxadiazol-2-yl)propyl)sulfamoyl)picolinamide |
| 3 | Reference Example D6 | ClO2S-C6H3(CN)-Cl | 5-chloro-2-(N-((1S,2R)-2-(2,3-dimethylphenyl)-1-(5-oxo-4,5-dihydro-1,3,4-oxadiazol-2-yl)propyl)sulfamoyl)benzamide |
| 4 | Reference Example D6 | ClO2S-C6H3(CN)-Br | 5-bromo-2-(N-((1S,2R)-2-(2,3-dimethylphenyl)-1-(5-oxo-4,5-dihydro-1,3,4-oxadiazol-2-yl)propyl)sulfamoyl)benzamide |
| 5 | Reference Example D1 | ClO2S-C6H3(CN)-Cl | 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide |
| 6 | Reference Example D3 | ClO2S-C6H3(CN)-Cl | 5-chloro-2-(N-((1S,4R)-2-(2-fluoronaphthalen-1-yl)-1-(5-oxo-4,5-dihydro-1,3,4-oxadiazol-2-yl)propyl)sulfamoyl)benzamide |
| 7 | Reference Example D7 | ClO2S-C6H3(CN)-Cl | 5-chloro-2-(N-((1S,2R)-2-(5-fluoro-2,3-dimethylphenyl)-1-(5-oxo-4,5-dihydro-1,3,4-oxadiazol-2-yl)propyl)sulfamoyl)benzamide |
| 8 | Reference Example D20 | ClO2S-C6H3(CN)-Cl | 5-chloro-2-(N-((1S,2R)-2-(8-fluoronaphthalen-1-yl)-1-(5-oxo-4,5-dihydro-1,3,4-oxadiazol-2-yl)propyl)sulfamoyl)benzamide |
| 9 | Reference Example D8 | ClO2S-C6H3(CN)-Cl | 5-chloro-2-(N-((1S,2R)-2-(3-fluoronaphthalen-1-yl)-1-(5-oxo-4,5-dihydro-1,3,4-oxadiazol-2-yl)propyl)sulfamoyl)benzamide |
| 10 | Reference Example D1 | ClO2S-C6H3(CN)-CH3 | 2-(N-((1S,2R)-2-(3-6-fluoro-2,3-dimethylphenyl)-1-(5-oxo-4,5-dihydro-1,3,4-oxadiazol-2-yl)propyl)sulfamoyl)-5-methylbenzamide |

TABLE 7-1-continued

| Example | Starting Material | ArSO2Cl | Name of the Synthesized Compound |
|---|---|---|---|
| 11 | Reference Example D45 | ClO₂S–(phenyl with NC, Cl) | 5-chloro-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide |

TABLE 7-2

| Example | Starting Material | ArSO2Cl | Name of the Synthesized Compound |
|---|---|---|---|
| 12 | Reference Example D3 | ClO₂S–(phenyl with NC, Me) | 2-(N-((1S,2R)-2-(2-Fluoronaphthalen-1-yl)-1-(5-oxo-4,5-dihydro-1,3,4-oxadiazol-2-yl)propyl)sulfamoyl)-5-methylbenzamide |
| 13 | Reference Example D46 | ClO₂S–(phenyl with NC, Cl) | 5-chloro-2-(N-((1S,2R)-2-(2,3-difluoro-5,6-dimethylphenyl)-1-(5-oxo-4,5-dihydro-1,3,4-oxadiazol-2-yl)propyl)sulfamoyl)benzamide |
| 14 | Reference Example D4 | ClO₂S–(phenyl with NC, Cl) | 5-chloro-2-(N-((1S,2R)-2-(3-chloro-6-fluoro-2-methylphenyl)-1-(5-oxo-4,5-dihydro-1,3,4-oxadiazol-2-yl)propyl)sulfamoyl)benzamide |
| 15 | Reference Example D3 | ClO₂S–(phenyl with NC, Br) | 5-bromo-2-(N-((1S,2R)-2-(2-fluoronaphthalen-1-yl)-1-(5-oxo-4,5-dihydro-1,3,4-oxadiazol-2-yl)propyl)sulfamoyl)benzamide |
| 16 | Reference Example D1 | Reference Example E20 | 5-Cyclopropyl-2-(N-((1S,2R)-2-(6-Fluoro-2,3-dimethylphenyl)-1-(5-oxo-4,5-dihydro-1,3,4-oxadiazol-2-yl)propyl)sulfamoyl)benzamide |
| 17 | Reference Example D15 | ClO₂S–(phenyl with NC, Cl) | 5-chloro-2-(N-((1S)-2-(2-chloro-6-fluoro-3-methylphenyl)-1-(5-oxo-4,5-dihydro-1,3,4-oxadiazol-2-yl)propyl)sulfamoyl)benzamide |
| 18 | Reference Example D1 | Reference Example E21 | 5-Ethyl-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide |
| 19 | Reference Example D1 | Reference Example E22 | 6-Chloro-3-(N-((1S,2R)-2-(6-fluoro-2,3-dimethylphenyl)-1-(5-oxo-4,5-dihydro-1,3,4-oxadiazol-2-yl)propyl)sulfamoyl)picolinamide |
| 20 | Reference Example D1 | ClO₂S–(phenyl with NC) | 2-(N-((1S,2R)-2-(6-fluoro-2,3-dimethylphenyl)-1-(5-oxo-4,5-dihydro-1,3,4-oxadiazol-2-yl)propyl)sulfamoyl)benzamide |
| 21 | Reference Example D16 | ClO₂S–(phenyl with NC, Cl) | 5-chloro-2-(N-((1S,2R)-2-(2-fluoro-5-methylphenyl)-1-(5-oxo-4,5-dihydro-1,3,4-oxadiazol-2-yl)propyl)sulfamoyl)benzamide |
| 22 | Reference Example D17 | ClO₂S–(phenyl with NC, Cl) | 5-chloro-2-(N-((1S,2R)-2-(2-fluoro-6-methylphenyl)-1-(5-oxo-4,5-dihydro-1,3,4-oxadiazol-2-yl)propyl)sulfamoyl)benzamide |

TABLE 7-3

| Example | Starting Material | ArSO2Cl | Name of the Synthesized Compound |
|---|---|---|---|
| 23 | Reference Example D18 | 4-Cl, 2-CN benzenesulfonyl chloride (ClO2S, NC, Cl) | 5-chloro-2-(N-((1S,2S)-2-(2-fluoro-6-methylphenyl)-1-(5-oxo-4,5-dihydro-1,3,4-oxadiazol-2-yl)propyl)sulfamoyl)benzamide |
| 24 | Reference Example D37 | 4-Cl, 2-CN benzenesulfonyl chloride | 5-chloro-(N-((1S,2R)-1-(5-oxo-4,5-dihydro-1,3,4-oxadiazol-2-yl)-2-(o-tolyl)propyl)sulfamoyl)benzamide |
| 25 | Reference Example D4 | 4-Br, 2-CN benzenesulfonyl chloride | 5-bromo-2-(N-((1S,2R)-2-(3-chloro-6-fluoro-2-methylphenyl)-1-(5-oxo-4,5-dihydro-1,3,4-oxadiazol-2-yl)propyl)sulfamoyl)benzamide |
| 26 | Reference Example D47 | 4-Cl, 2-CN benzenesulfonyl chloride | 5-chloro-2-(N-((1S,2R)-2-(3-cyclopropyl-6-fluoro-2-methylphenyl)-1-(5-oxo-4,5-dihydro-1,3,4-oxadiazol-2-yl)propyl)sulfamoyl)benzamide |
| 27 | Reference Example D48 | 4-Cl, 2-CN benzenesulfonyl chloride | 5-chloro-2-(N-((1S,2R)-2-(6-fluoro-2-methyl-3-(trifluoromethyl)phenyl)-1-(5-oxo-4,5-dihydro-1,3,4-oxadiazol-2-yl)propyl)sulfamoyl)benzamide |
| 28 | Reference Example D19 | 4-Cl, 2-CN benzenesulfonyl chloride | 5-chloro-2-(N-((1S,2R)-2-(3,6-difluoro-2-methylphenyl)-1-(5-oxo-4,5-dihydro-1,3,4-oxadiazol-2-yl)propyl)sulfamoyl)benzamide |
| 29 | Reference Example D49 | 4-Cl, 2-OMe benzenesulfonyl chloride | 3-((1S,2R)-1-(4-chloro-2-methoxyphenylsulfonamido)-1-(5-oxo-4,5-dihydro-1,3,4-oxadiazol-2-yl)propan-2-yl)-4-fluoro-2-methylbenzamide |
| 30 | Reference Example D5 | 4-Cl, 2-CN benzenesulfonyl chloride | 2-(N-((1S,2R)-2-(3-bromo-6-fluoro-2-methylphenyl)-1-(5-oxo-4,5-dihydro-1,3,4-oxadiazol-2-yl)propyl)sulfamoyl)-5-chlorobenzamide |
| 31 | Reference Example D1 | Reference Example E18 | 3-chloro-6-(N-((1S,2R)-2-(6-fluoro-2,3-dimethylphenyl)-1-(5-oxo-4,5-dihydro-1,3,4-oxadiazol-2-yl)propyl)sulfamoyl)picolinamide |
| 32 | Reference Example D2 | 4-Cl, 2-CN benzenesulfonyl chloride | 5-chloro-2-(N-((1S,2S)-2-(6-fluoro-2,3-dimethylphenyl)-1-(5-oxo-4,5-dihydro-1,3,4-oxadiazol-2-yl)propyl)sulfamoyl)benzamide |
| 33 | Reference Example D57 | 4-Cl, 2-CN benzenesulfonyl chloride | 5-chloro-2-(N-((1R,2S)-2-(6-fluoro-2,3-dimethylphenyl)-1-(5-oxo-4,5-dihydro-1,3,4-oxadiazol-2-yl)propyl)sulfamoyl)benzamide |

TABLE 7-4

| | | | |
|---|---|---|---|
| 34 | Reference Example D58 | 4-Cl, 2-CN benzenesulfonyl chloride | 5-chloro-2-(N-((1R,2R)-2-(6-fluoro-2,3-dimethylphenyl)-1-(5-oxo-4,5-dihydro-1,3,4-oxadiazol-2-yl)propyl)sulfamoyl)benzamide |

TABLE 7-4-continued

| | | | |
|---|---|---|---|
| 35 | Reference Example D5 | ClO₂S–[benzene with NC, Br] | 5-bromo-2-(N-((1S,2R)-2-(3-bromo-6-fluoro-2-methylphenyl)-1-(5-oxo-4,5-dihydro-1,3,4-oxadiazol-2-yl)propyl)sulfamoyl)benzamide |
| 36 | Reference Example D1 | Reference Example E67 | 2-(N-((1S,2R)-2-(6-fluoro-2,3-dimethylphenyl)-1-(5-oxo-4,5-dihydro-1,3,4-oxadiazol-2-yl)propyl)sulfamoyl)-4-(morpholine-4-carbonyl)benzamide |
| 37 | Reference Example D1 | Reference Example E68 | 3-(N-((1S,2R)-2-(6-fluoro-2,3-dimethylphenyl)-1-(5-oxo-4,5-dihydro-1,3,4-oxadiazol-2-yl)propyl)sulfamoyl)-N1,N1-dimethylterephthalamide |
| 38 | Reference Example D1 | Reference Example E16 | 4-carbamoyl-2-chloro-5-(N-((1S,2R)-2-(6-fluoro-2,3-dimethylphenyl)-1-(5-oxo-4,5-dihydro-1,3,4-oxadiazol-2-yl)propyl)sulfamoyl)benzoic acid |
| 39 | Reference Example D1 | Reference Example E69 | 2-chloro-5-(N-((1S,2R)-2-(6-fluoro-2,3-dimethylphenyl)-1-(5-oxo-4,5-dihydro-1,3,4-oxadiazol-2-yl)propyl)sulfamoyl)-N1,N1-dimethyl terephthalamide |
| 40 | Reference Example D1 | Reference Example E32 | 2-chloro-5-(N-((1S,2R)-2-(6-fluoro-2,3-dimethylphenyl)-1-(5-oxo-4,5-dihydro-1,3,4-oxadiazol-2-yl)propyl)sulfamoyl)isonicotinamide |
| 41 | Reference Example D1 | ClO₂S–[benzene with NC, CF₃] | 2-(N-((1S,2R)-2-(6-fluoro-2,3-dimethylphenyl)-1-(5-oxo-4,5-dihydro-1,3,4-oxadiazol-2-yl)propyl)sulfamoyl)-5-(trifluoromethyl)benzamide |
| 42 | Reference Example D5 | ClO₂S–[benzene with NC, CF₃] | 2-(N-((1S,2R)-2-(3-bromo-6-fluoro-2-methylphenyl)-1-(5-oxo-4,5-dihydro-1,3,4-oxadiazol-2-yl)propyl)sulfamoyl)-5-(trifluoromethyl)benzamide |
| 43 | Reference Example D44 | ClO₂S–[benzene with NC, Cl] | 5-chloro-2-[[(1S,2R)-3,3,3-trideuterio-2-(6-fluoro-2,3-dimethylphenyl)-1-(2-oxo-3H-1,3,4-oxadiazol-5-yl)propyl]sulfamoyl]benzamide |
| 44 | Reference Example D11 | ClO₂S–[benzene with Br] | 4-bromo-N-((1S,2R)-2-(naphthalen-1-yl)-1-(5-oxo-4,5-dihydro-1,3,4-oxadiazol-2-yl)propyl)benzenesulfonamide |

TABLE 7-5

| Example | Starting Material | ArSO2Cl | Name of the Synthesized Compound |
|---|---|---|---|
| 45 | Reference Example D27 | ClO₂S–[benzene with Br] | N-((1S,2R)-2-(benzo[b]thiophen-4-yl)-1-(5-oxo-4,5-dihydro-1,3,4-oxadiazol-2-yl)propyl)-4-bromobenzenesulfonamide |
| 46 | Reference Example D11 | ClO₂S–[benzene with Cl, Cl] | 2,4-dichloro-N-((1S,2R)-2-(naphthalen-1-yl)-1-(5-oxo-4,5-dihydro-1,3,4-oxadiazol-2-yl)propyl)benzenesulfonamide |
| 47 | Reference Example D21 | ClO₂S–[benzene with Cl, cyclopropyl] | 2-chloro-4-cyclopropyl-N-((1S,2R)-1-(5-oxo-4,5-dihydro-1,3,4-oxadiazol-2-yl)-2-(5,6,7,8-tetrahydronaphthalen-1-yl)propyl)benzenesulfonamide |
| 48 | Reference Example D51 | ClO₂S–[pyridine with Br] | 5-bromo-N-((1S)-2-(3-methyl-2,3-dihydro-1H-inden-4-yl)-1-(5-oxo-4,5-dihydro-1,3,4-oxadiazol-2-yl)propyl)pyridine-2-sulfonamide |

TABLE 7-5-continued

| Example | Starting Material | ArSO2Cl | Name of the Synthesized Compound |
|---|---|---|---|
| 49 | Reference Example D22 | 5-bromopyridine-2-sulfonyl chloride | N-((1S,2R)-2-(9H-fluoren-1-yl)-1-(5-oxo-4,5-dihydro-1,3,4-oxadiazol-2-yl)propyl)-5-bromopyridine-2-sulfonamide |
| 50 | Reference Example D23 | 5-bromopyridine-2-sulfonyl chloride | N-((1S,2R)-2-(9H-fluoren-4-yl)-1-(5-oxo-4,5-dihydro-1,3,4-oxadiazol-2-yl)propyl)-5-bromopyridine-2-sulfonamide |
| 51 | Reference Example D11 | 4-nitrobenzenesulfonyl chloride | N-((1S,2R)-2-(naphthalen-1-yl)-1-(5-oxo-4,5-dihydro-1,3,4-oxadiazol-2-yl)propyl)-4-nitrobenzene sulfonamide |
| 52 | Reference Example D21 | 5-chloropyridine-2-sulfonyl chloride | 5-chloro-N-((1S,2R)-1-(5-oxo-4,5-dihydro-1,3,4-oxadiazol-2-yl)-2-(5,6,7,8-tetrahydronaphthalen-1-yl)propy)pyridine-2-sulfonamide |
| 53 | Reference Example D21 | 4-bromo-3-methoxybenzenesulfonyl chloride | 4-bromo-3-methoxy-N-((1S,2R)-1-(5-oxo-4,5-dihydro-1,3,4-oxadiazol-2-yl)-2-(5,6,7,8-tetrahydronaphthalen-1-yl)propyl)benzene sulfonamide |
| 54 | Reference Example D21 | 4-chloro-2-nitrobenzenesulfonyl chloride | 4-chloro-2-nitro-N-((1S,2R)-1-(5-oxo-4,5-dihydro-1,3,4-oxadiazol-2-yl)-2-(5,6,7,8-tetrahydronaphthalen-1-yl)propyl)benzene sulfonamide |
| 55 | Reference Example D21 | 2,4-dimethoxybenzenesulfonyl chloride | 2,4-dimethoxy-N-((1S,2R)-1-(5-oxo-4,5-dihydro-1,3,4-oxadiazol-2-yl)-2-(5,6,7,8-tetrahydronaphthalen-1-yl)propyl)benzene sulfonamide |

TABLE 7-6

| Example | Starting Material | ArSO2Cl | Name of the Synthesized Compound |
|---|---|---|---|
| 56 | Reference Example D24 | 4-chloro-2-methoxybenzenesulfonyl chloride | 4-chloro-N-((1S,2R)-2-(6-fluoro-naphthalen-1-yl)-1-(5-oxo-4,5-dihydro-1,3,4-oxadiazol-2-yl)propyl)-2-methoxybenzenesulfonamide |
| 57 | Reference Example D21 | 2-methoxy-4-nitrobenzenesulfonyl chloride | 2-methoxy-4-nitro-N-((1S,2R)-1-(5-oxo-4,5-dihydro-1,3,4-oxadiazol-2-yl)-2-(5,6,7,8-tetrahydronaphthalen-1-yl)propyl)benzenesulfonamide |
| 58 | Reference Example D21 | methyl 5-(chlorosulfonyl)-4-methoxythiophene-3-carboxylate | methyl 4-methoxy-5-(N-((1S,2R)-1-(5-oxo-4,5-dihydro-1,3,4-oxadiazol-2-yl)-2-(5,6,7,8-tetrahydronaphthalen-1-yl)propyl)sulfamoyl)thiophene-3-carboxylate |

TABLE 7-6-continued

| Example | Starting Material | ArSO2Cl | Name of the Synthesized Compound |
|---|---|---|---|
| 59 | Reference Example D10 | benzo[c][1,2,5]thiadiazole-4-sulfonyl chloride | N-((1S,2R)-2-(2,3-dihydro-1H-inden-4-yl)-1-(5-oxo-4,5-dihydro-1,3,4-oxadiazol-2-yl)propyl)benzo[c][1,2,5]thiadiazole-4-sulfonamide |
| 60 | Reference Example D10 | 4-bromo-2-fluorobenzenesulfonyl chloride | 4-bromo-N-((1S,2R)-2-(2,3-dihydro-1H-inden-4-yl)-1-(5-oxo-4,5-dihydro-1,3,4-oxadiazol-2-yl)propyl)-2-fluorobenzenesulfonamide |
| 61 | Reference Example D10 | 3-chloro-2-fluorobenzenesulfonyl chloride | 3-chloro-N-((1S,2R)-2-(2,3-dihydro-1H-inden-4-yl)-1-(5-oxo-4,5-dihydro-1,3,4-oxadiazol-2-yl)propy)-2-fluorobenzenesulfonamide |
| 62 | Reference Example D33 | 4-chloro-2-methoxybenzenesulfonyl chloride | N-((1S,2R)-2-(benzo[b]thiophen-3-yl)-1-(5-oxo-4,5-dihydro-1,3,4-oxadiazol-2-yl)propyl)-4-chloro-2-methoxybenzenesulfonamide |
| 63 | Reference Example D40 | 4-chloro-2-methoxybenzenesulfonyl chloride | N-((1S,2R)-2-(benzo[d]thiazol-4-yl)-1-(5-oxo-4,5-dihydro-1,3,4-oxadiazol-2-yl)propyl)-4-chloro-2-methoxybenzenesulfonamide |
| 64 | Reference Example D30 | 4-chloro-2-methoxybenzenesulfonyl chloride | 4-chloro-N-((1S,2R)-2-(2,3-dihydrobenzofuran-7-yl)-1-(5-oxo-4,5-dihydro-1,3,4-oxadiazol-2-yl)propyl)-2-methoxybenzenesulfonamide |
| 65 | Reference Example D31 | 4-chloro-2-methoxybenzenesulfonyl chloride | 4-chloro-2-methoxy-N-((1S,2R)-2-(2-methyl naphthalen-1-yl)-1-(5-oxo-4,5-dihydro-1,3,4-oxadiazol-2-yl)propyl)benzenesulfonamide |
| 66 | Reference Example D29 | 4-chloro-2-methoxybenzenesulfonyl chloride | 4-chloro-N-((1S,2R)-2-(2,3-dihydrobenzofuran-4-yl)-1-(5-oxo-4,5-dihydro-1,3,4-oxadiazol-2-yl)propyl)-2-methoxybenzenesulfonamide |

TABLE 7-7

| Example | Starting Material | ArSO2Cl | Name of the Synthesized Compound |
|---|---|---|---|
| 67 | Reference Example D53 | 4-chloro-2-methoxybenzenesulfonyl chloride | 4-chloro-2-methoxy-N-((1S,2R)-2-(2-methyl-2,3-dihydro-1H-inden-4-yl)-1-(5-oxo-4,5-dihydro-1,3,4-oxadiazol-2-yl)propyl)benzenesulfonamide |
| 68 | Reference Example D10 | naphthalene-1-sulfonyl chloride | N-((1S,2R)-2-(2,3-dihydro-1H-inden-4-yl)-1-(5-oxo-4,5-dihydro-1,3,4-oxadiazol-2-yl)propyl)naphthalene-1-sulfonamide |

TABLE 7-7-continued

| Example | Starting Material | ArSO2Cl | Name of the Synthesized Compound |
|---|---|---|---|
| 69 | Reference Example D52 | 4-chloro-2-methoxybenzenesulfonyl chloride | 4-chloro-2-methoxy-N-((1S,2S)-2-(3-methyl-2,3-dihydro-1H-inden-4-yl)-1-(5-oxo-4,5-dihydro-1,3,4-oxadiazol-2-yl)propyl)benzenesulfonamide |
| 70 | Reference Example D28 | 4-chloro-2-methoxybenzenesulfonyl chloride | 4-chloro-2-methoxy-N-((1S,2R)-2-(2-methyl-[1,1'-biphenyl]-3-yl)-1-(5-oxo-4,5-dihydro-1,3,4-oxadiazol-2-yl)propyl)benzenesulfonamide |
| 71 | Reference Example D13 | 4-chloro-2-methoxybenzenesulfonyl chloride | 4-chloro-2-methoxy-N-((1S,2R)-2-(8-methylnaphthalen-1-yl)-1-(5-oxo-4,5-dihydro-1,3,4-oxadiazol-2-yl)propyl)benzenesulfonamide |
| 72 | Reference Example D35 | 4-chloro-2-methoxybenzenesulfonyl chloride | 4-chloro-2-methoxy-N-((1S,2R)-2-(3-methyl-2,3-dihydrobenzofuran-4-yl)-1-(5-oxo-4,5-dihydro-1,3,4-oxadiazol-2-yl)propyl)benzenesulfonamide |
| 73 | Reference Example D36 | 4-chloro-2-methoxybenzenesulfonyl chloride | 4-chloro-2-methoxy-N-((1S,2S)-2-(3-methyl-2,3-dihydrobenzofuran-4-yl)-1-(5-oxo-4,5-dihydro-1,3,4-oxadiazol-2-yl)propyl)benzenesulfonamide |
| 74 | Reference Example D34 | 4-chloro-2-methoxybenzenesulfonyl chloride | 4-chloro-N-((1S)-2-(2,3-difluorophenyl)-1-(5-oxo-4,5-dihydro-1,3,4-oxadiazol-2-yl)propyl)-2-methoxybenzenesulfonamide |
| 75 | Reference Example D32 | 4-chloro-2-methoxybenzenesulfonyl chloride | 4-chloro-N-((1S,2R)-2-(3-fluoro-2-methylphenyl)-1-(5-oxo-4,5-dihydro-1,3,4-oxadiazol-2-yl)propyl)-2-methoxybenzenesulfonamide |
| 76 | Reference Example D3 | 4-chloro-2-methoxybenzenesulfonyl chloride | 4-chloro-N-((1S,2R)-2-(2-fluoronaphthalen-1-yl)-1-(5-oxo-4,5-dihydro-1,3,4-oxadiazol-2-yl)propyl)-2-methoxybenzenesulfonamide |
| 77 | Reference Example D9 | 4-chloro-2-methoxybenzenesulfonyl chloride | 4-chloro-N-((1S,2R)-2-(4-fluoro-2,3-dimethylphenyl)-1-(5-oxo-4,5-dihydro-1,3,4-oxadiazol-2-yl)propyl)-2-methoxybenzenesulfonamide |

TABLE 7-8

| Example | Starting Material | ArSO2Cl | Name of the Synthesized Compound |
|---|---|---|---|
| 78 | Reference Example D55 | 4-chloro-2-methoxybenzenesulfonyl chloride | (S)-4-chloro-2-methoxy-N-(2-(8-methylnaphthalen-1-yl)-1-(5-oxo-4,5-dihydro-1,3,4-oxadiazol-2-yl)ethyl)benzenesulfonamide |
| 79 | Reference Example D38 | 4-chloro-2-methoxybenzenesulfonyl chloride | 4-chloro-N-((1S)-2-(2,6-difluoro-3-methylphenyl)-1-(5-oxo-4,5-dihydro-1,3,4-oxadiazol-2-yl)propyl)-2-methoxybenzenesulfonamide |
| 80 | Reference Example D39 | 4-chloro-2-methoxybenzenesulfonyl chloride | 4-chloro-N-((1S)-2-(2-fluoro-3-methylphenyl)-1-(5-oxo-4,5-dihydro-1,3,4-oxadiazol-2-yl)propyl)-2-methoxybenzenesulfonamide |

TABLE 7-8-continued

| Example | Starting Material | ArSO2Cl | Name of the Synthesized Compound |
|---|---|---|---|
| 81 | Reference Example D13 | Reference Example E57 | 5-chloro-4,4-difluoro-N-((1S,2R)-2-(8-methylnaphthalen-1-yl)-1-(5-oxo-4,5-dihydro-1,3,4-oxadiazol-2-yl)propyl)chroman-8-sulfonamide |
| 82 | Reference Example D25 | (structure: ClO2S, OMe, Cl on benzene) | 4-chloro-N-((1S,2R)-2-(5-fluoronaphthalen-1-yl)-1-(5-oxo-4,5-dihydro-1,3,4-oxadiazol-2-yl)propyl)-2-methoxybenzenesulfonamide |
| 83 | Reference Example D1 | (structure: ClO2S, OMe, Cl on benzene) | 4-chloro-N-((1S,2R)-2-(6-fluoro-2,3-dimethylphenyl)-1-(5-oxo-4,5-dihydro-1,3,4-oxadiazol-2-yl)propyl)-2-methoxybenzenesulfonamide |
| 84 | Reference Example D1 | (structure: ClO2S, NC, Cl on benzene) | 4-chloro-2-cyano-N-((1S,2R)-2-(6-fluoro-2,3-dimethylphenyl)-1-(5-oxo-4,5-dihydro-1,3,4-oxadiazol-2-yl)propyl)benzenesulfonamide |
| 85 | Reference Example D14 | (structure: ClO2S, OMe, Cl on benzene) | 4-chloro-N-((1S,2R)-2-(2-isopropyl-3-methylphenyl)-1-(5-oxo-4,5-dihydro-1,3,4-oxadiazol-2-yl)propyl)-2-methoxybenzenesulfonamide |
| 86 | Reference Example D12 | (structure: ClO2S, OMe, Cl on benzene) | 4-chloro-N-((1S,2R)-2-(3-ethyl-2-methylphenyl)-1-(5-oxo-4,5-dihydro-1,3,4-oxadiazol-2-yl)propyl)-2-methoxybenzenesulfonamide |
| 87 | Reference Example D42 | (structure: ClO2S, OMe, Cl on benzene) | 4-chloro-N-((1S,2R)-2-(2-ethyl-3-methylphenyl)-1-(5-oxo-4,5-dihydro-1,3,4-oxadiazol-2-yl)propyl)-2-methoxybenzenesulfonamide |
| 88 | Reference Example D1 | Reference Example E7 | 5-chloro-N-((1S,2R)-2-(6-fluoro-2,3-dimethylphenyl)-1-(5-oxo-4,5-dihydro-1,3,4-oxadiazol-2-yl)propyl)-4-oxochroman-8-sulfonamide |

TABLE 7-9

| Example | Starting Material | ArSO2Cl | Name of the Synthesized Compound |
|---|---|---|---|
| 89 | Reference Example D50 | (structure: ClO2S, OMe, Cl on benzene) | N-((1S)-2-(2-bromo-5,6-difluoro-3-methylphenyl)-1-(5-oxo-4,5-dihydro-1,3,4-oxadiazol-2-yl)propyl)-4-chloro-2-methoxybenzenesulfonamide |
| 90 | Reference Example D46 | (structure: ClO2S, OMe, Cl on benzene) | 4-chloro-N-((1S,2R)-2-(2,3-difluoro-5,6-dimethylphenyl)-1-(5-oxo-4,5-dihydro-1,3,4-oxadiazol-2-yl)propyl)-2-methoxybenzenesulfonamide |
| 91 | Reference Example D1 | Reference Example E50 | 4-chloro-N-((1S,2R)-2-(6-fluoro-2,3-dimethylphenyl)-1-(5-oxo-4,5-dihydro-1,3,4-oxadiazol-2-yl)propyl)-2-(isoxazol-5-yl)benzenesulfonamide |
| 92 | Reference Example D1 | (structure: ClO2S, NC, Br on benzene) | 4-bromo-2-cyano-N-((1S,2R)-2-(6-fluoro-2,3-dimethylphenyl)-1-(5-oxo-4,5-dihydro-1,3,4-oxadiazol-2-yl)propyl)benzenesulfonamide |
| 93 | Reference Example D1 | Reference Example E64 | 5-chloro-N-((1S,2R)-2-(6-fluoro-2,3-dimethylphenyl)-1-(5-oxo-4,5-dihydro-1,3,4-oxadiazol-2-yl)propyl)-4-methyl-3-oxo-3,4-dihydro-2H-benzo[b][1,4]oxazine-8-sulfonamide |
| 94 | Reference Example D1 | Reference Example E61 | 5-chloro-4-ethyl-N-(1S,2R)-2-(6-fluoro-2,3-dimethylphenyl)-1-(5-oxo-4,5-dihydro-1,3,4-oxadiazol-2-yl)propyl)-3,4-dihydro-2H-benzo[b][1,4]oxazine-8-sulfonamide |

TABLE 7-9-continued

| Example | Starting Material | ArSO2Cl | Name of the Synthesized Compound |
|---|---|---|---|
| 95 | Reference Example D1 | Reference Example E2 | 5-chloro-8-(N-((1S,2R)-2-(6-fluoro-2,3-dimethylphenyl)-1-(5-oxo-4,5-dihydro-1,3,4-oxadiazol-2-yl)propyl)sulfamoyl)-4-methylchroman-4-yl acetate |
| 96 | Reference Example D45 | (ClO2S, NC, Br-substituted benzene structure) | 5-bromo-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide |
| 97 | Reference Example D1 | Reference Example E23 | N-((1S,2R)-2-(6-fluoro-2,3-dimethylphenyl)-1-(5-oxo-4,5-dihydro-1,3,4-oxadiazol-2-yl)propyl)-2,2-dimethyl-4-oxochroman-8-sulfonamide |
| 98 | Reference Example D1 | (ClO2S, NC-substituted benzene structure) | 2-cyano-N-((1S,2R)-2-(6-fluoro-2,3-dimethylphenyl)-1-(5-oxo-4,5-dihydro-1,3,4-oxadiazol-2-yl)propyl)benzenesulfonamide |

TABLE 7-10

| Example | Starting Material | ArSO2Cl | Name of the Synthesized Compound |
|---|---|---|---|
| 99 | Reference Example D1 | Reference Example E62 | 4-(cyclopropanecarbonyl)-N-((1S,2R)-2-(6-fluoro-2,3-dimethylphenyl)-1-(5-oxo-4,5-dihydro-1,3,4-oxadiazol-2-yl)propyl)-3,4-dihydro-2H-benzo[b][1,4]oxazine-8-sulfonamide |
| 100 | Reference Example D4 | Reference Example E2 | 5-chloro-8-(N-((1S,2R)-2-(3-chloro-6-fluoro-2-methylphenyl)-1-(5-oxo-4,5-dihydro-1,3,4-oxadiazol-2-yl)propyl)sulfamoyl)-4-methylchroman-4-yl acetate |
| 101 | Reference Example D1 | Reference Example E63 | 5-chloro-4-(2,2-difluoroethyl)-N-((1S,2R)-2-(6-fluoro-2,3-dimethylphenyl)-1-(5-oxo-4,5-dihydro-1,3,4-oxadiazol-2-yl)propyl)-3-oxo-3,4-dihydro-2H-benzo[b][1,4]oxazine-8-sulfonamide |
| 102 | Reference Example D1 | Reference Example E66 | 5-chloro-4-(2,2-difluoroethyl)-N-((1S,2R)-2-(6-fluoro-2,3-dimethylphenyl)-1-(5-oxo-4,5-dihydro-1,3,4-oxadiazol-2-yl)propyl)-3,4-dihydro-2H-benzo[b][1,4]oxazine-8-sulfonamide |
| 103 | Reference Example D1 | (ClO2S, methyl ester, Cl-substituted benzene structure) | methyl 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzoate |
| 104 | Reference Example D49 | (ClO2S, OMe, Cl-substituted benzene structure) | 4-chloro-N-((1S,2R)-2-(3-cyano-6-fluoro-2-methylphenyl)-1-(5-oxo-4,5-dihydro-1,3,4-oxadiazol-2-yl)propyl)-2-methoxybenzenesulfonamide |
| 105 | Reference Example D1 | Reference Example E18 | 5-chloro-6-cyano-N-((1S,2R)-2-(6-fluoro-2,3-dimethylphenyl)-1-(5-oxo-4,5-dihydro-1,3,4-oxadiazol-2-yl)propyl)pyridine-2-sulfonamide |
| 106 | Reference Example D1 | Reference Example E6 | 8-(N-((1S,2R)-2-(6-fluoro-2,3-dimethylphenyl)-1-(5-oxo-4,5-dihydro-1,3,4-oxadiazol-2-yl)propyl)sulfamoyl)-4-(trifluoromethyl)chroman-4-yl acetate |
| 107 | Reference Example D1 | Reference Example E25 | 4-chloro-N-((1S,2R)-2-(6-fluoro-2,3-dimethylphenyl)-1-(5-oxo-4,5-dihydro-1,3,4-oxadiazol-2-yl)propyl)-8-oxo-5,6,7,8-tetrahydronaphthalene-1-sulfonamide |
| 108 | Reference Example D1 | Reference Example E46 | 2-(6-chloro-3-(N-((1S,2R)-2-(6-fluoro-2,3-dimethylphenyl)-1-(5-oxo-4,5-dihydro-1,3,4-oxadiazol-2-yl)propyl)sulfamoyl)-2-methoxyphenyl)propan-2-yl acetate |

TABLE 7-11

| Example | Starting Material | ArSO2Cl | Name of the Synthesized Compound |
|---|---|---|---|
| 109 | Reference Example D1 | Reference Example E10 | methyl 3-chloro-6-(N-((1S,2R)-2-(6-fluoro-2,3-dimethylphenyl)-1-(5-oxo-4,5-dihydro-1,3,4-oxadiazol-2-yl)propyl)sulfamoyl)picolinate |

TABLE 7-11-continued

| Example | Starting Material | ArSO2Cl | Name of the Synthesized Compound |
|---|---|---|---|
| 110 | Reference Example D1 | 2,6-difluorobenzenesulfonyl chloride | 2,6-difluoro-N-((1S,2R)-2-(6-fluoro-2,3-dimethylphenyl)-1-(5-oxo-4,5-dihydro-1,3,4-oxadiazol-2-yl)propyl)benzenesulfonamide |
| 111 | Reference Example D1 | 4-chloro-2,6-difluorobenzenesulfonyl chloride | 4-chloro-2,6-difluoro-N-((1S,2R)-2-(6-fluoro-2,3-dimethylphenyl)-1-(5-oxo-4,5-dihydro-1,3,4-oxadiazol-2-yl)propyl)benzenesulfonamide |
| 112 | Reference Example D1 | Reference Example E27 | 5-chloro-N-((1S,2R)-2-(6-fluoro-2,3-dimethylphenyl)-1-(5-oxo-4,5-dihydro-1,3,4-oxadiazol-2-yl)propyl)-3-methoxypyridine-2-sulfonamide |
| 113 | Reference Example D1 | Reference Example E37 | 5-chloro-N-((1S,2R)-2-(6-fluoro-2,3-dimethylphenyl)-1-(5-oxo-4,5-dihydro-1,3,4-oxadiazol-2-yl)propyl)-6-(morpholine-4-carobnyl)pyridine-2-sulfonamide |
| 114 | Reference Example D1 | Reference Example E35 | 5-chloro-N-((1S,2R)-2-(6-fluoro-2,3-dimethylphenyl)-1-(5-oxo-4,5-dihydro-1,3,4-oxadiazol-2-yl)propyl)-6-(pyrrolidine-1-carbonyl)pyridine-2-sulfonamide |
| 115 | Reference Example D1 | Reference Example E43 | 5-chloro-N-((1S,2R)-2-(6-fluoro-2,3-dimethylphenyl)-1-(5-oxo-4,5-dihydro-1,3,4-oxadiazol-2-yl)propyl)-6-(6-azaspiro[3,4]octane-6-carbonyl)pyridine-2-sulfonamide |
| 116 | Reference Example D1 | Reference Example E39 | 6-(3-oxa-8-azabicyclo[3.2.1]octane-8-carbonyl)-5-chloro-N-((1S,2R)-2-(6-fluoro-2,3-dimethylphenyl)-1-(5-oxo-4,5-dihydro-1,3,4-oxadiazol-2-yl)propyl)pyridine-2-sulfonamide |
| 117 | Reference Example D1 | Reference Example E40 | 6-(8-oxa-3-azabicyclo[3.2.1]octane-3-carbonyl)-5-chloro-N-((1S,2R)-2-(6-fluoro-2,3-dimethylphenyl)-1-(5-oxo-4,5-dihydro-1,3,4-oxadiazol-2-yl)propyl)pyridine-2-sulfonamide |
| 118 | Reference Example D1 | Reference Example E11 | methyl 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)nicotinate |

TABLE 7-12

| Example | Starting Material | ArSO2Cl | Name of the Synthesized Compound |
|---|---|---|---|
| 119 | Reference Example D1 | Reference Example E73 | methyl 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)nicotinate |
| 120 | Reference Example D1 | Reference Example E45 | 1-(5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)-3-methoxypyridin-4-yl)ethyl acetate |
| 121 | Reference Example D1 | Reference Example E28 | methyl 5-chloro-4-fluoro-2-(N-((1S,2R)-2-(6-fluoro-2,3-dimethylphenyl)-1-(5-oxo-4,5-dihydro-1,3,4-oxadiazol-2-yl)propyl)sulfamoyl)benzoate |
| 122 | Reference Example D1 | Reference Example E14 | methyl 5-chloro-2-(N-((1S,2R)-2-(5-fluoro-2,3-dimethylphenyl)-1-(5-oxo-4,5-dihydro-1,3,4-oxadiazol-2-yl)propyl)sulfamoyl)-4-methoxybenzoate |
| 123 | Reference Example D1 | Reference Example E5 | 5-chloro-8-(N-((1S,2R)-2-(6-fluoro-2,3-dimethylphenyl)-1-(5-oxo-4,5-dihydro-1,3,4-oxadiazol-2-yl)propyl)sulfamoyl)-4-(trifluoromethyl)chroman-4-yl acetate |
| 124 | Reference Example D5 | Reference Example E7 | N-((1S,2R)-2-(3-bromo-6-fluoro-2-methylphenyl)-1-(5-oxo-4,5-dihydro-1,3,4-oxadiazol-2-yl)propyl)-5-chloro-4-oxochroman-8-sulfonamide |
| 125 | Reference Example D59 | 4-chloro-2-methoxybenzenesulfonyl chloride | (S)-4-chloro-N-(2-(6-fluoro-2,3-dimethylphenyl)-2-methyl-1-(5-oxo-4,5-dihydro-1,3,4-oxadiazol-2-yl)propyl)-2-methoxybenzenesulfonamide |
| 126 | Reference Example D54 | 4-chloro-2-methoxybenzenesulfonyl chloride | (S)-4-chloro-N-(2-(6-fluoro-2,3-dimethylphenyl)-1-(5-oxo-4,5-dihydro-1,3,4-oxadiazol-2-yl)ethyl)-2-methoxybenzenesulfonamide |
| 127 | Reference Example D60 | 4-chloro-2-methoxybenzenesulfonyl chloride | (S)-4-chloro-N-((1-(6-fluoro-2,3-dimethylphenyl)cyclopropyl)(5-oxo-4,5-dihydro-1,3,4-oxadiazol-2-yl)methyl)-2-methoxybenzenesulfonamide |

TABLE 7-12-continued

| Example | Starting Material | ArSO2Cl | Name of the Synthesized Compound |
|---|---|---|---|
| 128 | Reference Example D43 | (ClO2S, methoxy, Cl-substituted benzene) | 4-chloro-N-((1S,2R)-2-(6-fluoro-2,3-dimethylphenyl)-1-(5-oxo-4,5-dihydro-1,3,4-oxadiazol-2-yl)butyl)-2-methoxybenzenesulfonamide |

Example 129

5-Chloro-8-(N-((1S,2R)-2-(6-fluoro-2,3-dimethylphenyl)-1-(5-oxo-4,5-dihydro-1,3,4-oxadiazol-2-yl)propyl)sulfamoyl)-4-methyl-d3-chroman-4-yl acetate To a pyridine (1.5 mL) solution of 5-((1S,2R)-1-amino-2-(6-fluoro-2,3-dimethylphenyl)propyl)-1,3,4-oxadiazol-2(3H)-one monohydrochloride (45 mg) obtained from Reference Example F1, 5-chloro-8-(chlorosulfonyl)-4-methyl-d3-chroman-4-ylacetate (80 mg) obtained in Reference Example E1 was added, and the reaction solution was stirred at room temperature for 12 hours. The reaction solution was concentrated under reduced pressure, and the obtained residue was purified by silica gel column chromatography (eluent: hexane/ethyl acetate) to obtain the title compound (59 mg) as a 1:1 diastereomer mixture.

Examples 130 to 185

According to the method of Example 129, the following compounds of Examples 130 to 185 were synthesized. The necessary raw materials are listed in the following table.

TABLE 8-1

| Example | Starting Material | ArSO2Cl | Name of the Synthesized Compound |
|---|---|---|---|
| 130 | Reference Example F6 | (ClO2S-pyridine-Br) | 5-bromo-N-((1S,2R)-1-(5-oxo-4,5-dihydro-1,3,4-oxadiazol-2-yl)-2-(quinoline-8-yl)propyl)pyridine-2-sulfonamide |
| 131 | Reference Example F5 | (ClO2S, Br, SO2Me-benzene) | N-((1S,2R)-2-(2,3-dihydro-1H-inden-4-yl)-1-(5-oxo-4,5-dihydro-1,3,4-oxadiazol-2-yl)propyl)-4-fluoro-3-(methylsulfonyl)benzenesulfonamide |
| 132 | Reference Example F5 | (ClO2S-quinoline) | N-((1S,2R)-2-(2,3-dihydro-1H-inden-4-yl)-1-(5-oxo-4,5-dihydro-1,3,4-oxadiazol-2-yl)propyl)quinoline-8-sulfonamide |
| 133 | Reference Example F5 | (ClO2S-benzene-isoxazole) | N-((1S,2R)-2-(2,3-dihydro-1H-inden-4-yl)-1-(5-oxo-4,5-dihydro-1,3,4-oxadiazol-2-yl)propyl)-2-(isoxazol-4-yl)benzenesulfonamide |
| 134 | Reference Example F5 | (ClO2S-benzene-OMe) | N-((1S,2R)-2-(2,3-dihydro-1H-inden-4-yl)-1-(5-oxo-4,5-dihydro-1,3,4-oxadiazol-2-yl)propyl)-2-methoxybenzenesulfonamide |
| 135 | Reference Example F5 | (ClO2S, Et, Br-benzene) | 4-bromo-N-((1S,2R)-2-(2,3-dihydro-1H-inden-4-yl)-1-(5-oxo-4,5-dihydro-1,3,4-oxadiazol-2-yl)propyl)-2-ethylbenzenesulfonamide |

TABLE 8-1-continued

| Example | Starting Material | ArSO2Cl | Name of the Synthesized Compound |
|---|---|---|---|
| 136 | Reference Example F5 | (8-quinolinyl, 3-methyl) | N-((1S,2R)-2-(2,3-dihydro-1H-inden-4-yl)-1-(5-oxo-4,5-dihydro-1,3,4-oxadiazol-2-yl)propyl)-3-methylquinoline-8-sulfonamide |
| 137 | Reference Example F5 | (4-bromo-2-methoxyphenyl) | 4-bromo-N-((1S,2R)-2-(2,3-dihydro-1H-inden-4-yl)-1-(5-oxo-4,5-dihydro-1,3,4-oxadiazol-2-yl)propyl)-2-methoxybenzenesulfonamide |
| 138 | Reference Example F5 | (2-(difluoromethoxy)phenyl) | 2-(difluoromethoxy)-N-((1S,2R)-2-(2,3-dihydro-1H-inden-4-yl)-1-(5-oxo-4,5-dihydro-1,3,4-oxadiazol-2-yl)propyl)benzenesulfonamide |

TABLE 8-2

| Example | Starting Material | ArSO2Cl | Name of the Synthesized Compound |
|---|---|---|---|
| 139 | Reference Example F5 | (2,3-dihydrobenzo[b]thiophene-6-yl 1,1-dioxide) | N-((1S,2R)-2-(2,3-dihydro-1H-inden-4-yl)-1-(5-oxo-4,5-dihydro-1,3,4-oxadiazol-2-yl)propyl)-2,3-dihydrobenzo[b]thiophene-6-sulfonamide 1,1-dioxide |
| 140 | Reference Example F5 | (5,6,7,8-tetrahydronaphthalen-1-yl) | N-((1S,2R)-2-(2,3-dihydro-1H-inden-4-yl)-1-(5-oxo-4,5-dihydro-1,3,4-oxadiazol-2-yl)propyl)-5,6,7,8-tetrahydronaphthalene-1-sulfonamide |
| 141 | Reference Example F5 | (2-methoxypyridin-3-yl) | N-((1S,2R)-2-(2,3-dihydro-1H-inden-4-yl)-1-(5-oxo-4,5-dihydro-1,3,4-oxadiazol-2-yl)propyl)-2-methoxypyridine-3-sulfonamide |
| 142 | Reference Example F5 | E34 | 1-(3-chloro-6-(N-((1S,2R)-2-(2,3-dihydro-1H-inden-4-yl)-1-(5-oxo-4,5-dihydro-1,3,4-oxadiazol-2-yl)propyl)sulfamoyl)pyridin-2-yl)ethylacetate |
| 143 | Reference Example F5 | (5-nitroquinolin-8-yl) | N-((1S,2R)-2-(2,3-dihydro-1H-inden-4-yl)-1-(5-oxo-4,5-dihydro-1,3,4-oxadiazol-2-yl)propyl)-5-nitroquinoline-8-sulfonamide |
| 144 | Reference Example F1 | Reference Example E44 | 1-(6-chloro-3-(N-((1S,2R)-2-(6-fluoro-2,3-dimethylphenyl)-1-(5-oxo-4,5-dihydro-1,3,4-oxadiazol-2-yl)propyl)sulfamoyl)-2-methoxyphenyl)ethyl acetate |
| 145 | Reference Example F1 | Reference Example E47 | 4-chloro-2-(2,2-difluoroethoxy)-N-((1S,2R)-2-(6-fluoro-2,3-dimethylphenyl)-1-(5-oxo-4,5-dihydro-1,3,4-oxadiazol-2-yl)propyl)benzenesulfonamide |
| 146 | Reference Example F1 | Reference Example E48 | 4-chloro-2-(difluoromethoxy)-N-((1S,2R)-2-(6-fluoro-2,3-dimethylphenyl)-1-(5-oxo-4,5-dihydro-1,3,4-oxadiazol-2- |

TABLE 8-2-continued

| Example | Starting Material | ArSO2Cl | Name of the Synthesized Compound |
|---|---|---|---|
| 147 | Reference Example F1 | Reference Example E19 | yl)propyl)benzenesulfonamide 2-acetyl-4-chloro-N-((1S,2R)-2-(6-fluoro-2,3-dimethylphenyl)-1-(5-oxo-4,5-dihydro-1,3,4-oxadiazol-2-yl)propyl)benzenesulfonamide |
| 148 | Reference Example F1 | 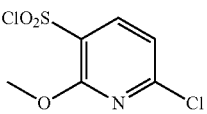 | 6-chloro-N-((1S,2R)-2-(6-fluoro-2,3-dimethylphenyl)-1-(5-oxo-4,5-dihydro-1,3,4-oxadiazol-2-yl)propyl)-2-methoxypyridine-3-sulfonamide |

TABLE 8-3

| Example | Starting Material | ArSO2Cl | Name of the Synthesized Compound |
|---|---|---|---|
| 149 | Reference Example F1 | E54 | 4-chloro-N-((1S,2R)-2-(6-fluoro-2,3-dimethylphenyl)-1-(5-oxo-4,5-dihydro-1,3,4-oxadiazol-2-yl)propyl)-2-(5-oxo-4,5-dihydro-1,3,4-oxadiazol-2-yl)benzenesulfonamide |
| 150 | Reference Example F2 | 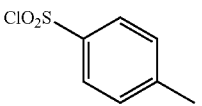 | N-((1S,2R)-2-(2,3-dimethylphenyl)-1-(5-oxo-4,5-dihydro-1,3,4-oxadiazol-2-yl)propyl)-4-methylbenzenesulfonamide |
| 151 | Reference Example F1 | 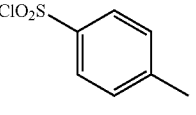 | N-((1S,2R)-2-(6-fluoro-2,3-dimethylphenyl)-1-(5-oxo-4,5-dihydro-1,3,4-oxadiazol-2-yl)propyl)-4-methylbenzenesulfonamide |
| 152 | Reference Example F1 | E60 | N-((1S,2R)-2-(6-fluoro-2,3-dimethylphenyl)-1-(5-oxo-4,5-dihydro-1,3,4-oxadiazol-2-yl)propyl)-1H-indole-4-sulfonamide |
| 153 | Reference Example F1 | 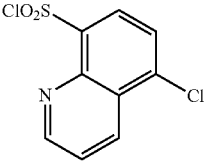 | 5-chloro-N-((1S,2R)-2-(6-fluoro-2,3-dimethylphenyl)-1-(5-oxo-4,5-dihydro-1,3,4-oxadiazol-2-yl)propyl)quinoline-8-sulfonamide |
| 154 | Reference Example F1 | 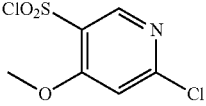 | 6-chloro-N-((1S,2R)-2-(6-fluoro-2,3-dimethylphenyl)-1-(5-oxo-4,5-dihydro-1,3,4-oxadiazol-2-yl)propyl)-4-methoxypyridine-3-sulfonamide |
| 155 | Reference Example F1 | Reference Example E38 | 5-chloro-N-((1S,2R)-2-(6-fluoro-2,3-dimethylphenyl)-1-(5-oxo-4,5-dihydro-1,3,4-oxadiazol-2-yl)propyl)-6-(2-oxa-6-azaspiro[3.4]octane-6-carbonyl)pyridine-2-sulfonamide |
| 156 | Reference Example F1 | Reference Example E42 | 5-chloro-N-((1S,2R)-2-(6-fluoro-2,3-dimethylphenyl)-1-(5-oxo-4,5-dihydro-1,3,4-oxadiazol-2-yl)propyl)-6-(2-oxa-7-azaspiro[3.5]nonane-7-carbonyl)pyridine-2-sulfonamide |
| 157 | Reference Example F1 | Reference Example E71 | N-(5-chloro-8-(N-((1S,2R)-2-(6-fluoro-2,3-dimethylphenyl)-1-(5-oxo-4,5-dihydro-1,3,4-oxadiazol-2-yl)propyl)sulfamoyl)chroman-4-yl)acetamide |
| 158 | Reference Example F1 | 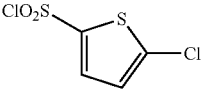 | 5-chloro-N-((1S,2R)-2-(6-fluoro-2,3-dimethylphenyl)-1-(5-oxo-4,5-dihydro-1,3,4-oxadiazol-2-yl)propyl)thiophene-2-sulfonamide |

TABLE 8-4

| Example | Starting Material | ArSO2Cl | Name of the Synthesized Compound |
|---|---|---|---|
| 159 | Reference Example F1 | Reference Example E8 | 5-fluoro-N-((1S,2R)-2-(6-fluoro-2,3-dimethylphenyl)-1-(5-oxo-4,5-dihydro-1,3,4-oxadiazol-2-yl)propyl)-4-oxochroman-8-sulfonamide |
| 160 | Reference Example F1 | 2-chloro-1-methyl-1H-imidazole-4-sulfonyl chloride | 2-chloro-N-((1S,2R)-2-(6-fluoro-2,3-dimethylphenyl)-1-(5-oxo-4,5-dihydro-1,3,4-oxadiazol-2-yl)propyl)-1-methyl-1H-imidazole-4-sulfonamide |
| 161 | Reference Example F1 | 4-chloro-3-(1H-tetrazol-5-yl)benzenesulfonyl chloride | 4-chloro-N-((1S,2R)-2-(6-fluoro-2,3-dimethylphenyl)-1-(5-oxo-4,5-dihydro-1,3,4-oxadiazol-2-yl)propyl)-3-(1H-tetrazol-5-yl)benzenesulfonamide |
| 162 | Reference Example F1 | 2-oxoindoline-5-sulfonyl chloride | N-((1S,2R)-2-(6-fluoro-2,3-dimethylphenyl)-1-(5-oxo-4,5-dihydro-1,3,4-oxadiazol-2-yl)propyl)-2-oxoindoline-5-sulfonamide |
| 163 | Reference Example F1 | 1,3-dioxoisoindoline-5-sulfonyl chloride | N-((1S,2R)-2-(6-fluoro-2,3-dimethylphenyl)-1-(5-oxo-4,5-dihydro-1,3,4-oxadiazol-2-yl)propyl)-1,3-dioxoisoindoline-5-sulfonamide |
| 164 | Reference Example F1 | 2,3-dihydrobenzo[b][1,4]dioxin-5-sulfonyl chloride | N-((1S,2R)-2-(6-fluoro-2,3-dimethylphenyl)-1-(5-oxo-4,5-dihydro-1,3,4-oxadiazol-2-yl)propyl)-2,3-dihydrobenzo[b][1,4]dioxin-5-sulfonamide |
| 165 | Reference Example F1 | 2-oxo-2,3-dihydro-1H-benzo[d]imidazole-5-sulfonyl chloride | N-((1S,2R)-2-(6-fluoro-2,3-dimethylphenyl)-1-(5-oxo-4,5-dihydro-1,3,4-oxadiazol-2-yl)propyl)-2-oxo-2,3-dihydro-1H-benzo[d]imidazole-5-sulfonamide |
| 166 | Reference Example F1 | 2,3-dihydrobenzo[b]thiophene-6-sulfonyl chloride 1,1-dioxide | N-((1S,2R)-2-(6-fluoro-2,3-dimethylphenyl)-1-(5-oxo-4,5-dihydro-1,3,4-oxadiazol-2-yl)propyl)-2,3-dihydrobenzo[b]thiophene-6-sulfonamide 1,1-dioxide |
| 167 | Reference Example F1 | Reference Example E2 | 8-(N-((1S,2R)-2-(3-bromo-6-fluoro-2-methylphenyl)-1-(5-oxo-4,5-dihydro-1,3,4-oxadiazol-2-yl)propyl)sulfamoyl)-5-chloro-4-methylchroman-4-yl acetate |

TABLE 8-5

| Example | Starting Material | ArSO2Cl | Name of the Synthesized Compound |
|---|---|---|---|
| 168 | Reference Example F1 | (3-oxo-3,4-dihydro-2H-benzo[b][1,4]oxazine-5-sulfonyl chloride) | N-((1S,2R)-2-(6-fluoro-2,3-dimethylphenyl)-1-(5-oxo-4,5-dihydro-1,3,4-oxadiazol-2-yl)propyl)-3-oxo-3,4-dihydro-2H-benzo[b][1,4]oxazine-5-sulfonamide |
| 169 | Reference Example F1 | (4-fluoro-3-(methylsulfonyl)benzenesulfonyl chloride) | 4-fluoro-N-((1S,2R)-2-(6-fluoro-2,3-dimethylphenyl)-1-(5-oxo-4,5-dihydro-1,3,4-oxadiazol-2-yl)propyl)-3-(methylsulfonyl)benzenesulfonamide |
| 170 | Reference Example F1 | (2,4-difluoro-6-methoxybenzenesulfonyl chloride) | 2,4-difluoro-N-((1S,2R)-2-(6-fluoro-2,3-dimethylphenyl)-1-(5-oxo-4,5-dihydro-1,3,4-oxadiazol-2-yl)propyl)-6-methoxybenzenesulfonamide |
| 171 | Reference Example F1 | (4-methyl-3-(piperidin-1-ylsulfonyl)benzenesulfonyl chloride) | N-((1S,2R)-2-(6-fluoro-2,3-dimethylphenyl)-1-(5-oxo-4,5-dihydro-1,3,4-oxadiazol-2-yl)propyl)-4-methyl-3-(piperidin-1-ylsulfonyl)benzenesulfonamide |
| 172 | Reference Example F1 | (2,3-dioxo-1,2,3,4-tetrahydroquinoxaline-6-sulfonyl chloride) | N-((1S,2R)-2-(6-fluoro-2,3-dimethylphenyl)-1-(5-oxo-4,5-dihydro-1,3,4-oxadiazol-2-yl)propyl)-2,3-dioxo-1,2,3,4-tetrahydroquinoxaline-6-sulfonamide |
| 173 | Reference Example F1 | (2,3-dihydrobenzo[b][1,4]dioxin-6-sulfonyl chloride) | N-((1S,2R)-2-(6-fluoro-2,3-dimethylphenyl)-1-(5-oxo-4,5-dihydro-1,3,4-oxadiazol-2-yl)propyl)-2,3-dihydrobenzo[b][1,4]dioxin-6-sulfonamide |
| 174 | Reference Example F1 | (8-oxo-5,6,7,8-tetrahydronaphthalene-2-sulfonyl chloride) | N-((1S,2R)-2-(6-fluoro-2,3-dimethylphenyl)-1-(5-oxo-4,5-dihydro-1,3,4-oxadiazol-2-yl)propyl)-8-oxo-5,6,7,8-tetrahydronaphthalene-2-sulfonamide |
| 175 | Reference Example F1 | (1-oxo-1,3-dihydroisobenzofuran-4-sulfonyl chloride) | N-((1S,2R)-2-(6-fluoro-2,3-dimethylphenyl)-1-(5-oxo-4,5-dihydro-1,3,4-oxadiazol-2-yl)propyl)-1-oxo-1,3-dihydroisobenzofuran-4-sulfonamide |

TABLE 8-5-continued

| Example | Starting Material | ArSO2Cl | Name of the Synthesized Compound |
|---|---|---|---|
| 176 | Reference Example F1 | 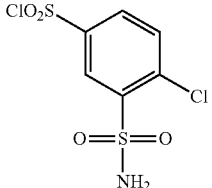 | 4-chloro-N1-((1S,2R)-2-(6-fluoro-2,3-dimethylphenyl)-1-(5-oxo-4,5-dihydro-1,3,4-oxadiazol-2-yl)propyl)benzene-1,3-disulfonamide |

TABLE 8-6

| Example | Starting Material | ArSO2Cl | Name of the Synthesized Compound |
|---|---|---|---|
| 177 | Reference Example F1 | 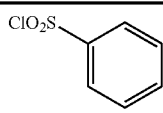 | N-((1S,2R)-2-(6-fluoro-2,3-dimethylphenyl)-1-(5-oxo-4,5-dihydro-1,3,4-oxadiazol-2-yl)propyl)benzenesulfonamide |
| 178 | Reference Example F1 | 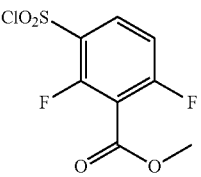 | methyl 2,6-difluoro-3-(N-((1S,2R)-2-(6-fluoro-2,3-dimethylphenyl)-1-(5-oxo-4,5-dihydro-1,3,4-oxadiazol-2-yl)propyl)sulfamoyl)benzoate |
| 179 | Reference Example F1 | 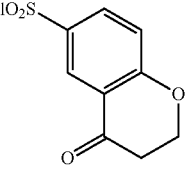 | N-((1S,2R)-2-(6-fluoro-2,3-dimethylphenyl)-1-(5-oxo-4,5-dihydro-1,3,4-oxadiazol-2-yl)propyl)-4-oxochroman-6-sulfonamide |
| 180 | Reference Example F1 | Reference Example E53 | methyl 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)-4-nitrobenzoate |
| 181 | Reference Example F1 | 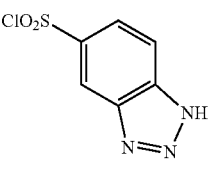 [SMILES: O=S(=O)(Cl)c1ccc2[nH]nnc2c1] | N-((1S,2R)-2-(6-fluoro-2,3-dimethylphenyl)-1-(5-oxo-4,5-dihydro-1,3,4-oxadiazol-2-yl)propyl)-1H-benzo[d][1,2,3]triazole-5-sulfonamide |
| 182 | Reference Example F1 | 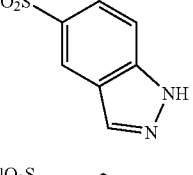 | N-((1S,2R)-2-(6-fluoro-2,3-dimethylphenyl)-1-(5-oxo-4,5-dihydro-1,3,4-oxadiazol-2-yl)propyl)-1H-indazole-5-sulfonamide |
| 183 | Reference Example F1 | 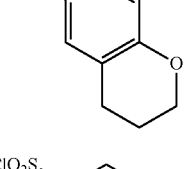 | N-((1S,2R)-2-(6-fluoro-2,3-dimethylphenyl)-1-(5-oxo-4,5-dihydro-1,3,4-oxadiazol-2-yl)propyl)chroman-6-sulfonamide |
| 184 | Reference Example F1 | 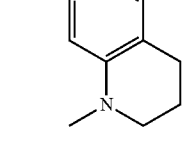 | N-((1S,2R)-2-(6-fluoro-2,3-dimethylphenyl)-1-(5-oxo-4,5-dihydro-1,3,4-oxadiazol-2-yl)propyl)-1-methyl-1,2,3,4-tetrahydroquinoline-7-sulfonamide |

TABLE 8-6-continued

| Example | Starting Material | ArSO2Cl | Name of the Synthesized Compound |
|---|---|---|---|
| 185 | Reference Example F10 | (structure: ClO2S-phenyl with OMe and Cl) | (S)-4-chloro-N-(2-(6-fluoro-2,3-dimethylphenyl)-1-(5-oxo-4,5-dihydro-1,3,4-oxadiazol-2-yl)allyl)-2-methoxybenzenesulfonamide |

TABLE 8-7

| Example | Starting Material | ArSO2Cl | Name of the Synthesized Compound |
|---|---|---|---|
| 338 | Reference Example F1 | (structure: ClO2S-phenyl with OCF3 and Br) | 4-bromo-N-((1S,2R)-(6-fluoro-2,3-dimethylphenyl)-1-(5-oxo-4,5-dihydro-1,3,4-oxadiazol-2-yl)propyl)-2-(trifluoromethoxy)benzenesulfonamide |
| 339 | Reference Example F1 | (structure: ClO2S-phenyl with 2F and Br) | 4-bromo-2,5-difluoro-N-((1S,2R)-(6-fluoro-2,3-dimethylphenyl)-1-(5-oxo-4,5-dihydro-1,3,4-oxadiazol-2-yl)propyl)benzenesulfonamide |
| 340 | Reference Example F1 | (structure: ClO2S-phenyl with NO2) | N-((1S,2R)-(6-fluoro-2,3-dimethylphenyl)-1-(5-oxo-4,5-dihydro-1,3,4-oxadiazol-2-yl)propyl)-4-nitrobenzenesulfonamide |
| 341 | Reference Example F1 | (structure: ClO2S-phenyl with CN) | 4-cyano-N-((1S,2R)-(6-fluoro-2,3-dimethylphenyl)-1-(5-oxo-4,5-dihydro-1,3,4-oxadiazol-2-yl)propyl)benzenesulfonamide |
| 342 | Reference Example F1 | (structure: ClO2S-phenyl with OMe and CN) | 4-cyano-N-((1S,2R)-(6-fluoro-2,3-dimethylphenyl)-1-(5-oxo-4,5-dihydro-1,3,4-oxadiazol-2-yl)propyl)-2-methoxybenzenesulfonamide |
| 343 | Reference Example F1 | (structure: ClO2S-phenyl with CN and Br) | 4-bromo-3-cyano-N-((1S,2R)-(6-fluoro-2,3-dimethylphenyl)-1-(5-oxo-4,5-dihydro-1,3,4-oxadiazol-2-yl)propyl)benzenesulfonamide |

Example 186

2,4-difluoro-N-((1S,2R)-2-(6-fluoro-2,3-dimethylphenyl)-1-(5-oxo-4,5-dihydro-1,3,4-oxadiazol-2-yl)propyl)-3-(2-hydroxypropan-2-yl)benzenesulfonamide Step 1

Methyl 3-(chlorosulfonyl)-2,6-difluorobenzoate (33 mg) was added to a pyridine (1.0 mL) solution of 5-((1S,2R)-1-amino-2-(6-fluoro-2,3-dimethylphenyl)propyl)-1,3,4-oxadiazol-2(3H)-one monohydrochloride (20 mg) obtained from Reference Example F1, and the reaction solution was stirred for 12 hours at room temperature. The reaction solution was concentrated under reduced pressure, and the obtained residue was purified by silica gel column chromatography (eluent: hexane/ethyl acetate) to obtain methyl 2,6-difluoro-3-(N-((1S,2R)-2-(6-fluoro-2,3-dimethylphenyl)-1-(5-oxo-4,5-dihydro-1,3,4-oxadiazol-2-yl)propyl)sulfamoyl)benzoate (12.5 mg).

Step 2

To a THF (2.0 mL) solution of methyl 2,6-difluoro-3-(N-((1S,2R)-2-(6-fluoro-2,3-dimethylphenyl)-1-(5-oxo-4,5-dihydro-1,3,4-oxadiazol-2-yl)propyl)sulfamoyl)benzoate (12.5 mg) obtained from the above Step 1, a diethyl ether (3.0 M, 84 µL) solution of methylmagnesium bromide was added dropwise at 0° C., and the reaction solution was stirred for 1 hour at room temperature. A saturated ammonium chloride aqueous solution (10 mL) was added dropwise in an ice bath, ethyl acetate (10 mL) was added, and the layers were separated. The organic layer was washed successively with hydrochloric acid (1 M, 10 mL), water (10 mL) and saturated saline (10 mL), dried over anhydrous magnesium sulfate, and concentrated under reduced pressure. The residue was purified by silica gel column chromatography (eluent: hexane/ethyl acetate) to obtain the title compound.

Examples 187 to 195

According to the method of Example 186, the following compounds of Examples 187 to 195 were synthesized. The necessary raw materials are listed in the following table.

TABLE 9

| Example | Starting Material | ArSO2Cl | Name of the Synthesized Compound |
|---|---|---|---|
| 187 | Reference Example F5 | [structure] | 4-chloro-N-((1S,2R)-2-(2,3-dihydro-1H-inden-4-yl)-1-(5-oxo-4,5-dihydro-1,3,4-oxadiazol-2-yl)propyl)-2-(2-hydroxypropan-2-yl)benzenesulfonamide |
| 188 | Reference Example F5 | [structure] | 4-bromo-N-((1S,2R)-2-(2,3-dihydro-1H-inden-4-yl)-1-(5-oxo-4,5-dihydro-1,3,4-oxadiazol-2-yl)propyl)-3-(2-hydroxypropan-2-yl)benzenesulfonamide |
| 189 | Reference Example F5 | [structure] | N-((1S,2R)-2-(2,3-dihydro-1H-inden-4-yl)-1-(5-oxo-4,5-dihydro-1,3,4-oxadiazol-2-yl)propyl)-2,4-difluoro-3-(2-hydroxypropan-2-yl)benzenesulfonamide |
| 190 | Reference Example F5 | [structure] | N-((1S,2R)-2-(2,3-dihydro-1H-inden-4-yl)-1-(5-oxo-4,5-dihydro-1,3,4-oxadiazol-2-yl)propyl)-4-(2-hydroxypropan-2-yl)-3-methoxythiophene-2-sulfonamide |
| 191 | Reference Example F5 | [structure] | N-((1S,2R)-2-(2,3-dihydro-1H-inden-4-yl)-1-(5-oxo-4,5-dihydro-1,3,4-oxadiazol-2-yl)propyl)-3-(2-hydroxypropan-2-yl)-2,4-dimethoxybenzenesulfonamide |
| 192 | Reference Example F5 | Reference Example E10 | 5-chloro-N-((1S,2R)-2-(2,3-dihydro-1H-inden-4-yl)-1-(5-oxo-4,5-dihydro-1,3,4-oxadiazol-2-yl)propyl)-6-(2-hydroxypropan-2-yl)pyridine-2-sulfonamide |
| 193 | Reference Example F1 | Reference Example E10 | 5-chloro-N-((1S,2R)-2-(6-fluoro-2,3-dimethylphenyl)-1-(5-oxo-4,5-dihydro-1,3,4-oxadiazol-2-yl)propyl)-6-(2-hydroxypropan-2-yl)pyridine-2-sulfonamide |
| 194 | Reference Example F1 | [structure] | N-((1S,2R)-2-(6-fluoro-2,3-dimethylphenyl)-1-(5-oxo-4,5-dihydro-1,3,4-oxadiazol-2-yl)propyl)-8-hydroxy-8-methyl-5,6,7,8-tetrahydronaphthalene-2-sulfonamide |

TABLE 9-continued

| Example | Starting Material | ArSO2Cl | Name of the Synthesized Compound |
|---|---|---|---|
| 195 | Reference Example F1 | ClO2S- (4-oxo-chroman-6-yl) | N-((1S,2R)-2-(6-fluoro-2,3-dimethylphenyl)-1-(5-oxo-4,5-dihydro-1,3,4-oxadiazol-2-yl)propyl)-4-hydroxy-4-methylchroman-6-sulfonamide |

Example 196

5-fluoro-2-(N-((1S,2R)-2-(6-fluoro-2,3-dimethylphenyl)-1-(5-oxo-4,5-dihydro-1,3,4-oxadiazol-2-yl)propyl)sulfamoyl)-4-(2-hydroxypropan-2-yl)benzamide

Step 1

From 5-((1S,2R)-1-amino-2-(6-fluoro-2,3-dimethylphenyl)propyl)-1,3,4-oxadiazol-2(3H)-one monohydrochloride (60 mg) obtained from Reference Example F1 and methyl 2-fluoro-5-(chlorosulfonyl)-4-cyanobenzoate (94 mg) obtained in Reference Example E15, in accordance with the method of Example 129, methyl 4-(cyano-2-fluoro-5 (N-((1S,2R)-2-(6-fluoro-2,3-dimethylphenyl)-1-(5-oxo-4,5-dihydro-1,3,4-oxadiazol-2-yl)propyl)sulfamoyl)benzoate (49 mg) was obtained.

Step 2

From methyl 4-cyano-2-fluoro-5-(N-((1S,2R)-2-(6-fluoro-2,3-dimethylphenyl)-1-(5-oxo-4,5-dihydro-1,3,4-oxadiazol-2-yl)propyl)sulfamoyl)benzoate (49 mg) obtained from the above Step 1, according to the method of Example 186 Step 2, 2-cyano-4-fluoro-N-((1S,2R)-2-(6-fluoro-2,3-dimethylphenyl)-1-(5-oxo-4,5-dihydro-1,3,4-oxadiazol-2-yl)propyl)-5-(2-hydroxypropan-2-yl)benzenesulfonamide (27.5 mg) was obtained.

Step 3

From 2-cyano-4-fluoro-N-((1S,2R)-2-(6-fluoro-2,3-dimethylphenyl)-1-(5-oxo-4,5-dihydro-1,3,4-oxadiazol-2-yl)propyl)-5-(2-hydroxypropan-2-yl)benzenesulfonamide (27.5 mg) obtained from the above Step 2, according to the method of Example 1 Step 3, the title compound was obtained.

Examples 197 to 199

According to the method of Example 129, Example 186 Step 2, Example 1 Step 3, the following compounds of Examples 197 to 199 were synthesized. The necessary raw materials are listed in the following table. However, for Example 199, the synthesis was carried out using 1-propynyl magnesium bromide instead of methyl magnesium bromide.

TABLE 10

| Example | Starting Material | ArSO2Cl | Name of the Synthesized Compound |
|---|---|---|---|
| 197 | Reference Example F1 | Reference Example E13 | 2-(N-((1S,2R)-2-(5-fluoro-2,3-dimethylphenyl)-1-(5-oxo-4,5-dihydro-1,3,4-oxadiazol-2-yl)propyl)sulfamoyl)-4-(2-hydroxypropan-2-yl)benzamide |
| 198 | Reference Example F1 | Reference Example E16 | 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)-4-(2-hydroxypropan-2-yl)benzamide |
| 199 | Reference Example F1 | Reference Example E13 | 2-(N-((1S,2R)-2-(6-fluoro-2,3-dimethylphenyl)-1-(5-oxo-4,5-dihydro-1,3,4-oxadiazol-2-yl)propyl)sulfamoyl)-4-(hydroxyhepta-2,5-diyn-4-yl)benzamide |

Example 200

5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide Isomer A and Isomer B 1:1 diastereomer mixture of 5-chloro-8-(N-((1S,2R)-2-(6-fluoro-2,3-dimethylphenyl)-1-(5-oxo-4,5-dihydro-1,3,4-oxadiazol-2-yl)propyl)sulfamoyl)-4-methyl-d3-chroman-4-yl acetate (59 mg) obtained from Example 129 was dissolved in methanol (2.0 mL) and water (1.0 mL), lithium hydroxide (5 mg) was added, and the reaction solution was stirred at 55° C. for 1 hour. After concentrating the reaction solution, hydrochloric acid (1 M, 10 mL) and ethyl acetate (10 mL) were added to the residue, and the layers were separated. The aqueous layer was extracted with ethyl acetate (10 mL), and the combined organic layers were washed with saturated saline (10 mL). The organic layer was dried over anhydrous sodium sulfate and concentrated under reduced pressure. The residue was purified by reverse phase HPLC (water/acetonitrile), and the fractions were concentrated to give each of two diastereomeric products. The substance eluted first was designated Compound A, and the substance eluted later was designated as Compound B.

Examples 201 to 229

According to the method of Example 200, the following compounds of Examples 201 to 229 were synthesized. In the case of separating the diastereomers, the previously eluted compound was designated as A and the later eluted compound as B. The ratio of diastereomers is 1:1 mixture unless otherwise specified. The necessary raw materials are listed in the following table.

TABLE 11-1

| Example | Starting Material | ArSO2Cl | Name of the Synthesized Compound |
|---|---|---|---|
| 201 | Reference Example F5 | Reference Example E33 | 2,4-dichloro-N-((1S,2R)-2-(2,3-dihydro-1H-inden-4-yl)-1-(5-oxo-4,5-dihydro-1,3,4-oxadiazol-2-yl)propyl)-3-(1-hydroxyethyl)benzenesulfonamide (diastereomer mixture) |
| 202 | Reference Example F5 | Reference Example E34 | 5-chloro-N-((1S,2R)-2-(2,3-dihydro-1H-inden-4-yl)-1-(5-oxo-4,5-dihydro-1,3,4-oxadiazol-2-yl)propyl)-6-(1-hydroxyethyl)pyridine-2-sulfonamide (diastereomer mixture) |
| 203 | Reference Example F2 | Reference Example E44 | 4-chloro-N-((1S,2R)-2-(2,3-dimethylphenyl)-1-(5-oxo-4,5-dihydro-1,3,4-oxadiazol-2-yl)propyl)-3-(1-hydroxyethyl)-2-methoxybenzenesulfonamide (diastereomer mixture) |
| 204 | Reference Example F1 | Reference Example E44 | 4-chloro-N-((1S,2R)-2-(6-fluoro-2,3-dimethylphenyl)-1-(5-oxo-4,5-dihydro-1,3,4-oxadiazol-2-yl)propyl)-3-(1-hydroxyethyl)-2-methoxybenzenesulfonamide (diastereomer mixture) |
| 205 | Reference Example F3 | Reference Example E44 | 4-chloro-N-((1S,2R)-2-(2-fluoronaphthalene-1-yl)-1-(5-oxo-4,5-dihydro-1,3,4-oxadiazol-2-yl)propyl)-3-(1-hydroxyethyl)-2-methoxybenzenesulfonamide(diastereomer mixture) |
| 206A | Reference Example F9 | Reference Example E44 | 4-chloro-N-((1S,2R)-2-(3-ethyl-6-fluoro-2-methylphenyl)-1-(5-oxo-4,5-dihydro-1,3,4-oxadiazol-2-yl)propyl)-3-(1-hydroxyethyl)-2-methoxybenzenesulfonamide |
| 207-A 207-B | Reference Example F1 | Reference Example E2 | 5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methylchroman-8-sulfonamide |
| 208A 208-B | Reference Example F1 | Reference Example E44 | 4-chloro-N-((1S,2R)-2-(6-fluoro-2,3-dimethylphenyl)-1-(5-oxo-4,5-dihydro-1,3,4-oxadiazol-2-yl)propyl)-3-(1-hydroxyethyl)-2-methoxybenzenesulfonamide |
| 209A 207-B | Reference Example F7 | Reference Example E2 | 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methylchroman-8-sulfonamide |
| 210 | Reference Example F1 | ClO2S-  structure with methyl 5-chloro-2-(chlorosulfonyl)benzoate | 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzoic acid |

TABLE 11-2

| Example | Starting Material | ArSO2Cl | Name of the Synthesized Compound |
|---|---|---|---|
| 211A | Reference Example F1 | Reference Example E6 | N-((1S,2R)-2-(5-fluoro-2,3-dimethylphenyl)-1-(5-oxo-4,5-dihydro-1,3,4-oxadiazol-2-yl)propyl)-4-hydroxy-4-(tifluoromethyl)chroman-8-sulfonamide |
| 212 | Reference Example F1 | Reference Example E46 | 4-chloro-N-((1S,2R)-2-(6-fluoro-2,3-dimethylphenyl)-1-(5-oxo-4,5-dihydro-1,3,4-oxadiazol-2-yl)propyl)-3-(2-hydroxypropan-2-yl)-2-methoxybenzenesulfonamide |
| 213 | Reference Example F1 | Reference Example E11 | 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)nicotinic acid |
| 214 | Reference Example F1 | Reference Example E73 | 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)nicotinic acid |
| 215 | Reference Example F1 | Reference Example E10 | 3-chloro-6-(N-((1S,2R)-2-(6-fluoro-2,3-dimethylphenyl)-1-(5-oxo-4,5-dihydro-1,3,4-oxadiazol-2-yl)propyl)sulfamoyl)picolinic acid |
| 216 | Reference Example F1 | Reference Example E45 | 5-chloro-N-((1S,2R)-2-(6-fluoro-2,3-dimethylphenyl)-1-(5-oxo-4,5-dihydro-1,3,4-oxadiazol-2-yl)propyl)-4-(1-hydroxyethyl)-3-methoxypyridine-2-sulfonamide (diastereomer mixture) |
| 217 | Reference Example F1 | Reference Example E28 | 5-chloro-4-fluoro-2-(N-((1S,2R)-2-(6-fluoro-2,3-dimethylphenyl)-1-(5-oxo-4,5-dihydro-1,3,4-oxadiazol-2-yl)propyl)sulfamoyl)benzoic acid |
| 218 | Reference Example F1 | Reference Example E12 | 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)-4-methylbenzoic acid |
| 219 | Reference Example F1 | Reference Example E29 | 5-chloro-3-fluoro-2-(N-((1S,2R)-2-(6-fluoro-2,3-dimethylphenyl)-1-(5-oxo-4,5-dihydro-1,3,4-oxadiazol-2-yl)propyl)sulfamoyl)benzoic acid |
| 220A 220-B | Reference Example F1 | Reference Example E5 | 5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-(tifluoromethyl)chroman-8-sulfonamide |

TABLE 11-2-continued

| Example | Starting Material | ArSO2Cl | Name of the Synthesized Compound |
|---|---|---|---|
| 221 | Reference Example F1 | Reference Example E72 | 5-chloro-N-((1S,2R)-2-(6-fluoro-2,3-dimethylphenyl)-1-(5-oxo-4,5-dihydro-1,3,4-oxadiazol-2-yl)propyl)-6-(2,2,2-trifluoro-1-hydroxyethyl)pyridine-2-sulfonamide (diastereomer mixture) |

TABLE 11-3

| Example | Starting Material | ArSO2Cl | Name of the Synthesized Compound |
|---|---|---|---|
| 222A 222-B | Reference Example F8 | Reference Example E2 | N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methylchroman-8-sulfonamide |
| 223 | Reference Example F1 | Reference Example E17 | 7-(N-((1S,2R)-2-(6-fluoro-2,3-dimethylphenyl)-1-(5-oxo-4,5-dihydro-1,3,4-oxadiazol-2-yl)propyl)sulfamoyl)-2,3-dihydrobenzo[b][1,4]dioxin-6-Carboxylic Acid |
| 224A 224-B | Reference Example F1 | Reference Example E3 | 5-fluoro-N-((1S,2R)-2-(6-fluoro-2,3-dimethylphenyl)-1-(5-oxo-4,5-dihydro-1,3,4-oxadiazol-2-yl)propyl)-4-hydroxy-4-methylchroman-8-sulfonamide |
| 225A | Reference Example F1 | Reference Example E4 | N-((1S,2R)-2-(6-fluoro-2,3-dimethylphenyl)-1-(5-oxo-4,5-dihydro-1,3,4-oxadiazol-2-yl)propyl)-4-hydroxy-4-methyl-5-(tifluoromethyl)chroman-8-sulfonamide |
| 226A 226-B | Reference Example F8 | Reference Example E1 | N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methyl-d3-chroman-8-sulfonamide |

TABLE 11-4

| Example | Starting Material | ArSO2Cl | Name of the Synthesized Compound |
|---|---|---|---|
| 227A 227-B | Reference Example F8 | Reference Example E3 | N-((1S,2R)-2-(3-bromo-6-fluoro-2-methylphenyl)-1-(5-oxo-4,5-dihydro-1,3,4-oxadiazol-2-yl)propyl)-5-fluoro-4-hydroxy-4-methyl-d3-chroman-8-sulfonamide |
| 228A 228-B | Reference Example F7 | Reference Example E1 | 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-d3-chroman-8-sulfonamide |
| 229A 229-B | Reference Example F7 | Reference Example E3 | N-((1S,2R)-2-(3-chloro-6-fluoro-2-methylphenyl)-1-(5-oxo-4,5-dihydro-1,3,4-oxadiazol-2-yl)propyl)-5-fluoro-4-hydroxy-4-methylchroman-8-sulfonamide |

Example 230

5-fluoro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide Isomer A and Isomer B Step 1

Using 5-((1S,2R)-1-amino-2-(6-fluoro-2,3-dimethylphenyl)propyl)-1,3,4-oxadiazol-2(3H)-one monohydrochloride (40 mg) obtained from Reference Example F1 and 5-fluoro-4-oxochroman-8-sulfonyl chloride (60 mg) obtained from Reference Example E8, 5-fluoro-N-((1S,2R)-2-(6-fluoro-2,3-dimethylphenyl)-1-(5-oxo-4,5-dihydro-1,3,4-oxadiazol-2-yl)propyl)-4-oxochroman-8-sulfonamide (44 mg) was obtained in accordance with the method of Example 129.

Step 2

Sodium borohydride (13.5 mg) was added to an ethanol (2.0 mL) solution of 5-fluoro-N-((1S,2R)-2-(6-fluoro-2,3-dimethylphenyl)-1-(5-oxo-4,5-dihydro-1,3,4-oxadiazol-2-yl)propyl)-4-oxochroman-8-sulfonamide (44 mg) obtained from the above Step 1 and the reaction solution was stirred at room temperature for 30 minutes. After concentrating the reaction solution under reduced pressure, water (10 mL) and ethyl acetate (10 mL) were added to the residue, separated, and the aqueous layer was extracted with ethyl acetate (10 mL). The combined organic layer was washed with saturated saline (10 mL), dried over anhydrous sodium sulfate, and concentrated under reduced pressure. The residue was purified by reverse phase HPLC (water/acetonitrile), and the fractions were concentrated to obtain each of two diastereomeric products. The substance eluted first was designated as Compound A, and the substance eluted later was designated as Compound B.

Examples 231 to 244

According to the method of Example 129 and Example 230 Step 2, the compounds of Examples 231 to 244 shown below were synthesized. In the case of separating the diastereomers, the first eluted compound was designated as A and the later eluted compound as B. The ratio of diastereomers is 1:1 mixture unless otherwise specified. The necessary raw materials are listed in the following table.

TABLE 12-1

| Example | Starting Material | ArSO2Cl | Name of the Synthesized Compound |
|---|---|---|---|
| 231 | Reference Example F5 | ClO2S-C6H3(Cl)(C(O)CH3) (structure) | 4-chloro-N-((1S,2R)-2-(2,3-dihydro-1H-inden-4-yl)-1-(5-oxo-4,5-dihydro-1,3,4-oxadiazol-2-yl)propyl)-3-(1-hydroxyethyl)benzenesulfonamide (diastereomer mixture) |
| 232 | Reference Example F4 | Reference Example E7 | 5-chloro-4-hydroxy-N-((1S,2R)-2-(8-methylnaphthalene-1-yl)-1-(5-oxo-4,5-dihydro-1,3,4-oxadiazol-2-yl)propyl)chroman-8-sulfonamide (diastereomer mixture) |
| 233 | Reference Example F3 | Reference Example E7 | 5-chloro-N-((1S,2R)-2-(2-fluoronaphthalene-1-yl)-1-(5-oxo-4,5-dihydro-1,3,4-oxadiazol-2-yl)propyl)-4-hydroxychroman-8-sulfonamide (diastereomer mixture) |
| 234A | Reference Example F3 | Reference Example E7 | 5-chloro-N-((1S,2R)-2-(2-fluoronaphthalene-1-yl)-1-(5-oxo-4,5-dihydro-1,3,4-oxadiazol-2-yl)propyl)-4-hydroxychroman-8-sulfonamide |
| 235A 235-B | Reference Example F1 | Reference Example E7 | 5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide |
| 236 | Reference Example F1 | Reference Example E19 | 4-chloro-N-((1S,2R)-2-(6-fluoro-2,3-dimethylphenyl)-1-(5-oxo-4,5-dihydro-1,3,4-oxadiazol-2-yl)propyl)-2-(1-hydroxyethyl)benzenesulfonamide (diastereomer mixture) |
| 237A | Reference Example F1 | Reference Example E23 | N-((1S,2R)-2-(6-fluoro-2,3-dimethylphenyl)-1-(5-oxo-4,5-dihydro-1,3,4-oxadiazol-2-yl)propyl)-4-hydroxy-2,2-dimethylchroman-8-sulfonamide |
| 238A | Reference Example F7 | Reference Example E7 | 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxychroman-8-sulfonamide |
| 239A | Reference Example F9 | Reference Example E7 | 5-chloro-N-((1S,2R)-2-(3-ethyl-6-fluoro-2-methylphenyl)-1-(5-oxo-4,5-dihydro-1,3,4-oxadiazol-2-yl)propyl)-4-hydroxychroman-8-sulfonamide |

TABLE 12-2

| Example | Starting Material | ArSO2Cl | Name of the Synthesized Compound |
|---|---|---|---|
| 240 | Reference Example F1 | Reference Example E25 | 4-chloro-N-((1S,2R)-2-(6-fluoro-2,3-dimethylphenyl)-1-(5-oxo-4,5-dihydro-1,3,4-oxadiazol-2-yl)propyl)-8-hydroxy-5,6,7,8-tetrahydronaphthalene-1-sulfonamide (diastereomer mixture) |
| 241 | Reference Example F1 | Reference Example E8 | 5-fluoro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide (diastereomer mixture) |
| 242 | Reference Example F1 | Reference Example E30 | 5,7-difluoro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide (diastereomer mixture) |
| 243A 243-B | Reference Example F8 | Reference Example E7 | N-((1S,2R)-2-(3-bromo-6-fluoro-2-methylphenyl)-1-(5-oxo-4,5-dihydro-1,3,4-oxadiazol-2-yl)propyl)-5-chloro-4-hydroxychroman-8-sulfonamide |
| 244A 244-B | Reference Example F1 | Reference Example E9 | N-((1S,2R)-2-(6-fluoro-2,3-dimethylphenyl)-1-(5-oxo-4,5-dihydro-1,3,4-oxadiazol-2-yl)propyl)-4-hydroxy-5-(tifluoromethyl)chroman-8-sulfonamide |

Example 245

5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)nicotinamide

Step 1

Using (2S,3R)-2-amino-3-(6-fluoro-2,3-dimethylphenyl) butanoic acid (100 mg) obtained from Reference Example D1 and methyl 5-chloro-2-(chlorosulfonyl)nicotinate (140 mg) obtained from Reference Example E11, according to the method of Example 1 Steps 1, 2, methyl 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)nicotinate (174 mg) was obtained.

Step 2

Methyl 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)nicotinate (174 mg) obtained from the above Step 1 was dissolved in THF (2.5 mL) and water (2.5 mL), lithium hydroxide (30 mg) was added, and the reaction solution was stirred at 50° C. for 16 hours. The reaction solution was added to hydrochloric acid (1 M, 15 mL) and extracted with ethyl acetate (15 mL). The organic layer was washed with saturated saline (20 mL), dried over anhydrous magnesium sulfate, and concentrated under reduced pressure. The residue was purified by silica gel column chromatography (eluent: hexane/ethyl acetate/2% acetic acid) to obtain 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)nicotinic acid (145 mg).

Step 3

To a toluene (1.2 mL) solution of 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)nicotinic acid (10 mg) obtained from the above Step 2, DMF (30 μL) and thionyl chloride (60 μL) were sequentially added, and the reaction solution was stirred at 95° C. for 40 minutes. The reaction solution was allowed to cool to room temperature and then concentrated under reduced pressure. The THF (2.0 mL) solution of the residue was slowly added dropwise to 28% aqueous ammonia solution (1.0 mL) at −10° C., and the reaction solution was stirred at room temperature for 30 min. The reaction solution was added to hydrochloric acid (1 M, 10 mL) and extracted with ethyl acetate (10 mL). The organic layer was washed with saturated saline (10 mL), dried over anhydrous sodium sulfate, and concentrated under reduced pressure. The residue was purified by silica gel column chromatography (eluent: hexane/ethyl acetate) to give the title compound.

Examples 246 to 264

Compounds of Examples 246 to 264 shown below were synthesized according to the procedures of Example 1 Steps 1 and 2, and Example 245 Step 2 and 3. The necessary raw materials are listed in the following table.

TABLE 13-1

| Example | Starting Material | ArSO2Cl | Amine | Name of the Synthesized Compound |
|---|---|---|---|---|
| 246 | Reference Example D1 | (structure) | \NH/ | 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)-N,N-dimethylbenzamide |
| 247 | Reference Example D1 | (structure) | azetidine-NH | 2-(azetidine-1-carbonyl)-4-chloro-N-((1S,2R)-2-(6-fluoro-2,3-dimethylphenyl)-1-(5-oxo-4,5-dihydro-1,3,4-oxadiazol-2-yl)propyl)benzenesulfonamide |
| 248 | Reference Example D1 | (structure) | H2N-CH2CH2-OH | 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)-N-(2-hydroxyethyl)benzamide |
| 249 | Reference Example D4 | Reference Example E11 | NH3 | 5-chloro-2-(N-((1S,2R)-2-(3-chloro-6-fluoro-2-methylphenyl)-1-(5-oxo-4,5-dihydro-1,3,4-oxadiazol-2-yl)propyl)sulfamoyl)nicotinamide |
| 250 | Reference Example D1 | Reference Example E73 | NH3 | 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)nicotinamide |
| 251 | Reference Example D1 | Reference Example E73 | MeNH2 | 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)-N-methylnicotinamide |
| 252 | Reference Example D1 | Reference Example E10 | MeNH2 | 3-chloro-6-(N-((1S,2R)-2-(6-fluoro-2,3-dimethylphenyl)-1-(5-oxo-4,5-dihydro-1,3,4-oxadiazol-2-yl)propyl)sulfamoyl)-N-methylpicolinamide |
| 253 | Reference Example D1 | Reference Example E10 | \NH/ | 3-chloro-6-(N-((1S,2R)-2-(6-fluoro-2,3-dimethylphenyl)-1-(5-oxo-4,5-dihydro-1,3,4-oxadiazol-2-yl)propyl)sulfamoyl)-N,N-dimethylpicolinamide |

TABLE 13-2

| Example | Starting Material | ArSO2Cl | Amine | Name of the Synthesized Compound |
|---|---|---|---|---|
| 254 | Reference Example D4 | Reference Example E73 | NH3 | 5-bromo-2-(N-((1S,2R)-2-(3-chloro-6-fluoro-2-methylphenyl)-1-(5-oxo-4,5-dihydro-1,3,4-oxadiazol-2-yl)propyl)sulfamoyl)nicotinamide |

TABLE 13-2-continued

| Example | Starting Material | ArSO2Cl | Amine | Name of the Synthesized Compound |
|---|---|---|---|---|
| 255 | Reference Example D1 | Reference Example E28 | NH$_3$ | 5-chloro-4-fluoro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide |
| 256 | Reference Example D1 | (structure: 3-chloro-5-chloro-2-(chlorosulfonyl)benzoic acid methyl ester) | NH$_3$ | 3,5-dichloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide |
| 257 | Reference Example D1 | Reference Example E12 | NH$_3$ | 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)-4-methylbenzamide |
| 258 | Reference Example D1 | Reference Example E29 | NH$_3$ | 5-chloro-3-fluoro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide |
| 259 | Reference Example D1 | Reference Example E14 | NH$_3$ | 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)-4-methoxybenzamide |
| 260 | Reference Example D1 | Reference Example E31 | NH$_3$ | 2-(N-((1S,2R)-2-(6-fluoro-2,3-dimethylphenyl)-1-(5-oxo-4,5-dihydro-1,3,4-oxadiazol-2-yl)propyl)sulfamoyl)-4,5-dimethoxybenzamide |
| 261 | Reference Example D1 | Reference Example E17 | NH$_3$ | 7-(N-((1S,2R)-2-(6-fluoro-2,3-dimethylphenyl)-1-(5-oxo-4,5-dihydro-1,3,4-oxadiazol-2-yl)propyl)sulfamoyl)-2,3-dihydrobenzo[b][1,4]dioxin-6-carboxamide |

TABLE 13-3

| Example | Starting Material | ArSO2Cl | Amine | Name of the Synthesized Compound |
|---|---|---|---|---|
| 262 | Reference Example D1 | Reference Example E53 | NH$_3$ | 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)-4-nitrobenzamide |
| 263 | Reference Example D1 | Reference Example E47 | NH$_3$ | 4-(2,2-difluoroethoxy)-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide |
| 264 | Reference Example D5 | Reference Example E11 | NH$_3$ | 2-(N-((1S,2R)-2-(3-bromo-6-fluoro-2-methylphenyl)-1-(5-oxo-4,5-dihydro-1,3,4-oxadiazol-2-yl)propyl)sulfamoyl)-5-chloronicotinamide |

Example 265

4-amino-N-((1S,2R)-2-(2-fluoronaphthalen-1-yl)-1-(5-oxo-4,5-dihydro-1,3,4-oxadiazol-2-yl)propyl)-2-methoxybenzenesulfonamide Step 1

Using (2S,3R)-2-amino-3-(2-fluoronaphthalen-1-yl)butanoic acid (45 mg) obtained in Reference Example D3 and 2-methoxy-4-nitrobenzene-1-sulfonyl chloride (60 mg), according to the method of Example 1, Steps 1 and 2, N-((1S,2R)-2-(2-fluoronaphthalen-1-yl)-1-(5-oxo-4,5-dihydro-1,3,4-oxadiazol-2-yl)propyl)-2-methoxy-4-nitrobenzenesulfonamide (32 mg) was obtained.

Step 2

N-((1S,2R)-2-(2-fluoronaphthalen-1-yl)-1-(5-oxo-4,5-dihydro-1,3,4-oxadiazol-2-yl)propyl)-2-methoxy-4-nitrobenzenesulfonamide (32 mg) obtained from the above Step 1 was dissolved in ethanol (2.0 mL) and water (1.0 mL), iron (30 mg) and ammonium chloride (20 mg) were sequentially added, and the reaction solution was stirred at 80° C. for 1 hour. The reaction solution was filtered through CELITE, and the residue was washed with ethyl acetate (10 mL). The combined filtrates were concentrated and the residue was purified by silica gel column chromatography (eluent: hexane/ethyl acetate) to give the title compound.

Examples 266 to 272

Compounds of Examples 266 to 272 shown below were synthesized according to the method of Example 1 Steps 1 and 2 and Example 265 Step 2. The necessary raw materials are listed in the following table.

TABLE 14

| Example | Starting Material | ArSO2Cl | Name of the Synthesized Compound |
|---|---|---|---|
| 266 | Reference Example D21 | Cl-SO2-C6H4-NO2 (4-nitro) | 4-amino-N-((1S,2R)-1-(5-oxo-4,5-dihydro-1,3,4-oxadiazol-2-yl)-2-(5,6,7,8-tetrahydronaphthalen-1-yl)propyl)benzenesulfonamide |
| 267 | Reference Example D10 | Cl-SO2-(3-methyl-4-nitrophenyl) | 4-amino-N-((1S,2R)-2-(2,3-dihydro-1H-inden-4-yl)-1-(5-oxo-4,5-dihydro-1,3,4-oxadiazol-2-yl)propyl)-2-methylbenzenesulfonamide |
| 268 | Reference Example D10 | Cl-SO2-(5-nitroquinolin-8-yl) | 5-amino-N-((1S,2R)-2-(2,3-dihydro-1H-inden-4-yl)-1-(5-oxo-4,5-dihydro-1,3,4-oxadiazol-2-yl)propyl)quinoline-8-sulfonamide |
| 269 | Reference Example D13 | Cl-SO2-(3-methoxy-4-nitrophenyl) | 4-amino-2-methoxy-N-((1S,2R)-2-(8-methylnaphthalen-1-yl)-1-(5-oxo-4,5-dihydro-1,3,4-oxadiazol-2-yl)propyl)benzenesulfonamide |
| 270 | Reference Example D10 | Cl-SO2-(3-methoxy-4-nitrophenyl) | 4-amino-N-((1S,2R)-2-(2,3-dihydro-1H-inden-4-yl)-1-(5-oxo-4,5-dihydro-1,3,4-oxadiazol-2-yl)propyl)-2-methoxybenzenesulfonamide |
| 271 | Reference Example D1 | Cl-SO2-(4-chloro-2-nitrophenyl) | 2-amino-4-chloro-N-((1S,2R)-2-(6-fluoro-2,3-dimethylphenyl)-1-(5-oxo-4,5-dihydro-1,3,4-oxadiazol-2-yl)propyl)benzenesulfonamide |
| 272 | Reference Example D1 | Reference Example E53 | methyl 4-amino-5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzoate |

Example 273

5-chloro-N-((1S,2R)-2-(6-fluoro-2,3-dimethylphenyl)-1-(5-oxo-4,5-dihydro-1,3,4-oxadiazol-2-yl)propyl)-4-(2-hydroxyethyl)-3-oxo-3,4-dihydro-2H-benzo[b][1,4]oxazine-8-sulfonamide

Step 1

Using (2S,3R)-2-amino-3-(6-fluoro-2,3-dimethylphenyl) butanoic acid (50 mg) obtained in Reference Example D1 and 4-(2-(benzyloxy)ethyl)-5-chloro-3,4-dihydro-2H-benzo[b][1,4]oxazine-8-sulfonyl chloride (142 mg) obtained in Reference Example E65, according to the method of Example 1 Steps 1 and 2, 4-(2-(benzyloxy)ethyl)-5-chloro-N-((1S,2R)-2-(6-fluoro-2,3-dimethylphenyl)-1-(5-oxo-4,5-dihydro-1,3,4-oxadiazol-2-yl)propyl)-3-oxo-3,4-dihydro-2H-benzo[b][1,4]oxazine-8-sulfonamide (22 mg) was obtained.

Step 2

To a THF (1.5 mL) solution of 4-(2-(benzyloxy)ethyl)-5-chloro-N-((1S,2R)-2-(6-fluoro-2,3-dimethylphenyl)-1-(5-oxo-4,5-dihydro-1,3,4-oxadiazol-2-yl)propyl)-3-oxo-3,4-dihydro-2H-benzo[b][1,4]oxazine-8-sulfonamide (20 mg) obtained from the above Step 1, 20 wt % palladium hydroxide (30 mg) was added, and the reaction mixture was stirred at room temperature for 30 minutes under hydrogen atmosphere. The reaction solution was filtered through CELITE, and the residue was washed with hexane/ethyl acetate=1/1 (10 mL), and the combined filtrate was concentrated under reduced pressure. The residue was purified by silica gel column chromatography (eluent: hexane/ethyl acetate) to obtain the title compound.

Example 274

N-(5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)phenyl)acetamide To a dichloromethane (1.0 mL) solution of 2-Amino-4-chloro-N-((1S,2R)-2-(6-fluoro-2,3-dimethylphenyl)-1-(5-oxo-4,5-dihydro-1,3,4-oxadiazol-2-yl)propyl)benzenesulfonamide (5.0 mg) obtained from Example 271, Pyridine (5.0 µL) and acetic anhydride (4.0 µL) were sequentially added, and the reaction solution was stirred at room temperature for 3 hours. The reaction solution was added to hydrochloric acid (1 M, 5.0 mL) and extracted with ethyl acetate (10 mL). The organic layer was washed with saturated saline (10 mL), dried over anhydrous sodium sulfate, and concentrated under reduced pressure. The residue was purified by silica gel column chromatography (eluent: hexane/ethyl acetate) to give the title compound.

Example 275

5-chloro-N-((1S,2R)-2-(6-fluoro-2,3-dimethylphenyl)-1-(5-oxo-4,5-dihydro-1,3,4-oxadiazol-2-yl)propyl)-3,4-dihydro-2H-benzo[b][1,4]oxazine-8-sulfonamide

Step 1

From 5-((1S,2R)-1-amino-2-(6-fluoro-2,3-dimethylphenyl)propyl)-1,3,4-oxadiazol-2(3H)-one monohydrochloride (14.3 mg) obtained in Reference Example F1 and tert-butyl 5-chloro-8-(chlorosulfonyl)-2H-benzo[b][1,4]oxazin-4(3H)-carboxylate (25.3 mg) obtained in Reference Example E58, according to the method of Example 129, tert-butyl 5-chloro-8-(N-((1S,2R)-2-(6-fluoro-2,3-dimethylphenyl)-1-(5-oxo-4,5-dihydro-1,3,4-oxadiazol-2-yl)propyl)sulfamoyl)-2H-benzo[b][1,4]oxazine-4(3H)-carboxylate (30.4 mg) was obtained.

Step 2

To tert-butyl 5-chloro-8-(N-((1S,2R)-2-(6-fluoro-2,3-dimethylphenyl)-1-(5-oxo-4,5-dihydro-1,3,4-oxadiazol-2-yl)propyl)sulfamoyl)-2H-benzo[b][1,4]oxazin-4(3H)-carboxylate (30.4 mg) obtained from the above Step 1, hydrochloric acid-1,4-dioxane (4 M, 5.0 mL) was added, and the reaction solution was stirred at room temperature for 1 hour. The reaction solution was concentrated under reduced pressure, and the obtained residue was purified by reversed phase HPLC (water/acetonitrile) to obtain the title compound.

Examples 276 to 283

Compounds of Examples 276 to 283 shown below were synthesized according to the method of Example 129 and Example 275 Step 2. The necessary raw materials are listed in the following table.

TABLE 15

| Example | Starting Material | ArSO2Cl | Name of the Synthesized Compound |
| --- | --- | --- | --- |
| 276 | Reference Example D10 | Reference Example E56 | methyl 6-amino-3-(N-((1S,2R)-2-(2,3-dihydro-1H-inden-4-yl)-1-(5-oxo-4,5-dihydro-1,3,4-oxadiazol-2-yl)propyl)sulfamoyl)-2-methoxybenzoate |
| 277 | Reference Example D1 | Reference Example E52 | 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)-N-methylbenzamide |
| 278 | Reference Example D1 | Reference Example E70 | 4-amino-5-chloro-N-((1S,2R)-2-(6-fluoro-2,3-dimethylphenyl)-1-(5-oxo-4,5-dihydro-1,3,4-oxadiazol-2-yl)propyl)chroman-8-sulfonamide |
| 279 | Reference Example D1 | Reference Example E55 | 2-(1-aminocyclopropyl)-4-chloro-N-((1S,2R)-2-(6-fluoro-2,3-dimethylphenyl)-1-(5-oxo-4,5-dihydro-1,3,4-oxadiazol-2-yl)propyl)benzenesulfonamide |
| 280 | Reference Example D1 | Reference Example E59 | N-((1S,2R)-2-(6-fluoro-2,3-dimethylphenyl)-1-(5-oxo-4,5-dihydro-1,3,4-oxadiazol-2-yl)propyl)-3,4-dihydro-2H-benzo[b][1,4]oxazine-8-sulfonamide |
| 281 | Reference Example D1 | Reference Example E24 | N-((1S,2R)-2-(6-fluoro-2,3-dimethylphenyl)-1-(5-oxo-4,5-dihydro-1,3,4-oxadiazol-2-yl)propyl)-1,2,3,4-tetrahydroisoquinoline-5-sulfonamide |
| 282 | Reference Example D1 | Reference Example E51 | N-(benzyloxy)-5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide |
| 283 | Reference Example D1 | Reference Example E41 | 6-(3-aminopyrrolidine-1-carbonyl)-5-chloro-N-((1S,2R)-2-(6-fluoro-2,3-dimethylphenyl)-1-(5-oxo-4,5-dihydro-1,3,4-oxadiazol-2-yl)propyl)pyridine-2-sulfonamide |

Example 284

4-acetyl-5-chloro-N-((1S,2R)-2-(2,3-dimethylphenyl)-1-(5-oxo-4,5-dihydro-1,3,4-oxadiazol-2-yl)propyl)-3,4-dihydro-2H-benzo[b][1,4]oxazine-8-sulfonamide To a dichloromethane (1.0 mL) solution of 5-chloro-N-((1S,2R)-2-(6-fluoro-2,3-dimethylphenyl)-1-(5-oxo-4,5-dihydro-1,3,4-oxadiazol-2-yl)propyl)-3,4-dihydro-2H-benzo[b][1,4]oxazine-8-sulfonamide (31.5 mg) obtained in Example 275, triethylamine (40 µL) and acetic anhydride (20 µL) were sequentially added, and the reaction solution was stirred at room temperature for 2 hours. The reaction solution was concentrated under reduced pressure, and the obtained residue was purified by reversed phase HPLC (water/acetonitrile) to obtain the title compound.

Example 285

2-(N-((1S,2R)-2-(6-fluoro-2,3-dimethylphenyl)-1-(5-oxo-4,5-dihydro-1,3,4-oxadiazol-2-yl)propyl)sulfamoyl)-N-hydroxybenzamide

Step 1

Using (2S,3R)-2-amino-3-(6-fluoro-2,3-dimethylphenyl) butanoic acid (125 mg) obtained in Reference Example D1 and tert-butylbenzyloxy (5-chloro-2-(chlorosulfonyl)benzoyl)carbamate (280 mg) obtained in Reference Example E51 as a starting material, according to the method of Example 1 Step 1, (2S,3R)-2-(2-((benzyloxy)(tert-butoxycarbonyl)carbamoyl)-4-chlorophenylsulfonamido)-3-(6-fluoro-2,3-dimethylphenyl)butanoic acid (250 mg) was synthesized.

Step 2

(2S,3R)-2-(2-((benzyloxy)(tert-butoxycarbonyl)carbamoyl)-4-chlorophenylsulfonamido)-3-(6-fluoro-2,3-dimethylphenyl)butanoic acid (250 mg) obtained in the above Step 1 was dissolved in hydrochloric acid-1,4-dioxane (4 M, 4 mL), and the reaction solution was stirred at 45° C. for 2.5 hours. The reaction solution was concentrated under reduced pressure and the residue was purified by silica gel column chromatography (eluent: hexane/ethyl acetate/2% acetic acid) to give (2S,3R)-2-(2-((benzyloxy)carbamoyl)-4-chlorophenylsulfonamido)-3-(6-fluoro-2,3-dimethylphenyl)butanoic acid (215 mg).

Step 3

From (2S,3R)-2-(2-((benzyloxy)carbamoyl)-4-chlorophenylsulfonamido)-3-(6-fluoro-2,3-dimethylphenyl)butanoic acid (215 mg) obtained from the above Step 2, according to the method of Example 1 Step 2, N-(benzyloxy)-5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide (75 mg) was given.

Step 4

To a methanol (4.0 mL) solution of N-(benzyloxy)-5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide (75 mg) obtained from the above Step 3, 10% palladium-carbon (55 mg) was added, and the reaction solution was stirred under a hydrogen atmosphere for 1.5 hours. Insoluble matter was removed by CELITE filtration, and the residue was washed with methanol (10 mL). The combined filtrate was concentrated under reduced pressure, and the residue was purified by silica gel column chromatography (eluent: hexane/ethyl acetate) to give the title compound.

Example 286

5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)-N-hydroxybenzamide To dichloromethane (3.0 mL) solution of N-(benzyloxy)-5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide (66 mg) obtained from Example 285 Step 3, boron tribromide (1.0 M, 170 μL) was added at −60° C., and the reaction solution was stirred at 0° C. for 1 hour. Methanol (1.0 mL) was added to the reaction solution, and the mixture was concentrated under reduced pressure. The residue was purified by silica gel column chromatography (eluent: hexane/ethyl acetate/2% acetic acid) to obtain the title compound.

Example 287

5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzothioamide To a toluene (500 μL) solution of 5-chloro-2-((1S,2R)-2-(6-fluoro-2,3-dimethylphenyl)-1-(2-oxo-3H-1,3,4-oxadiazol-5-yl)propyl)sulfamoyl)benzamide (15 mg) obtained in Example 5, Lawesson's reagent (20 mg) was added at room temperature, and the reaction solution was stirred at 100° C. for 12 hours. After allowing to cool to room temperature and concentrating under reduced pressure, the obtained residue was purified by silica gel column chromatography (eluent: hexane/ethyl acetate) to obtain the title compound.

Example 288

5-chloro-N-((1S,2R)-2-(6-fluoro-2,3-dimethylphenyl)-1-(5-oxo-4,5-dihydro-1,3,4-oxadiazol-2-yl)propyl)-4-methyl-3,4-dihydro-2H-benzo[b][1,4]oxazine-8-sulfonamide To a methanol (1.0 mL) solution of 5-chloro-N-((1S,2R)-2-(6-fluoro-2,3-dimethylphenyl)-1-(5-oxo-4,5-dihydro-1,3,4-oxadiazol-2-yl)propyl)-3,4-dihydro-2H-benzo[b][1,4]oxazine-8-sulfonamide (48 mg) obtained in Example 275, acetic acid (20 μL) and aqueous 37% formaldehyde solution (30 μL) were added successively, and the reaction solution was stirred at room temperature for 30 minutes. Sodium borohydride (12 mg) was added to the reaction solution, and the mixture was further stirred for 20 minutes. Water (15 mL) was added to the reaction solution, and the mixture was extracted with ethyl acetate/hexane=1/1 (15 mL). The organic layer was washed with saturated saline (10 mL), dried over anhydrous sodium sulfate, and concentrated under reduced pressure. The residue was purified by reverse phase HPLC (water/acetonitrile) to give the title compound.

Example 289

5-chloro-N-((1S,2R)-2-(3-chloro-6-fluoro-2-methylphenyl)-1-(5-oxo-4,5-dihydro-1,3,4-oxadiazol-2-yl)propyl)-4-methyl-3,4-dihydro-2H-benzo[b][1,4]oxazine-8-sulfonamide

Step 1

From 5-((1S,2R)-1-amino-2-(3-chloro-6-fluoro-2-methylphenyl)propyl)-1,3,4-oxadiazol-2 (3H)-one monohydrochloride (10.3 mg) obtained in Reference Example F7 and tert-butyl 5-chloro-8-(chlorosulfonyl)-2H-benzo[b][1,4]oxazin-4 (3H)-carboxylate (25.3 mg) obtained from Reference Example E58, according to the method of Example 129, tert-butyl 5-chloro-8-(N-((1S,2R)-2-(3-chloro-6-fluoro-2-methylphenyl)-1-(5-oxo-4,5-dihydro-1,3,4-oxadiazol-2-yl)propyl)sulfamoyl)-2H-benzo[b][1,4]oxazin-4 (3H)-carboxylate (25.4 mg) was obtained.

Step 2

To tert-butyl 5-chloro-8-(N-((1S,2R)-2-(3-chloro-6-fluoro-2-methylphenyl)-1-(5-oxo-4,5-dihydro-1,3,4-oxadiazol-2-yl)propyl)sulfamoyl)-2H-benzo[b][1,4]oxazin-4 (3H)-carboxylate (25.4 mg) obtained from the above Step 1, hydrochloric acid-1,4-dioxane (4 M, 5.0 mL) was added, and the reaction solution was stirred at room temperature for 1 hour. The reaction solution was concentrated under reduced pressure, and the obtained residue was purified by reversed phase HPLC (water/acetonitrile) to obtain 5-chloro-N-((1S,2R)-2-(3-chloro-6-fluoro-2-methylphenyl)-1-(5-oxo-4,5-dihydro-1,3,4-oxadiazol-2-yl)propyl)-3,4-dihydro-2H-benzo[b][1,4]oxazine-8-sulfonamide (15.2 mg).

Step 3

From 5-chloro-N-((1S,2R)-2-(3-chloro-6-fluoro-2-methylphenyl)-1-(5-oxo-4,5-dihydro-1,3,4-oxadiazol-2-yl)propyl)-3,4-dihydro-2H-benzo[b][1,4]oxazine-8-sulfonamide (15.2 mg) obtained from the above Step 2, according to the method of Example 288, the title compound was synthesized.

Example 290

4-chloro-N-((1S)-2-(6-fluoro-2,3-dimethylphenyl)-2-hydroxy-1-(5-oxo-4,5-dihydro-1,3,4-oxadiazol-2-yl)ethyl)-2-methoxybenzenesulfonamide Step 1

Using (2S)-2-amino-3-(6-fluoro-2,3-dimethylphenyl)-3-hydroxypropionic acid (139 mg) obtained from Reference Example D56 and 4-chloro-2-methoxybenzenesulfonyl chloride (175 mg), according to the method of Example 1 Step 1, (2S)-2-(4-chloro-2-methoxyphenylsulfonamido)-3-(6-fluoro-2,3-dimethylphenyl)-3-hydroxypropionic acid (163 mg) was synthesized.

Step 2

To a DMF (10 mL) solution of (2S)-2-(4-chloro-2-methoxyphenylsulfonamido)-3-(6-fluoro-2,3-dimethylphenyl)-3-hydroxypropionic acid (163 mg) obtained from the above Step 1, Imidazole (753 mg) and tert-butyldimethylchlorosilane (563 mg) were sequentially added, and the reaction solution was stirred at 60° C. for 12 hours. The reaction solution was added to water (20 mL) and extracted with ethyl acetate/hexane=1/1 (30 mL). The organic layer was washed with saturated saline (20 mL), dried over anhydrous sodium sulfate, and concentrated under reduced pressure. The residue was dissolved in methanol (10 mL) and THF (2.0 mL), potassium carbonate (1.0 g) and water (2.0 mL) were added, and the reaction solution was stirred at room temperature for 2 hours. The reaction solution was added to hydrochloric acid (1 M, 20 mL) and extracted with ethyl acetate/hexane=1/1 (30 mL). The organic layer was washed with saturated saline (20 mL), dried over anhydrous sodium sulfate, and concentrated under reduced pressure. The residue was purified by silica gel column chromatography (eluent: hexane/ethyl acetate) to obtain (2S)-3-((tert-butyldimethylsilyl)oxy)-2-(4-chloro-2-methoxyphenylsulfonamido)-3-(6-fluoro-2,3-dimethylphenyl)propionic acid (175 mg).

Step 3

From (2S)-3-((tert-butyldimethylsilyl)oxy)-2-(4-chloro-2-methoxyphenylsulfonamido)-3-(6-fluoro-2,3-dimethylphenyl)propionic acid (175 mg) obtained from the above Step 2, according to the method of Example 1 Step 2, N-((1S)-2-((tert-butyldimethylsilyl)oxy)-2-(6-fluoro-2,3-dimethylphenyl)-1-(5-oxo-4,5-dihydro-1,3,4-oxadiazol-2-yl)ethyl)-4-chloro-2-methoxybenzenesulfonamide (126 mg) was obtained.

Step 4

To a THF (6.0 mL) solution of N-((1S)-2-((tert-butyldimethylsilyl)oxy)-2-(6-fluoro-2,3-dimethylphenyl)-1-(5-oxo-4,5-dihydro-1,3,4-oxadiazol-2-yl)ethyl)-4-chloro-2-methoxybenzenesulfonamide (126 mg) obtained in the above Step 3, acetic acid (600 µL) and tetra-n-butylammonium fluoride (6.0 mL) were sequentially added, and the mixture was stirred at room temperature for 2 hours. The reaction solution was added to water (20 mL) and extracted with ethyl acetate/hexane=1/1 (30 mL). The organic layer was washed with saturated saline (20 mL), dried over anhydrous sodium sulfate, and concentrated under reduced pressure. The residue was purified by silica gel column chromatography (eluent: hexane/ethyl acetate) to give the title compound as a diastereomeric mixture.

Example 291

4-chloro-N-((1R)-2-fluoro-2-(6-fluoro-2,3-dimethylphenyl)-1-(5-oxo-4,5-dihydro-1,3,4-oxadiazol-2-yl)ethyl)-2-methoxybenzenesulfonamide To a dichloromethane (200 µL) solution of 4-chloro-N-((1S)-2-(6-fluoro-2,3-dimethylphenyl)-2-hydroxy-1-(5-oxo-4,5-dihydro-1,3,4-oxadiazol-2-yl)ethyl)-2-methoxybenzenesulfonamide (5.6 mg) obtained from Example 290, DAST (10 µL) was added, and the mixture was stirred at room temperature for 2 hours. Saturated aqueous sodium hydrogen carbonate solution (5.0 mL) was added to the reaction solution, and the mixture was extracted with ethyl acetate/hexane=1/1 (10 mL). The organic layer was washed with saturated saline (5.0 mL), dried over anhydrous sodium sulfate, and concentrated under reduced pressure. The residue was purified by reverse phase HPLC (water/acetonitrile) to obtain the title compound as a diastereomeric mixture.

Example 292

5-chloro-4-fluoro-N-((1S,2R)-2-(2-fluoronaphthalen-1-yl)-1-(5-oxo-4,5-dihydro-1,3,4-oxadiazol-2-yl)propyl)chroman-8-sulfonamide From 5-chloro-N-((1S,2R)-2-(2-fluoronaphthalen-1-yl)-1-(5-oxo-4,5-dihydro-1,3,4-oxadiazol-2-yl)propyl)-4-hydroxychroman-8-sulfonamide (13 mg) obtained in Example 233, according to the method of Example 291, the title compound was obtained as a 1:1 diastereomeric mixture.

Example 293

5-chloro-N-((1S,2R)-2-(6-fluoro-2,3-dimethylphenyl)-1-(5-oxo-4,5-dihydro-1,3,4-oxadiazol-2-yl)propyl)-6-(2,2,2-trifluoroacetyl)pyridine-2-sulfonamide From 5-chloro-N-((1S,2R)-2-(6-fluoro-2,3-dimethylphenyl)-1-(5-oxo-4,5-dihydro-1,3,4-oxadiazol-2-yl)propyl)-6-(2,2,2-trifluoro-1-hydroxyethyl)pyridine-2-sulfonamide (15.6 mg) obtained in Example 221, according to the method of Reference Example E46 Step 1, the title compound was obtained.

Example 294

3-acetyl-4-chloro-N-((1S,2R)-2-(6-fluoro-2,3-dimethylphenyl)-1-(5-oxo-4,5-dihydro-1,3,4-oxadiazol-2-yl)propyl)-2-methoxybenzenesulfonamide From 4-chloro-N-((1S,2R)-2-(6-fluoro-2,3-dimethylphenyl)-1-(5-oxo-4,5-dihydro-1,3,4-oxadiazol-2-yl)propyl)-3-(1-hydroxyethyl)-2-methoxybenzenesulfonamide obtained in Example 204, the title compound was obtained according to the method of Reference Example E46 Step 1.

Example 295

5-chloro-N-((1S,2R)-2-(2,3-dimethylphenyl)-1-(5-oxo-4,5-dihydro-1,3,4-oxadiazol-2-yl)propyl)-2H-chromene-8-sulfonamide Step 1

From (2S,3R)-2-amino-3-(2,3-dimethylphenyl)butanoic acid (58 mg) obtained in Reference Example D6 and 5-chloro-4-oxochroman-8-sulfonyl chloride (88 mg) obtained in Reference Example E7, in accordance with the procedures of Example 1 Steps 1 and 2, 5-chloro-N-((1S,2R)-2-(2,3-dimethylphenyl)-1-(5-oxo-4,5-dihydro-1,3,4-oxadiazol-2-yl)propyl)-4-oxochroman-8-sulfonamide (63.4 mg) was obtained.

Step 2

From 5-chloro-N-((1S,2R)-2-(2,3-dimethylphenyl)-1-(5-oxo-4,5-dihydro-1,3,4-oxadiazol-2-yl)propyl)-4-oxochroman-8-sulfonamide (63.4 mg) obtained from the Step 1 above, according to the method of Example 230 Step 2, 5-chloro-N-((1S,2R)-2-(2,3-dimethylphenyl)-1-(5-oxo-4,5-dihydro-1,3,4-oxadiazol-2-yl)propyl)-4-hydroxychroman-8-sulfonamide (48 mg) was obtained as a diastereomeric mixture.

Step 3

To a toluene (2.0 mL) solution of 5-chloro-N-((1S,2R)-2-(2,3-dimethylphenyl)-1-(5-oxo-4,5-dihydro-1,3,4-oxadiazol-2-yl)propyl)-4-hydroxychroman-8-sulfonamide (10 mg) obtained from the above Step 2, p-toluenesulfonic acid monohydrate (2.0 mg) was added, and the reaction solution was stirred at 110° C. for 30 minutes. The reaction solution was added to water (5 mL) and extracted with ethyl acetate (10 mL). The organic layer was washed with saturated saline (10 mL), dried over anhydrous sodium sulfate, and concentrated under reduced pressure. The residue was purified by silica gel column chromatography (eluent: hexane/ethyl acetate) to give the title compound.

Example 296

4-chloro-N-((1S,2R)-2-(2,3-dihydro-1H-inden-4-yl)-1-(5-oxo-4,5-dihydro-1,3,4 oxadiazol-2-yl)propyl)-2-(hydroxymethyl)benzenesulfonamide Step 1

Using (2S,3R)-2-amino-3-(2,3-dihydro-1H-inden-4-yl)butanoic acid (50 mg) obtained from Reference Example D10 and methyl 5-chloro-2-(chlorosulfonyl)benzoate (71 mg), according to the method of steps 1 and 2 of Example 1, methyl 5-chloro-2-(N-((1S,2R)-2-(2,3-dihydro-1H-inden-4-yl)-1-(5-oxo-4,5-dihydro-1,3,4-oxadiazol-2-yl)propyl)sulfamoyl)benzoate (43 mg) was obtained.

Step 2

To a THF (2.0 mL) solution of methyl 5-chloro-2-(N-((1S,2R)-2-(2,3-dihydro-1H-inden-4-yl)-1-(5-oxo-4,5-dihydro-1,3,4-oxadiazol-2-yl)propyl)sulfamoyl)benzoate (15 mg) obtained in the above Step 1, a THF solution of lithium borohydride (2 M, 100 μL) was added, and the reaction solution was stirred at 60° C. for 1 hour. The reaction solution was added to water (10 mL) and extracted with ethyl acetate (15 mL). The organic layer was washed with saturated saline (10 mL), dried over anhydrous sodium sulfate, and concentrated under reduced pressure. The residue was purified by silica gel column chromatography (eluent: hexane/ethyl acetate) to give the title compound.

Example 297

4-chloro-N-((1S,2R)-2-(6-fluoro-2,3-dimethylphenyl)-1-(5-oxo-4,5-dihydro-1,3,4-oxadiazol-2-yl)propyl)-2-methoxy-3-(1-(methoxymethoxy)ethyl)benzenesulfonamide To a toluene (1.5 mL) solution of 4-chloro-N-((1S,2R)-2-(6-fluoro-2,3-dimethylphenyl)-1-(5-oxo-4,5-dihydro-1,3,4-oxadiazol-2-yl)propyl)-3-(1-hydroxyethyl)-2-methoxybenzenesulfonamide (10 mg) obtained from Example 204, N,N-diisopropylethylamine (25 μL) and chloromethyl methyl ether (10 μL) were sequentially added, and the reaction solution was stirred at room temperature for 3 hours. The reaction solution was concentrated under reduced pressure, and the residue was purified by silica gel column chromatography (eluent: hexane/ethyl acetate) to obtain the title compound.

Example 298

4-chloro-N-((1S,2R)-2-(4-fluoro-4'-methoxy-2-methyl-[1,1'-biphenyl]-3-yl)-1-(5-oxo-4,5-dihydro-1,3,4-oxadiazol-2-yl)propyl)-2-methoxybenzenesulfonamide Step 1

Using (2S,3R)-2-amino-3-(3-bromo-6-fluoro-2-methylphenyl)butanoic acid (200 mg) obtained in Reference Example D5 and 4-chloro-2-methoxybenzenesulfonyl chloride (280 mg), according to the method of steps 1 and 2 of Example 1, N-((1S,2R)-2-(3-bromo-6-fluoro-2-methylphenyl)-1-(5-oxo-4,5-dihydro-1,3,4-oxadiazol-2-yl)propyl)-4-chloro-2-methoxybenzenesulfonamide (262 mg) was synthesized.

Step 2

To a 1,4-dioxane (1.0 mL) solution of N-((1S,2R)-2-(3-bromo-6-fluoro-2-methylphenyl)-1-(5-oxo-4,5-dihydro-1,3,4-oxadiazol-2-yl)propyl)-4-chloro-2-methoxybenzenesulfonamide (11 mg), 4-methoxyphenylboronic acid (5.0 mg), [1,1'-bis (diphenylphosphino) ferrocene] palladium (II) dichloride dichloromethane adduct (4.0 mg), and a sodium carbonate aqueous solution (2 M, 100 μL) was added sequentially at room temperature, and the reaction solution was stirred at 100° C. for 1 hour. The reaction solution was allowed to cool to room temperature, insoluble matter was removed by CELITE filtration, and the residue was washed with hexane/ethyl acetate=1/1 (10 mL). The combined filtrate was concentrated under reduced pressure, and the obtained residue was purified by reverse phase HPLC (water/acetonitrile) to give the title compound.

Examples 299-324

Using N-((1S,2R)-2-(3-bromo-6-fluoro-2-methylphenyl)-1-(5-oxo-4,5-dihydro-1,3,4-oxadiazol-2-yl)propyl)-4- chloro-2-methoxybenzenesulfonamide obtained from Example 298 Step 1, according to the method of Example 298, Step 2, compounds of Examples 299 to 324 shown below were synthesized. The boronic acids or boronic acid esters used are listed in the following table.

TABLE 16-1

| Example | Reagent | ArSO2Cl |
|---|---|---|
| 299 | 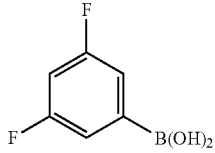 | 4-chloro-2-methoxy-N-((1S,2R)-1-(5-oxo-4,5-dihydro-1,3,4-oxadiazol-2-yl)-2-3',4',5'-trifluoro-2-methyl-[1,1'-biphenyl]-3-yl)propyl)benzenesulfonamide |
| 300 | 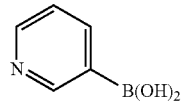 | 4-chloro-N-((1S,2R)-2-(6-fluoro-2-methyl-3-(pyridin-3-yl)phenyl)-1-(5-oxo-4,5-dihydro-1,3,4-oxadiazol-2-yl)propyl)-2-methoxybenzenesulfonamide |
| 301 | 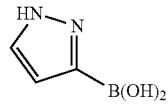 | 4-chloro-N-((1S,2R)-2-(6-fluoro-2-methyl-3-(1H-pyrazol-3-yl)phenyl)-1-(5-oxo-4,5-dihydro-1,3,4-oxadiazol-2-yl)propyl)-2-methoxybenzenesulfonamide |
| 302 | 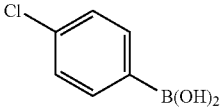 | 4-chloro-N-((1S,2R)-2-(4'-chloro-4-fluoro-2-methyl-[1,1'-biphenyl]-3-yl)-1-(5-oxo-4,5-dihydro-1,3,4-oxadiazol-2-yl)propyl)-2-methoxybenzenesulfonamide |
| 303 | 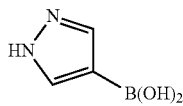 | 4-chloro-N-((1S,2R)-2-(6-fluoro-2-methyl-3-(1H-pyrazol-4-yl)phenyl)-1-(5-oxo-4,5-dihydro-1,3,4-oxadiazol-2-yl)propyl)-2-methoxybenzenesulfonamide |
| 304 | 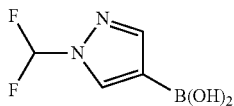 | 4-chloro-N-((1S,2R)-2-(3-(1-(difluoromethyl)-1H-pyrazol-4-yl)-6-fluoro-2-methylphenyl)-1-(5-oxo-4,5-dihydro-1,3,4-oxadiazol-2-yl)propyl)-2-methoxybenzenesulfonamide |
| 305 | 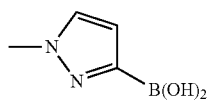 | 4-chloro-N-((1S,2R)-2-(6-fluoro-2-methyl-3-(1-methyl-1H-pyrazol-3-yl)phenyl)-1-(5-oxo-4,5-dihydro-1,3,4-oxadiazol-2-yl)propyl)-2-methoxybenzenesulfonamide |
| 306 | 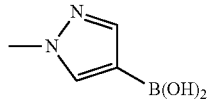 | 4-chloro-N-((1S,2R)-2-(6-fluoro-2-methyl-3-(1-methyl-1H-pyrazol-4-yl)phenyl)-1-(5-oxo-4,5-dihydro-1,3,4-oxadiazol-2-yl)propyl)-2-methoxybenzenesulfonamide |
| 307 | 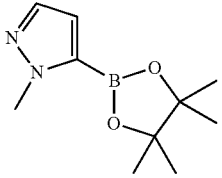 | 4-chloro-N-((1S,2R)-2-(6-fluoro-2-methyl-3-(1-methyl-1H-pyrazol-5-yl)phenyl)-1-(5-oxo-4,5-dihydro-1,3,4-oxadiazol-2-yl)propyl)-2-methoxybenzenesulfonamide |
| 308 | 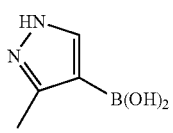 | 4-chloro-N-((1S,2R)-2-(6-fluoro-2-methyl-3-(3-methyl-1H-pyrazol-4-yl)phenyl)-1-(5-oxo-4,5-dihydro-1,3,4-oxadiazol-2-yl)propyl)-2-methoxybenzenesulfonamide |

TABLE 16-2

| Example | Reagent | ArSO2Cl |
|---|---|---|
| 309 | 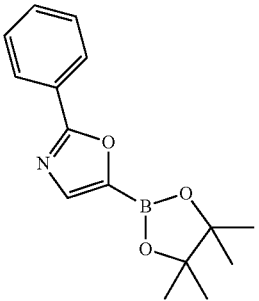 [SMILES: CC1(C)OB(c2cnc(-c3ccccc3)o2)OC1(C)C] | 4-chloro-N-((1S,2R)-2-(6-fluoro-2-methyl-3-(2-phenyloxazol-5-yl)phenyl)-1-(5-oxo-4,5-dihydro-1,3,4-oxadiazol-2-yl)propyl)-2-methoxybenzenesulfonamide |
| 310 | 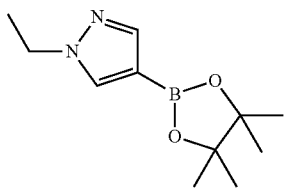 [SMILES: CCn1cc(B2OC(C)(C)C(C)(C)O2)cn1] | 4-chloro-N-((1S,2R)-2-(3-(1-ethyl-1H-pyrazol-4-yl)-6-fluoro-2-methylphenyl)-1-(5-oxo-4,5-dihydro-1,3,4-oxadiazol-2-yl)propyl)-2-methoxybenzenesulfonamide |
| 311 | 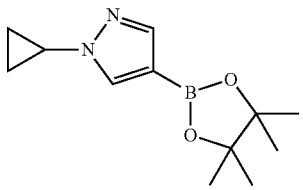 [SMILES: CC1(C)OB(c2cnn(C3CC3)c2)OC1(C)C] | 4-chloro-N-((1S,2R)-2-(3-(1-cyclopropyl-1H-pyrazol-4-yl)-6-fluoro-2-methylphenyl)-1-(5-oxo-4,5-dihydro-1,3,4-oxadiazol-2-yl)propyl)-2-methoxybenzenesulfonamide |
| 312 | 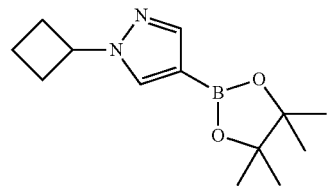 [SMILES: CC1(C)OB(c2cnn(C3CCC3)c2)OC1(C)C] | 4-chloro-N-((1S,2R)-2-(3-(1-cyclobutyl-1-pyrazol-4-yl)-6-fluoro-2-methylphenyl)-1-(5-oxo-4,5-dihydro-1,3,4-oxadiazol-2-yl)propyl)-2-methoxybenzenesulfonamide |
| 313 | 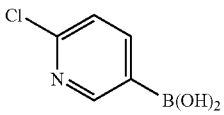 | 4-chloro-N-((1S,2R)-2-(3-(6-chloropyridin-3-yl)-6-fluoro-2-methylphenyl)-1-(5-oxo-4,5-dihydro-1,3,4-oxadiazol-2-yl)propyl)-2-methoxybenzenesulfonamide |
| 314 | 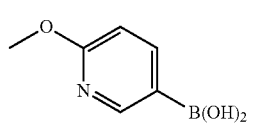 | 4-chloro-N-((1S,2R)-2-(6-fluoro-3-(6-methoxypyridin-3-yl)-2-methylphenyl)-1-(5-oxo-4,5-dihydro-1,3,4-oxadiazol-2-yl)propyl)-2-methoxybenzenesulfonamide |
| 315 | 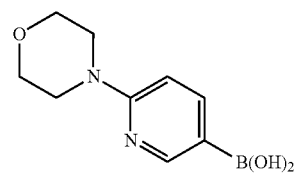 [SMILES: OB(O)c1ccc(N2CCOCC2)nc1] | 4-chloro-N-((1S,2R)-2-(6-fluoro-2-methyl-3-(6-morpholinopyridin-3-yl)phenyl)-1-(5-oxo-4,5-dihydro-1,3,4-oxadiazol-2-yl)propyl)-2-methoxybenzenesulfonamide |
| 316 | 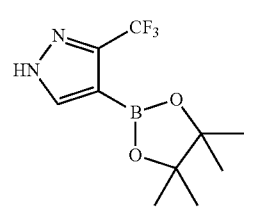 [SMILES: CC1(C)OB(c2c[nH]nc2C(F)(F)F)OC1(C)C] | 4-chloro-N-((1S,2R)-2-(6-fluoro-2-methyl-3-(3-(tifluoromethyl)-1H-pyrazol-4-yl)phenyl)-1-(5-oxo-4,5-dihydro-1,3,4-oxadiazol-2-yl)propyl)-2-methoxybenzenesulfonamide |

TABLE 16-2-continued

| Example | Reagent | ArSO2Cl |
|---|---|---|
| 317 | 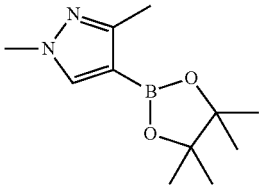 | 4-chloro-N-((1S,2R)-2-(3-(1,3-dimethyl-1H-pyrazol-4-yl)-6-fluoro-2-methylphenyl)-1-(5-oxo-4,5-dihydro-1,3,4-oxadiazol-2-yl)propyl)-2-methoxybenzenesulfonamide |
| 318 | 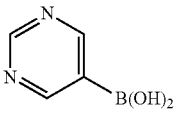 | 4-chloro-N-((1S,2R)-2-(6-fluoro-2-methyl-3-(pyrimidin-5-yl)phenyl)-1-(5-oxo-4,5-dihydro-1,3,4-oxadiazol-2-yl)propyl)-2-methoxybenzenesulfonamide |
| 319 | 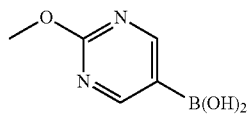 | 4-chloro-N-((1S,2R)-2-(6-fluoro-3-(2-methoxypyrimidin-5-yl)-2-methylphenyl)-1-(5-oxo-4,5-dihydro-1,3,4-oxadiazol-2-yl)propyl)-2-methoxybenzenesulfonamide |

TABLE 16-3

| Example | Reagent | ArSO2Cl |
|---|---|---|
| 320 | 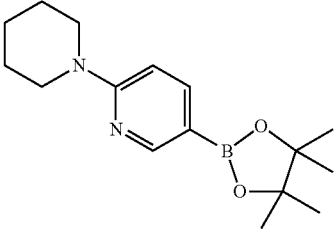 [SMILES: CC1(C)OB(c2ccc(N3CCCCC3)nc2)OC1(C)C] | 4-chloro-N-((1S,2R)-2-(6-fluoro-2-methyl-3-(6-(piperidin-1-yl)pyridin-3-yl)phenyl)-1-(5-oxo-4,5-dihydro-1,3,4-oxadiazol-2-yl)propyl)-2-methoxybenzenesulfonamide |
| 321 | 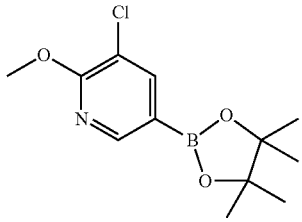 | 4-chloro-N-((1S,2R)-2-(3-(5-chloro-6-methoxypyridin-3-yl)-6-fluoro-2-methyphenyl)-1-(5-oxo-4,5-dihydro-1,3,4-oxadiazol-2-yl)propyl)-2-methoxybenzenesulfonamide |
| 322 | 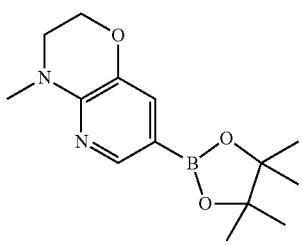 | 4-chloro-N-((1S,2R)-2-(6-fluoro-2-methyl-3-(4-methyl-3,4-dihydro-2H-pyrido[3,2-b][1,4]oxazine-7-yl)phenyl)-1-(5-oxo-4,5-dihydro-1,3,4-oxadiazol-2-yl)propyl)-2-methoxybenzenesulfonamide |

TABLE 16-3-continued

| Example | Reagent | ArSO2Cl |
|---|---|---|
| 323 | (morpholine-carbonyl pyridine with B(OH)₂) | 4-chloro-N-((1S,2R)-2-(6-fluoro-2-methyl-3-(5-(morpholine-4-carbonyl)pyridin-3-yl)phenyl)-1-(5-oxo-4,5-dihydro-1,3,4-oxadiazol-2-yl)propyl)-2-methoxybenzenesulfonamide |
| 324 | (1-methyl-1H-pyrazol-4-yl boronic acid) | 5-chloro-2-(N-((1S,2R)-2-(6-fluoro-2-methyl-3-(1-methyl-1H-pyrazol-4-yl)phenyl)-1-(5-oxo-4,5-dihydro-1,3,4-oxadiazol-2-yl)propyl)sulfamoyl)benzamide |

Example 325

4-chloro-N-((1S,2R)-2-(6-fluoro-2,3-dimethylphenyl)-1-(5-oxo-4,5-dihydro-1,3,4-oxadiazol-2-yl)propyl)-3-(1-methyl-1H-pyrazol-4-yl)benzenesulfonamide

Step 1

From (2S,3R)-2-amino-3-(6-fluoro-2,3-dimethylphenyl)butanoic acid (200 mg) obtained from Reference Example D1 and 3-bromo-4-chlorobenzenesulfonyl chloride (306 mg), according to the method of Steps 1 and 2 of Example 1, 3-bromo-4-chloro-N-((1S,2R)-2-(6-fluoro-2,3-dimethylphenyl)-1-(5-oxo-4,5-dihydro-1,3,4-oxadiazol-2-yl)propyl)benzenesulfonamide (274 mg) was synthesized.

Step 2

To a 1,4-dioxane (0.7 ml) solution of 3-bromo-4-chloro-N-((1S,2R)-2-(6-fluoro-2,3-dimethylphenyl)-1-(5-oxo-4,5-dihydro-1,3,4-oxadiazol-2-yl)propyl)benzenesulfonamide (5.6 mg) obtained from the above Step 1, (1-methyl-1H-pyrazol-4-yl)boronic acid (6.2 mg), [1,1'-bis(diphenylphosphino)ferrocene] palladium (II) dichloride dichloromethane adduct (5.0 mg), a sodium carbonate aqueous solution (2 M, 100 µL) were added sequentially at room temperature, and the reaction solution was stirred for 4 hours at 100° C. The reaction solution was allowed to cool to room temperature, insoluble matter was removed by CELITE filtration, and the residue was washed with hexane/ethyl acetate=1/1 (10 mL). The combined filtrate was concentrated under reduced pressure, and the obtained residue was purified by reverse phase HPLC (water/acetonitrile) to give the title compound.

Example 326

6-chloro-2'-fluoro-N-((1S,2R)-2-(6-fluoro-2,3-dimethylphenyl)-1-(5-oxo-4,5-dihydro-1,3,4-oxadiazol-2-yl)propyl)-[1,1'-biphenyl]-3-sulfonamide Using 3-bromo-4-chloro-N-((1S,2R)-2-(6-fluoro-2,3-dimethylphenyl)-1-(5-oxo-4,5-dihydro-1,3,4-oxadiazol-2-yl)propyl)benzenesulfonamide obtained from Example 325 Step 1 and (2-fluorophenyl)boronic acid, the title compound was synthesized according to the method of Example 325 Step 2.

Example 327

4-chloro-N-((1S,2R)-2-(6-fluoro-2-methyl-3-(phenylethynyl)phenyl)-1-(5-oxo-4,5-dihydro-1,3,4-oxadiazol-2-yl)propyl)-2-methoxybenzenesulfonamide To a DMF (1.0 mL) solution of N-((1S,2R)-2-(3-bromo-6-fluoro-2-methylphenyl)-1-(5-oxo-4,5-dihydro-1,3,4-oxadiazol-2-yl)propyl)-4-chloro-2-methoxybenzenesulfonamide (10.9 mg) obtained from Example 298 Step 1, dichlorobis (triphenylphosphine) palladium (II) (1.5 mg), copper (I) iodide (1.5 mg), triethylamine (30 µL) and ethynylbenzene (20 µL) were sequentially added at room temperature, the reaction solution was added at 100° C., and the mixture was stirred for 4 hours. The reaction solution was allowed to cool to room temperature, and insoluble matter was removed by CELITE filtration, and the residue was washed with hexane/ethyl acetate=1/1 (10 mL). The combined filtrate was concentrated under reduced pressure, and the obtained residue was purified by reverse phase HPLC (water/acetonitrile) to give the title compound.

Example 328

4-amino-5-chloro-N-((1S,2R)-2-(3-chloro-6-fluoro-2-methylphenyl)-1-(5-oxo-4,5-dihydro-1,3,4-oxadiazol-2-yl)propyl)-4-methylchroman-8-sulfonamide To a benzene (1.5 ml) solution of 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methylchroman-8-sulfonamide (17 mg) obtained from Example 209A, trimethylsilylazide (50 µL), boron trifluoride-dimethylethercomplex (100 µL) were sequentially added, and the reaction solution was stirred for 1 hour at room temperature. To the reaction solution, a saturated sodium bicarbonate aqueous solution (10 mL) was added, and the mixture was extracted with ethyl acetate/hexane=1/1 (10 mL). The organic layer was washed with saturated saline (10 mL), dried with anhydride sodium sulfate, and concentrated under reduced pressure. The obtained residue was dissolved in THF (1.5 ml) and water (50 µL). Triphenylphosphine (15 mg) was added to the residue, and the reaction solution was stirred for 2 hours at room temperature. Insoluble matter was removed by CELITE filtration, and the residue was washed with ethyl acetate/hexane=1/1 (10 mL). The combined filtrate was concentrated under reduced pressure, and the obtained residue was purified by reverse phase HPLC (water/acetonitrile) to give the title compound as a 1:1 diastereomeric mixture.

Example 329

4-amino-N-((1S,2R)-2-(3-bromo-6-fluoro-2-methylphenyl)-1-(5-oxo-4,5-dihydro-1,3,4-oxadiazol-2-yl)propyl)-5-chloro-4-methyl-chroman-8-sulfonamide The title compound was prepared using N-((1S,2R)-2-(3-bromo-6-fluoro-2-methylphenyl)-1-(5-oxo-4,5-dihydro-1,3, 4-oxadiazol-2-yl)propyl)-5-chloro-4-hydroxy-4-methyl-chroman-8-sulfonamide obtained in Example 222A according to the method of example 328.

Example 330

4-amino-5-chloro-N-((1S,2R)-2-(3-chloro-6-fluoro-2-methylphenyl)-1-(5-oxo-4,5-dihydro-1,3, 4-oxadiazol-2-yl)propyl)-4-methyl chroman-8-sulfonamide isomer A and isomer B To a 1,4-dioxane solution (1.0 mL) of a diastereomeric mixture of 4-amino-5-chloro-N-((1S,2R)-2-(3-chloro-6-fluoro-2-methylphenyl)-1-(5-oxo-4,5-dihydro-1,3,4-oxadiazol-2-yl)propyl)-4-methylchroman-8-sulfonamide (6.4 mg) obtained in Example 328, triethylamine (100 μL) and di-tert-butyl dicarbonate (54 mg) were added at room temperature, and the reaction solution was stirred for 4 hours. The reaction solution was concentrated under reduced pressure, the obtained residue was purified by reverse phase HPLC (water/acetonitrile), and the fractions were concentrated to give each of two diastereomeric products. The substance eluted first was designated Compound A, and the substance eluted later was designated as Compound B. The obtained Compounds A and B were each dissolved in hydrochloric acid-dioxane (4 M, 2.0 mL), and the reaction solution was stirred at 70° C. for 4 hours. The reaction solution was allowed to cool to room temperature and concentrated under reduced pressure. The substance obtained from compound A was designated as compound 330A, and the substance obtained from compound B as compound 330B.

Example 331

2-(N-((1S,2R)-2-(6-fluoro-2,3-dimethylphenyl)-1-(5-oxo-4,5-dihydro-1,3,4-oxadiazol-2-yl)propyl)sulfamoyl)-4-(1,3,4-oxadiazol-2-yl)benzamide Step 1

Using (2S,3R)-2-amino-3-(6-fluoro-2,3-dimethylphenyl) butanoic acid (80 mg) obtained in Reference Example D1 and ethyl 3-(chlorosulfonyl)-4-cyanobenzoate (146 mg) obtained in Reference Example E13, according to the method of steps 1 and 2 of Example 1, ethyl 4-cyano-3-(N-((1S,2R)-2-(6-fluoro-2,3-dimethylphenyl)-1-(5-oxo-4,5-dihydro-1,3,4-oxadiazol-2-yl)propyl)sulfamoyl)benzoate (40 mg) was obtained.

Step 2

To a DMSO (1 mL) solution of ethyl 4-cyano-3-(N-((1S, 2R)-2-(6-fluoro-2,3-dimethylphenyl)-1-(5-oxo-4,5-dihydro-1,3,4-oxadiazol-2-yl)propyl)sulfamoyl)benzoate (40 mg) obtained from the above Step 1, 30% hydrogen peroxide water (0.5 ml) and potassium carbonate (20 mg) were added, and the reaction solution was stirred at 70° C. for 1 hour. 1M hydrochloric acid was added to the reaction solution, and the mixture was extracted with ethyl acetate. The organic layer was washed with saturated saline, dried over anhydrous magnesium sulfate, concentrated under reduced pressure, and the obtained residue was purified by reversed phase HPLC (water/acetonitrile) to give 4-carbamoyl-3-(N-((1S, 2R)-2-(6-fluoro-2,3-dimethylphenyl)-1-(5-oxo-4,5-dihydro-1,3,4-oxadiazol-2-yl)propyl)sulfamoyl)benzoic acid (8.9 mg).

Step 3

To a dichloromethane (1.5 mL) solution of 4-carbamoyl-3-(N-((1S,2R)-2-(6-fluoro-2,3-dimethylphenyl)-1-(5-oxo-4, 5-dihydro-1,3,4-oxadiazol-2-yl)propyl)sulfamoyl)benzoic acid (16 mg) obtained from the above Step 2, (isocyanoimino) triphenylphosphorane (36 mg) was added thereto, and the reaction solution was stirred at room temperature for 72 hours. The reaction solution was concentrated under reduced pressure, and the obtained residue was purified by reversed phase HPLC (water/acetonitrile) to obtain the title compound (1.1 mg).

Example 332

5-bromo-2-(N-((1S,2R)-2-(6-fluoro-2,3-dimethylphenyl)-1-(5-thioxo-4,5-dihydro-1,3,4-oxadiazol-2-yl)propyl)sulfamoyl)benzamide Step 1

(2S,3R)-2-amino-3-(6-fluoro-2,3-dimethylphenyl)butanoic acid (300 mg) obtained from Reference Example D1 was dissolved in water (5.0 mL) and 1,4-dioxane (5.0 mL), triethylamine (570 μL) was added, and it was cooled to 0° C. 4-Bromo-2-cyanobenzene-1-sulfonyl chloride (362 mg) was added to the reaction solution, and the mixture was stirred at the same temperature for 45 minutes. The reaction solution was added to hydrochloric acid (1 M, 15 mL) and extracted with ethyl acetate (15 mL). The organic layer was washed with saturated saline (20 mL), dried over anhydrous magnesium sulfate, and concentrated under reduced pressure. The residue was purified by silica gel column chromatography (eluent: hexane/ethyl acetate/2% acetic acid) to give (2S,3R)-2-(4-bromo-2-cyanophenylsulfonamido)-3-(6-fluoro-2,3-dimethylphenyl)butanoic acid (465 mg).

Step 2

To a THF (1.5 mL) solution of (2S,3R)-2-(4-bromo-2-cyanophenylsulfonamido)-3-(6-fluoro-2,3-dimethylphenyl) butanoic acid (22 mg) obtained from the above Step 1, CDI (13 mg) was added, the reaction solution was stirred at room temperature for 30 minutes, then hydrazine•monohydrate (12 μL) was added and the mixture was stirred for 20 minutes. The reaction solution was concentrated under reduced pressure, and the obtained residue was dissolved in ethanol (1.2 mL), carbon disulfide (10 μL) and potassium hydroxide (10 mg) were sequentially added, and the reaction solution was stirred at 90° C. for 12 hours. The reaction solution was added to hydrochloric acid (1 M, 10 mL) and extracted with ethyl acetate (10 mL). The organic layer was washed with saturated saline (10 mL), dried over anhydrous magnesium sulfate, and concentrated under reduced pressure. The residue was purified by silica gel column chromatography (eluent: hexane/ethyl acetate) to give the title compound.

Examples 333 to 335

According to the method of Example 332 steps 1 and 2, the compounds of Examples 333 to 335 shown below were synthesized. The raw materials are listed in the following table.

TABLE 17

| Example | Starting Material | ArSO2Cl | Name of the Synthesized Compound |
|---|---|---|---|
| 333 | Reference Example D10 | (2,6-dichloro-3-methoxycarbonylphenylsulfonyl chloride) | methyl 2,6-dichloro-3-(N-((1S,2R)-2-(2,3-dihydro-1H-inden-4-yl)-1-(5-thioxo-4,5-dihydro-1,3,4-oxadiazol-2-yl)propyl)sulfamoyl)benzoate |
| 334 | Reference Example D10 | (2-chloro-5-chlorosulfonyl-methylbenzoate) | methyl 2-chloro-5-(N-((1S,2R)-2-(2,3-dihydro-1H-inden-4-yl)-1-(5-thioxo-4,5-dihydro-1,3,4-oxadiazol-2-yl)propyl)sulfamoyl)benzoate |
| 335 | Reference Example D26 | (4-bromobenzene-1-sulfonyl chloride) | 4-bromo-N-((1S,2R)-2-(5,5-dimethyl-5,6,7,8-tetrahydronaphthalen-1-yl)-1-(5-thioxo-4,5-dihydro-1,3,4-oxadiazol-2-yl)propyl)benzenesulfonamide |

Example 336

4-chloro-N-((1S,2R)-2-(2,3-dihydro-1H-inden-4-yl)-1-(5-thioxo-4,5-dihydro-1,3,4-oxadiazol-2-yl)propyl)-3-(2-hydroxypropan-2-yl)benzenesulfonamide Step 1

Using (2S,3R)-2-amino-3-(2,3-dihydro-1H-inden-4-yl) butanoic acid (20 mg) and 3-acetyl-4-chlorobenzene-1-sulfonyl chloride (20 mg) obtained in Reference Example D10, according to the method of Example 332 steps 1 and 2, 3-acetyl-4-chloro-N-((1S,2R)-2-(2,3-dihydro-1H-inden-4-yl)-1-(5-thioxo-4,5-dihydro-1,3,4-oxadiazol-2-yl)propyl)benzenesulfonamide (12 mg) was obtained.

Step 2

From 3-acetyl-4-chloro-N-((1S,2R)-2-(2,3-dihydro-1H-inden-4-yl)-1-(5-thioxo-4,5-dihydro-1,3,4-oxadiazol-2-yl)propyl)benzenesulfonamide (12 mg) obtained from the above Step 1, the title compound was obtained according to the method of Example 186 Step 2.

Example 337

5-chloro-2-(N-((1S,2R)-2-(6-fluoro-2,3-dimethylphenyl)-1-(5-oxo-4,5-dihydro-1,3,4 oxadiazol-2-yl)propyl)-N-methylsulfamoyl)benzamide Step 1

Using (2S,3R)-2-amino-3-(6-fluoro-2,3-dimethylphenyl) butanoic acid (530 mg) obtained from Reference Example D1 and 4-chloro-2-cyanobenzene-1-sulfonyl chloride (660 mg), according to the method of Example 1 Step 1, (2S,3R)-2-(4-chloro-2-cyanophenylsulfonamido)-3-(6-fluoro-2,3-dimethylphenyl)butanoic acid (777 mg) was obtained.

Step 2

To a THF (500 µL) solution of (2S,3R)-2-(4-chloro-2-cyanophenylsulfonamido)-3-(6-fluoro-2,3-dimethylphenyl) butanoic acid (11 mg) obtained from the above Step 1, CDI (15 mg) was added, and the reaction solution was stirred for 1 hour at room temperature. Methanol (1.0 mL) was added to the reaction solution, and the mixture was further stirred for 16 hours. The reaction solution was added to water (10 mL) and extracted with diethyl ether (15 mL). The organic layer was washed with saturated saline (10 mL), dried over anhydrous magnesium sulfate, and concentrated under reduced pressure to give methyl (2S,3R)-2-(4-chloro-2-cyanophenyl)-3-(6-fluoro-2,3-dimethylphenyl)butanoate (12 mg).

Step 3

To methyl (2S,3R)-2-(4-chloro-2-cyanophenylsulfonamido)-3-(6-fluoro-2,3-dimethylphenyl)butanoate (100 mg) obtained from the above Step 2, Methanol (2 mL), dichloromethane (2 mL), and a hexane solution of trimethylsilyl diazomethane (0.6 M, 800 µL) were sequentially added, and the reaction solution was stirred at room temperature for 1 hour. By concentrating the reaction solution under reduced pressure, methyl (2S,3R)-2-(4-chloro-2-cyano-N-methylphenylsulfonamido)-3-(6-fluoro-2,3-dimethylphenyl)butanoate (101 mg) was obtained.

Step 4

Methyl (2S,3R)-2-(4-chloro-2-cyano-N-methylphenylsulfonamido)-3-(6-fluoro-2,3-dimethylphenyl)butanoate (101 mg) obtained from the Step 3 above, according to the method of Example 245 Step 2, (2S,3R)-2-(4-chloro-2-cyano-N-methylphenylsulfonamido)-3-(6-fluoro-2,3-dimethylphenyl)butanoic acid (8.5 mg) was obtained.

Step 5

To (2S,3R)-2-(4-chloro-2-cyano-N-methylphenylsulfonamide)-3-(6-fluoro-2,3-dimethylphenyl)butanoic acid (8.5 mg) obtained from the above Step 4, according to the method of Example 1 Step 2, 4-chloro-2-cyano-N-((1S,2R)-2-(6-fluoro-2,3-dimethylphenyl)-1-(5-oxo-4,5-dihydro-1,3,4-oxadiazol-2-yl)propyl)-N-methylbenzenesulfonamide (6.0 mg) was obtained.

Step 6

From 4-chloro-2-cyano-N-((1S,2R)-2-(6-fluoro-2,3-dimethylphenyl)-1-(5-oxo-4,5-dihydro-1,3,4-oxadiazol-2-yl)propyl)-N-methylbenzenesulfonamide (6.0 mg) obtained from the above Step 5, according to the method of Example 1 Step 3, the title compound was obtained.

Example 344

6-chloro-N-((1S,2R)-2-(6-fluoro-2,3-dimethylphenyl)-1-(5-oxo-4,5-dihydro-1,3,4-oxadiazol-2-yl)propyl)-4'-methoxy-[1,1'-biphenyl]-3-sulfonamide Using 3-bromo-4-chloro-N-((1S,2R)-2-(6-fluoro-2,3-dimethylphenyl)-1-(5-oxo-4,5-dihydro-1,3,4-oxadiazol-2-yl)propyl)benzenesulfonamide and (4-methoxyphenyl)boronic acid obtained from Example 325 step 1, the title compound was synthesized according to the method of Example 325 Step 2.

Example 345

3-N-((1S,2R)-2-(6-fluoro-2,3-dimethylphenyl)-1-(5-oxo-4,5-dihydro-1,3,4-oxadiazol-2-yl)propyl)sulfamoyl)-2'-methoxy-[1,1'-biphenyl]-4-carboxamide

Step 1

From (2S,3R)-2-amino-3-(6-fluoro-2,3-dimethylphenyl)butanoic acid obtained from Reference Example D1 and 5-bromo-2-cyanobenzenesulfonyl chloride, according to the method of steps 1 and 2 of Example 1, 5-bromo-2-cyano-N-((1S,2R)-2-(6-fluoro-2,3-dimethylphenyl)-1-(5-oxo-4,5-dihydro-1,3,4-oxadiazol-2-yl)propyl)benzenesulfonamide was synthesized.

Step 2

Using 5-bromo-2-cyano-N-((1S,2R)-2-(6-fluoro-2,3-dimethylphenyl)-1-(5-oxo-4,5-dihydro-1,3,4-oxadiazol-2-yl)propyl)benzenesulfonamide obtained from the above Step 1 and 2-methoxyphenylboronic acid, according to the method of Example 325 Step 2 and Example 1 Step 3, the title compound was obtained.

Example 346

4-(N-((1S,2R)-2-(6-fluoro-2,3-dimethylphenyl)-1-(5-oxo-4,5-dihydro-1,3,4-oxadiazol-2 yl)propyl)sulfamoyl)-3-methoxybenzamide From 4-cyano-N-((1S,2R)-(6-fluoro-2,3-dimethylphenyl)-1-(5-oxo-4,5-dihydro-1,3,4-oxadiazol-2-yl)propyl)-2-methoxybenzenesulfonamide obtained in Example 342, the title compound was obtained according to the method of Example 1 Step 3.

Example 347

4-(N-((1S,2R)-(6-fluoro-2,3-dimethylphenyl)-1-(5-oxo-4,5-dihydro-1,3,4-oxadiazol-2 yl)propyl)sulfamoyl)benzamide From 4-cyano-N-((1S,2R)-(6-fluoro-2,3-dimethylphenyl)-1-(5-oxo-4,5-dihydro-1,3,4-oxadiazol-2-yl)propyl)benzenesulfonamide obtained in Example 341, according to the method of Example 1 Step 3, the title compound was obtained.

Example 348

4-bromo-N-((1S,2R)-2-(naphthalen-1-yl)-1-(5-oxo-4,5-dihydro-1,2,4-oxadiazol-3-yl)propyl)benzenesulfonamide

Step 1

Using (2S,3R)-2-amino-3-(naphthalen-1-yl)butanoic acid obtained in Reference Example D11 and 4-bromobenzenesulfonyl chloride, according to the method of Step 1 of Example 1, (2S,3R)-2-((4-bromophenyl)sulfonamido)-3-(naphthalen-1-yl)butanoic acid was obtained.

Step 2

To a DMF (2.5 ml) solution of (2S,3R)-2-((4-bromophenyl)sulfonamido)-3-(naphthalen-1-yl)butanoic acid (283 mg) obtained from the above Step 1, ammonium chloride (41 mg), HOBt (103 mg), triethylamine (0.264 ml) and WSC (146 mg) were added, and the reaction solution was stirred at room temperature for 3 hours. The reaction solution was added to water and extracted with ethyl acetate. The organic layer was washed with saturated saline, dried over anhydrous magnesium sulfate and concentrated under reduced pressure to obtain (2S,3R)-2-((4-bromophenyl)sulfonamido)-3-(naphthalen-1-yl)butanamide as a crude product.

Step 3

To a DMF (2 ml) solution of (2S,3R)-2-((4-bromophenyl)sulfonamido)-3-(naphthalen-1-yl)butanamide obtained from the above Step 2, cyanuric chloride (59 mg) was added at 0° C., and the reaction solution was stirred at room temperature for 1 hour. The reaction solution was added to water and extracted with a mixed solvent of ethyl acetate/toluene. The organic layer was washed with saturated saline, dried over anhydrous sodium sulfate, and concentrated under reduced pressure. The residue was purified by silica gel column chromatography (eluent: hexane/ethyl acetate) to give 4-bromo-N-((1S,2R)-1-cyano-2-(naphthalen-1-yl)propyl)benzene sulfonamide (137 mg).

Step 4

To an ethanol (2 ml) solution of 4-bromo-N-((1S,2R)-1-cyano-2-(naphthalen-1-yl)propyl)benzenesulfonamide (137 mg) obtained from the above Step 3, water (0.66 ml) and a 50% aqueous solution of hydroxylamine (0.060 ml) were added, and the reaction solution was stirred at room temperature overnight. The reaction solution was concentrated under reduced pressure, added to water and extracted with ethyl acetate. The organic layer was washed with saturated saline, dried over anhydrous sodium sulfate and concentrated under reduced pressure to give (2S,3R)-2-((4-bromophenyl)sulfonamido)-N-hydroxy-(3-naphthalen-1-yl)butanamide (130 mg) as a crude product.

Step 5

To a DMF (1.0 ml) solution of (2S,3R)-2-((4-bromophenyl)sulfonamido)-N-hydroxy-3-(naphthalen-1-yl)butanamide (20 mg) obtained from the above Step 4, Pyridine (0.004 ml) and 2-ethylhexyl chloroformate (0.009 ml) were added, and the reaction solution was stirred at room temperature for 1 hour. Further, xylene was added, and the reaction solution was stirred overnight at 100° C. Water was added to the reaction solution, and the mixture was extracted with a mixed solvent of ethyl acetate/hexane. The organic layer was washed with saturated saline, dried over anhydrous sodium sulfate, and concentrated under reduced pressure. The obtained residue was subjected to silica gel column chromatography (eluent: hexane/ethyl acetate) to give the title compound (37 mg).

Example 349

4-chloro-N-((1S,2R)-2-(6-fluoro-2,3-dimethylphenyl)-1-(5-oxo-4,5-dihydro-1,2,4-oxadiazol-3-yl)propyl)-2-methoxybenzenesulfonamide Step 1

Using (2S,3R)-2-amino-3-(6-fluoro-2,3-dimethylphenyl)butanoic acid obtained in Reference Example D1 and 4-chloro-2-methoxybenzenesulfonyl chloride, according to the method of Example 1 Step 1, (2S,3R)-2-((4-chloro-2-methoxyphenyl)sulfonamido)-3-(6-fluoro-2,3-dimethylphenyl)butanoic acid was obtained.

Step 2

From (2S,3R)-2-((4-chloro-2-methoxyphenyl)sulfonamido)-3-(6-fluoro-2,3-dimethylphenyl)butanoic acid obtained from the above Step 1, the titled compound was obtained according to the method of Example 348 Step 2 to Step 5.

Example 350

(2S,3R)-2-((4-chloro-2-methoxyphenyl)sulfonamido)-3-(6-fluoro-2,3-dimethylphenyl)butanoic acid (142 mg) obtained from Example 348 Step 1 was dissolved in a DMF (3.3 mL), and WSC (130 mg), HOBt (100 mg), N, N-diisopropylethylamine (200 µL) and thiosemicarbazide (70 mg) were sequentially added, and the reaction solution was stirred at 80° C. for 4 hours. The reaction solution was added to a saturated aqueous solution of ammonium chloride (15 mL) and extracted with ethyl acetate (20 mL). The organic layer was washed with saturated saline (15 mL), dried over anhydrous magnesium sulfate, and concentrated under reduced pressure. The residue was purified by silica gel column chromatography (eluent: hexane/ethyl acetate). The obtained residue was dissolved in ethanol (1.5 mL), a 20% aqueous sodium hydroxide solution (2.0 mL) was added, and the reaction solution was stirred at 80° C. for 12 hours. The reaction solution was added to hydrochloric acid (1 M, 5.0 mL) and extracted with ethyl acetate (10 mL). The organic layer was washed with saturated saline (5.0 mL), dried over anhydrous sodium sulfate, and concentrated under reduced pressure. The residue was purified by silica gel column chromatography (eluent: hexane/ethyl acetate) to give the title compound.

Comparative Example 1

According to the method described in Non-Patent Document 11, a compound of the following formula was obtained.

[Formula 49]

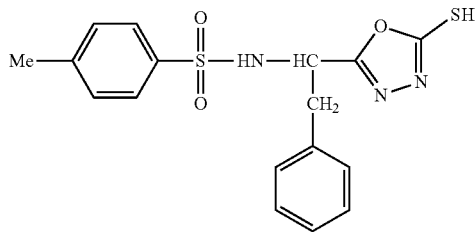

$^1$H NMR (CD3OD) δ: 7.54 (d, J=8.4 Hz, 2H), 7.17-7.29 (m, 5H), 7.08-7.14 (m, 2H), 4.55-4.61 (m, 1H), 3.00-3.13 (m, 2H), 2.39 (s, 3H)

Hereinafter, the structural formulas and physical properties of Example Compounds 1 to 350 are shown.

TABLE 18-1

| Example | Structural Formula | Physical Property Value |
|---|---|---|
| 1 |  | 1H NMR (CD3OD) δ: 7.74-7.78 (m, 3H), 6.97 (dd, J = 8.2, 5.7 Hz, 1H), 6.71 (dd, J = 11.7, 8.4 Hz, 1H), 4.78-4.81 (m, 1H), 3.51-3.61 (m, 1H), 2.20 (s, 3H), 2.17 (s, 3H), 1.44 (d, J = 7.0 Hz, 3H); LC/MS RT 1.67 min, m/z [M − H]$^-$ 525, 527 |

TABLE 18-1-continued

| Example | Structural Formula | Physical Property Value |
|---|---|---|
| 2 | | 1H NMR (CD3OD) δ: 8.20 (1H, d, J = 8.1 Hz), 7.65 (1H, d, J = 8.4 Hz), 7.03-7.00 (1H, m), 6.98-6.96 (2H, m), 4.63-4.61 (1H, m), 3.40-3.36 (1H, m), 2.91-2.82 (4H, m), 2.03-1.99 (2H, m), 1.41 (3H, d, J = 7.0 Hz); LC/MS RT 1.66 min, m/z [M − H]⁻ 476, 478 |
| 3 | | 1H NMR (CD3OD) δ: 7.77 (d, J = 8.4 Hz, 1H), 7.59 (d, J = 2.2 Hz, 1H), 7.53 (dd, J = 8.4, 2.2 Hz, 1H), 7.03 (dd, J = 7.0, 2.2 Hz, 1H), 6.90-6.99 (m, 2H), 4.53 (d, J = 9.5 Hz, 1H), 3.52-3.61 (m, 1H), 2.20 (s, 3H), 2.18 (s, 3H), 1.35 (d, J = 7.0 Hz, 3H); LC/MS RT 1.63 min, m/z [M − H]⁻ 463, 465 |
| 4 | | 1H NMR (CD3OD) δ: 7.74 (s, 1H), 7.67-7.69 (m, 2H), 7.01-7.07 (m, J = 6.2 Hz, 1H), 6.91-6.99 (m, 2H), 4.54 (d, J = 9.5 Hz, 1H), 3.51-3.65 (m, 1H), 2.20 (s, 3H), 2.17 (s, 3H), 1.35 (d, J = 7.0 Hz, 3H); LC/MS RT 1.65 min, m/z [M − H]⁻ 507, 509 |
| 5 | | 1H NMR (CD3OD) δ: 7.84 (d, J = 8.4 Hz, 1H), 7.62 (d, J = 2.2 Hz, 1H), 7.58 (dd, J = 8.4, 2.2 Hz, 1H), 6.98 (dd, J = 8.2, 5.7 Hz, 1H), 6.72 (dd, J = 11.7, 8.4 Hz, 1H), 4.82 (d, J = 11.4 Hz, 1H), 3.50-3.60 (m, 1H), 2.20 (s, 3H), 2.17 (s, 3H), 1.45 (d, J = 7.0 Hz, 3H); LC/MS RT 1.65 min, m/z [M − H]⁻ 481, 483 |

TABLE 18-2
| Example | Structural Formula | Physical Property Value |
|---|---|---|
| 6 | 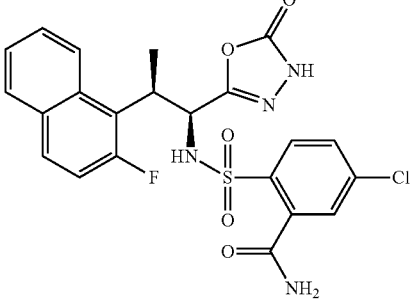 | 1H NMR (CD3OD) δ: 8.11 (d, J = 8.8 Hz, 1H), 7.76-7.89 (m, 3H), 7.62 (d, J = 2.2 Hz, 1H), 7.51-7.59 (m, 2H), 7.40-7.47 (m, 1H), 7.22 (dd, J = 11.5, 9.0 Hz, 1H), 4.90-4.98 (m, 1H), 4.09-4.18 (m, 1H), 1.60 (d, J = 7.0 Hz, 3H); LC/MS RT 1.66 min, m/z [M − H]⁻ 503, 505 |
| 7 | 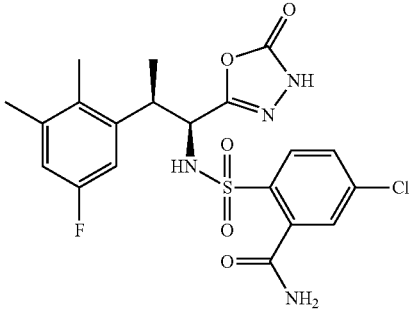 [SMILES: Cc1cc(F)cc([C@@H](C)[C@H](NS(=O)(=O)c2ccc(Cl)cc2C(N)=O)c2n[nH]c(=O)o2)c1C] | 1H NMR (CD3OD) δ: 7.75 (d, J = 8.4 Hz, 1H), 7.59 (d, J = 2.2 Hz, 1H), 7.53 (dd, J = 8.4, 2.2 Hz, 1H), 6.80 (dd, J = 10.4, 2.7 Hz, 1H), 6.69 (dd, J = 9.2, 2.7 Hz, 1H), 4.55 (d, J = 8.8 Hz, 1H), 3.53-3.65 (m, 1H), 2.21 (s, 3H), 2.15 (s, 3H), 1.33 (d, J = 7.0 Hz, 3H); LC/MS RT 1.65 min, m/z [M − H]⁻ 481, 483 |
| 8 | 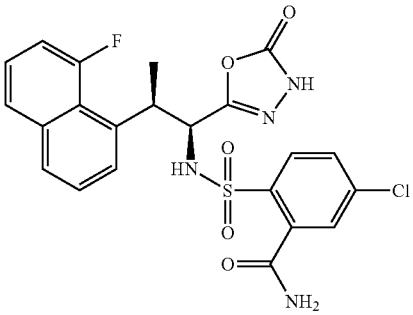 [SMILES: C[C@H](c1cccc2cccc(F)c12)[C@H](NS(=O)(=O)c1ccc(Cl)cc1C(N)=O)c1n[nH]c(=O)o1] | 1H NMR (CD3OD) δ: 7.62-7.79 (m, 2H), 7.46-7.52 (m, 2H), 7.38-7.45 (m, 2H), 7.29-7.35 (m, 1H), 7.20-7.28 (m, 2H), 4.82-4.86 (m, 1H), 4.44-4.62 (m, 1H), 1.50 (d, J = 7.0 Hz, 3H); LC/MS RT 1.64 min, m/z [M − H]⁻ 503, 505 |
| 9 | 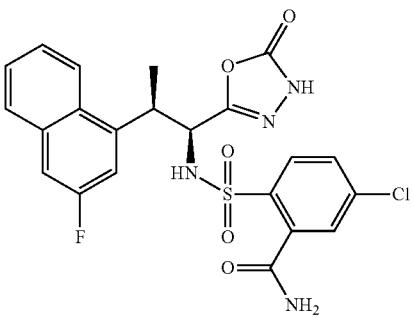 [SMILES: C[C@H](c1cc(F)cc2ccccc12)[C@H](NS(=O)(=O)c1ccc(Cl)cc1C(N)=O)c1n[nH]c(=O)o1] | 1H NMR (CD3OD) δ: 8.01-8.11 (m, 1H), 7.75-7.85 (m, 1H), 7.43-7.59 (m, 4H), 7.22-7.38 (m, 3H), 4.78 (d, J = 7.3 Hz, 1H), 4.20 (t, J = 7.0 Hz, 1H), 1.52 (d, J = 7.0 Hz, 3H); LC/MS RT 1.67 min, m/z [M − H]⁻ 503, 505 |

TABLE 18-2-continued

| Example | Structural Formula | Physical Property Value |
| --- | --- | --- |
| 10 | | 1H-NMR (CDCl3) δ: 7.85 (1H, d, J = 7.7 Hz), 7.67 (1H, s), 7.36-7.33 (1H, m), 6.92-6.88 (2H, m), 6.69 (1H, dd, J = 11.7, 8.4 Hz), 6.00 (1H, s), 5.87 (1H, s), 4.89 (1H, t, J = 10.1 Hz), 3.45 (1H, s), 2.42 (3H, s), 2.17-2.15 (6H, m), 1.44 (3H, d, J = 6.6 Hz); LC/MS RT 1.59 min, m/z [M − H]⁻ 461 |

TABLE 18-3

| Example | Structural Formula | Physical Property Value |
| --- | --- | --- |
| 11 | | 1H NMR (CD3OD) δ: 7.84 (d, J = 8.4 Hz, 1H), 7.62 (d, J = 2.2 Hz, 1H), 7.58 (dd, J = 8.4, 2.2 Hz, 1H), 6.98 (dd, J = 8.4, 5.9 Hz, 1H), 6.75 (dd, J = 11.7, 8.8 Hz, 1H), 4.78 (d, J = 11.0 Hz, 1H), 3.50-3.60 (m, 1H), 2.52-2.59 (m, 2H), 2.24 (s, 3H), 1.46 (d, J = 7.0 Hz, 3H), 1.06 (t, J = 7.5 Hz, 3H), ; LC/MS RT 1.73 min, m/z [M − H]⁻ 495, 497 |
| 12 | | 1H NMR (CD3OD) δ: 8.10 (br d, J = 8.8 Hz, 1H), 7.76-7.84 (m, 2H), 7.72 (d, J = 8.1 Hz, 1H), 7.54 (t, J = 7.5 Hz, 1H), 7.39-7.45 (m, 2H), 7.33 (d, J = 8.1 Hz, 1H), 7.21 (dd, J = 11.4, 9.2 Hz, 1H), 4.91 (d, J = 11.7 Hz, 1H), 4.07-4.21 (m, 1H), 2.39 (s, 3H), 1.60 (d, J = 6.6 Hz, 3H); LC/MS RT 1.61 min, m/z [M − H]⁻ 483 |
| 13 | | 1H NMR (CD3OD) δ: 7.86 (d, J = 8.4 Hz, 1H), 7.63 (d, J = 1.8 Hz, 1H), 7.57-7.61 (m, 1H), 6.91 (dd, J = 11.0, 8.4 Hz, 1H), 4.78 (d, J = 11.0 Hz, 1H), 3.55-3.66 (m, 1H), 2.18 (s, 3H), 2.16 (s, 3H), 1.47 (d, J = 7.0 Hz, 3H); LC/MS RT 1.68 min, m/z [M − H]⁻ 499, 501 |

TABLE 18-3-continued

| Example | Structural Formula | Physical Property Value |
|---|---|---|
| 14 | | 1H NMR (CD3OD) δ: 7.86 (d, J = 8.4 Hz, 1H), 7.63 (d, J = 1.8 Hz, 1H), 7.59 (dd, J = 8.4, 2.2 Hz, 1H), 7.25 (dd, J = 8.8, 5.1 Hz, 1H), 6.88 (t, J = 10.0 Hz, 1H), 4.80 (d, J = 11.4 Hz, 1H), 3.55-3.65 (m, 1H), 2.37 (s, 3H), 1.47 (d, J = 7.0 Hz, 3H); LC/MS RT 1.68 min, m/z [M − H]⁻ 501, 503 |
| 15 | | 1H NMR (CD3OD) δ: 8.11 (d, J = 8.8 Hz, 1H), 7.69-7.92 (m, 5H), 7.54 (br t, J = 7.7 Hz, 1H), 7.42 (t, J = 7.2 Hz, 1H), 7.21 (dd, J = 11.4, 9.2 Hz, 1H), 4.89-5.01 (m, 1H), 4.10-4.24 (m, 1H), 1.60 (br d, J = 6.6 Hz, 3H); LC/MS RT 1.68 min, m/z [M − H]⁻ 547, 549 |

TABLE 18-4

| Example | Structural Formula | Physical Property Value |
|---|---|---|
| 16 | | 1H NMR (CD3OD) δ: 7.69 (d, J = 8.1 Hz, 1H), 7.29 (d, J = 1.8 Hz, 1H), 7.21 (dd, J = 8.2, 2.0 Hz, 1H), 6.97 (d, J = 8.4, 5.9 Hz, 1H), 6.71 (dd, J = 12.1, 8.4 Hz, 1H), 4.76 (d, J = 11.4 Hz, 1H), 3.46-3.60 (m, 1H), 2.18 (s, 3H), 2.16 (s, 3H), 1.95-2.04 (m, 1H), 1.45 (d, J = 7.0 Hz, 3H), 1.06 (dd, J = 8.4, 1.8 Hz, 2H), 0.72-0.90 (m, 2H); LC/MS RT 1.67 min, m/z [M − H]⁻ 487 |
| 17 | | 1H NMR (CD3OD) δ: 7.84 (d, J = 8.4 Hz, 1H), 7.53-7.66 (m, 2H), 7.12-7.22 (m, 1H), 6.89-7.03 (m, 1H), 4.71-4.82 (m, 1H), 3.86-4.04 (m, 1H), 2.28 (s, 3H), 1.47 (br d, J = 6.2 Hz, 3H); LC/MS RT 1.66 min, m/z [M − H]⁻ 501, 503 |

TABLE 18-4-continued

| Example | Structural Formula | Physical Property Value |
|---|---|---|
| 18 | | 1H NMR (CD3OD) δ: 7.74 (d, J = 8.4 Hz, 1H), 7.45 (d, J = 1.8 Hz, 1H), 7.37 (dd, J = 8.2, 1.6 Hz, 1H), 6.97 (dd, J = 8.4, 5.9 Hz, 1H), 6.71 (dd, J = 11.7, 8.4 Hz, 1H), 4.78 (d, J = 11.0 Hz, 1H), 3.47-3.63 (m, 1H), 2.71 (q, J = 7.7 Hz, 2H), 2.18 (s, 3H), 2.16 (s, 3H), 1.45 (d, J = 7.0 Hz, 3H), 1.21-1.28 (m, 3H); LC/MS RT 1.66 min, m/z [M − H]⁻ 475 |
| 19 | | 1H NMR (CD3OD) δ: 8.32 (d, J = 8.4 Hz, 1H), 7.70 (d, J = 8.4 Hz, 1H), 6.98 (dd, J = 8.4, 5.9 Hz, 1H), 6.72 (dd, J = 12.1, 8.4 Hz, 1H), 4.84 (d, J = 11.4 Hz, 1H), 3.55-3.68 (m, 1H), 2.22 (s, 3H), 2.18 (s, 3H), 1.48 (d, J = 7.0 Hz, 3H); LC/MS RT 1.65 min, m/z [M − H]⁻ 482, 484 |
| 20 | | 1H NMR (CD3OD) δ: 7.87 (d, J = 7.6 Hz, 1H), 7.53-7.70 (m, 3H), 6.97 (dd, J = 8.2, 5.7 Hz, 1H), 6.71 (dd, J = 11.7, 8.4 Hz, 1H), 4.80 (d, J = 11.0 Hz, 1H), 3.50-3.52 (m, 1H), 2.19 (s, 3H), 2.17 (s, 3H), 1.44 (d, J = 6.6 Hz, 3H); LC/MS RT 1.54 min, m/z [M − H]⁻ 447 |

TABLE 18-5

| Example | Structural Formula | Physical Property Value |
|---|---|---|
| 21 | | 1H NMR (CD3OD) δ: 7.76 (d, J = 8.4 Hz, 1H), 7.61 (d, J = 2.2 Hz, 1H), 7.52-7.55 (m, 1H), 6.96-7.05 (m, 2H), 6.83 (s, 1H), 4.59 (d, J = 9.5 Hz, 1H), 3.37-3.44 (m, 1H), 2.22 (s, 3H), 1.41 (d, J = 7.0 Hz, 3H); LC/MS RT 1.60 min, m/z [M − H]⁻ 467, 469 |

| Example | Structural Formula | Physical Property Value |
|---|---|---|
| 22 | 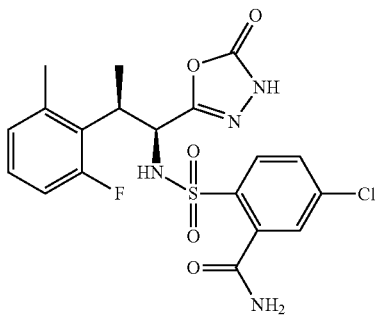 [SMILES: Cc1cccc(F)c1[C@@H](C)[C@H](NS(=O)(=O)c1ccc(Cl)cc1C(N)=O)c1n[nH]c(=O)o1] | LC/MS RT 1.6 min, m/z [M − H]⁻ 467, 469 |
| 23 | 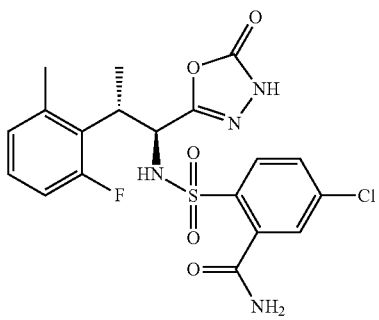 [SMILES: Cc1cccc(F)c1[C@H](C)[C@H](NS(=O)(=O)c1ccc(Cl)cc1C(N)=O)c1n[nH]c(=O)o1] | 1H NMR (CD3OD) δ: 7.73 (d, J = 8.4 Hz, 1H), 7.52-7.59 (m, 2H), 7.07 (td, J = 7.9, 5.5 Hz, 1H), 6.90-6.97 (m, 1H), 6.66-6.77 (m, 1H), 4.77 (d, J = 11.4 Hz, 1H), 3.43-3.59 (m, 1H), 2.38 (s, 3H), 1.46 (d, J = 7.0 Hz, 3H); LC/MS RT 1.58 min, m/z [M − H]⁻ 467, 469 |
| 24 | 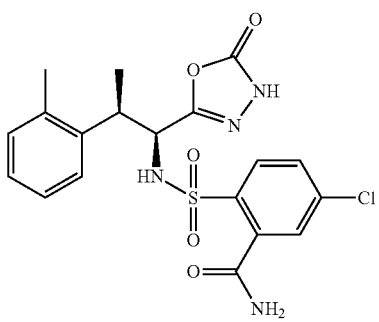 [SMILES: Cc1ccccc1[C@@H](C)[C@H](NS(=O)(=O)c1ccc(Cl)cc1C(N)=O)c1n[nH]c(=O)o1] | 1H NMR (cdcl3) δ: 7.73 (d, J = 8.4 Hz, 1H), 7.55 (d, J = 1.8 Hz, 1H), 7.43 (d, J = 8.4 Hz, 1H), 7.00-7.16 (m, 4H), 4.56 (dd, J = 15.8, 7.7 Hz, 1H), 3.37-3.62 (m, 1H), 2.29 (s, 3H), 1.38 (d, J = 7.0 Hz, 3H); LC/MS RT 1.56 min, m/z [M − H]⁻ 449, 451 |
| 25 | 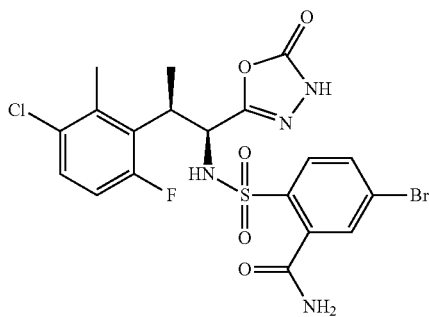 [SMILES: Cc1c(Cl)ccc(F)c1[C@@H](C)[C@H](NS(=O)(=O)c1ccc(Br)cc1C(N)=O)c1n[nH]c(=O)o1] | 1H NMR (CD3OD) δ: 7.74-7.79 (m, 3H), 7.25 (dd, J = 8.9, 5.0 Hz, 1H), 6.85-6.94 (m, 1H), 4.77-4.83 (m, 1H), 3.55-3.65 (m, 1H), 2.37 (s, 3H), 1.47 (d, J = 7.0 Hz, 3H); LC/MS RT 1.70 min, m/z [M − H]⁻ 545, 547 |

TABLE 18-6

| Example | Structural Formula | Physical Property Value |
| --- | --- | --- |
| 26 | | 1H NMR (CD3OD) δ: 7.84 (d, J = 8.4 Hz, 1H), 7.62 (d, J = 2.2 Hz, 1H), 7.58 (dd, J = 8.4, 2.2 Hz, 1H), 6.94 (dd, J = 8.5, 5.9 Hz, 1H), 6.73 (dd, J = 11.9, 8.5 Hz, 1H), 4.77 (d, J = 11.4 Hz, 1H), 3.50-3.65 (m, 1H), 2.39 (s, 3H), 1.73-1.83 (m, 1H), 1.46 (d, J = 7.0 Hz, 3H), 0.80-0.98 (m, 2H), 0.37-0.55 (m, 2H); LC/MS RT 1.76 min, m/z [M − H]− 507, 509 |
| 27 | | 1H-NMR (CDCl3) δ: 8.26 (1H, br s), 7.94 (1H, d, J = 8.1 Hz), 7.55-7.47 (3H, m), 6.90 (2H, t, J = 9.7 Hz), 6.19-6.14 (1H, m), 4.90 (1H, t, J = 10.1 Hz), 3.56 (1H, br s), 2.39 (3H, s), 1.48 (3H, d, J = 7.0 Hz), 1.24 (1H, s). ; LC/MS RT 1.73 min, m/z [M − H]− 535, 537 |
| 28 | | 1H NMR (CD3OD) δ: 7.86 (d, J = 8.4 Hz, 1H), 7.63 (d, J = 2.2 Hz, 1H), 7.59 (dd, J = 8.4, 2.2 Hz, 1H), 6.83-6.95 (m, 2H), 4.78 (d, J = 11.0 Hz, 1H), 3.45-3.56 (m, J = 2.2 Hz, 3H), 1.46 (d, J = 7.0 Hz, 3H); LC/MS RT 1.60 min, m/z [M − H]− 485, 487 |
| 29 | | 1H-NMR (CDCl3) δ: 8.88 (1H, s), 7.80 (1H, d, J = 8.4 Hz), 7.24-7.21 (1H, m), 7.03-7.01 (1H, m), 6.94-6.93 (1H, m), 6.84 (1H, dd, J = 11.4, 8.4 Hz), 6.02-5.95 (2H, m), 5.89 (1H, s), 4.80 (1H, t, J = 10.8 Hz), 3.93 (3H, s), 3.46 (1H, s), 2.35 (3H, s), 1.49 (3H, d, J = 5.9 Hz). ; LC/MS RT 1.38 min, m/z [M − H]− 497, 499 |
| 30 | | 1H NMR (CD3OD) δ: 7.85 (d, J = 8.4 Hz, 1H), 7.63 (d, J = 2.2 Hz, 1H), 7.57-7.61 (m, 1H), 7.44 (dd, J = 8.8, 5.1 Hz, 1H), 6.80-6.86 (m, 1H), 4.79 (d, J = 11.0 Hz, 1H), 3.55-3.65 (m, 1H), 2.43 (s, 3H), 1.47 (d, J = 7.0 Hz, 3H); LC/MS RT 1.70 min, m/z [M − H]− 545, 547 |

TABLE 18-7

| Example | Structural Formula | Physical Property Value |
|---|---|---|
| 31 | | 1H NMR (CD3OD) δ: 8.16 (d, J = 8.4 Hz, 1H), 8.02 (d, J = 8.1 Hz, 1H), 6.98 (dd, J = 8.6, 5.3 Hz, 1H), 6.65-6.80 (m, 1H), 4.83-4.91 (m, 1H), 3.55-3.65 (m, 1H), 2.22 (s, 3H), 2.18 (s, 3H), 1.47 (d, J = 7.3 Hz, 3H); LC/MS RT 1.52 min, m/z [M − H]⁻ 482, 484 |
| 32 | | 1H NMR (CD3OD) δ: 7.67 (1H, d, J = 8.8 Hz), 7.54-7.52 (2H, m), 6.95-6.92 (1H, m), 6.59-6.53 (1H, m), 4.79 (1H, d, J = 11.0 Hz), 3.56-3.54 (1H, m), 2.24 (3H, s), 2.19 (3H, s), 1.15 (3H, d, J = 7.0 Hz); LC/MS RT 1.66 min, m/z [M − H]⁻ 481, 483 |
| 33 | | 1H NMR (CD3OD) δ: 7.84 (d, J = 8.4 Hz, 1H), 7.53-7.70 (m, 2H), 6.98 (dd, J = 8.2, 5.7 Hz, 1H), 6.72 (dd, J = 12.1, 8.4 Hz, 1H), 4.79 (d, J = 11.4 Hz, 1H), 3.48-3.61 (m, 1H), 2.20 (s, 3H), 2.17 (s, 3H), 1.45 (d, J = 7.0 Hz, 3H); LC/MS RT 1.66 min, m/z [M − H]⁻ 481, 483 |
| 34 | | 1H NMR (CD3OD) δ: 7.68 (dd, J = 7.9, 0.9 Hz, 1H), 7.51-7.58 (m, 2H), 6.94 (dd, J = 8.2, 6.0 Hz, 1H), 6.52-6.66 (m, 1H), 4.80 (d, J = 11.0 Hz, 1H), 3.51-3.68 (m, 1H), 2.25 (s, 3H), 2.20 (s, 3H), 1.16 (3H, d, J = 6.6 Hz, 3H); LC/MS RT 1.66 min, m/z [M − H]⁻ 481, 483 |

TABLE 18-7-continued

| Example | Structural Formula | Physical Property Value |
|---|---|---|
| 35 | | 1H NMR (CD3OD) δ: 7.77 (s, 3H), 7.41-7.51 (m, 1H), 6.72-6.91 (m, 1H), 4.79 (d, J = 11.0 Hz, 1H), 3.52-3.73 (m, 1H), 2.43 (s, 3H), 1.47 (d, J = 7.0 Hz, 3H); LC/MS RT 1.73 min, m/z [M − H]⁻ 589, 591 |

TABLE 18-8

| Example | Structural Formula | Physical Property Value |
|---|---|---|
| 36 | | 1H-NMR (CDCl3) δ: 9.73 (1H, br s), 7.87 (1H, s), 7.64-7.56 (2H, m), 7.06-7.04 (1H, m), 6.91 (1H, dd, J = 8.2, 5.7 Hz), 6.70-6.65 (2H, m), 6.47 (1H, s), 4.87 (1H, t, J = 10.6 Hz), 3.78-3.76 (4H, m), 3.64-3.62 (2H, m), 3.48-3.46 (1H, m), 3.41-3.39 (2H, m), 2.16-2.14 (6H, m), 1.46 (3H, d, J = 6.6 Hz). ; LC/MS RT 1.50 min, m/z [M − H]⁻ 560 |
| 37 | | 1H-NMR (CDCl3) δ: 7.86 (1H, s), 7.65-7.55 (2H, m), 7.06-7.03 (1H, m), 6.93-6.89 (1H, m), 6.71-6.66 (1H, m), 6.14 (1H, s), 6.03 (1H, s), 4.96 (1H, t, J = 10.3 Hz), 3.43-3.41 (1H, m), 3.11 (3H, s), 2.94 (3H, s), 2.15 (6H, s), 1.51 (3H, d, J = 7.0 Hz); LC/MS RT 1.51 min, m/z [M − H]⁻ 518 |
| 38 | | 1H NMR (CD3OD) δ: 8.18 (1H, s), 7.67 (1H, s), 6.96 (1H, dd, J = 8.4, 5.9 Hz), 6.71 (1H, dd, J = 11.7, 8.4 Hz), 4.81 (1H, d, J = 11.0 Hz), 3.56 (1H, s), 3.33 (1H, s), 2.20 (3H, s), 2.16 (3H, s), 1.45 (3H, d, J = 6.6 Hz). ; LC/MS RT 1.46 min, m/z [M − H]⁻ 525, 527 |

TABLE 18-8-continued

| Example | Structural Formula | Physical Property Value |
|---|---|---|
| 39 | | 1H NMR (CD3OD) δ: 7.88 (1H, s), 7.72 (1H, s), 6.99-6.94 (1H, m), 6.70 (1H, dd, J = 11.7, 8.4 Hz), 4.77 (1H, d, J = 11.0 Hz), 3.58 (1H, s), 3.13 (3H, s), 2.90 (3H, s), 2.22 (3H, s), 2.17 (3H, s), 1.44-1.42 (3H, m); LC/MS RT 1.58 min, m/z [M − H]⁻ 552, 554 |
| 40 | | 1H NMR (CD3OD) δ: 8.76 (s, 1H), 7.62 (s, 1H), 6.98 (dd, J = 8.2, 6.0 Hz, 1H), 6.73 (dd, J = 11.9, 8.6 Hz, 1H), 4.83-4.86 (m, 1H), 3.51-3.73 (m, 1H), 2.22 (s, 3H), 2.18 (s, 3H), 1.45 (d, J = 6.6 Hz, 3H); LC/MS RT 1.61 min, m/z [M − H]⁻ 482, 484 |

TABLE 18-9

| Example | Structural Formula | Physical Property Value |
|---|---|---|
| 41 | | 1H NMR (CD3OD) δ: 8.06 (d, J = 9.2 Hz, 1H), 7.87-7.91 (m, 2H), 6.97 (dd, J = 8.3, 5.7 Hz, 1H), 6.72 (dd, J = 11.7, 8.3 Hz, 1H), 4.83 (d, J = 11.0 Hz, 1H), 3.49-3.66 (m, 1H), 2.20 (s, 3H), 2.17 (s, 3H), 1.45 (d, J = 7.0 Hz, 3H); LC/MS RT 1.72 min, m/z [M − H]⁻ 515 |
| 42 | | 1H NMR (CD3OD) δ: 8.08 (d, J = 8.1 Hz, 1H), 7.88-7.94 (m, 2H), 7.44 (dd, J = 8.8, 5.1 Hz, 1H), 6.82 (dd, J = 11.4, 8.8 Hz, 1H), 4.79-4.85 (m, 1H), 3.56-3.71 (m, 1H), 2.18 (s, 3H), 1.47 (d, J = 7.0 Hz, 3H); LC/MS RT 1.78 min, m/z [M − H]⁻ 579, 581 |

TABLE 18-9-continued

| Example | Structural Formula | Physical Property Value |
|---|---|---|
| 43 | | 1H NMR (CD3OD) δ: 7.84 (d, J = 8.4 Hz, 1H), 7.55-7.65 (m, 2H), 6.98 (dd, J = 8.4, 5.9 Hz, 1H), 6.72 (dd, J = 11.7, 8.4 Hz, 1H), 4.79 (d, J = 11.0 Hz, 1H), 3.54 (br d, J = 11.4 Hz, 1H), 2.20 (s, 3H), 2.17 (s, 3H); LC/MS RT 1.64 min, m/z [M − H]⁻ 484, 486 |
| 44 | | 1H NMR (CD3OD) δ: 8.01 (d, J = 8.4 Hz, 1H), 7.78-7.86 (m, 1H), 7.71 (dd, J = 8.6, 2.0 Hz, 1H), 7.50 (s, 4H), 7.37-7.47 (m, 3H), 7.09-7.25 (m, 1H), 4.57 (d, J = 9.2 Hz, 1H), 4.05-4.23 (m, 1H), 1.54 (d, J = 6.6 Hz, 3H); LC/MS RT 1.82 min, m/z [M − H]⁻ 486, 488 |
| 45 | | 1H NMR (CD3OD) δ: 7.76-7.85 (m, 1H), 7.65-7.74 (m, 2H), 7.54 (s, 2H), 7.51 (d, J = 5.5 Hz, 1H), 7.34 (d, J = 5.5 Hz, 1H), 7.29 (t, J = 7.7 Hz, 1H), 7.14-7.23 (m, 1H), 4.67 (d, J = 9.5 Hz, 1H), 3.44-3.58 (m, 1H), 1.55 (d, J = 7.0 Hz, 3H); LC/MS RT 1.78 min, m/z [M − H]⁻ 492, 494 |

TABLE 18-10

| Example | Structural Formula | Physical Property Value |
|---|---|---|
| 46 | | LC/MS RT 1.89 min, m/z [M − H]⁻ 476, 478 |
| 47 | | 1H NMR (CD3OD) δ: 7.83 (d, J = 8.4 Hz, 1H), 7.15 (d, J = 1.8 Hz, 1H), 7.08 (dd, J = 8.1, 1.8 Hz, 1H), 6.90-7.00 (m, 2H), 6.83 (d, J = 7.0 Hz, 1H), 4.29 (d, J = 10.6 Hz, 1H), 3.54-3.63 (m, 1H), 2.59-2.83 (m, 4H), 1.90-1.98 (m, 1H), 1.61-1.82 (m, 4H), 1.37 (d, J = 7.0 Hz, 3H), 1.03-1.12 (m, 2H), 0.76-0.87 (m, 2H); LC/MS RT 1.97 min, m/z [M − H]⁻ 486 |

TABLE 18-10-continued

| Example | Structural Formula | Physical Property Value |
|---|---|---|
| 48 | | 1H NMR (CD3OD) δ: 8.58-8.67 (m, 1H), 8.08-8.34 (m, 1H), 7.78-7.96 (m, 1H), 6.89-7.18 (m, 3H), 4.72 (d, J = 10.3 Hz, 0.5H), 4.41 (d, J = 11.0 Hz, 0.5H), 3.36-3.50 (m, 2H), 2.93-3.10 (m, 1H), 2.70 (dt, J = 15.9, 8.2 Hz, 1H), 1.98-2.27 (m, 1H), 1.67-1.85 (m, 1H), 1.46 (d, J = 6.6 Hz, 1.5H), 1.35 (d, J = 6.6 Hz, 1.5H), 1.15 (d, J = 7.0 Hz, 1.5H), 1.10 (d, J = 7.0 Hz, 1.5H); LC/MS RT 1.79 min, m/z [M − H]⁻ 491, 493 |
| 49 | | 1H NMR (CD3OD) δ: 8.53 (dd, J = 2.2, 0.7 Hz, 1H), 8.11 (dd, J = 8.2, 2.4 Hz, 1H), 7.76 (d, J = 7.3 Hz, 1H), 7.64 (d, J = 7.3 Hz, 1H), 7.55 (d, J = 7.3 Hz, 1H), 7.26-7.41 (m, 4H), 7.16 (d, J = 7.7 Hz, 1H), 4.68 (d, J = 9.9 Hz, 1H), 3.87 (s, 2H), 3.49-3.61 (m, 1H), 1.50 (d, J = 7.0 Hz, 3H); LC/MS RT 1.83 min, m/z [M − H]⁻ 525, 527 |
| 50 | | 1H NMR (CD3OD) δ: 8.44 (d, J = 2.2 Hz, 1H), 8.02-8.09 (m, 2H), 7.68 (d, J = 8.4 Hz, 1H), 7.57 (d, J = 7.3 Hz, 1H), 7.09-7.46 (m, 5H), 4.83-4.85 (m, 1H), 4.30-4.442 (m, 1H), 3.65 (s, 2H), 1.51 (d, J = 7.0 Hz, 3H); LC/MS RT 1.82 min, m/z [M − H]⁻ 525, 527 |

TABLE 18-11

| Example | Structural Formula | Physical Property Value |
|---|---|---|
| 51 | | 1H NMR (CD3OD) δ: 8.07-8.19 (m, 2H), 8.00 (d, J = 8.8 Hz, 1H), 7.76 (d, J = 8.4 Hz, 3H), 7.63-7.70 (m, 1H), 7.47-7.54 (m, 1H), 7.34-7.45 (m, 3H), 4.63 (d, J = 8.1 Hz, 1H), 4.06-4.21 (m, 1H), 1.54 (d, J = 7.0 Hz, 3H); LC/MS RT 1.73 min, m/z [M − H]⁻ 453 |
| 52 | | 1H NMR (CD3OD) δ: 8.52 (d, J = 2.6 Hz, 1H), 8.01 (dd, J = 8.4, 2.6 Hz, 1H), 7.90 (d, J = 8.4 Hz, 1H), 6.97 (d, J = 4.8 Hz, 2H), 6.83-6.91 (m, 1H), 4.50 (d, J = 10.3 Hz, 1H), 3.51-3.61 (m, 1H), 2.55-2.96 (m, 4H), 1.54-1.91 (m, 4H), 1.36 (d, J = 6.6 Hz, 3H); LC/MS RT 1.77 min, m/z [M − H]⁻ 447, 449 |

TABLE 18-11-continued

| Example | Structural Formula | Physical Property Value |
|---|---|---|
| 53 | | 1H NMR (CD3OD) δ: 7.94 (d, J = 8.4 Hz, 1H), 7.91 (d, J = 2.2 Hz, 1H), 7.72 (dd, J = 8.4, 2.2 Hz, 1H), 6.99-7.02 (m, 1H), 6.91-6.97 (m, 1H), 6.84 (d, J = 7.3 Hz, 1H), 4.54 (d, J = 9.5 Hz, 1H), 3.58-3.69 (m, 4H), 2.63-2.85 (m, 4H), 1.64-1.88 (m, 4H), 1.32 (d, J = 6.6 Hz, 3H); LC/MS RT 1.92 min, m/z [M − H]⁻ 520, 522 |
| 54 | | LC/MS RT 1.94 min, m/z [M − H]⁻ 491, 493 |
| 55 | | 1H NMR (CD3OD) δ: 7.66 (d, J = 8.7 Hz, 1H), 6.93-7.00 (m, 2H), 6.83 (d, J = 7.0 Hz, 1H), 6.51-6.56 (m, 2H), 4.25 (d, J = 11.0 Hz, 1H), 3.91 (s, 3H), 3.82 (s, 3H), 3.47-3.61 (m, 1H), 2.60-2.79 (m, 4H), 1.59-1.85 (m, 4H), 1.40 (d, J = 7.0 Hz, 3H); LC/MS RT 1.77 min, m/z [M − H]⁻ 472 |

TABLE 18-12

| Example | Structural Formula | Physical Property Value |
|---|---|---|
| 56 | | 1H NMR (CD3OD) δ: 8.13 (dd, J = 9.5, 5.5 Hz, 1H), 7.67 (d, J = 8.4 Hz, 2H), 7.37-7.53 (m, 3H), 7.30 (td, J = 8.8, 2.6 Hz, 1H), 7.08 (d, J = 1.8 Hz, 1H), 6.97 (dd, J = 8.4, 1.8 Hz, 1H), 4.48 (d, J = 10.3 Hz, 1H), 4.11-4.21 (m, 1H), 3.94 (s, 3H), 1.60 (d, J = 7.0 Hz, 3H); LC/MS RT 1.80 min, m/z [M − H]⁻ 490, 492 |

TABLE 18-12-continued

| Example | Structural Formula | Physical Property Value |
|---|---|---|
| 57 | | 1H NMR (CD3OD) δ: 8.00 (d, J = 8.4 Hz, 1H), 7.83-7.91 (m, 2H), 6.91-7.02 (m, 2H), 6.78-6.86 (m, 1H), 4.36 (d, J = 10.6 Hz, 1H), 4.05 (s, 3H), 3.53-3.63 (m, 1H), 2.59-2.87 (m, 4H), 1.62-1.87 (m, 4H), 1.40 (d, J = 7.0 Hz, 3H); LC/MS RT 1.83 min, m/z [M − H]⁻ 487, 489 |
| 58 | | 1H NMR (CD3OD) δ: 8.28-8.34 (m, 1H), 6.92-7.00 (m, 2H), 6.80-6.89 (m, 1H), 4.43 (d, J = 10.6 Hz, 1H), 3.95 (s, 3H), 3.84 (s, 3H), 3.47-3.60 (m, 1H), 2.60-2.85 (m, 4H), 1.60-1.87 (m, 4H), 1.33 (d, J = 6.6 Hz, 3H); LC/MS RT 1.80 min, m/z [M − H]⁻ 506 |
| 59 | | 1H NMR (CD3OD) δ: 8.12-8.30 (m, 2H), 7.74 (dd, J = 8.8, 7.3 Hz, 1H), 6.72-7.02 (m, 3H), 4.52 (d, J = 10.3 Hz, 1H), 3.30-3.40 (m, 1H), 2.68-2.92 (m, 4H), 1.88-2.01 (m, 2H), 1.38 (d, J = 7.0 Hz, 3H); LC/MS RT 1.69 min, m/z [M − H]⁻ 456 |
| 60 | | 1H NMR (cdcl3) δ: 7.60 (t, J = 8.1 Hz, 1H), 7.31-7.37 (m, 1H), 7.20-7.26 (m, 1H), 7.06-7.10 (m, 1H), 7.01-7.06 (m, 1H), 6.88 (d, J = 7.3 Hz, 1H), 5.46 (br s, 1H), 4.52 (br t, J = 7.9 Hz, 1H), 3.29-3.41 (m, 1H), 2.70-2.90 (m, 4H), 1.95-2.07 (m, 2H), 1.38 (d, J = 7.0 Hz, 3H); LC/MS RT 1.87 min, m/z [M − H]⁻ 494, 496 |

TABLE 18-13

| Example | Structural Formula | Physical Property Value |
|---|---|---|
| 61 | | 1H NMR (cdcl3) δ: 7.62-7.69 (m, 1H), 7.52-7.59 (m, 1H), 7.15 (t, J = 8.1 Hz, 1H), 7.03 (s, 2H), 6.86-6.92 (m, 1H), 5.46 (br s, 1H), 4.54 (br t, J = 8.1 Hz, 1H), 3.30-3.46 (m, 1H), 2.72-2.91 (m, 4H), 1.96-2.09 (m, 2H), 1.37-1.42 (m, 1H), 1.40 (d, J = 7.0 Hz, 2H); LC/MS RT 1.82 min, m/z [M − H]⁻ 450, 452 |

TABLE 18-13-continued

| Example | Structural Formula | Physical Property Value |
|---|---|---|
| 62 | | 1H NMR (CD3OD) δ: 7.79-7.87 (m, 1H), 7.73 (d, J = 7.7 Hz, 1H), 7.65 (d, J = 8.4 Hz, 1H), 7.40 (s, 1H), 7.27-7.36 (m, 2H), 7.07 (d, J = 1.8 Hz, 1H), 6.95 (dd, J = 8.4, 2.2 Hz, 1H), 4.46 (d, J = 9.9 Hz, 1H), 3.93 (s, 3H), 3.70-3.78 (m, 1H), 1.59 (d, J = 7.0 Hz, 3H); LC/MS RT 1.77 min, m/z [M − H]⁻ 478, 480 |
| 63 | | 1H NMR (CD3OD) δ: 9.16 (1H, s), 7.91-7.88 (1H, m), 7.66 (1H, d, J = 8.4 Hz), 7.39-7.31 (2H, m), 7.07-7.07 (1H, m), 6.99-6.97 (1H, m), 3.95 (3H, s), 3.49-3.48 (1H, m), 3.15-3.13 (1H, m), 1.66 (3H, d, J = 7.0 Hz); LC/MS RT 1.62 min, m/z [M − H]⁻ 479, 481 |
| 64 | | 1H NMR (CD3OD) δ: 7.70 (d, J = 8.4 Hz, 1H), 7.24 (d, J = 1.8 Hz, 1H), 7.08-7.11 (m, 1H), 6.99-7.04 (m, 1H), 6.80 (d, J = 7.0 Hz, 1H), 6.61-6.73 (m, 1H), 4.55 (d, J = 10.6 Hz, 1H), 4.44-4.51 (m, 2H), 3.94 (s, 3H), 3.19-3.28 (m, 1H), 3.09 (t, J = 8.6 Hz, 2H), 1.45 (d, J = 7.0 Hz, 3H); LC/MS RT 1.68 min, m/z [M − H]⁻ 464, 466 |
| 65 | | 1H NMR (CD3OD) δ: 8.07-8.21 (m, 1H), 7.74 (d, J = 8.4 Hz, 2H), 7.58 (d, J = 8.4 Hz, 1H), 7.44-7.53 (m, 1H), 7.31-7.42 (m, 1H), 7.20 (d, J = 8.4 Hz, 1H), 7.10 (d, J = 1.8 Hz, 1H), 5.96-7.06 (m, 1H), 5.16 (d, J = 11.7 Hz, 1H), 4.07-4.15 (m, 1H), 3.95 (s, 3H), 2.49 (s, 3H), 1.77 (d, J = 7.3 Hz, 2.3H), 1.66 (d, J = 7.3 Hz, 0.7H); LC/MS RT 1.82 min, m/z [M − H]⁻ 486, 488 |

TABLE 18-14

| Example | Structural Formula | Physical Property Value |
|---|---|---|
| 66 | | 1H NMR (CD3OD) δ: 7.67-7.77 (m, 1H), 7.10-7.15 (m, 1H), 7.01-7.05 (m, 1H), 6.97-7.01 (m, 1H), 6.63 (d, J = 7.7 Hz, 1H), 6.52 (d, J = 7.7 Hz, 1H), 4.36-4.56 (m, 2H), 4.30 (d, J = 11.4 Hz, 1H), 3.94 (s, 3H), 3.21-3.29 (m, 1H), 3.13 (t, J = 8.6 Hz, 2H), 1.46 (d, J = 7.0 Hz, 3H); LC/MS RT 1.62 min, m/z [M − H]⁻ 464, 466 |
| 67 | | 1H NMR (CD3OD) δ: 7.71 (dd, J = 8.4, 0.7 Hz, 1H), 7.10 (d, J = 1.8 Hz, 1H), 7.02 (dd, J = 8.2, 1.6 Hz, 2H), 6.91-6.99 (m, 2H), 4.29 (dd, J = 11.2, 1.6 Hz, 1H), 3.94 (s, 3H), 3.30-3.36 (m, 1H), 2.91-3.16 (m, 2H), 2.28-2.55 (m, 3H), 1.44 (d, J = 7.0 Hz, 3H), 1.11 (d, J = 6.4 Hz, 1.5H), 1.0 (d, J = 6.4 Hz, 1.5H); LC/MS RT 1.89 min, m/z [M − H]⁻ 476, 478 |
| 68 | | 1H NMR (CD3OD) δ: 8.62 (d, J = 8.8 Hz, 1H), 8.19 (dd, J = 7.3, 1.1 Hz, 1H), 8.09 (d, J = 8.4 Hz, 1H), 7.95 (d, J = 8.4 Hz, 1H), 7.64-7.71 (m, 1H), 7.56-7.62 (m, 1H), 7.48-7.56 (m, 1H), 6.92 (d, J = 4.8 Hz, 2H), 6.83 (d, J = 4.4 Hz, 1H), 4.20 (d, J = 10.6 Hz, 1H), 3.20-3.30 (m, 1H), 2.68-2.83 (m, 4H), 1.83-1.89 (m, 2H), 1.33 (d, J = 7.0 Hz, 3H); LC/MS RT 1.82 min, m/z [M − H]⁻ 448 |
| 69 | | LC/MS RT 1.86 min, m/z [M − H]⁻ 476, 478 |
| 70 | | 1H NMR (CD3OD) δ: 7.75 (d, J = 8.4 Hz, 1H), 7.26-7.43 (m, 3H), 7.09-7.21 (m, 5H), 7.04 (dd, J = 8.4, 1.8 Hz, 1H), 6.96 (dd, J = 7.1, 1.6 Hz, 1H), 4.37 (d, J = 10.6 Hz, 1H), 3.95 (s, 3H), 3.61-3.68 (m, 1H), 2.13 (s, 3H), 1.49 (d, J = 7.0 Hz, 3H); LC/MS RT 1.93 min, m/z [M − H]⁻ 512, 514 |

TABLE 18-15

| Example | Structural Formula | Physical Property Value |
|---|---|---|
| 71 | | 1H NMR (CD3OD) δ: 7.72 (d, J = 8.4 Hz, 1H), 7.64 (d, J = 7.3 Hz, 1H), 7.59-7.62 (m, 1H), 7.46 (d, J = 6.2 Hz, 1H), 7.31-7.37 (m, 1H), 7.21-7.29 (m, 2H), 7.06 (d, J = 1.8 Hz, 1H), 7.00 (dd, J = 8.4, 1.8 Hz, 1H), 4.61-4.74 (m, 1H), 4.37 (d, J = 10.6 Hz, 1H), 3.90 (s, 3H), 2.96 (s, 3H), 1.67 (d, J = 7.0 Hz, 3H); LC/MS RT 1.81 min, m/z [M − H]⁻ 486,488 |
| 72 | | 1H NMR (CD3OD) δ: 7.72 (d, J = 8.4 Hz, 1H), 7.11 (d, J = 1.8 Hz, 1H), 7.01-7.09 (m, 2H), 6.71 (d, J = 7.7 Hz, 1H), 6.52 (d, J = 8.1 Hz, 1H), 4.28-4.33 (m, 1H), 4.23 (d, J = 11.0 Hz, 1H), 4.07-4.15 (m, 1H), 3.94 (s, 3H), 3.41-3.50 (m, 1H), 3.33-3.39 (m, 1H), 1.51 (d, J = 7.0 Hz, 3H), 1.21 (d, J = 7.0 Hz, 3H); LC/MS RT 1.69 min, m/z [M − H]⁻ 478,480 |
| 73 | | 1H NMR (CD3OD) δ: 7.76 (d, J = 8.4 Hz, 1H), 7.10-7.14 (m, 1H), 6.97-7.09 (m, 2H), 6.62-6.67 (m, 1H), 6.51-6.62 (m, 1H), 4.50-4.57 (m, 1H), 4.38-4.48 (m, 1H), 4.11-4.16 (m, 1H), 3.94 (s, 3H), 3.33-3.46 (m, 2H), 1.41 (d, J = 7.0 Hz, 3H), 1.20-1.24 (m, 3H); LC/MS RT 1.66 min, m/z [M − H]⁻ 478,480 |
| 74 | | 1H NMR (CD3OD) δ: 7.71 (d, J = 8.4 Hz, 1H), 6.98-7.17 (m, 5H), 4.54 (d, J = 11.0 Hz, 0.34H), (d, J = 11.0 Hz, 0.68H), 3.95 (s, 1H), 3.85 (s, 2H), 3.48-3.59 (m, 1H), 1.51 (d, J = 7.0 Hz, 2H), 1.17 (d, J = 7.0 Hz, 1H),; LC/MS RT 1.67 min, m/z [M − H]⁻ 458,460 |
| 75 | | 1H NMR (CD3OD) δ: 7.72 (d, J = 8.4 Hz, 1H), 7.08-7014 (m, 2H), 6.95-7.06 (m, 1H), 6.95-7.06 (m, 1H), 6.84 (t, J = 9.0 Hz, 1H), 4.34 (d, J = 11.0 Hz, 1H), 3.94 (s, 3H), 3.52-3.63 (m, 1H), 2.17 (d, J = 2.2 Hz, 3H), 1.44 (d, J = 7.0 Hz, 3H); LC/MS RT 1.70 min, m/z [M − H]⁻ 454,456 |

TABLE 18-16

| Example | Structural Formula | Physical Property Value |
| --- | --- | --- |
| 76 | | LC/MS RT 1.78 min, m/z [M − H]⁻ 490,492 |
| 77 | | 1H NMR (CD3OD) δ: 7.71 (d, J = 8.4 Hz, 1H), 7.11 (d, J = 1.8 Hz, 1H), 6.94-7.06 (m, 2H), 6.73-6.86 (m, 1H), 4.30 (d, J = 10.6 Hz, 1H), 3.94 (s, 3H), 3.54-3.64 (m, 1H), 2.20 (s, 3H), 2.10 (s, 3H), 1.41 (d, J = 7.0 Hz, 3H); LC/MS RT 1.78 min, m/z [M − H]⁻ 468,470 |
| 78 | | 1H NMR (CD3OD) δ: 7.68 (d, J = 7.3 Hz, 2H), 7.51 (d, J = 8.4 Hz, 1H), 7.28-7.37 (m, 2H), 7.20 (t, J = 7.6 Hz, 1H), 7.09-7.15 (m, 1H), 7.02 (d, J = 1.8 Hz, 1H), 6.88 (dd, J = 8.4, 1.8 Hz, 1H), 4.39 (dd, J = 9.0, 6.4 Hz, 1H), 3.89-3.99 (m, 1H), 3.88 (s, 3H), 3.62-3.69 (m, 1H), 2.89 (s, 3H); LC/MS RT 1.80 min, m/z [M − H]⁻ 472,474 |
| 79 | | 1H NMR (CD3OD) δ: 7.73 (d, J = 8.4 Hz, 0.5H), 7.66 (d, J = 8.4 Hz, 0.5H), 6.98-7.17 (m, 3H), 6.75 (t, J = 9.3 Hz, 1H), 4.66 (d, J = 11.0 Hz, 0.5H), 4.57 (d, J = 11.4 Hz, 0.5H), 3.95 (s, 1.5H), 3.82 (s, 1.5H), 3.61-3.78 (m, 1H), 2.15 (s, 3H), 1.52 (d, J = 7.0 Hz, 1.5H), 1.15 (d, J = 7.0 Hz, 1.5H); LC/MS RT 1.76 min, m/z [M − H]⁻ 472,474 |
| 80 | | 1H NMR (CD3OD) δ: 7.61-7.80 (m, 1H), 6.76-7.19 (m, 5H), 4.55 (d, J = 11.0 Hz, 0.33H), 4.40 (d, J = 11.0 Hz, 0.67H), 3.94 (s, 2H), 3.80 (s, 1H), 3.39-3.49 (m, 1H), 2.15-2.20 (m, 3H), 1.48 (d, J = 7.0 Hz, 2H), 1.14 (d, J = 7.0 Hz, 1H); LC/MS RT 1.73, 1.76 min, m/z [M − H]⁻ 454,456 |

TABLE 18-17

| Example | Structural Formula | Physical Property Value |
|---|---|---|
| 81 | | 1H NMR (CD3OD) δ: 7.80 (d, J = 8.4 Hz, 1H), 7.64 (d, J = 8.5 Hz, 1H), 7.61 (d, J = 7.4 Hz, 1H), 7.43-7.50 (m, 1H), 7.34 (t, J = 7.3 Hz, 1H), 7.22-7.29 (m, 2H), 7.12 (d, J = 8.4 Hz, 1H), 4.64-4.76 (m, 1H), 4.36-4.49 (m, 3H), 2.96 (s, 3H), 2.47-2.58 (m, 2H), 1.68 (d, J = 7.0 Hz, 3H); LC/MS RT 1.88 min, m/z [M − H]⁻ 548,550 |
| 82 | | 1H NMR (DMSO-d6) δ:11.63 (br s, 1H), 7.31 (br dd, J = 8.1 Hz, 1H), 7.88 (d, J = 8.1 Hz, 1H), 7.80 (d, J = 8.8 Hz, 1H), 7.46-7.62 (m, J = 8.4 Hz, 4H), 7.30 (dd, J = 10.4, 7.9 Hz, 1H), 7.10-7.26 (m, 2H), 7.01 (dd, J = 8.6, 1.6 Hz, 1H), 4.33-4.50 (m, 1H), 4.06-4.22 (m, 1H), 3.86 (s, 3H), 1.45 (d, J = 6.6 Hz, 3H); LC/MS RT 1.82 min, m/z [M − H]⁻ 490,492 |
| 83 | | 1H NMR (CD3OD) δ: 7.74 (d, J = 8.4 Hz, 1H), 7.11 (d, J = 1.8 Hz, 1H), 7.03-7.07 (m, 1H), 6.96 (dd, J = 8.2, 5.7 Hz, 1H), 6.69 (dd, J = 11.7, 8.4 Hz, 1H), 4.68 (br d, J = 11.0 Hz, 1H), 3.95 (s, 3H), 3.61-3.68 (m, 1H), 2.21 (s, 3H), 2.17 (s, 3H), 1.47 (d, J = 6.6 Hz, 3H); LC/MS RT 1.77 min, m/z [M − H]⁻ 468,470 |
| 84 | | 1H NMR (CD3OD) δ: 7.87 (d, J = 8.4 Hz, 1H), 7.62 (dd, J = 8.4, 1.8 Hz, 1H), 7.54 (d, J = 2.2 Hz, 1H), 6.98 (dd, J = 8.4, 5.9 Hz, 1H), 6.72 (dd, J = 11.7, 8.4 Hz, 1H), 4.80 (d, J = 11.4 Hz, 1H), 3.52-3.63 (m, 1H), 2.22 (s, 3H), 2.17 (s, 3H), 1.45 (d, J = 7.0 Hz, 3H); LC/MS RT 1.77 min, m/z [M − H]⁻ 463,465 |
| 85 | | 1H NMR (CD3OD) δ: 7.73 (d, J = 8.1 Hz, 1H), 7.08-7.16 (m, 1H), 6.89-7.07 (m, 4H), 4.40 (d, J = 10.3 Hz, 1H), 3.95 (s, 3H), 3.71-3.83 (m, 1H), 3.45-3.58 (m, 1H), 2.33 (s, 3H), 1.43 (d, J = 6.6 Hz, 3H), 1.24 (d, J = 7.3 Hz, 6H); LC/MS RT 1.88 min, m/z [M − H]⁻ 478,480 |

TABLE 18-18

| Example | Structural Formula | Physical Property Value |
|---|---|---|
| 86 | | 1H NMR (CD3OD) δ: 7.73 (d, J = 8.4 Hz, 1H), 7.11 (d, J = 1.8 Hz, 1H), 6.92-7.05 (m, 4H), 4.35 (d, J = 11.0 Hz, 1H), 3.95 (s, 3H), 3.52-3.62 (m, 1H), 2.55-2.78 (m, 2H), 2.24 (s, 3H), 1.44 (d, J = 6.6 Hz, 3H), 1.08 (t, J = 7.3 Hz, 3H); LC/MS RT 1.82 min, m/z [M − H]⁻ 464,466 |
| 87 | | 1H NMR (CD3OD) δ: 7.72 (d, J = 8.4 Hz, 1H), 7.10 (d, J = 1.8 Hz, 1H), 6.98-7.06 (m, 3H), 6.94 (d, J = 2.2 Hz, 1H), 4.29 (d, J = 10.6 Hz, 1H), 3.94 (s, 3H), 3.58-3.63 (m, 1H), 2.51-2.66 (m, 2H), 2.21 (s, 3H), 1.43 (d, J = 6.6 Hz, 3H), 1.08 (t, J = 7.5 Hz, 3H); LC/MS RT 1.84 min, m/z [M − H]⁻ 464,466 |
| 88 | | 1H NMR (CD3OD) δ: 7.88 (d, J = 8.4 Hz, 1H), 7.14 (d, J = 8.4 Hz, 1H), 6.87-7.06 (m, 1H), 6.67-6.77 (m, 1H), 4.70-4.78 (m, 3H), 3.63-3.71 (m, 1H), 2.84-2.95 (m, 2H), 2.22 (s, 3H), 2.17 (s, 3H), 1.51 (d, J = 7.0 Hz, 3H); LC/MS RT 1.71 min, m/z [M − H]⁻ 508,510 |
| 89 | | 1H NMR (CD3OD) δ: 7.74 (d, J = 8.4 Hz, 1H), 7.10-7.27 (m, 2H), 7.04 (dd, J = 8.4, 1.8 Hz, 1H), 4.64-4.75 (m, 1H), 4.06-4.22 (m, 1H), 3.96 (s, 3H), 2.32 (s, 3H), 1.51 (d, J = 7.0 Hz, 3H); LC/MS RT 1.84 min, m/z [M − H]⁻ 550,552 |
| 90 | | 1H NMR (CD3OD) δ: 7.75 (d, J = 8.4 Hz, 1H), 7.12 (d, J = 2.2 Hz, 1H), 7.05 (dd, J = 8.4, 1.8 Hz, 1H), 6.89 (dd, J = 9.8 Hz, 1H), 4.66 (d, J = 11.4 Hz, 1H), 3.95 (s, 3H), 3.63-3.72 (m, 1H), 2.18 (s, 3H), 2.17 (s, 3H), 1.50 (d, J = 6.6 Hz, 3H); LC/MS RT 1.80 min, m/z [M − H]⁻ 486,488 |

TABLE 18-19

| Example | Structural Formula | Physical Property Value |
|---|---|---|
| 91 | | 1H NMR (CD3OD) δ: 8.51 (d, J = 1.8 Hz, 1H), 8.09-8.21 (m, 1H), 7.768-7.73 (m, 2H), 6.92-7.01 (m, 2H), 6.63-6.78 (m, 1H), 4.61-4.71 (m, 1H), 3.53-3.75 (m, 1H), 2.19 (s, 3H), 2.17 (s, 3H), 1.38 (d, J = 7.0 Hz, 3H); LC/MS RT 1.82 min, m/z [M − H]$^-$ 505,507 |
| 92 | | LC/MS RT 1.79 min, m/z [M − H]$^-$ 507,509 |
| 93 | | 1H NMR (CD3OD) δ: 7.45 (1H, d, J = 8.4 Hz), 7.21 (1H, d, J = 8.4 Hz), 6.96 (1H, dd, J = 8.6, 5.9 Hz), 6.70 (1H, dd, J = 12.1, 8.6 Hz), 4.66-4.80 (4H, m), 3.46 (3H, s), 2.19 (3H, s), 2.16 (3H, s), 1.49 (3H, d, J = 6.6 Hz); LC/MS RT 1.71 min, m/z [M − H]$^-$ 523,525 |
| 94 | | 1H-NMR (CDCl3) δ: 7.77 (1H, s), 7.42 (1H, d, J = 8.4 Hz), 7.00 (1H, d, J = 8.4 Hz), 6.93 (1H, dd, J = 8.3, 5.9 Hz), 6.69 (1H, dd, J = 11.5, 8.3 Hz), 5.43 (1H, d, J = 10.6 Hz), 4.86 (1H, t, J = 10.6 Hz), 4.34-4.29 (1H, m), 4.23-4.19 (1H, m), 3.41 (1H, br s), 3.10-3.07 (2H, m), 2.98-2.83 (2H, m), 2.18-2.17 (6H, m), 1.56-1.53 (3H, m), 1.27-1.23 (3H, m).; LC/MS RT 1.85 min, m/z [M − H]$^-$ 523,525 |
| 95 | | 1H-NMR (CDCl3) δ: 8.88 (1H, s), 7.68-7.64 (1H, m), 6.98-6.92 (2H, m), 6.73-6.68 (1H, m), 5.48-5.43 (1H, m), 4.95-4.81 (1H, m), 4.55-4.49 (1H, m), 4.34-4.20 (1H, m), 3.45 (1H, s), 2.92-2.82 (1H, m), 2.20-2.18 (6H, m), 2.08 (2H, s), 2.02 (1H, s), 1.98-1.93 (1H, m), 1.86 (1H, s), 1.76 (2H, s), 1.57-1.51 (3H, m).; LC/MS RT 1.82, 1.87 min, m/z [M − H]$^-$ 566,568 |

TABLE 18-20

| Example | Structural Formula | Physical Property Value |
|---|---|---|
| 96 | | 1H NMR (CD3OD) δ: 7.74-7.78 (m, 3H), 6.98 (dd, J = 8.4, 5.9 Hz, 1H), 6.75 (dd, J = 11.7, 8.4 Hz, 1H), 4.79 (d, J = 11.0 Hz, 1H), 3.51-3.63 (m, 1H), 2.47-2.68 (m, 2H), 2.24 (s, 3H), 1.45 (d, J = 7.0 Hz, 3H), 1.06 (t, J = 7.5 Hz, 3H); LC/MS RT 1.75 min, m/z [M − H]⁻ 539,541 |
| 97 | | 1H-NMR (CDCl3) δ: 8.06-7.99 (2H, m), 7.80 (1H, s), 7.07 (1H, t, J = 7.7 Hz), 6.93 (1H, dd, J = 8.5, 5.9 Hz), 6.69 (1H, dd, J = 11.5, 8.5 Hz), 5.28 (1H, d, J = 10.6 Hz), 4.86 (1H, t, J = 10.6 Hz), 3.46 (1H, br s), 2.92 (1H, d, J = 16.9 Hz), 2.69 (1H, d, J = 16.9 Hz), 2.20 (3H, s), 2.18 (3H, s), 1.64 (3H, s), 1.58-1.56 (3H, m), 1.46 (3H, s).; LC/MS RT 1.77 min, m/z [M − H]⁻ 502 |
| 98 | | LC/MS RT 1.66 min, m/z [M − H]⁻ 429 |
| 99 | | 1H-NMR (CDCl3) δ: 8.11 (1H, br s), 7.66-7.63 (2H, m), 6.98-6.90 (2H, m), 6.71-6.66 (1H, m), 5.44 (1H, d, J = 10.5 Hz), 4.82 (1H, t, J = 10.5 Hz), 4.56-4.52 (1H, m), 4.47-4.42 (1H, m), 4.01-3.95 (1H, m), 3.44-3.37 (1H, m), 2.17-2.16 (6H, m), 1.89 (1H, br s), 1.55 (3H, d, J = 7.0 Hz), 1.21-1.10 (2H, m), 0.92-0.89 (2H, m); LC/MS RT 1.69 min, m/z [M − H]⁻ 529 |
| 100 | | LC/MS RT 1.83, 1.90 min, m/z [M − H]⁻ 586,588 |

TABLE 18-21

| Example | Structural Formula | Physical Property Value |
|---------|-------------------|------------------------|
| 101 | | 1H NMR (CD3OD) δ: 7.51 (1H, d, J = 8.6 Hz), 7.24 (1H, d, J = 8.6 Hz), 6.97 (1H, dd, J = 8.2, 5.7 Hz), 6.71 (1H, dd, J = 11.9, 8.2 Hz), 6.04 (1H, tt, J = 55.5, 3.9 Hz), 4.82-4.58 (7H, m), 3.67-3.62 (1H, m), 2.19 (3H, s), 2.16 (3H, s), 1.47 (3H, d, J = 7.0 Hz); LC/MS RT 1.76 min, m/z [M − H]⁻ 573,575 |
| 102 | | 1H-NMR (CDCl3) δ: 7.67 (1H, br s), 7.46 (1H, d, J = 8.4 Hz), 7.01 (1H, d, J = 8.4 Hz), 6.94 (1H, dd, J = 8.4, 5.5 Hz), 6.70 (1H, dd, J = 11.4, 8.4 Hz), 6.24 (1H, tt, J = 56.3, 4.5 Hz), 5.41 (1H, d, J = 10.5 Hz), 4.88 (1H, t, J = 10.5 Hz), 4.42-4.37 (1H, m), 4.29-4.25 (1H, m), 3.42 (1H, br s), 3.32-3.17 (4H, m), 2.19-2.17 (6H, m), 1.55-1.54 (3H, m).; LC/MS RT 1.87 min, m/z [M − H]⁻ 559,561 |
| 103 | | LC/MS RT 1.87 min, m/z [M − H]⁻ 496,498 |
| 104 | | 1H-NMR (CDCl3) δ: 8.21 (1H, br s), 7.79 (1H, d, J = 8.4 Hz), 7.49 (1H, dd, J = 8.6, 5.3 Hz), 7.04-7.01 (1H, m), 6.96-6.92 (2H, m), 5.60-5.56 (1H, m), 4.79 (1H, t, J = 10.6 Hz), 3.95 (3H, s), 3.43 (1H, br s), 2.53 (3H, s), 1.55 (3H, d, J = 7.0 Hz).; LC/MS RT 1.64 min, m/z [M − H]⁻ 479,481 |
| 105 | | LC/MS RT 1.71 min, m/z [M − H]⁻ 464,466 |

TABLE 18-22

| Example | Structural Formula | Physical Property Value |
|---|---|---|
| 106 | | 1H-NMR (CDCl3) δ: 7.92-7.86 (1H, m), 7.56-7.46 (1H, m), 7.08-7.00 (1H, m), 6.97-6.92 (1H, m), 6.73-6.67 (1H, m), 5.52-5.45 (1H, m), 4.96-4.83 (1H, m), 4.61-4.37 (3H, m), 3.49 (1H, br s), 2.90-2.82 (1H, m), 2.54-2.48 (1H, m), 2.19-2.16 (6H, m), 2.09-2.09 (3H, m), 1.57-1.50 (2H, m); LC/MS RT 1.81 1.85 min, m/z [M − H]⁻ 586 |
| 107 | | LC/MS RT 1.90 min, m/z [M − H]⁻ 506,508 |
| 108 | | LC/MS RT 1.98 min, m/z [M − H]⁻ 568,570 |
| 109 | | LC/MS RT 1.71 min, m/z [M − H]⁻ 497,499 |
| 110 | | 1H NMR (CD3OD) δ: 7.53-7.63 (m, 1H), 7.02-7.19 (m, 2H), 6.95-7.01 (m, 1H), 6.72 (dd; J = 11.9, 8.6 Hz, 1H), 4.82-4.98 (m, 1H), 3.65-3.74 (m, 1H), 2.24 (s, 3H), 2.18 (s, 3H), 1.46 (d, J = 7.0 Hz, 3H); LC/MS RT 1.69 min, m/z [M − H]⁻ 440 |

TABLE 18-23

| Example | Structural Formula | Physical Property Value |
|---|---|---|
| 111 | | LC/MS RT 1.79 min, m/z [M − H]⁻ 474,476 |
| 112 | | 1H NMR (CD3OD) δ: 8.05 (d, J = 1.8 Hz, 1H), 7.76 (d, J = 1.8 Hz, 1H), 6.97 (dd, J = 8.2, 5.7 Hz, 1H), 6.70 (dd, J = 11.7, 8.4 Hz, 1H), 4.82 (d, J = 11.4 Hz, 1H), 3.99 (s, 3H), 3.66-3.76 (m, 1H), 2.25 (s, 3H), 2.18 (s, 3H), 1.51 (d, J = 7.0 Hz, 3H); LC/MS RT 1.62 min, m/z [M − H]⁻ 469,471 |
| 113 | | 1H NMR (CD3OD) δ: 8.16 (d, J = 8.4 Hz, 1H), 7.97 (d, J = 8.4 Hz, 1H), 6.99 (dd, J = 8.6, 6.0 Hz, 1H), 6.73 (dd, J = 11.9, 8.6 Hz, 1H), 4.94 (d, J = 11.4 Hz, 1H), 3.75-3.83 (m, 4H), 3.63-3.72 (m, 2H), 3.55-3.62 (m, 1H), 3.22-3.27 (m, 2H), 2.21 (s, 3H), 2.19 (s, 3H), 1.47 (d, J = 7.3 Hz, 3H); LC/MS RT 1.57 min, m/z [M − H]⁻ 552,554 |
| 114 | | 1H NMR (CD3OD) δ: 8.17 (d, J = 8.4 Hz, 1H), 7.98 (d, J = 8.4 Hz, 1H), 6.99 (dd, J = 8.4, 5.9 Hz, 1H), 6.73 (dd, J = 11.7, 8.4 Hz, 1H), 4.94 (d, J = 11.4 Hz, 1H), 3.58-3.66 (m, 3H), 3.21-3.29 (m, 2H), 2.21 (s, 3H), 2.19 (s, 3H), 1.94-2.01 (m, 4H), 1.46 (d, J = 7.0 Hz, 3H); LC/MS RT 1.65 min, m/z [M − H]⁻ 536,538 |

TABLE 18-23-continued

| Example | Structural Formula | Physical Property Value |
|---|---|---|
| 115 | | 1H NMR (CD3OD) δ: 8.16 (d, J = 8.4 Hz, 1H), 7.93-8.02 (m, 1H), 6.99 (dd, J = 8.2, 6.0 Hz, 1H), 6.72 (dd, J = 11.7, 8.4 Hz, 1H), 4.94 (dd, J = 11.2, 3.1 Hz, 1H), 3.53-3.64 (m, 3H), 3.29-3.36 (m, 2H), 3.23-3.29 (m, 2H), 2.21 (s, 3H), 2.18 (s, 3H), 1.92-2.08 (m, 6H), 1.46 (br d, J = 7.0 Hz, 3H); LC/MS RT 1.83 min, m/z [M − H]⁻ 576,578 |

TABLE 18-24

| Example | Structural Formula | Physical Property Value |
|---|---|---|
| 116 | | 1H NMR (CD3OD) δ: 8.16 (dd, J = 8.4, 5.1 Hz, 1H), 7.97 (dd, J = 11.7, 8.4 Hz, 1H), 6.96-7.02 (m, 1H), 6.73 (dd, J = 11.5, 8.4 Hz, 1H), 4.88-4.99 (m, 1H), 4.43-4.50 (m, 1H), 4.21-4.28 (m, 2H), 3.56-3.64 (m, 1H), 3.37-3.49 (m, 1H), 3.16 (d, J = 12.8 Hz, 1H), 2.96 (d, J = 12.8 Hz, 1H), 2.21 (s, 3H), 2.18 (s, 3H), 1.88-2.07 (m, 4H), 1.47 (d, J = 7.0 Hz, 3H); LC/MS RT 1.61 min, m/z [M − H]⁻ 578,580 |
| 117 | | 1H NMR (CD3OD) δ: 8.17 (dd, J = 8.4, 2.6 Hz, 1H), 7.97 (dd, J = 8.4, 2.2 Hz, 1H), 6.99 (dd, J = 8.4, 5.7 Hz, 1H), 6.73 (dd, J = 11.5, 8.4 Hz, 1H), 4.91-4.97 (m, 1H), 4.66-4.73 (m, 1H), 3.80-3.90 (m, 2H), 3.54-3.77 (m, 4H), 2.19-2.22 (m, 3H), 2.18 (s, 3H), 2.03-2.12 (m, 4H), 1.46 (d, J = 7.0 Hz, 3H); LC/MS RT 1.62 min, m/z [M − H]⁻ 578,580 |
| 118 | | LC/MS RT 1.72 min, m/z [M − H]⁻ 497,499 |

TABLE 18-24-continued

| Example | Structural Formula | Physical Property Value |
| --- | --- | --- |
| 119 | | LC/MS RT 1.73 min, m/z [M − H]⁻ 541,543 |
| 120 | | LC/MS RT 1.80 min, m/z [M − H]⁻ 555,557 |

TABLE 18-25

| Example | Structural Formula | Physical Property Value |
| --- | --- | --- |
| 121 | | LC/MS RT 1.93 min, m/z [M − H]⁻ 514,516 |
| 122 | | LC/MS RT 1.91 min, m/z [M − H]⁻ 526,528 |

TABLE 18-25-continued

| Example | Structural Formula | Physical Property Value |
|---|---|---|
| 123 | | 1H-NMR (CDCl3) δ: 8.56 (0.5H, s), 8.04 (0.5H, s), 7.83-7.78 (1H, m), 7.07-7.04 (1H, m), 6.96-6.93 (1H, m), 6.74-6.68 (1H, m), 5.43-5.40 (1H, m), 4.97-4.91 (0.5H, m), 4.84-4.79 (0.5H, m), 4.60-4.42 (2H, m), 3.51 (1H, s), 2.94 (1H, s), 2.53-2.44 (1H, m), 2.22-2.17 (9H, m), 1.57-1.50 (3H, m).; LC/MS RT 1.89, 1.94 min, m/z [M − H]⁻ 620,622 |
| 124 | | 1H NMR (CD3OD) δ: 7.88 (d, J = 8.4 Hz, 1H), 7.43 (dd, J = 8.8, 5.5 Hz, 1H), 7.15 (d, J = 8.4 Hz, 1H), 6.82 (dd, J = 11.2, 9.0 Hz, 1H), 4.69-4.80 (m, 3H), 3.63-3.79 (m, 1H), 2.85-2.92 (m, 2H), 2.44 (s, 3H), 1.54 (d, J = 7.0 Hz, 3H); LC/MS RT 1.77 min, m/z [M − H]⁻ 572,574 |
| 125 | | 1H-NMR (CDCl3) δ: 8.47 (1H, br s), 7.67 (1H, d, J = 8.4 Hz), 6.96-6.93 (2H, m), 6.82-6.82 (1H, m), 6.65 (1H, dd, J = 14.5, 8.2 Hz), 5.67 (1H, d, J = 9.6 Hz), 5.01 (1H, dd, J = 9.6, 1.6 Hz), 3.88 (3H, s), 2.29 (3H, s), 2.15 (3H, s), 1.66 (3H, d, J = 4.0 Hz), 1.58 (3H, d, J = 3.7 Hz).; LC/MS RT 1.87 min, m/z [M − H]⁻ 482,484 |

TABLE 18-26

| Example | Structural Formula | Physical Property Value |
|---|---|---|
| 126 | | 1H NMR (CD3OD) δ: 7.63 (1H, d, J = 8.4 Hz), 7.07 (1H, s), 6.98-6.94 (2H, m), 6.70-6.66 (1H, m), 4.40 (1H, t, J = 7.7 Hz), 3.94 (3H, s), 3.26-3.23 (1H, m), 3.16-3.11 (1H, m), 2.17 (3H, s), 2.14 (3H, s); LC/MS RT 1.76 min, m/z [M − H]⁻ 454,456 |
| 127 | | 1H NMR (CD3OD) δ: 7.72 (1H, dd, J = 14.3, 8.4 Hz), 7.12-7.06 (1H, m), 7.05-6.99 (2H, m), 6.72-6.63 (1H, m), 4.34-4.16 (1H, m), 3.86-3.81 (3H, m), 2.37-2.30 (3H, m), 2.19 (3H, s), 1.57-1.54 (1H, m), 1.35-1.28 (1H, m), 0.93-0.87 (1H, m), 0.72-0.67 (1H, m); LC/MS RT 1.85 min, m/z [M − H]⁻ 480,482 |

TABLE 18-26-continued

| Example | Structural Formula | Physical Property Value |
| --- | --- | --- |
| 128 | | 1H-NMR (CDCl3) δ: 7.84 (1H, br s), 7.78 (1H, d, J = 8.1 Hz), 7.00 (1H, dd, J = 8.4, 1.8 Hz), 6.95-6.91 (2H, m), 6.68 (1H, dd, J = 11.7, 8.4 Hz), 5.46 (1H, d, J = 10.3 Hz), 4.82 (1H, t, J = 10.6 Hz), 3.94 (3H, s), 3.28-3.22 (1H, m), 2.27-2.25 (1H, m), 2.19-2.16 (6H, m), 1.96-1.87 (1H, m), 0.79 (3H, t, J = 7.3 Hz).; LC/MS RT 1.85 min, m/z [M − H]⁻ 482,484 |
| 129 | | 1H NMR (CD3OD) δ: 7.58-7.73 (m, 1H), 6.91-7.11 (m, 2H), 6.62-6.81 (m, 1H), 4.71-4.82 (m, 1H), 4.49-4.61 (m, 2H), 3.57-3.79 (m, 1H), 2.70-2.95 (m, 1H), 2.28-2.38 (m, 0.5H), 2.20-2.25 (m, 3H), 2.16-2.24 (m, 3H), 2.08-2.14 (m, 0.5H), 1.98-2.02 (m, 3H), 1.42-1.56 (m, 3H); LC/MS RT 1.81, 1.87 min, m/z [M − H]⁻ 569,571 |
| 130 | | 1H NMR (CD3OD) δ: 8.87 (dd, J = 4.2, 1.6 Hz, 1H), 8.39 (d, J = 2.6 Hz, 1H), 8.12-8.36 (m, 1H), 7.98 (dd, J = 8.2, 2.4 Hz, 1H), 7.69-7.86 (m, 1H), 7.55-7.68 (m, 2H), 7.42-7.51 (m, 2H), 5.21 (d, J = 7.7 Hz, 1H), 4.40-4.53 (m, 1H), 1.55 (d, J = 7.3 Hz, 3H); LC/MS RT 1.82 min, m/z [M − H]⁻ 488,490 |

TABLE 18-27

| Example | Structural Formula | Physical Property Value |
| --- | --- | --- |
| 131 | | 1H NMR (CD3OD) δ: 8.28 (dd, J = 6.2, 2.6 Hz, 1H), 8.08 (ddd, J = 8.7, 4.5, 2.6 Hz, 1H), 7.43-7.54 (m, 1H), 7.00-7.09 (m, 2H), 6.98 (d, J = 2.2 Hz, 1H), 4.42 (d, J = 10.6 Hz, 1H), 3.31-3.41 (m, 1H), 3.28 (s, 3H), 2.79-2.87 (m, 4H), 1.92-2.07 (m, 2H), 1.42 (d, J = 7.0 Hz, 3H); LC/MS RT 1.67 min, m/z [M − H]⁻ 494 |

TABLE 18-27-continued

| Example | Structural Formula | Physical Property Value |
|---|---|---|
| 132 | | 1H NMR (CD3OD) δ: 9.01 (dd, J = 4.2, 1.6 Hz, 1H), 8.28-8.45 (m, 2H), 8.15 (d, J = 7.0 Hz, 1H), 7.64-7.71 (m, 1H), 7.57-7.63 (m, 1H), 6.91-7.00 (m, 2H), 6.85-6.91 (m, 1H), 4.45 (d, J = 10.6 Hz, 1H), 3.28-3.42 (m, 1H), 2.68-2.94 (m, 4H), 1.78-2.08 (m, 2H), 1.45 (d, J = 7.0 Hz, 3H); LC/MS RT 1.72 min, m/z [M − H]⁻ 449 |
| 133 | | 1H NMR (CD3OD) δ: 8.88 (s, 1H), 8.59 (s, 1H), 8.01-8.08 (m, 1H), 7.56-7.65 (m, 1H), 7.45-7.54 (m, 1H), 7.36-7.42 (m, 1H), 6.98-7.06 (m, 2H), 6.85-6.93 (m, 1H), 4.23 (d, J = 11.0 Hz, 1H), 3.19-3.31 (m, 1H), 2.75-2.82 (m, 4H), 1.82-2.08 (m, 2H), 1.35 (d, J = 7.0 Hz, 3H); LC/MS RT 1.76 min, m/z [M − H]⁻ 465 |
| 134 | | 1H NMR (cdcl3) δ: 7.81 (dd, J = 7.7, 1.8 Hz, 1H), 7.73 (br s, 1H), 7.43-7.50 (m, 1H), 7.03-7.07 (m, 2H), 7.00 (t, J = 7.7 Hz, 1H), 6.90-6.95 (m, 2H), 5.48 (d, J = 10.6 Hz, 1H), 4.47 (t, J = 10.3 Hz, 1H), 3.95 (s, 3H), 3.14-3.33 (m, 1H), 2.77-2.88 (m, 4H), 1.95-2.10 (m, 2H), 1.49 (d, J = 7.0 Hz, 3H); LC/MS RT 1.69 min, m/z [M − H]⁻ 428 |
| 135 | | 1H NMR (CD3OD) δ: 7.72 (d, J = 8.4 Hz, 1H), 7.47 (d, J = 1.8 Hz, 1H), 7.42 (dd, J = 8.4, 2.2 Hz, 1H), 6.98-7.03 (m, 2H), 6.89-6.95 (m, 1H), 4.28 (d, J = 10.3 Hz, 1H), 3.25-3.33 (m, 1H), 2.88-3.11 (m, 2H), 2.75-2.85 (m, 4H), 1.84-2.10 (m, 2H), 1.39 (d, J = 7.0 Hz, 3H), 1.25 (t, J = 7.5 Hz, 3H); LC/MS RT 2.02 min, m/z [M − H]⁻ 506,508 |

TABLE 18-28

| Example | Structural Formula | Physical Property Value |
|---|---|---|
| 136 | | 1H NMR (CD3OD) δ: 8.86 (d, J = 2.2 Hz, 1H), 8.24 (dd, J = 7.3, 1.5 Hz, 1H), 8.12 (s, 1H), 8.06 (dd, J = 8.1, 1.5 Hz, 1H), 7.61 (t, J = 7.6 Hz, 1H), 6.82-7.03 (m, 3H), 4.40 (d, J = 11.0 Hz, 1H), 3.32-3.40 (m, 1H), 2.70-2.89 (m, 4H), 2.54 (s, 3H), 1.79-2.13 (m, 2H), 1.45 (d, J=7.0 Hz, 3H); LC/MS RT 1.79 min, m/z [M − H]⁻ 463 |
| 137 | | 1H NMR (CD3OD) δ: 7.64 (d, J = 8.4 Hz, 1H), 7.24 (d, J = 1.5 Hz, 1H), 7.18 (dd, J = 8.4, 1.8 Hz, 1H), 6.97-7.07 (m, 2H), 6.90-6.96 (m, 1H), 4.30 (d, J = 11.0 Hz, 1H), 3.94 (s, 3H), 3.32-3.38 (m, 1H), 2.78-2.89 (m, 4H), 1.90-2.11 (m, 2H), 1.44 (d, J = 7.0 Hz, 3H); LC/MS RT 1.82 min, m/z [M − H]⁻ 506,508 |
| 138 | | 1H NMR (CD3OD) δ: 7.89 (dd, J = 7.9, 1.6 Hz, 1H), 7.59 (td, J = 8.0, 1.6 Hz, 1H), 7.26-7.33 (m, 3H), 6.99-7.05 (m, 2H), 6.92-6.96 (m, 1H), 4.41 (d, J = 10.6 Hz, 1H), 3.36-3.42 (m, 1H), 2.78-2.91 (m, 4H), 1.91-2.04 (m, 2H), 1.40 (d, J = 7.0 Hz, 3H); LC/MS RT 1.78 min, m/z [M − H]⁻ 464 |
| 139 | | 1H NMR (CD3OD) δ: 8.00 (d, J = 1.8 Hz, 1H), 7.94 (dd, J = 8.1, 1.8 Hz, 1H), 7.58 (d, J = 8.1 Hz, 1H), 6.99-7.07 (m, 2H), 6.94-6.99 (m, 1H), 4.41 (d, J = 10.3 Hz, 1H), 3.56-3.60 (m, 2H), 3.39-3.46 (m, 2H), 3.25-3.29 (m, 1H), 2.78-2.87 (m, 4H), 1.93-2.06 (m, 2H), 1.40 (d, J = 7.0 Hz, 3H); LC/MS RT 1.60 min, m/z [M − H]⁻ 488 |

TABLE 18-28-continued
| Example | Structural Formula | Physical Property Value |
|---|---|---|
| 140 | 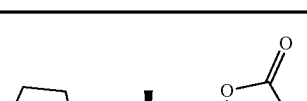 | 1H NMR (CD3OD) δ: 7.39-7.43 (m, 1H), 7.36-3.38 (m, 1H), 7.10 (d, J = 8.1 Hz, 1H), 7.00-7.06 (m, 2H), 6.93-6.98 (m, 1H), 4.30 (d, J = 11.0 Hz, 1H), 3.30-3.35 (m, 1H), 2.74-2.87 (m, 8H), 1.91-2.10 (m, 2H), 1.77-1.82 (m, 4H), 1.41 (d, J = 6.6 Hz, 3H); LC/MS RT 1.91 min, m/z [M − H]⁻ 452 |
TABLE 18-29
| Example | Structural Formula | Physical Property Value |
|---|---|---|
| 141 | | 1H NMR (CD3OD) δ: 8.53-8.55 (m, 1H), 8.23-8.31 (m, 1H), 8.10 (dd, J = 7.5, 2.0 Hz, 1H), 7.39-7.50 (m, 1H), 7.00-7.05 (m, 2H), 4.32 (d, J = 10.6 Hz, 1H), 4.03 (s, 3H), 3.45-3.52 (m, 1H), 2.76-2.93 (m, 4H), 1.93-2.12 (m, 2H), 1.44 (d, J = 7.0 Hz, 3H); LC/MS RT 1.65 min, m/z [M − H]⁻ 429 |
| 142 | | LC/MS RT 1.80 min, m/z [M − H]⁻ 519,521 |
| 143 | | 1H NMR (CD3OD) δ: 8.86-9.01 (m, 1H), 8.29-8.55 (m, 1H), 7.95-8.24 (m, 1H), 7.37-7.52 (m, 1H), 6.63-7.24 (m, 4H), 4.26-4.46 (m, 1H), 3.14-3.39 (m, 1H), 2.71-2.88 (m, 4H), 1.81-2.10 (m, 2H), 1.43 (d, J = 7.0 Hz, 3H); LC/MS RT 1.80 min, m/z [M − H]⁻ 494 |

TABLE 18-29-continued

| Example | Structural Formula | Physical Property Value |
|---|---|---|
| 144 | | LC/MS RT 1.92 min, m/z [M − H]⁻ 554,556 |
| 145 | | LC/MS RT 1.86 min, m/z [M − H]⁻ 518,520 |

TABLE 18-30

| Example | Structural Formula | Physical Property Value |
|---|---|---|
| 146 | | 1H NMR (CD3OD) δ: 7.90 (d, J = 8.4 Hz, 1H), 7.37 (dd, J = 8.4, 1.8 Hz, 1H), 7.33-7.35 (m, 1H), 6.88-7.05 (m, 1H), 6.70 (dd, J = 11.7, 8.4 Hz, 1H), 5.29-5.43 (m, 1H), 4.74 (d, J = 11.4 Hz, 1H), 3.59-3.75 (m, 1H), 2.22 (s, 3H), 2.18 (s, 3H), 1.45 (d, J = 7.0 Hz, 3H); LC/MS RT 1.86 min, m/z [M − H]⁻ 504, 506 |
| 147 | | LC/MS RT 1.83 min, m/z [M − H]⁻ 480, 482 |

TABLE 18-30-continued

| Example | Structural Formula | Physical Property Value |
|---|---|---|
| 148 | | 1H NMR (CD3OD) δ: 8.10 (d, J = 8.1 Hz, 1H), 7.10 (d, J = 8.1 Hz, 1H), 6.97 (dd, J = 8.4, 5.9 Hz, 1H), 6.70 (dd, J = 11.7, 8.4 Hz, 1H), 4.69 (d, J = 11.4 Hz, 1H), 4.03 (s, 3H), 3.60-3.74 (m, 1H), 2.22 (s, 3H), 2.18 (s, 3H), 1.47 (d, J = 7.0 Hz, 3H); LC/MS RT 1.77 min, m/z [M − H]⁻ 469, 471 |
| 149 | | 1H NMR (CD3OD) δ: 8.14-8.23 (m, 2H), 8.05-8.10 (m, 1H), 6.99 (dd, J = 8.4, 6.0 Hz, 1H), 6.75 (dd, J = 11.9, 8.4 Hz, 1H), 5.40 (d, J = 11.4 Hz, 1H), 3.65-3.77 (m, 1H), 2.23 (s, 3H), 2.20 (s, 3H), 1.40 (d, J = 7.0 Hz, 3H); LC/MS RT 1.66 min, m/z [M − H]⁻ 522, 524 |
| 150 | | 1H NMR (cdcl3) δ: 8.28-8.53 (m, 1H), 7.54 (br d, J = 8.1 Hz, 2H), 7.18 (br d, J = 8.1 Hz, 2H), 6.90-7.08 (m, 3H), 5.17 (br d, J = 9.2 Hz, 1H), 4.40 (t, J = 9.9 Hz, 1H), 3.49 (s, 2H), 3.44-3.61 (m, 1H), 2.38 (s, 3H), 2.20 (s, 3H), 2.11 (s, 3H), 1.34 (d, J = 7.0 Hz, 3H); LC/MS RT 1.72 min, m/z [M − H]⁻ 400 |

TABLE 18-31

| Example | Structural Formula | Physical Property Value |
|---|---|---|
| 151 | | 1H NMR (cdcl3) δ: 5.27 (d, J = 9.9 Hz, 1H), 7.69 (d, J = 8.4 Hz, 2H), 7.26 (d, J = 7.7 Hz, 4H), 6.94 (dd, J = 8.1, 5.9 Hz, 1H), 6.71 (dd, J = 11.4, 8.4 Hz, 1H), 5.27 (br d, J = 9.9 Hz, 1H), 4.79 (t, J = 10.3 Hz, 1H), 3.31-3.48 (m, 1H), 2.38 (s, 3H), 2.17 (s, 3H), 2.15 (s, 3H), 1.42 (br d, J = 7.0 Hz, 3H); LC/MS RT 1.72 min, m/z [M − H]⁻ 418 |

TABLE 18-31-continued

| Example | Structural Formula | Physical Property Value |
|---|---|---|
| 152 | | 1H-NMR (CDCl3) δ: 8.75 (1H, s), 7.72 (1H, d, J = 7.7 Hz), 7.55 (1H, d, J = 8.1 Hz), 7.38-7.37 (1H, m), 7.22 (1H, t, J = 7.9 Hz), 6.91-6.86 (2H, m), 6.66-6.61 (1H, m), 5.48 (1H, d, J = 10.4 Hz), 4.74 (1H, t, J = 10.4 Hz), 3.34 (1H, br s), 2.12 (3H, s), 2.08 (3H, s), 1.36 (3H, d, J = 6.6 Hz); LC/MS RT 1.60 min, m/z [M − H]⁻ 443 |
| 153 | | 1H NMR (CD3OD) δ: 9.09 (dd, J = 4.2, 1.6 Hz, 1H), 8.69 (d, J = 8.9 Hz, 1H), 8.34 (d, J = 8.1 Hz, 1H), 7.82 (d, J = 8.1 Hz, 1H), 7.70-7.76 (m, 1H), 6.91 (dd, J = 8.4, 5.9 Hz, 1H), 6.55-6.68 (m, 1H), 4.80 (d, J = 11.4 Hz, 1H), 3.62-3.70 (m, 1H), 2.18 (s, 3H), 2.13 (s, 3H), 1.49 (d, J = 6.6 Hz, 3H); LC/MS RT 1.80 min, m/z [M − H]⁻ 489, 491 |
| 154 | | 1H-NMR (CDCl3) δ: 8.63 (1H, s), 6.98-6.93 (1H, m), 6.92 (1H, s), 6.71 (1H, dd, J = 11.7, 8.4 Hz), 5.57 (1H, br s), 4.94-4.90 (1H, m), 4.03 (3H, s), 3.45 (1H, s), 2.18 (6H, s), 1.53 (3H, d, J = 7.0 Hz); LC/MS RT 1.65 min, m/z [M − H]⁻ 469, 471 |
| 155 | | 1H-NMR (CDCl3) δ: 7.95-7.91 (2H, m), 6.96-6.92 (1H, m), 6.70 (1H, dd, J = 11.5, 8.4 Hz), 4.98 (1H, t, J = 11.5 Hz), 4.76 (1H, d, J = 6.2 Hz), 4.62 (2H, t, J = 6.2 Hz), 4.58-4.55 (1H, m), 4.05-3.77 (1H, m), 3.70-3.66 (2H, m), 3.52-3.25 (4H, m), 2.31-2.21 (2H, m), 2.18 (3H, s), 2.14 (3H, d, J = 9.2 Hz), 1.53 (3H, d, J = 6.6 Hz). ; LC/MS RT 1.54 min, m/z [M − H]⁻ 578, 580 |

TABLE 18-32

| Example | Structural Formula | Physical Property Value |
|---|---|---|
| 156 | | 1H-NMR (CDCl3) δ: 7.95-7.92 (2H, m), 6.94 (1H, dd, J = 8.3, 5.9 Hz), 6.68 (1H, dd, J = 11.4, 8.3 Hz), 4.95 (1H, d, J = 10.6 Hz), 4.51-4.45 (4H, m), 3.82-3.80 (1H, m), 3.58-3.51 (1H, m), 3.44 (1H, br s), 3.16-3.03 (2H, m), 2.18 (3H, s), 2.15 (3H, s), 2.02-1.98 (2H, m), 1.92-1.88 (2H, m), 1.53 (3H, d, J = 7.0 Hz); LC/MS RT 1.56 min, m/z [M − H]⁻ 592, 594 |
| 157 | | 1H-NMR (CDCl3) δ: 10.23 (1H, s), 7.64 (1H, d, J = 8.4 Hz), 7.02 (1H, d, J = 8.4 Hz), 6.92 (1H, dd, J = 8.4, 5.9 Hz), 6.68 (1H, dd, J = 11.7, 8.4 Hz), 6.30 (1H, d, J = 6.2 Hz), 5.58 (1H, d, J = 10.3 Hz), 5.23 (1H, s), 4.79 (1H, t, J = 10.4 Hz), 4.54-4.51 (1H, m), 4.21-4.17 (1H, m), 3.54 (1H, s), 3.48 (1H, s), 2.19 (3H, s), 2.18 (3H, s), 1.96 (3H, s), 1.53 (3H, d, J = 7.0 Hz); LC/MS RT 1.61 min, m/z [M − H]⁻ 551, 553 |
| 158 | | 1H-NMR (CDCl3) δ: 8.12 (1H, br s), 7.37 (1H, d, J = 4.0 Hz), 6.97 (1H, dd, J = 8.3, 5.7 Hz), 6.86 (1H, d, J = 4.0 Hz), 6.72 (1H, dd, J = 11.7, 8.3 Hz), 5.24 (1H, br s), 4.84 (1H, t, J = 10.1 Hz), 3.48-3.43 (1H, m), 2.19 (3H, s), 2.17 (3H, s), 1.45 (3H, d, J = 7.0 Hz). ; LC/MS RT 1.79 min, m/z [M − H]⁻ 444, 446 |
| 159 | | ; LC/MS RT 1.65 min, m/z [M − H]⁻ 492 |

TABLE 18-32-continued

| Example | Structural Formula | Physical Property Value |
|---|---|---|
| 160 | | 1H-NMR (CDCl3) δ: 8.52 (1H, br s), 7.48 (1H, s), 6.96-6.92 (1H, m), 6.73-6.68 (1H, m), 5.53 (1H, d, J = 9.5 Hz), 4.80 (1H, t, J = 9.5 Hz), 3.66 (3H, s), 3.48 (1H, br s), 2.21 (3H, s), 2.19 (3H, s), 1.56-1.55 (3H, m). ; LC/MS RT 1.53 min, m/z [M − H]⁻ 442, 444 |

TABLE 18-33

| Example | Structural Formula | Physical Property Value |
|---|---|---|
| 161 | | 1H-NMR (CDCl3) δ: 8.34-8.54 (1H, m), 7.98 (1H, dd, J = 8.5, 2.4 Hz), 7.65 (1H, d, J = 8.5 Hz), 6.93-6.89 (1H, m), 6.67 (1H, dd, J = 11.4, 8.4 Hz), 6.16-6.14 (1H, m), 4.91 (1H, t, J = 10.3 Hz), 3.51 (2H, br s), 2.16 (1H, s), 2.14 (3H, s), 2.12 (3H, s), 1.53 (3H, d, J = 7.0 Hz). ; LC/MS RT 1.58 min, m/z [M − H]⁻ 506, 508 |
| 162 | | 1H NMR (CD3OD) δ: 7.64 (dd, J = 8.1, 1.8 Hz, 1H), 7.60 (s, 1H), 6.97 (dd, J = 8.4, 5.5 Hz, 1H), 6.92 (d, J = 8.1 Hz, 1H), 6.71 (dd, J = 11.9, 8.1 Hz, 1H), 4.67 (d, J = 11.0 Hz, 1H), 3.53-3.56 (m, 3H), 2.17 (s, 3H), 2.16 (s, 3H), 1.46 (d, J = 6.6 Hz, 3H); LC/MS RT 1.49 min, m/z [M − H]⁻ 459 |
| 163 | | 1H NMR (CD3OD) δ: 8.11-8.21 (m, 2H), 7.90-7.98 (m, 1H), 6.97 (dd, J = 8.4, 5.9 Hz, 1H), 6.72 (dd, J = 11.7, 8.4 Hz, 1H), 4.77 (d, J = 11.0 Hz, 1H), 3.53-3.72 (m, 1H), 2.18 (s, 3H), 2.16 (s, 3H), 1.47 (d, J = 7.0 Hz, 3H); LC/MS RT 1.58 min, m/z [M − H]⁻ 473 |

TABLE 18-33-continued

| Example | Structural Formula | Physical Property Value |
|---|---|---|
| 164 | | 1H NMR (CD3OD) δ: 7.30 (dd, J = 8.1, 1.5 Hz, 1H), 7.01 (dd, J = 8.1, 1.5 Hz, 1H), 6.96 (dd, J = 8.4, 5.9 Hz, 1H), 6.86 (t, J = 8.0 Hz, 1H), 6.70 (dd, J = 11.9, 8.6 Hz, 1H), 4.74 (d, J = 11.0 Hz, 1H), 4.37-4.45 (m, 2H), 4.19-4.34 (m, 2H), 3.61-3.77 (m, 1H), 2.21 (s, 3H), 2.17 (s, 3H), 1.49 (d, J = 6.6 Hz, 3H); LC/MS RT 1.67 min, m/z [M − H]⁻ 462 |
| 165 | | 1H NMR (CD3OD) δ: 7.47 (dd, J = 8.4, 1.8 Hz, 1H), 7.43 (d, J = 1.8 Hz, 1H), 7.07 (d, J = 8.3 Hz, 1H), 6.96 (dd, J = 8.3, 5.7 Hz, 1H), 6.70 (dd, J = 11.7, 8.4 Hz, 1H), 4.68 (d, J = 11.4 Hz, 1H), 3.53 (br dd, J = 10.8, 7.1 Hz, 1H), 2.17 (s, 3H), 2.15 (s, 3H), 1.43 (d, J = 6.6 Hz, 3H); LC/MS RT 1.42 min, m/z [M − H]⁻ 460 |

TABLE 18-34

| Example | Structural Formula | Physical Property Value |
|---|---|---|
| 166 | | LC/MS RT 1.59 min, m/z [M − H]⁻ 494 |
| 167 | | LC/MS RT 1.87, 1.92 min, m/z [M − H]⁻ 630, 632 |

TABLE 18-34-continued

| Example | Structural Formula | Physical Property Value |
|---|---|---|
| 168 | | 1H NMR (CD3OD) δ: 7.40 (dd, J = 8.1, 1.5 Hz, 1H), 7.16 (dd, J = 8.1, 1.1 Hz, 1H), 7.04 (t, J = 8.2 Hz, 1H), 6.98 (dd, J = 8.4, 5.7 Hz, 1H), 6.72 (dd, J = 11.5, 8.4 Hz, 1H), 4.68 (d, J = 11.4 Hz, 1H), 4.63-4.66 (m, 2H), 3.50-3.59 (m, 1H), 2.17 (s, 6H), 1.45 (d, J = 7.0 Hz, 3H); LC/MS RT 1.65 min, m/z [M − H]⁻ 475 |
| 169 | | 1H NMR (CD3OD) δ: 8.30 (dd, J = 6.2, 2.2 Hz, 1H), 8.12 (ddd, J = 8.7, 4.5, 2.6 Hz, 1H), 7.52 (t, J = 9.1 Hz, 1H), 6.98 (dd, J = 8.4, 5.9 Hz, 1H), 6.73 (dd, J = 11.7, 8.4 Hz, 1H), 4.75 (d, J = 11.4 Hz, 1H), 3.52-3.64 (m, 1H), 3.28(s, 3H), 2.20 (s, 3H), 2.17 (s, 3H), 1.47 (d, J = 6.6 Hz, 3H); LC/MS RT 1.65 min, m/z [M − H]⁻ 500 |
| 170 | | 1H NMR (CD3OD) δ: 6.97 (dd, J = 8.4, 5.9 Hz, 1H), 6.68-6.78 (m, 2H), 6.59-6.67 (m, 1H), 4.80 (d, J = 11.4 Hz, 1H), 3.94 (s, 3H), 3.63-3.75 (m, 1H), 2.23 (s, 3H), 2.18 (s, 3H), 1.50 (d, J = 6.6 Hz, 3H); LC/MS RT 1.71 min, m/z [M − H]⁻ 470 |

TABLE 18-35

| Example | Structural Formula | Physical Property Value |
|---|---|---|
| 171 | | 1H NMR (CD3OD) δ: 8.22 (d, J = 1.8 Hz, 1H), 7.83 (dd, J = 8.1, 2.2 Hz, 1H), 7.51 (d, J = 8.1 Hz, 1H), 6.93-7.03 (m, 1H), 6.66-6.80 (m, 1H), 4.71 (d, J = 11.3 Hz, 1H), 3.51-3.64 (m, 1H), 3.07-3.26 (m, 4H), 2.64 (s, 3H), 2.18 (s, 3H), 2.17 (s, 3H), 1.55-1.71 (m, 6H), 1.43 (d, J = 6.6 Hz, 3H); LC/MS RT 1.89 min, m/z [M − H]⁻ 565 |

TABLE 18-35-continued

| Example | Structural Formula | Physical Property Value |
|---|---|---|
| 172 | | 1H NMR (CD3OD) δ: 7.59 (d, J = 1.9 Hz, 1H), 7.50 (dd, J = 8.6, 1.9 Hz, 1H), 7.21 (d, J = 8.3 Hz, 1H), 6.97 (dd, J = 8.3, 5.7 Hz, 1H), 6.71 (dd, J = 11.7, 8.4 Hz, 1H), 4.70 (d, J = 11.0 Hz, 1H), 3.51-3.58 (m, 1H), 2.17 (s, 3H), 2.16 (s, 3H), 1.45 (d, J = 7.0 Hz, 3H); LC/MS RT 1.39 min, m/z [M − H]⁻ 488 |
| 173 | | 1H NMR (CD3OD) δ: 7.19-7.25 (m, 2H), 6.97 (dd, J = 8.4, 5.9 Hz, 1H), 6.87 (d, J = 8.4 Hz, 1H), 6.72 (dd, J = 11.7, 8.4 Hz, 1H), 4.66 (d, J = 11.4 Hz, 1H), 4.22-4.31 (m, 4H), 3.40-3.65 (m, 1H), 2.16 (s, 6H), 1.44 (d, J = 7.3 Hz, 3H); LC/MS RT 1.67 min, m/z [M − H]⁻ 462 |
| 174 | | LC/MS RT 1.68 min, m/z [M − H]⁻ 472 |
| 175 | | 1H NMR (CD3OD) δ: 8.05 (dd, J = 7.5, 2.0 Hz, 2H), 7.73 (t, J = 7.7 Hz, 1H), 6.97 (dd, J = 8.6, 5.9 Hz, 1H), 6.72 (dd, J = 11.7, 8.6 Hz, 1H), 5.52-5.71 (m, 2H), 4.72-4.79 (m, 1H), 3.54-3.61 (m, 1H), 2.17 (s, 3H), 2.16 (s, 3H), 1.46 (d, J = 7.0 Hz, 3H); LC/MS RT 1.65 min, m/z [M − H]⁻ 460 |

TABLE 18-36

| Example | Structural Formula | Physical Property Value |
|---|---|---|
| 176 | | 1H NMR (CD3OD) δ: 8.43 (d, J = 2.2 Hz, 1H ), 7.88-7.95 (m, 1H), 7.72 (d, J = 8.1 Hz, 1H), 6.98 (dd, J = 8.4, 5.9 Hz, 1H), 6.73 (dd, J = 11.4, 8.4 Hz, 1H), 4.23 (d, J = 10.6 Hz, 1H), 3.43-3.55 (m, 1H), 2.25 (s, 3H), 2.20 (s, 3H), 1.46 (d, J = 7.0 Hz, 3H); LC/MS RT 1.61 min, m/z [M − H]⁻ 517, 519 |
| 177 | | 1H NMR (cdcl3) δ: 8.27 (brs, 1H), 7.77-7.89 (m, 2H), 7.40-7.59 (m, 3H), 6.94 (dd, J = 8.3, 5.7 Hz, 1H), 6.71 (dd, J = 11.7, 8.3 Hz, 1H), 5.31 (br d, J = 10.3 Hz, 1H), 4.82 (t, J = 10.3 Hz, 1H), 3.36-3.47 (m, 1H), 2.17 (s, 3H), 2.15 (s, 3H), 1.43 (d, J = 5.9 Hz, 3H); LC/MS RT 1.66 min, m/z [M − H]⁻ 404 |
| 178 | | LC/MS RT 1.75 min, m/z [M − H]⁻ 498 |
| 179 | | LC/MS RT 1.64 min, m/z [M − H]⁻ 474 |

TABLE 18-36-continued

| Example | Structural Formula | Physical Property Value |
|---|---|---|
| 180 | 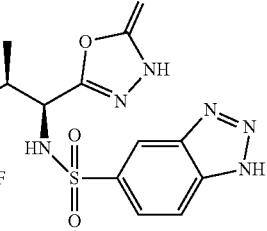 | LC/MS RT 1.90 min, m/z [M − H]⁻ 541, 543 |

TABLE 18-37

| Example | Structural Formula | Physical Property Value |
|---|---|---|
| 181 | 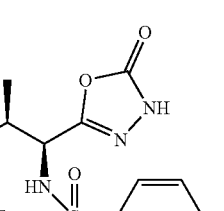 | 1H NMR (CD3OD) δ: 8.38 (s, 1H), 7.93 (d, J = 9.0 Hz, 1H), 7.83 (dd, J = 8.8, 1.8 Hz, 1H), 6.95 (dd, J = 8.3, 5.7 Hz, 1H), 6.70 (dd, J = 11.7, 8.3 Hz, 1H), 4.75 (d, J = 11.0 Hz, 1H), 3.50-3.65 (m, 1H), 2.16 (s, 3H), 2.14 (s, 3H), 1.45 (d, J = 7.0 Hz, 3H); LC/MS RT 1.50 min, m/z [M − H]⁻ 445 |
| 182 | 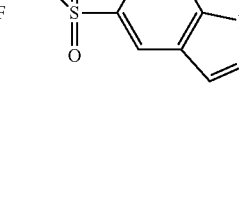 | 1H NMR (CD3OD) δ: 8.28 (s, 1H), 8.19 (s, 1H), 7.73 (dd, J = 8.8, 1.5 Hz, 1H), 7.61 (d, J = 8.8 Hz, 1H), 6.94 (dd, J = 8.4, 5.9 Hz, 1H), 6.69 (dd, J = 11.7, 8.4 Hz, 1H), 4.72 (d, J = 11.4 Hz, 1H), 3.47-3.65 (m, 1H), 2.16 (s, 3H), 2.14 (s, 3H), 1.43 (d, J = 7.0 Hz, 3H); LC/MS RT 1.53 min, m/z [M − H]⁻ 444 |
| 183 | | 1H NMR (CD3OD) δ: 7.40-7.48 (m, 2H), 6.97 (dd, J = 8.4, 5.9 Hz, 1H), 6.69-6.79 (m, 2H), 4.65 (d, J = 11.4 Hz, 1H), 4.16-4.22 (m, 2H), 3.48-3.60 (m, 1H), 2.78 (t, J = 6.2 Hz, 2H), 2.17 (s, 6H), 1.94-2.04 (m, 2H), 1.45 (d, J = 7.0 Hz, 3H); LC/MS RT 1.72 min, m/z [M − H]⁻ 460 |

TABLE 18-37-continued

| Example | Structural Formula | Physical Property Value |
|---|---|---|
| 184 | | 1H NMR (CD3OD) δ: 6.84-7.00 (m, 4H), 6.71 (dd, J = 11.7, 8.4 Hz, 1H), 4.66 (d, J = 11.4 Hz, 1H), 3.47-3.56 (m, 1H), 3.20-3.28 (m, 2H), 2.89 (s, 3H), 2.72 (t, J = 6.4 Hz, 2H), 2.15-2.18 (m, 6H), 1.85-1.99 (m, 2H), 1.44 (d, J = 7.0 Hz, 3H); LC/MS RT 1.73 min, m/z [M − H]⁻ 473 |
| 185 | | 1H-NMR (CDCl3) δ: 8.47 (1H, br s), 7.70 (1H, d, J = 8.8 Hz), 7.02 (1H, dd, J = 8.2, 6.0 Hz), 6.97 (1H, dd, J = 8.4, 1.8 Hz), 6.90-6.89 (1H, m), 6.72 (1H, t, J = 8.8 Hz), 5.74-5.73 (1H, m), 5.67 (1H, br s), 5.30-5.30 (1H, m), 5.14 (1H, d, J = 9.2 Hz), 3.92 (3H, s), 2.19 (3H, s), 2.11 (3H, s).; LC/MS RT 1.80 min, m/z [M − H]⁻ 466, 468 |

TABLE 18-38

| Example | Structural Formula | Physical Property Value |
|---|---|---|
| 186 | | 1H NMR (CD3OD) δ: 7.69-7.82 (m, 1H), 6.91-7.10 (m, 2H), 6.71 (dd, J = 11.7, 8.4 Hz, 1H), 4.74 (d, J = 11.0 Hz, 1H), 3.59-3.71 (m, 1H), 2.21 (s, 3H), 2.18 (s, 3H), 1.66 (s, 6H), 1.46 (d, J = 6.6 Hz, 3H); LC/MS RT 1.68 min, m/z [M − H]⁻ 498 |
| 187 | | 1H NMR (CD3OD) δ: 7.94 (d, J = 8.8 Hz, 1H), 7.49 (d, J = 2.2 Hz, 1H), 7.32 (d, J = 8.8 Hz, 1H), 6.98-7.07 (m, 2H), 6.90-6.98 (m, 1H), 4.43 (d, J = 10.3 Hz, 1H), 3.19-3.27 (m, 1H), 2.74-2.91 (m, 4H), 1.90-2.08 (m, 2H), 1.71 (s, 3H), 1.65 (s, 3H), 1.42 (d, J = 7.0 Hz, 3H); LC/MS RT 1.93 min, m/z [M − H]⁻ 490, 492 |

TABLE 18-38-continued

| Example | Structural Formula | Physical Property Value |
|---|---|---|
| 188 | | 1H NMR (CD3OD) δ: 8.29 (d, J = 2.6 Hz, 1H), 7.67 (d, J = 8.1 Hz, 1H), 7.45 (dd, J = 8.2, 2.4 Hz, 1H), 6.90-7.10 (m, 3H), 4.34 (d, J = 10.6 Hz, 1H), 3.24-3.31 (m, 1H), 2.79-2.84 (m, 4H), 1.90-2.09 (m, 2H), 1.70 (s, 6H), 1.39 (d, J = 7.0 Hz, 3H); LC/MS RT 1.8 min, m/z [M − H]⁻ 534, 536 |
| 189 | | 1H NMR (CD3OD) δ: 7.69-7.76 (m, 1H), 6.89-7.14 (m, 4H), 4.39 (d, J = 11.0 Hz, 1H), 3.24-3.31 (m, 1H), 2.77-2.97 (m, 4H), 1.91-2.07 (m, 2H), 1.67 (s, 6H), 1.44 (d, J = 7.0 Hz, 3H); LC/MS RT 1.7 min, m/z [M − H]⁻ 492 |
| 190 | | 1H NMR (CD3OD) δ: 7.37-7.50 (m, 1H), 7.03 (s, 2H), 6.91-6.99 (m, 1H), 4.41 (d, J = 10.6 Hz, 1H), 4.06 (s, 3H), 3.32-3.36 (m, 1H), 2.77-2.96 (m, 4H), 1.93-2.06 (m, 2H), 1.54 (s, 3H), 1.50 (s, 3H), 1.35 (d, J = 7.0 Hz, 3H); LC/MS RT 1.67 min, m/z [M − H]⁻ 492 |

TABLE 18-39

| Example | Structural Formula | Physical Property Value |
|---|---|---|
| 191 | | 1H NMR (CD3OD) δ: 7.76 (d, J = 9.2 Hz, 1H), 6.97-7.08 (m, 2H), 6.81-6.95 (m, 2H), 4.32 (d, J = 11.0 Hz, 1H), 3.91 (s, 6H), 3.33-3.40 (m, 1H), 2.70-2.98 (m, 4H), 1.91-2.13 (m, 2H), 1.66 (s, 3H), 1.65 (s, 3H), 1.41 (d, J = 7.0 Hz, 3H); LC/MS RT 1.78 min, m/z [M − H]⁻ 516 |

TABLE 18-39-continued

| Example | Structural Formula | Physical Property Value |
|---|---|---|
| 192 | | 1H NMR (CD3OD) δ: 8.45-8.43 (2H, m), 8.02 (1H, d, J = 8.1 Hz), 7.82 (1H, d, J = 8.1 Hz), 7.04-7.02 (2H, m), 6.98-6.95 (1H, m), 4.63 (1H, s), 4.51 (1H, d, J = 11.0 Hz), 2.92-2.82 (4H, m), 2.05-1.97 (2H, m), 1.69 (3H, s), 1.68 (3H, s), 1.42 (3H, d, J = 7.0 Hz); LC/MS RT 1.74 min, m/z [M − H]⁻ 491, 493 |
| 193 | | 1H NMR (CD3OD) δ: 8.04 (d, J = 8.3 Hz, 1H), 8.02 (d, J = 8.3 Hz, 1H), 6.98 (dd, J = 8.4, 5.9 Hz, 1H), 6.71 (dd, J = 11.7, 8.4 Hz, 1H), 4.83 (d, J = 11.4 Hz, 1H), 3.55-3.68 (m, 1H), 2.23 (s, 3H), 2.18 (s, 3H), 1.67 (d, J = 6.6 Hz, 6H), 1.46 (d, J = 7.0 Hz, 3H); LC/MS RT 1.71 min, m/z [M − H]⁻ 497, 499 |
| 194 | | 1H NMR (CD3OD) δ: 8.01-8.15 (m, 1H), 7.46-7.69 (m, 1H), 7.14 (d, J = 8.1 Hz, 1H), 6.93-7.01 (m, 1H), 6.66-6.76 (m, 1H), 4.69 (d, J = 11.4 Hz, 1H), 3.47-3.61 (m, 1H), 2.72-2.88 (m, 2H), 2.07-2.25 (m, 6H), 1.76-1.94 (m, 4H), 1.39-1.52 (m, 6H); LC/MS RT 1.66 min, m/z [M − H]⁻ 488 |
| 195 | | 1H NMR (CD3OD) δ: 7.96 (dd, J = 6.8, 2.4 Hz, 1H), 7.50 (dt, J = 8.7, 2.6 Hz, 1H), 6.97 (dd, J = 8.4, 5.9 Hz, 1H), 6.77-6.83 (m, 1H), 6.68-6.76 (m, 1H), 4.67 (dd, J = 11.2, 3.1 Hz, 1H), 4.29-4.38 (m, 1H), 4.21-4.28 (m, 1H), 3.47-3.62 (m, 1H), 2.13-2.24 (m, 6H), 2.02-2.11 (m, 2H), 1.58 (d, J = 11.0 Hz, 3H), 1.39-1.49 (m, 3H); LC/MS RT 1.60 min, m/z [M − H]⁻ 490 |

TABLE 18-40

| Example | Structural Formula | Physical Property Value |
|---|---|---|
| 196 | 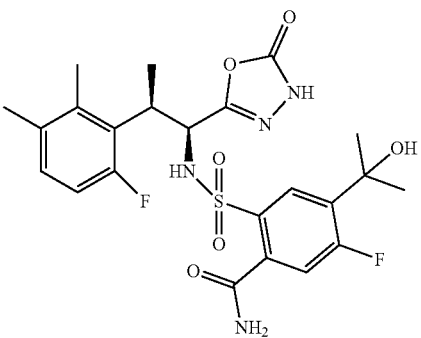 [SMILES: Cc1ccc(F)c([C@@H](C)[C@H](NS(=O)(=O)c2cc(C(C)(C)O)c(F)cc2C(N)=O)c2n[nH]c(=O)o2)c1C] | 1H NMR (CD3OD) δ: 8.25 (d, J = 7.3 Hz, 1H), 7.31 (d, J = 11.0 Hz, 1H), 6.97 (dd, J = 8.4, 5.9 Hz, 1H), 6.71 (dd, J = 11.7, 8.4 Hz, 1H), 4.79 (d, J = 11.0 Hz, 1H), 3.51-3.62 (m, 1H), 2.21 (s, 3H), 2.17 (s, 3H), 1.57 (s, 6H), 1.46 (d, J = 7.0 Hz, 3H); LC/MS RT 1.56 min, m/z [M − H]⁻ 523 |
| 197 | 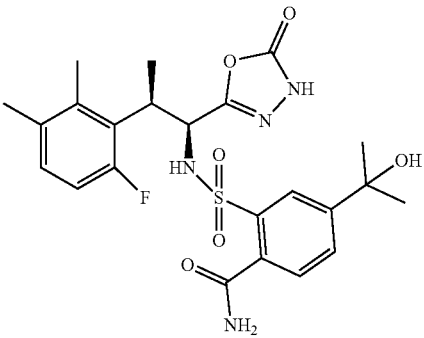 [SMILES: Cc1ccc(F)c([C@@H](C)[C@H](NS(=O)(=O)c2cc(C(C)(C)O)ccc2C(N)=O)c2n[nH]c(=O)o2)c1C] | 1H NMR (CD3OD) δ: 8.02 (d, J = 1.8 Hz, 1H), 7.74 (dd, J = 8.1, 1.8 Hz, 1H), 7.58 (d, J = 8.1 Hz, 1H), 6.97 (dd, J = 8.3, 5.7 Hz, 1H), 6.71 (dd, J = 11.7, 8.3 Hz, 1H), 4.80 (d, J = 11.0 Hz, 1H), 3.49-3.62 (m, 1H), 2.20 (s, 3H), 2.17 (s, 3H), 1.53 (s, 6H), 1.44 (d, J = 6.6 Hz, 3H); LC/MS RT 1.52 min, m/z [M − H]⁻ 505 |
| 198 | 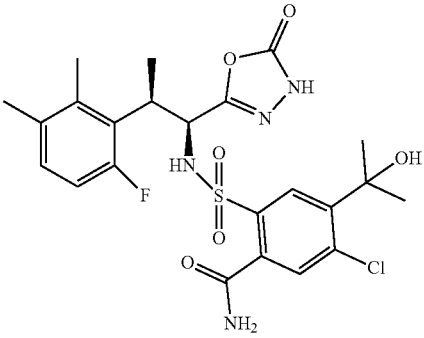 [SMILES: Cc1ccc(F)c([C@@H](C)[C@H](NS(=O)(=O)c2cc(C(C)(C)O)c(Cl)cc2C(N)=O)c2n[nH]c(=O)o2)c1C] | 1H NMR (CD3OD) δ: 8.41 (s, 1H), 7.60 (s, 1H), 6.97 (dd, J = 8.3, 6.0 Hz, 1H), 6.71 (dd, J = 11.7, 8.3 Hz, 1H), 4.80 (d, J = 11.0 Hz, 1H), 3.52-3.64 (m, 1H), 2.20 (s, 3H), 2.17 (s, 3H), 1.68 (s, 6H), 1.45 (d, J = 7.0 Hz, 3H); LC/MS RT 1.61 min, m/z [M − H]⁻ 539, 541 |
| 199 | 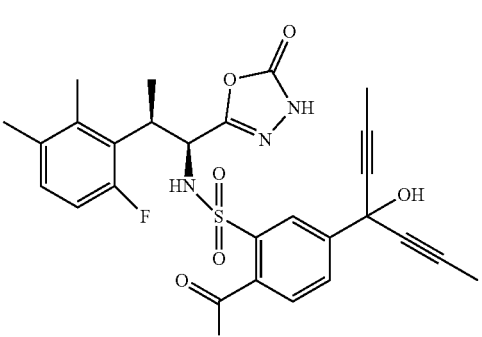 | 1H NMR (CD3OD) δ: 8.25 (d, J = 1.8 Hz, 1H), 7.95 (dd, J = 7.9, 2.0 Hz, 1H), 7.61 (d, J = 8.1 Hz, 1H), 6.93-7.02 (m, 1H), 6.66-6.75 (m, 1H), 4.75-4.85 (m, 1H), 3.52-3.62 (m, 1H), 2.20 (s, 3H), 2.17 (s, 3H), 1.88 (s, 6H), 1.40 (d, J = 6.2 Hz, 3H); LC/MS RT 1.63 min, m/z [M − H]⁻ 553 |

TABLE 18-40-continued

| Example | Structural Formula | Physical Property Value |
|---|---|---|
| 200A | | 1H NMR (CD3OD) δ: 7.61 (d, J = 8.4 Hz, 1H), 7.02 (d, J = 8.5 Hz, 1H), 6.96 (dd, J = 8.2, 5.7 Hz, 1H), 6.70 (dd, J = 11.7, 8.4 Hz, 1H), 4.71 (d, J = 11.4 Hz, 1H), 4.40-4.46 (m, 1H), 4.26 (td, J = 10.8, 2.6 Hz, 1H), 3.62-3.71 (m, 1H), 2.23 (s, 3H), 2.17 (s, 3H), 2.05-2.13 (m, 2H), 1.50 (d, J = 7.0 Hz, 3H); LC/MS RT 1.64 min, m/z [M − H]⁻ 527, 529 |

TABLE 18-41

| Example | Structural Formula | Physical Property Value |
|---|---|---|
| 200B | | 1H NMR (CD3OD) δ: 7.59 (d, J = 8.8 Hz, 1H), 7.02 (d, J = 8.4 Hz, 1H), 6.97 (dd, J = 8.4, 5.9 Hz, 1H), 6.71 (dd, J = 11.7, 8.4 Hz, 1H), 4.75 (d, J = 11.4 Hz, 1H), 4.41-4.48 (m, 1H), 4.32 (td, J = 10.7, 2.7 Hz, 1H), 3.63-3.73 (m, 1H), 2.22 (s, 3H), 2.18 (s, 3H), 2.05-2.13 (m, 2H), 1.48 (d, J = 7.0 Hz, 3H); LC/MS RT 1.71 min, m/z [M − H]⁻ 527, 529 |
| 201 | | 1H NMR (CD3OD) δ: 7.90 (dd, J = 8.6, 2.7 Hz, 1H), 7.47 (dd, J = 8.4, 2.2 Hz, 1H), 6.98-7.05 (m, 2H), 6.91-6.95 (m, 1H), 5.67 (dd, J = 6.8, 5.3 Hz, 1H), 4.34 (d, J = 11.0 Hz, 1H), 3.39-3.48 (m, 1H), 2.75-2.95 (m, 4H), 1.92-2.05 (m, 2H), 1.57 (d, J = 7.0 Hz, 3H), 1.44 (dd, J = 6.6, 1.5 Hz, 3H); LC/MS RT 1.74 min, m/z [M − H]⁻ 510, 512 |
| 202 | | 1H NMR (CD3OD) δ: 7.98 (d, J = 8.4 Hz, 1H), 7.79 (d, J = 8.8 Hz, 1H), 7.00-7.04 (m, 2H), 6.93-6.98 (m 1H), 5.19-5.29 (m, 1H), 4.48-4.54 (m, 1H), 3.33-3.42 (m, 1H), 2.70-3.01 (m, 4H), 1.97-2.10 (m, 2H), 1.38-1.52 (m, 6H); LC/MS RT 1.66 min, m/z [M − H]⁻ 477, 479 |

TABLE 18-41-continued

| Example | Structural Formula | Physical Property Value |
|---|---|---|
| 203 | | 1H NMR (CD3OD) δ: 7.64-7.72 (m, 1H), 7.27 (dd, J = 8.4, 1.5 Hz, 1H), 6.95-7.02 (m, 2H), 6.90-6.94 (m, 1H), 5.34-5.48 (m, 1H), 4.38 (d, J = 11.0 Hz, 1H), 4.00 (s, 3H), 3.60-3.76 (m, 1H), 2.20 (s, 3H), 2.19 (s, 3H), 1.57-1.65 (m, 3H), 1.37 (d, J = 7.0 Hz, 3H); LC/MS RT 1.68, 1.74 min, m/z [M − H]⁻ 494, 496 |
| 204 | | 1H NMR (CD3OD) δ: 7.69 (dd, J = 8.4, 7.0 Hz, 1H), 7.28 (dd, J = 8.8, 2.6 Hz, 1H), 6.96 (dd, J = 8.5, 5.7 Hz, 1H), 6.69 (dd, J = 11.7, 8.5 Hz, 1H), 5.30-5.52 (m, 1H), 4.70-4.77 (m, 1H), 4.01 (d, J = 1.5 Hz, 3H), 3.61-3.74 (m, 1H), 2.21 (s, 3H), 2.17 (s, 3H), 1.57-1.64 (m, 3H), 1.41-1.48 (m, 3H); LC/MS RT 1.70, 1.75 min, m/z [M − H]⁻ 512, 514 |

TABLE 18-42

| Example | Structural Formula | Physical Property Value |
|---|---|---|
| 205 | | 1H NMR (CD3OD) δ: 8.09-8.21 (m, 1H), 7.74-7.92 (m, 2H), 7.68-7.73 (m, 1H), 7.39-7.64 (m, 2H), 7.24-7.30 (m, 1H), 7.15-7.23 (m, 1H), 5.30-5.55 (m, 1H), 4.16-4.35 (m, 1H), 4.03 (d, J = 2.6 Hz, 3H), 3.80 (d, J = 9.5 Hz, 1H), 1.55-1.67 (m, 3H), 1.27-1.41 (m, 3H); LC/MS RT 1.72 1.77 min, m/z [M − H]⁻ 534, 536 |
| 206A | | 1H NMR (CD3OD) δ: 7.69 (d, J = 8.5 Hz, 1H), 7.28 (d, J = 8.5 Hz, 1H), 6.97 (dd, J = 8.4, 5.7 Hz, 1H), 6.73 (dd, J = 11.7, 8.3 Hz, 1H), 5.40-5.48 (m, 1H), 4.72 (d, J = 11.5 Hz, 1H), 4.01 (s, 3H), 3.64-3.75 (m, 1H), 2.51-2.60 (m, 2H), 2.25 (s, 3H), 1.62 (d, J = 6.8 Hz, 3H), 1.46 (d, J = 6.1 Hz, 3H), 1.06 (t, J = 7.4 Hz, 3H); LC/MS RT 1.78 min, m/z [M − H]⁻ 526, 528 |

TABLE 18-42-continued

| Example | Structural Formula | Physical Property Value |
|---|---|---|
| 207A | | 1H-NMR (CDCl3) δ: 7.78 (1H, br s), 7.67 (1H, d, J = 8.4 Hz), 6.99 (1H, d, J = 8.4 Hz), 6.93 (1H, dd, J = 8.3, 5.9 Hz), 6.70 (1H, dd, J = 11.5, 8.3 Hz), 5.41 (1H, d, J = 10.4 Hz), 4.89 (1H, t, J = 10.4 Hz), 4.49-4.44 (1H, m), 4.32-4.25 (1H, m), 3.46 (1H, br s), 3.25 (1H, s), 2.36-2.29 (1H, m), 2.19 (3H, s), 2.18 (3H, s), 2.10-2.05 (1H, m), 1.79 (3H, s), 1.55-1.53 (3H, m); LC/MS RT 1.64 min, m/z [M − H]⁻ 524, 526 |
| 207B | | 1H-NMR (CDCl3) δ: 8.41 (1H, s), 7.64 (1H, d, J = 8.4 Hz), 7.00 (1H, d, J = 8.4 Hz), 6.93 (1H, dd, J = 8.2, 5.9 Hz), 6.70 (1H, dd, J = 11.5, 8.2 Hz), 5.40 (1H, d, J = 11.0 Hz), 4.85 (1H, t, J = 11.0 Hz), 4.45-4.44 (1H, m), 4.33-4.30 (1H, m), 3.48 (1H, s), 3.40 (1H, s), 2.32-2.30 (1H, m), 2.19-2.16 (6H, m), 2.14-2.12 (1H, m), 1.78 (3H, s), 1.57-1.55 (3H, m); LC/MS RT 1.71 min, m/z [M − H]⁻ 524, 526 |
| 208A | | 1H NMR (cd3od) δ: 7.75 (d, J = 8.4 Hz, 1H), 7.33 (d, J = 8.4 Hz, 1H), 6.96 (dd, J = 8.3, 6.0 Hz, 1H), 6.69 (dd, J = 11.7, 8.3 Hz, 1H), 5.49 (q, J = 6.6 Hz, 1H), 4.73 (d, J = 11.4 Hz, 1H), 4.00 (s, 3H), 3.60-3.74 (m, 1H), 2.21 (s, 3H), 2.17 (s, 3H), 1.66 (d, J = 7.0 Hz, 3H), 1.44 (d, J = 7.0 Hz, 3H); LC/MS RT 1.70 min, m/z [M − H]⁻ 512, 514 |

TABLE 18-43

| Example | Structural Formula | Physical Property Value |
|---|---|---|
| 208B | | 1H NMR (CD3OD) δ: 7.70 (d, J = 8.8 Hz, 1H), 7.30 (d, J = 8.4 Hz, 1H), 6.96 (dd, J = 8.3, 6.0 Hz, 1H), 6.69 (dd, J = 11.7, 8.3 Hz, 1H), 5.38 (q, J = 6.6 Hz, 1H), 4.73 (d, J = 11.4 Hz, 1H), 4.00 (s, 3H), 3.60-3.74 (m, 1H), 2.21 (s, 3H), 2.17 (s, 3H), 1.58 (d, J = 7.0 Hz, 3H), 1.44 (d, J = 7.0 Hz, 3H); LC/MS RT 1.76 min, m/z [M − H]⁻ 512, 514 |

TABLE 18-43-continued

| Example | Structural Formula | Physical Property Value |
|---|---|---|
| 209A | | 1H-NMR (CDCl3) δ: 8.15 (1H, s), 7.66 (1H, d, J = 8.4 Hz), 7.19 (1H, dd, J = 8.6, 5.1 Hz), 6.99 (1H, d, J = 8.6 Hz), 6.78 (1H, dd, J = 10.8, 9.0 Hz), 5.52 (1H, d, J = 11.0 Hz), 4.87 (1H, t, J = 10.4 Hz), 4.47-4.44 (1H, m), 4.28-4.25 (1H, m), 3.48 (1H, s), 3.29 (1H, s), 2.37 (3H, s), 2.32-2.28 (1H, m), 2.09-2.06 (1H, m), 1.78 (3H, s), 1.54 (3H, d, J = 7.0 Hz). ; LC/MS RT 1.68 min, m/z [M − H]⁻ 544, 546 |
| 209B | | 1H-NMR (CDCl3) δ: 8.68 (1H, br s), 7.64 (1H, d, J = 8.8 Hz), 7.19 (1H, dd, J = 8.8, 4.9 Hz), 7.01 (1H, d, J = 8.8 Hz), 6.78 (1H, dd, J = 10.8, 8.8 Hz), 5.47-5.42 (1H, m), 4.81 (1H, t, J = 10.9 Hz), 4.45-4.42 (1H, m), 4.32 (1H, t, J = 10.9 Hz), 3.53 (1H, br s), 3.40 (1H, br s), 2.35 (3H, s), 2.33-2.27 (1H, m), 2.15-2.10 (1H, m), 1.78 (3H, s), 1.59-1.58 (3H, m). ; LC/MS RT 1.74 min, m/z [M − H]⁻ 544, 546 |
| 210 | | LC/MS RT 1.66 min, m/z [M − H]⁻ 482, 484 |
| 211A | | 1H-NMR (CDCl3) δ: 8.04 (1H, s), 7.86 (1H, dd, J = 8.2, 1.5 Hz), 7.77 (1H, d, J = 8.2 Hz), 7.03 (1H, t, J = 8.2 Hz), 6.92 (1H, dd, J = 8.3, 5.9 Hz), 6.68 (1H, dd, J = 11.5, 8.3 Hz), 5.58 (1H, d, J = 10.2 Hz), 4.86 (1H, t, J = 10.2 Hz), 4.48-4.43 (2H, m), 3.60 (1H, s), 3.25 (1H, s), 2.40-2.33 (1H, m), 2.24-2.20 (1H, m), 2.20 (3H, s), 2.18 (3H, s), 1.53 (3H, d, J = 7.0 Hz). ; LC/MS RT 1.67 min, m/z [M − H]⁻ 544 |

TABLE 18-44

| Example | Structural Formula | Physical Property Value |
|---|---|---|
| 212 | | 1H NMR (CD3OD) δ: 7.68 (d, J = 8.4 Hz, 1H), 7.31 (d, J = 8.4 Hz, 1H), 6.94-7.06 (m, 1H), 6.67-6.76 (m, 1H), 4.73-4.80 (m, 1H), 3.92 (s, 3H), 3.67-3.77 (m, 1H), 2.22 (s, 3H), 2.17 (s, 3H), 1.83 (s, 3H), 1.78 (s, 3H), 1.47 (d, J = 7.0 Hz, 3H); LC/MS RT 1.84 min, m/z [M − H]⁻ 526, 528 |
| 213 | | LC/MS RT 1.47 min, m/z [M − H]- 483, 485 |
| 214 | | LC/MS RT 1.49 min, m/z [M − H]⁻ 527, 529 |
| 215 | | LC/MS RT 1.49 min, m/z [M − H]⁻ 483, 485 |

TABLE 18-44-continued

| Example | Structural Formula | Physical Property Value |
|---|---|---|
| 216 | | 1H NMR (CD3OD) δ: 8.19 (d, J = 5.9 Hz, 1H), 6.98 (dd, J = 8.1, 5.9 Hz, 1H), 6.71 (dd, J = 11.7, 8.4 Hz, 1H), 5.35-5.44 (m, 1H), 4.86-4.91 (m, 1H), 4.03-4.06 (m, 3H), 3.66-3.77 (m, 1H), 2.27 (s, 3H), 2.20 (s, 3H), 1.56-1.63 (m, 3H), 1.51 (d, J = 6.6 Hz, 3H); LC/MS RT 1.62 min, m/z [M − H]⁻ 513, 515 |

TABLE 18-45

| Example | Structural Formula | Physical Property Value |
|---|---|---|
| 217 | | LC/MS RT 1.73 min, m/z [M − H]⁻ 500, 502 |
| 218 | | LC/MS RT 1.74 min, m/z [M − H]⁻ 496, 498 |
| 219 | | LC/MS RT 1.59 min, m/z [M − H]⁻ 500, 502 |

TABLE 18-45-continued

| Example | Structural Formula | Physical Property Value |
|---|---|---|
| 220A | | 1H-NMR (CDCl3) δ: 8.07 (1H, s), 7.86 (1H, d, J = 8.8 Hz), 7.07 (1H, d, J = 8.8 Hz), 6.94 (1H, dd, J = 8.3, 5.7 Hz), 6.70 (1H, dd, J = 11.7, 8.3 Hz), 5.49 (1H, d, J = 9.9 Hz), 4.86 (1H, t, J = 10.1 Hz), 4.74 (1H, s), 4.61-4.51 (1H, m), 4.39 (1H, t, J = 12.5 Hz), 3.49 (1H, s), 2.57-2.53 (1H, m), 2.36-2.34 (1H, m), 2.20-2.17 (6H, m), 1.52 (3H, d, J = 7.0 Hz).; LC/MS RT 1.74 min, m/z [M − H]⁻ 578, 580 |
| 220B | | 1H-NMR (CDCl3) δ: 8.26 (1H, s), 7.79 (1H, d, J = 8.6 Hz), 7.06 (1H, d, J = 8.6 Hz), 6.96-6.93 (1H, m), 6.73-6.68 (1H, m), 5.40 (1H, d, J = 10.6 Hz), 4.86 (1H, t, J = 10.6 Hz), 4.53-4.46 (3H, m), 3.41 (1H, s), 2.61-2.57 (1H, m), 2.37-2.34 (1H, m), 2.19-2.16 (6H, m), 1.52 (3H, d, J = 7.0 Hz).; LC/MS RT 1.80 min, m/z [M − H]⁻ 578, 580 |

TABLE 18-46

| Example | Structural Formula | Physical Property Value |
|---|---|---|
| 221 | | 1H-NMR (CDCl3) δ: 8.51-8.51 (1H, m), 8.28-8.27 (1H, m), 6.93 (1H, dd, J = 8.4, 5.9 Hz), 6.71-6.64 (1H, m), 6.05 (1H, br s), 5.60-5.55 (1H, m), 5.03-4.98 (1H, m), 3.54 (1H, s), 2.17 (6H, d, J = 3.7 Hz), 1.49 (3H, d, J = 7.0 Hz); LC/MS RT 1.72 min, m/z [M − H]⁻ 537, 539 |
| 222A | | 1H NMR (CD3OD) δ: 7.61 (d, J = 8.4 Hz, 1H), 7.42 (dd, J = 9.0, 5.3 Hz, 1H), 7.03 (d, J = 8.4 Hz, 1H), 6.81 (dd, J = 11.2, 9.0 Hz, 1H), 4.69 (d, J = 11.4 Hz, 1H), 4.39-4.47 (m, 1H), 4.22-4.33 (m, 1H), 3.63-3.78 (m, 1H), 2.44 (s, 3H), 2.17-2.24 (m, 1H), 2.05-2.15 (m, 1H), 1.75 (s, 3H), 1.52 (d, J = 6.6 Hz, 3H); LC/MS RT 1.70 min, m/z [M − H]⁻ 588, 590 |

TABLE 18-46-continued

| Example | Structural Formula | Physical Property Value |
|---|---|---|
| 222B | | 1H NMR (CD3OD) δ: 7.60 (d, J = 8.6 Hz, 1H), 7.43 (dd, J = 8.9, 5.1 Hz, 1H), 7.02 (d, J = 8.6 Hz, 1H), 6.82 (dd, J = 11.2, 8.9 Hz, 1H), 4.74 (d, J = 11.4 Hz, 1H), 4.39-4.47 (m, 1H), 4.33 (td, J = 10.8, 2.6 Hz, 1H), 3.65-3.77 (m, 1H), 2.44 (s, 3H), 2.22-2.31 (m, 1H), 2.05-2.12 (m, 1H), 1.75 (s, 3H), 1.50 (d, J = 7.0 Hz, 3H); LC/MS RT 1.76 min, m/z [M − H]⁻ 588, 590 |
| 223 | | LC/MS RT 1.61 min, m/z [M − H]⁻ 506 |
| 224A | | 1H NMR (CD3OD) δ: 7.70 (dd, J = 8.6, 5.9 Hz, 1H), 6.96 (dd, J = 8.6, 5.9 Hz, 1H), 6.61-6.82 (m, 2H), 4.70 (d, J = 11.4 Hz, 1H), 4.29-4.49 (m, 2H), 3.60-3.79 (m, 1H), 2.22 (s, 3H), 2.17 (s, 3H), 2.04-2.12 (m, 2H), 1.67 (d, J = 1.8 Hz, 3H), 1.50 (d, J = 7.0 Hz, 3H); LC/MS RT 1.6 min, m/z [M − H]⁻ 508 |

TABLE 18-47

| Example | Structural Formula | Physical Property Value |
|---|---|---|
| 224B | | 1H NMR (CD3OD) δ: 7.70 (dd, J = 8.8, 5.9 Hz, 1H), 6.97 (dd, J = 8.4, 5.9 Hz, 1H), 6.68-6.75 (m, 2H), 4.74 (d, J = 11.4 Hz, 1H), 4.38 (t, J = 5.5 Hz, 2H), 3.63-3.71 (m, 1H), 2.21 (s, 3H), 2.18 (s, 3H), 2.03-2.12 (m, 2H), 1.66 (d, J = 1.8 Hz, 3H), 1.48 (d, J = 7.0 Hz, 3H); LC/MS RT 1.65 min, m/z [M − H]⁻ 508 |

TABLE 18-47-continued

| Example | Structural Formula | Physical Property Value |
|---|---|---|
| 225A | | 1H NMR (CD3OD) δ: 7.79 (d, J = 8.4 Hz, 1H), 7.36 (d, J = 8.8 Hz, 1H), 6.97 (dd, J = 8.4, 5.9 Hz, 1H), 6.71 (dd, J = 11.7, 8.4 Hz, 1H), 4.79 (d, J = 11.4 Hz, 1H), 4.64-4.69 (m, 1H), 4.42-4.49 (m, 1H), 3.61-3.76 (m, 1H), 2.25-2.41 (m, 1H), 2.21 (s, 3H), 2.17 (s, 3H), 2.01-2.11 (m, 1H), 1.62 (s, 3H), 1.48 (d, J = 7.0 Hz, 3H); LC/MS RT 1.72 min, m/z [M − H]⁻ 558 |
| 226A | | 1H NMR (CD3OD) δ: 7.61 (d, J = 8.6 Hz, 1H), 7.42 (dd, J = 8.6, 5.1 Hz, 1H), 7.03 (d, J = 8.6 Hz, 1H), 6.81 (dd, J = 11.4, 8.6 Hz, 1H), 4.69 (d, J = 11.0 Hz, 1H), 4.35-4.46 (m, 1H), 4.26 (td, J = 10.9, 2.7 Hz, 1H), 3.66-3.75 (m, 1H), 2.44 (s, 3H), 2.15-2.26 (m, 1H), 2.05-2.13 (m, 1H), 1.52 (d, J = 6.6 Hz, 3H); LC/MS RT 1.70 min, m/z [M − H]⁻ 591, 593 |
| 226B | | LC/MS RT 1.76 min, m/z [M − H]⁻ 591, 593 |
| 227A | | 1H NMR (CD3OD) δ: 7.70 (dd, J = 8.8, 5.9 Hz, 1H), 7.42 (dd, J = 8.8, 5.1 Hz, 1H), 6.80 (dd, J = 11.0, 9.0 Hz, 1H), 6.72 (dd, J = 11.0, 9.0 Hz, 1H), 4.68 (d, J = 11.4 Hz, 1H), 4.31-4.42 (m, 2H), 3.66-3.74 (m, 1H), 2.42 (s, 3H), 2.04-2.15 (m, 2H), 1.67 (d, J = 1.8 Hz, 3H), 1.52 (d, J = 7.0 Hz, 3H); LC/MS RT 1.66 min, m/z [M − H]⁻ 572, 574 |

TABLE 18-48

| Example | Structural Formula | Physical Property Value |
|---|---|---|
| 227B | | 1H NMR (CD3OD) δ: 7.71 (dd, J = 8.8, 5.9 Hz, 1H), 7.43 (dd, J = 9.0, 5.3 Hz, 1H), 6.82 (dd, J = 11.4, 8.8 Hz, 1H), 6.73 (dd, J = 10.6, 8.8 Hz, 1H), 4.73 (d, J = 11.4 Hz, 1H), 4.38 (t, J = 5.5 Hz, 2H), 3.65-3.72 (m, 1H), 2.44 (s, 3H), 2.05-2.13 (m, 2H), 1.66 (d, J = 1.8 Hz, 3H), 1.50 (d, J = 6.6 Hz, 3H); LC/MS RT 1.71 min, m/z [M − H]⁻ 572, 574 |
| 228A | | 1H NMR (CD3OD) δ: 7.61 (d, J = 8.4 Hz, 1H), 7.24 (dd, J = 8.8, 5.1 Hz, 1H), 7.03 (d, J = 8.8 Hz, 1H), 6.87 (dd, J = 11.0, 8.8 Hz, 1H), 4.69 (d, J = 11.4 Hz, 1H), 4.41-4.47 (m, 1H), 4.26 (td, J = 10.9, 2.4 Hz, 1H), 3.65-3.72 (m, 1H), 2.39 (s, 3H), 2.15-2.25 (m, 1H), 2.05-2.13 (m, 1H), 1.52 (d, J = 6.6 Hz, 3H); LC/MS RT 1.68 min, m/z [M − H]⁻ 547, 549 |
| 228B | | 1H NMR (CD3OD) δ: 7.60 (d, J = 8.4 Hz, 1H), 7.24 (dd, J = 9.0, 4.9 Hz, 1H), 7.02 (d, J = 8.4 Hz, 1H), 6.87 (dd, J = 11.2, 9.0 Hz, 1H), 4.74 (d, J = 11.4 Hz, 1H), 4.41-4.46 (m, 1H), 4.29-4.36 (m, 1H), 3.64-3.74 (m, 1H), 2.38 (s, 3H), 2.22-2.29 (m, 1H), 2.05-2.13 (m, 1H), 1.50 (d, J = 7.0 Hz, 3H); LC/MS RT 1.74 min, m/z [M − H]⁻ 547, 549 |
| 229A | | 1H NMR (CD3OD) δ: 7.70 (dd, J = 8.8, 5.9 Hz, 1H), 7.42 (dd, J = 8.8, 5.1 Hz, 1H), 6.80 (dd, J = 11.2, 9.0 Hz, 1H), 6.72 (dd, J = 10.8, 9.0 Hz, 1H), 4.68 (d, J = 11.4 Hz, 1H), 4.31-4.42 (m, 2H), 3.66-3.74 (m, 1H), 2.44 (s, 3H), 2.05-2.11 (m, 2H), 1.67 (d, J = 1.8 Hz, 3H), 1.52 (d, J = 7.0 Hz, 3H); LC/MS RT 1.64 min, m/z [M − H]⁻ 528, 530 |
| 229B | | 1H NMR (CD3OD) δ: 7.71 (dd, J = 8.9, 5.9 Hz, 1H), 7.43 (dd, J = 8.9, 5.3 Hz, 1H), 6.82 (dd, J = 11.4, 8.8 Hz, 1H), 6.73 (dd, J = 10.6, 8.8 Hz, 1H), 4.73 (d, J = 11.4 Hz, 1H), 4.38 (t, J = 5.5 Hz, 2H), 3.63-3.78 (m, 1H), 2.44 (s, 3H), 2.04-2.16 (m, 2H), 1.66 (d, J = 1.8 Hz, 3H), 1.50 (d, J = 6.6 Hz, 3H); LC/MS RT 1.69 min, m/z [M − H]⁻ 528, 530 |

TABLE 18-49

| Example | Structural Formula | Physical Property Value |
| --- | --- | --- |
| 230A | | 1H NMR (CD3OD) δ: 7.73 (dd, J = 8.8, 6.2 Hz, 1H), 6.96 (dd, J = 8.4, 5.9 Hz, 1H), 6.66-6.77 (m, 2H), 4.69 (d, J = 11.4 Hz, 1H), 4.84-4.90 (m, 1H), 4.53-4.60 (m, 1H), 4.35 (ddd, J = 13.1, 10.9, 2.4 Hz, 1H), 3.62-3.71 (m, 1H), 2.21 (s, 3H), 2.17 (s, 3H), 1.95-2.12 (m, 2H), 1.49 (d, J = 7.0 Hz, 3H); LC/MS RT 1.57 min, m/z [M − H]⁻ 494 |
| 230B | | 1H NMR (CD3OD) δ: 7.77 (dd, J = 8.8, 6.2 Hz, 1H), 6.97 (dd, J = 8.2, 5.7 Hz, 1H), 6.68-6.78 (m, 2H), 4.85-4.93 (m, 1H), 4.74 (d, J = 11.4 Hz, 1H), 4.51-4.60 (m, 1H), 4.33 (td, J = 11.5, 3.3 Hz, 1H), 3.62-3.71 (m, 1H), 2.22 (s, 3H), 2.18 (s, 3H), 1.96-2.09 (m, 2H), 1.47 (d, J = 6.6 Hz, 3H); LC/MS RT 1.61 min, m/z [M − H]⁺ 494 |
| 231 | | 1H NMR (CD3OD) δ: 8.04-8.10 (m, 1H), 7.54-7.61 (m, 1H), 7.38-7.46 (m, 1H), 6.94-7.09 (m, 3H), 5.17 (q, J = 6.5 Hz, 1H), 4.36 (dd, J = 10.6, 5.1 Hz, 1H), 3.24-3.33 (m, 1H), 2.77-2.91 (m, 4H), 1.90-2.07 (m, 2H), 1.38-1.42 (m, 6H); LC/MS RT 1.72 min, m/z [M − H]⁻ 476, 478 |
| 232 | | 1H NMR (CD3OD) δ: 7.59-7.69 (m, 3H), 7.46 (dd, J = 7.3, 1.1 Hz, 1H), 7.30-7.38 (m, 1H), 7.22-7.29 (m, 2H), 7.02 (d, J = 8.4 Hz, 1H), 4.85-4.90 (m, 1H), 4.63-4.72 (m, 1H), 4.50-4.59 (m, 1H), 4.39 (d, J = 10.6 Hz, 1H), 4.26-4.35 (m, 1H), 2.96 (s, 3H), 1.97-2.05 (m, 2H), 1.68 (d, J = 6.6 Hz, 3H); LC/MS RT 1.65 min, m/z [M − H]⁻ 528, 530 |
| 233 | | 1H NMR (CD3OD) δ: 8.10 (d, J = 8.4 Hz, 1H), 7.75-7.93 (m, 2H), 7.63-7.75 (m, 1H), 7.51-7.60 (m, 1H), 7.39-7.48 (m, 1H), 7.16-7.29 (m, 1H), 7.05 (t, J = 9.0 Hz, 1H), 4.91-4.93 (m, 1H), 4.56-4.64 (m, 2H), 4.28-4.45 (m, 1H), 4.17-4.27 (m, 1H), 1.98-2.13 (m, 2H), 1.64 (d, J = 6.6 Hz, 3H); LC/MS RT 1.63, 1.68 min, m/z [M − H]⁻ 532, 534 |

TABLE 18-50

| Example | Structural Formula | Physical Property Value |
|---|---|---|
| 234A | | 1H-NMR (CDCl3) δ: 7.99 (1H, d, J = 8.8 Hz), 7.78 (1H, d, J = 8.1 Hz), 7.72-7.68 (2H, m), 7.65 (1H, s), 7.56 (1H, t, J = 7.9 Hz), 7.43 (1H, t, J = 7.3 Hz), 7.18-7.12 (1H, m), 6.99 (1H, d, J = 8.4 Hz), 5.57 (1H, d, J = 10.6 Hz), 5.05-5.00 (1H, m), 4.93 (1H, s), 4.51-4.48 (1H, m), 4.40-4.33 (1H, m), 4.00 (1H, s), 2.47 (1H, s), 2.16-2.07 (2H, m), 1.69-1.68 (3H, m).; LC/MS RT 1.63 min, m/z [M − H]⁻ 532, 534 |
| 235A | | 1H NMR (CD3OD) δ: 7.66 (d, J = 8.4 Hz, 1H), 7.05 (d, J = 8.4 Hz, 1H), 6.96 (dd, J = 8.1, 5.5 Hz, 1H), 6.69 (dd, J = 11.7, 8.4 Hz, 1H), 4.86-4.93 (m, 1H), 4.71 (d, J = 11.4 Hz, 1H), 4.53-4.61 (m, 1H), 4.29-4.39 (m, 1H), 3.63-3.71 (m, 1H), 2.21 (s, 3H), 2.17 (s, 3H), 2.01-2.06 (m, 2H), 1.49 (d, J = 7.0 Hz, 3H); LC/MS RT 1.61 min, m/z [M − H]⁻ 510, 512 |
| 235B | | 1H NMR (CD3OD) δ: 7.70 (d, J = 8.4 Hz, 1H), 7.07 (d, J = 8.4 Hz, 1H), 6.97 (dd, J = 8.3, 5.7 Hz, 1H), 6.71 (dd, J = 11.7, 8.3 Hz, 1H), 4.92-4.95 (m, 1H), 4.75 (d, J = 11.4 Hz, 1H), 4.53-4.60 (m, 1H), 4.26-4.39 (m, 1H), 3.58-3.75 (m, 1H), 2.22 (s, 3H), 2.18 (s, 3H), 1.95-2.14 (m, 2H), 1.47 (d, J = 7.0 Hz, 3H); LC/MS RT 1.67 min, m/z [M − H]⁻ 510, 512 |
| 236 | | 1H NMR (CD3OD) δ: 7.71-7.88 (m, 2H), 7.31-7.42 (m, 1H), 6.93-7.04 (m, 1H), 6.65-6.77 (m, 1H), 5.53-5.80 (m, 1H), 4.72-4.89 (m, 1H), 3.54-3.66 (m, 1H), 2.20 (d, J = 2.2 Hz, 3H), 2.17 (s, 3H), 1.48 (d, J = 7.0 Hz, 3H), 1.42-1.47 (m, 3H); LC/MS RT 1.70, 1.75 min, m/z [M − H]⁻ 482, 484 |
| 237A | | 1H-NMR (CDCl3) δ: 7.72-7.69 (1H, m), 7.61-7.59 (1H, m), 7.45 (1H, s), 6.99-6.90 (2H, m), 6.70-6.65 (1H, m), 5.34-5.32 (1H, m), 4.89-4.81 (2H, m), 3.49 (1H, br s), 2.35 (1H, s), 2.25 (1H, dd, J = 14.4, 6.0 Hz), 2.19 (3H, s), 2.17 (3H, s), 1.97 (1H, dd, J = 14.4, 7.3 Hz), 1.55-1.54 (6H, m), 1.48 (3H, s).; LC/MS RT 1.66 min, m/z [M − H]⁻ 504, 506 |

TABLE 18-51

| Example | Structural Formula | Physical Property Value |
|---|---|---|
| 238A | | 1H NMR (CD3OD) δ: 7.67 (d, J = 8.5 Hz, 1H), 7.08-7.17 (m, 1H), 7.04-7.07 (m, 1H), 6.86 (dd, J = 11.1, 8.9 Hz, 1H), 4.70 (d, J = 11.5 Hz, 1H), 4.89-4.94 (m, 1H), 4.53-4.61 (m, 1H), 4.29-4.40 (m, 1H), 3.64-3.77 (m, 1H), 2.38 (s, 3H), 2.00-2.12 (m, 2H), 1.51 (d, J = 7.6 Hz, 3H); LC/MS RT 1.65 min, m/z [M − H]⁻ 530, 532 |
| 239A | | 1H NMR (CD3OD) δ: 7.67 (d, J = 8.4 Hz, 1H), 7.05 (d, J = 8.4 Hz, 1H), 6.96 (dd, J = 8.4, 5.9 Hz, 1H), 6.73 (dd, J = 11.7, 8.4 Hz, 1H), 4.89-4.94 (m, 1H), 4.69 (d, J = 11.4 Hz, 1H), 4.51-4.61 (m, 1H), 4.27-4.43 (m, 1H), 3.59-3.77 (m, 1H), 2.47-2.68 (m, 2H), 2.25 (s, 3H), 2.03-2.13 (m, 2H), 1.50 (d, J = 7.0 Hz, 3H), 1.05 (t, J = 7.5 Hz, 3H); LC/MS RT 1.7 min, m/z [M − H]⁻ 524, 526 |
| 240 | | 1H NMR (CD3OD) δ: 7.76 (d, J = 8.4 Hz, 1H), 7.46 (d, J = 8.8 Hz, 1H), 6.96 (dd, J = 8.3, 6.0 Hz, 1H), 6.70 (dd, J = 11.7, 8.3 Hz, 1H), 5.60 (t, J = 3.1 Hz, 1H), 4.67 (d, J = 11.0 Hz, 1H), 3.44-3.51 (m, 1H), 2.96-3.06 (m, 1H), 2.52-2.65 (m, 1H), 2.18 (s, 3H), 2.16 (s, 3H), 1.97-2.10 (m, 2H), 1.78-1.84 (m, 1H), 1.66-1.77 (m, 1H), 1.41 (d, J = 7.0 Hz, 3H); LC/MS RT 1.89 min, m/z [M − H]⁻ 508, 510 |
| 241 | | 1H NMR (CD3OD) δ: 7.69-7.88 (m, 1H), 6.93-7.11 (m, 1H), 6.66-6.84 (m, 2H), 4.88-4.93 (m, 1H), 4.64-4.80 (m, 1H), 4.48-4.64 (m, 1H), 4.22-4.43 (m, 1H), 3.62-3.69 (m, 1H), 2.22 (s, 3H), 2.17 (s, 3H), 1.93-2.09 (2H, m), 1.44-1.52 (m, 3H); LC/MS RT 1.57, 1.61 min, m/z [M − H]⁻ 494 |

TABLE 18-51-continued

| Example | Structural Formula | Physical Property Value |
|---|---|---|
| 242 | | 1H NMR (CD3OD) δ: 6.94-7.02 (m, 1H), 6.67-6.78 (m, 1H), 6.53-6.65 (m, 1H), 4.79-4.87 (m, 1H), 4.48-4.71 (m, 2H), 4.25-4.42 (m, 1H), 3.57-3.82 (m, 1H), 2.23 (s, 3H), 2.18 (s, 3H), 1.95-2.11 (m, 2H), 1.50 (d, J = 6.2 Hz, 3H); LC/MS RT 1.59, 1.62 min, m/z [M − H]⁻ 512 |

TABLE 18-52

| Example | Structural Formula | Physical Property Value |
|---|---|---|
| 243A | | 1H NMR (CD3OD) δ: 7.67 (d, J = 8.4 Hz, 1H), 7.42 (dd, J = 8.8, 5.1 Hz, 1H), 7.06 (d, J = 8.4 Hz, 1H), 6.80 (dd, J = 11.0, 8.8 Hz, 1H), 4.90-4.95 (m, 1H), 4.69 (d, J = 11.4 Hz, 1H), 4.54-4.59 (m, 1H), 4.30-4.37 (m, 1H), 3.63-3.78 (m, 1H), 2.43 (s, 3H), 2.03-2.19 (m, 2H), 1.51 (d, J = 7.0 Hz, 3H); LC/MS RT 1.67 min, m/z [M − H]⁺ 574, 576 |
| 243B | | 1H NMR (CD3OD) δ: 7.70 (d, J = 8.7 Hz, 1H), 7.43 (dd, J = 8.8, 5.1 Hz, 1H), 7.07 (d, J = 8.7 Hz, 1H), 6.82 (dd, J = 11.2, 8.8 Hz, 1H), 4.92-4.95 (m, 1H), 4.75 (d, J = 11.4 Hz, 1H), 4.53-4.58 (m, 1H), 4.28-4.37 (m, 1H), 3.65-3.75 (m, 1H), 2.44 (s, 3H), 1.95-2.13 (m, 2H), 1.49 (d, J = 7.0 Hz, 3H); LC/MS RT 1.72 min, m/z [M − H]⁻ 574, 576 |
| 244A | | 1H NMR (CD3OD) δ: 7.85 (d, J = 8.3 Hz, 1H), 7.30 (d, J = 8.3 Hz, 1H), 6.96 (dd, J = 8.4, 5.9 Hz, 1H), 6.69 (dd, J = 11.7, 8.4 Hz, 1H), 5.00-5.04 (m, 1H), 4.74 (d, J = 11.4 Hz, 1H), 4.59-4.68 (m, 1H), 4.49-4.56 (m, 1H), 3.64-3.72 (m, 1H), 2.21 (s, 3H), 2.17 (s, 3H), 2.00-2.13 (m, 2H), 1.51 (d, J = 6.6 Hz, 3H); LC/MS RT 1.7 min, m/z [M − H]⁻ 544 |

TABLE 18-52-continued

| Example | Structural Formula | Physical Property Value |
|---|---|---|
| 244B | | 1H NMR (CD3OD) δ: 7.89 (d, J = 8.4 Hz, 1H), 7.33 (d, J = 8.4 Hz, 1H), 6.97 (dd, J = 8.3, 5.7 Hz, 1H), 6.71 (dd, J = 11.7, 8.3 Hz, 1H), 5.04-5.07 (m, 1H), 4.79 (d, J = 11.0 Hz, 1H), 4.46-4.65 (m, 2H), 3.63-3.77 (m, 1H), 2.22 (s, 3H), 2.18 (s, 3H), 1.95-2.14 (m, 2H), 1.47 (d, J = 6.6 Hz, 3H); LC/MS RT 1.76 min, m/z [M − H]⁻ 544 |
| 245 | | 1H NMR (CD3OD) δ: 8.51 (d, J = 2.6 Hz, 1H), 8.06 (d, J = 2.6 Hz, 1H), 6.98 (dd, J = 8.3, 6.0 Hz, 1H), 6.71 (dd, J = 11.7, 8.3 Hz, 1H), 4.89-4.94 (m, 1H), 3.63-3.70 (m, 1H), 2.26 (s, 3H), 2.20 (s, 3H), 1.49 (d, J = 6.6 Hz, 3H); LC/MS RT 1.47 min, m/z [M − H]⁻ 482, 484 |

TABLE 18-53

| Example | Structural Formula | Physical Property Value |
|---|---|---|
| 246 | | 1H NMR (CD3OD) δ: 7.73-7.97 (m, 1H), 7.51-7.68 (m, 1H), 7.46 (s, 1H), 6.99 (dd, J = 8.4, 5.7 Hz, 1H), 6.73 (dd, J = 11.8, 8.4 Hz, 1H), 4.80 (d, J = 11.2 Hz, 1H), 3.54-3.66 (m, 1H), 3.11 (s, 3H), 2.88 (s, 3H), 2.23 (s, 3H), 2.19 (s, 3H), 1.44-1.54 (m, 3H); LC/MS RT 1.79 min, m/z [M − H]⁺ 509, 511 |
| 247 | | 1H NMR (CD3OD) δ: 7.84 (d, J = 8.1 Hz, 1H), 7.58 (dd, J = 8.4, 2.2 Hz, 1H), 7.52 (d, J = 2.2 Hz, 1H), 6.96-7.01 (m, 1H), 6.71-6.75 (m, 1H), 4.74-4.85 (m, 1H), 3.93-4.32 (m, 4H), 3.53-3.67 (m, 1H), 2.32-2.46 (m, 2H), 2.21 (s, 3H), 2.18 (s, 3H), 1.43 (d, J = 7.3 Hz, 3H); LC/MS RT 1.81 min, m/z [M − H]⁻ 521, 523 |

TABLE 18-53-continued

| Example | Structural Formula | Physical Property Value |
|---|---|---|
| 248 | | 1H NMR (CD3OD) δ: 7.52-7.89 (m, 3H), 6.94-7.03 (m, 1H), 6.66-6.78 (m, 1H), 4.79 (d, J = 11.4 Hz, 1H), 3.43-3.88 (m, 5H), 2.21 (s, 3H), 2.15 (s, 3H), 1.49 (d, J = 7.7 Hz, 3H),; LC/MS RT 1.61, 1.66 min, m/z [M − H]⁻ 525, 527 |
| 249 | | 1H NMR (CD3OD) δ: 8.51 (d, J = 2.2 Hz, 1H), 8.06 (d, J = 2.2 Hz, 1H), 7.26 (dd, J = 8.9, 5.1 Hz, 1H), 6.88 (dd, J = 11.2, 8.9 Hz, 1H), 4.92 (d, J = 11.4 Hz, 1H), 3.61-3.74 (m, 1H), 2.42 (s, 3H), 1.50 (d, J = 7.0 Hz, 3H); LC/MS RT 1.51 min, m/z [M − H]⁻ 502, 504 |
| 250 | | 1H NMR (CD3OD) δ: 8.61 (d, J = 1.8 Hz, 1H), 8.20 (d, J = 2.2 Hz, 1H), 6.98 (dd, J = 8.4, 5.9 Hz, 1H), 6.71 (dd, J = 11.7, 8.4 Hz, 1H), 4.92 (d, J = 11.0 Hz, 1H), 3.56-3.83 (m, 1H), 2.25 (s, 3H), 2.20 (s, 3H), 1.48 (d, J = 6.6 Hz, 3H); LC/MS RT 1.49 min, m/z [M − H]⁻ 526, 528 |

TABLE 18-54

| Example | Structural Formula | Physical Property Value |
|---|---|---|
| 251 | | 1H NMR (CD3OD) δ: 8.60 (d, J = 2.2 Hz, 1H), 8.16 (d, J = 2.2 Hz, 1H), 6.99 (dd, J = 8.2, 5.7 Hz, 1H), 6.71 (dd, J = 11.7, 8.4 Hz, 1H), 4.88-4.93 (m, 1H), 3.55-3.75 (m, 1H), 2.93 (s, 3H), 2.26 (s, 3H), 2.23 (s, 3H), 1.48 (d, J = 7.0 Hz, 3H); LC/MS RT 1.56 min, m/z [M − H]⁻ 542, 544 |

TABLE 18-54-continued

| Example | Structural Formula | Physical Property Value |
|---|---|---|
| 252 | | 1H NMR (CD3OD) δ: 8.17 (d, J = 8.4 Hz, 1H), 8.02 (d, J = 8.4 Hz, 1H), 6.98 (dd, J = 8.6, 5.7 Hz, 1H), 6.66-6.79 (m, 1H), 4.83-4.90 (m, 1H), 3.56-3.71 (m, 1H), 2.94 (s, 3H), 2.23 (s, 3H), 2.18 (s, 3H), 1.48 (d, J = 7.0 Hz, 3H); LC/MS RT 1.57 min, m/z [M − H]⁻ 496, 498 |
| 253 | | 1H NMR (CD3OD) δ: 8.16 (d, J = 8.4 Hz, 1H), 7.98 (d, J = 8.4 Hz, 1H), 6.96-7.18 (m, 1H), 6.73 (dd, J = 11.7, 8.8 Hz, 1H), 4.92-4.98 (m, 1H), 3.57-3.67 (m, 1H), 3.12 (s, 3H), 2.85 (s, 3H), 2.21 (s, 3H), 2.19 (s, 3H), 1.46 (d, J = 7.0 Hz, 3H); LC/MS RT 1.56 min, m/z [M − H]⁻ 510, 512 |
| 254 | | 1H NMR (CD3OD) δ: 8.61 (d, J = 2.2 Hz, 1H), 8.20 (d, J = 2.2 Hz, 1H), 7.26 (dd, J = 9.0, 4.9 Hz, 1H), 6.88 (dd, J = 11.2, 9.0 Hz, 1H), 4.91 (d, J = 11.0 Hz, 1H), 3.61-3.76 (m, 1H), 2.42 (s, 3H), 1.50 (d, J = 7.0 Hz, 3H); LC/MS RT 1.53 min, m/z [M − H]⁻ 546, 548 |
| 255 | | 1H NMR (CD3OD) δ: 7.76-7.80 (m, 1H), 7.69-7.73 (m, 1H), 6.98 (dd, J = 8.3, 5.9 Hz, 1H), 6.73 (dd, J = 11.7, 8.3 Hz, 1H), 4.82 (d, J = 11.0 Hz, 1H), 3.51-3.65 (m, 1H), 2.22 (s, 3H), 2.18 (s, 3H), 1.46 (d, J = 7.0 Hz, 3H); LC/MS 1.71 min, m/z [M − H]⁻ 499, 501 |

TABLE 18-55

| Example | Structural Formula | Physical Property Value |
|---------|-------------------|------------------------|
| 256 | | 1H NMR (CD3OD) δ: 7.66 (d, J = 2.2 Hz, 1H), 7.41 (d, J = 2.2 Hz, 1H), 6.98 (dd, J = 8.3, 5.9 Hz, 1H), 6.70 (dd, J = 11.5, 8.3 Hz, 1H), 4.92-5.00 (m, 1H), 3.67-3.79 (m, 1H), 2.25 (s, 3H), 2.18 (s, 3H), 1.47 (d, J = 7.0 Hz, 3H); LC/MS RT 1.55 min, m/z [M − H]⁻ 515, 517 |
| 257 | | 1H NMR (CD3OD) δ: 7.73 (s, 1H), 7.61 (s, 1H), 6.98 (dd, J = 8.1, 5.9 Hz, 1H), 6.68-6.77 (m, 1H), 4.79-4.85 (m, 1H), 3.52-3.65 (m, 1H), 2.42 (s, 3H), 2.19 (s, 3H), 2.17 (s, 3H), 1.46 (d, J = 7.0 Hz, 3H); LC/MS RT 1.7 min, m/z [M − H]⁻ 495, 497 |
| 258 | | 1H NMR (CD3OD) δ: 7.43 (dd, J = 10.3, 2.2 Hz, 1H), 7.30 (d, J = 1.1 Hz, 1H), 6.98 (dd, J = 8.3, 5.7 Hz, 1H), 6.71 (dd, J = 11.7, 8.3 Hz, 1H), 4.94 (d, J = 11.4 Hz, 1H), 3.60-3.75 (m, 1H), 2.23 (s, 3H), 2.18 (s, 3H), 1.45 (d, J = 7.0 Hz, 3H); LC/MS RT 1.55 min, m/z [M − H]⁻ 499, 501 |
| 259 | | 1H NMR (CD3OD) δ: 7.66 (s, 1H), 7.48 (s, 1H), 6.98 (dd, J = 8.3, 5.9 Hz, 1H), 6.72 (dd, J = 11.9, 8.3 Hz, 1H), 4.80-4.85 (m, 1H), 3.97 (s, 3H), 3.52-3.60 (m, 1H), 2.20 (s, 3H), 2.17 (s, 3H), 1.46-1.50 (m, 3H); LC/MS RT 1.67 min, m/z [M − H]⁻ 511, 513 |

TABLE 18-55-continued

| Example | Structural Formula | Physical Property Value |
|---|---|---|
| 260 | | 1H NMR (CD3OD) δ: 7.35 (s, 1H), 7.16 (s, 1H), 6.97 (dd, J = 8.5, 5.7 Hz, 1H), 6.72 (dd, J = 11.7, 8.5 Hz, 1H), 4.79 (d, J = 11.0 Hz, 1H), 3.90 (s, 3H), 3.88 (s, 3H), 3.47-3.56 (m, 1H), 2.20 (s, 3H), 2.17 (s, 3H), 1.48 (d, J = 7.0 Hz, 3H); LC/MS RT 1.55 min, m/z [M − H]⁻ 507 |

TABLE 18-56

| Example | Structural Formula | Physical Property Value |
|---|---|---|
| 261 | | 1H NMR (CD3OD) δ: 7.26 (s, 1H), 7.10 (s, 1H), 6.97 (dd, J = 8.4, 5.9 Hz, 1H), 6.72 (dd, J = 12.1, 8.4 Hz, 1H), 4.75 (d, J = 11.4 Hz, 1H), 4.29-4.32 (m, 4H), 3.44-3.60 (m, 1H), 2.19 (s, 3H), 2.17 (s, 3H), 1.47 (d, J = 7.0 Hz, 3H); LC/MS RT 1.61 min, m/z [M − H]⁺ 505 |
| 262 | | 1H NMR (CD3OD) δ: 8.36 (s, 1H), 7.90 (s, 1H), 6.98 (dd, J = 8.3, 5.9 Hz, 1H), 6.73 (dd, J = 11.9, 8.3 Hz, 1H), 4.82-4.86 (m, 1H), 3.55-3.65 (m, 1H), 2.22 (s, 3H), 2.18 (s, 3H), 1.47 (d, J = 7.0 Hz, 3H); LC/MS RT 1.72 min, m/z [M − H]⁻ 526, 528 |
| 263 | | 1H NMR (CD3OD) δ: 7.60 (d, J = 8.4 Hz, 1H), 7.42 (d, J = 2.6 Hz, 1H), 7.21 (dd, J = 8.6, 2.7 Hz, 1H), 6.98 (dd, J = 8.4, 5.9 Hz, 1H), 6.72 (dd, J = 11.7, 8.4 Hz, 1H), 6.20 (tt, J = 55.0, 3.7 Hz, 1H), 4.80 (d, J = 11.0 Hz, 1H), 4.31 (tdd, J = 13.6, 3.7, 2.6 Hz, 2H), 3.51-3.58 (m, 1H), 2.20 (s, 3H), 2.17 (s, 3H), 1.46 (d, J = 6.6 Hz, 3H); LC/MS RT 1.67 min, m/z [M − H]⁻ 527 |

TABLE 18-56-continued

| Example | Structural Formula | Physical Property Value |
|---|---|---|
| 264 | | 1H NMR (CD3OD) δ: 8.51 (d, J = 2.2 Hz, 1H), 8.07 (d, J = 2.2 Hz, 1H), 7.45 (dd, J = 8.8, 5.5 Hz, 1H), 6.77-6.91 (m, 1H), 4.89-4.95 (m, 1H), 3.65-3.75 (m, 1H), 2.48 (s, 3H), 1.50 (d, J = 7.0 Hz, 3H); LC/MS RT 1.54 min, m/z [M − H]⁻ 546, 548 |
| 265 | | 1H NMR (CD3OD) δ: 8.10 (d, J = 8.8 Hz, 1H), 7.81 (d, J = 8.6 Hz, 1H), 7.75-7.79 (m, 1H), 7.54 (t, J = 7.7 Hz, 1H), 7.39-7.45 (m, 2H), 7.20 (dd, J = 11.7, 9.2 Hz, 1H), 6.11-6.24 (m, 2H), 4.73 (d, J = 11.4 Hz, 1H), 4.12-4.30 (m, 1H), 3.85 (s, 3H), 1.62 (d, J = 6.6 Hz, 3H); LC/MS RT 1.56 min, m/z [M − H]⁻ 471 |

TABLE 18-57

| Example | Structural Formula | Physical Property Value |
|---|---|---|
| 266 | | 1H NMR (CD3OD) δ: 7.37-7.45 (m, 2H), 6.94-7.08 (m, 2H), 6.85 (d, J = 6.6 Hz, 1H), 6.51-6.62 (m, 2H), 4.24 (d, J = 10.6 Hz, 1H), 3.36-3.48 (m, 1H), 2.59-2.75 (m, 4H), 1.59-1.85 (m, 4H), 1.29-1.44 (d, J = 6.6 Hz, 3H); LC/MS RT 1.61 min, m/z [M − H]⁻ 427 |
| 267 | | 1H NMR (CD3OD) δ: 7.52 (d, J = 9.2 Hz, 1H), 7.01 (s, 2H), 6.87-6.96 (m, 1H), 6.35-6.48 (m, 2H), 4.17 (d, J = 10.6 Hz, 1H), 3.20-3.35 (m, 1H), 2.75-2.84 (m, 4H), 2.42 (s, 3H), 1.85-2.09 (m, 2H), 1.38 (d, J = 7.0 Hz, 3H); LC/MS RT 1.58 min, m/z [M − H]⁻ 427 |

TABLE 18-57-continued

| Example | Structural Formula | Physical Property Value |
|---|---|---|
| 268 | | 1H NMR (CD3OD) δ: 8.82-8.91 (m, 1H), 8.48 (d, J = 8.4 Hz, 1H), 8.00 (d, J = 8.4 Hz, 1H), 7.36-7.45 (m, 1H), 6.83-7.06 (m, 3H), 6.68 (d, J = 8.4 Hz, 1H), 4.31 (d, J = 10.3 Hz, 1H), 3.34-3.46 (m, 1H), 2.72-2.82 (m, 4H), 1.81-2.10 (m, 2H), 1.43 (d, J = 6.6 Hz, 3H); LC/MS RT 1.57 min, m/z [M − H]− 464 |
| 269 | | 1H NMR (CD3OD) δ: 7.64 (d, J = 8.0 Hz, 1H), 7.60 (dd, J = 7.6, 1.9 Hz, 1H), 7.43-7.47 (m, 1H), 7.38 (d, J = 8.5 Hz, 1H), 7.34 (t, J = 7.8 Hz, 1H), 7.21-7.27 (m, 2H), 6.12-6.16 (m, 2H), 4.59-4.66 (m, 1H), 4.26 (d, J = 10.9 Hz, 1H), 3.80 (s, 3H), 2.95 (s, 3H), 1.66 (d, J = 6.6 Hz, 3H); LC/MS RT 1.58 min, m/z [M − H]− 467 |
| 270 | | 1H NMR (CD3OD) 7.38 (d, J = 8.4 Hz, 1H), 6.98-7.07 (m, 2H), 6.91-6.95 (m, 1H), 6.20 (d, J = 1.8 Hz, 1H), 6.16 (dd, J = 8.6, 2.0 Hz, 1H), 4.57-4.63 (m, 1H), 4.21 (d, J = 11.0 Hz, 1H), 3.83 (s, 3H), 2.73-2.91 (m, 4H), 1.89-2.04 (m, 2H), 1.43 (d, J = 6.6 Hz, 3H); LC/MS RT 1.55 min, m/z [M − H]− 443 |

TABLE 18-58

| Example | Structural Formula | Physical Property Value |
|---|---|---|
| 271 | | LC/MS RT 1.75 min, m/z [M − H]− 453, 455 |

TABLE 18-58-continued

| Example | Structural Formula | Physical Property Value |
|---|---|---|
| 272 | | LC/MS RT 1.8 min, m/z [M − H]⁻ 511, 513 |
| 273 | | 1H NMR (CD3OD) δ: 7.46 (1H, d, J = 8.6 Hz), 7.21 (1H, d, J = 8.6 Hz), 6.98-6.95 (1H, m), 6.71 (1H, dd, J = 11.9, 8.2 Hz), 4.79-4.66 (3H, m), 4.41-4.34 (1H, m), 4.24-4.18 (1H, m), 3.75-3.62 (3H, m), 2.19 (3H, s), 2.16 (3H, s), 1.49 (3H, d, J = 6.6 Hz); LC/MS RT 1.61 min, m/z [M − H]⁻ 553, 555 |
| 274 | | 1H NMR (CD3OD) δ: 7.53 (d, J = 8.8 Hz, 1H), 6.96-7.04 (m, 1H), 6.71-6.81 (m, 2H), 6.55-6.60 (m, 1H), 4.66 (d, J = 11.4 Hz, 1H), 3.50-3.66 (m, 1H), 2.23 (s, 3H), 2.21 (s, 3H), 2.17 (s, 3H), 1.45 (d, J = 6.6 Hz, 3H); LC/MS RT 1.92 min, m/z [M − H]⁻ 495, 497 |
| 275 | | 1H-NMR (CDCl3) δ: 7.63 (1H, s), 7.10 (1H, d, J = 8.4 Hz), 6.94-6.88 (2H, m), 6.69 (1H, dd, J = 11.5, 8.6 Hz), 5.38 (1H, d, J = 10.6 Hz), 4.86 (1H, t, J = 10.8 Hz), 4.41-4.40 (4H, m), 3.53-3.52 (2H, m), 2.18-2.17 (6H, m), 1.57-1.54 (3H, m).; LC/MS RT 1.71 min, m/z [M − H]⁻ 495, 497 |

TABLE 18-59

| Example | Structural Formula | Physical Property Value |
|---|---|---|
| 276 | | 1H-NMR (CDCl3) δ: 8.07 (1H, br s), 7.64 (1H, d, J = 8.8 Hz), 7.07-7.06 (2H, m), 6.95-6.93 (1H, m), 6.38 (1H, d, J = 8.8 Hz), 5.68 (2H, s), 5.45 (1H, d, J = 10.4 Hz), 4.37 (1H, t, J = 10.4 Hz), 3.95 (3H, s), 3.88 (3H, s), 3.28-3.21 (1H, m), 2.88-2.83 (4H, m), 2.04-1.99 (2H, m), 1.49 (3H, d, J = 7.0 Hz).; LC/MS RT 1.67 min, m/z [M − H]⁻ 501 |
| 277 | | 1H NMR (CD3OD) δ: 7.83 (d, J = 8.4 Hz, 1H), 7.58-7.60 (m, 1H), 7.55-7.57 (m, 1H), 6.94-7.02 (m, 1H), 6.67-6.77 (m, 1H), 4.76-4.82 (m, 1H), 3.57-3.76 (m, 1H), 2.92 (s, 3H), 2.21 (s, 3H), 2.17 (s, 3H), 1.46 (d, J = 7.0 Hz, 3H); LC/MS RT 1.74 min, m/z [M − H]⁻ 495, 497 |
| 278 | | LC/MS RT 1.34 min, m/z [M − H]⁻ 509, 511 |
| 279 | | LC/MS RT 1.4 min, m/z [M − H]⁻ 493, 495 |
| 280 | | 1H-NMR (CDCl3) δ: 8.12 (1H, br s), 7.15-7.13 (1H, m), 6.93-6.90 (1H, m), 6.75-6.64 (3H, m), 5.51 (1H, d, J = 10.6 Hz), 4.87 (1H, t, J = 10.6 Hz), 4.37-4.35 (2H, m), 3.93 (1H, br s), 3.43-3.40 (3H, m), 2.19 (3H, s), 2.17 (3H, s), 1.54 (3H, d, J = 7.0 Hz).; LC/MS RT 1.6 min, m/z [M − H]⁻ 461 |

TABLE 18-60

| Example | Structural Formula | Physical Property Value |
|---|---|---|
| 281 | | 1H NMR (CD3OD) δ: 7.90 (d, J = 1.0 Hz, 1H), 7.35-7.49 (m, 2H), 6.97 (t, J = 1.0 Hz, 1H), 6.73 (dd, J = 1.0 Hz, 1H), 4.70 (br d, J = 11.4 Hz, 1H), 4.28-4.52 (m, 2H), 3.38-3.83 (m, 5H), 2.17 (s, 5H), 1.49 (d, J = 1.0 Hz, 3H); LC/MS RT 1.29 min, m/z [M − H]⁻ 459 |
| 282 | | LC/MS RT 1.94 min, m/z [M − H]⁻ 587, 589 |
| 283 | | 1H NMR (CD3OD) δ: 7.94-7.99 (m, 1H), 7.84-7.91 (m, 1H), 6.81-6.93 (m, 1H), 6.61 (dd, J = 11.5, 8.6 Hz, 1H), 4.75 (d, J = 10.3 Hz, 1H), 3.37-3.89 (m, 5H), 2.88-3.03 (m, 1H), 2.24 (s, 3H), 2.14 (s, 3H), 1.75-1.85 (m, 1H), 1.36-1.53 (m, 4H); LC/MS RT 1.25 min, m/z [M − H]⁻ 551, 553 |
| 284 | | 1H-NMR (CDCl3) δ: 7.08 (1H, d, J = 8.8 Hz), 7.02-6.97 (3H, m), 6.88 (1H, d, J = 8.4 Hz), 5.42 (1H, d, J = 10.8 Hz), 4.56 (1H, t, J = 10.8 Hz), 4.47-4.36 (3H, m), 3.55-3.44 (3H, m), 2.24 (3H, s), 2.22 (3H, s), 2.17 (3H, s), 1.47 (3H, d, J = 7.0 Hz).; LC/MS RT 1.88 min, m/z [M − H]⁻ 519, 521 |

TABLE 18-60-continued

| Example | Structural Formula | Physical Property Value |
|---|---|---|
| 285 | 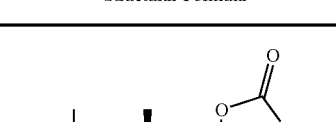 | 1H NMR (CD3OD) δ: 7.84-7.95 (m, 1H), 7.50-7.66 (m, 3H), 6.97 (dd, J = 8.4, 5.9 Hz, 1H), 6.71 (dd, J = 11.7, 8.4 Hz, 1H), 4.80 (d, J = 11.0 Hz, 1H), 3.50-3.63 (m, 1H), 2.20 (s, 3H), 2.17 (s, 3H), 1.44 (d, J = 6.6 Hz, 3H); LC/MS RT 1.48 min, m/z [[M − H]⁻ 463 |

TABLE 18-61

| Example | Structural Formula | Physical Property Value |
|---|---|---|
| 286 | 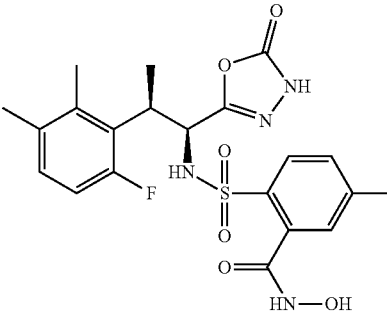 | 1H NMR (CD3OD) δ: 7.87 (d, J = 8.4 Hz, 1H), 7.62 (dd, J = 8.8, 2.2 Hz, 1H), 7.54 (d, J = 2.2 Hz, 1H), 6.98 (dd, J = 8.2, 5.7 Hz, 1H), 6.72 (dd, J = 11.9, 8.2 Hz, 1H), 4.80 (d, J = 11.0 Hz, 1H), 3.53-3.63 (m, 1H), 2.21 (s, 3H), 2.17 (s, 3H), 1.45 (d, J = 7.0 Hz, 3H); LC/MS RT 1.59 min, m/z [M − H]⁻ 497, 499 |
| 287 | 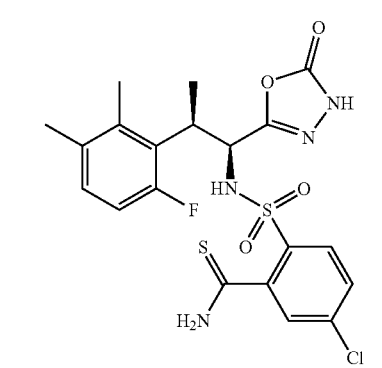 [SMILES: Cc1ccc(F)c([C@@H](C)[C@H](NS(=O)(=O)c2ccc(Cl)cc2C(N)=S)c2n[nH]c(=O)o2)c1C] | 1H-NMR (CDCl3) δ: 8.70 (1H, s), 8.51-8.48 (1H, m), 7.87-7.84 (2H, m), 7.44 (1H, dd, J = 8.6, 2.1 Hz), 7.39 (1H, d, J = 2.1 Hz), 6.93 (1H, dd, J = 8.4, 5.9 Hz), 6.71-6.65 (2H, m), 4.87 (1H, t, J = 10.1 Hz), 3.53-3.48 (1H, m), 2.18-2.17 (6H, m), 1.43 (3H, d, J = 7.0 Hz).; LC/MS RT 1.72 min, m/z [M − H]⁻ 497, 499 |
| 288 | 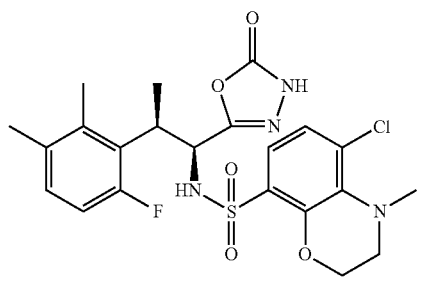 | LC/MS RT 1.76 min, m/z [M − H]⁻ 509, 511 |

TABLE 18-61-continued

| Example | Structural Formula | Physical Property Value |
|---|---|---|
| 289 | | LC/MS RT 1.8 min, m/z [M − H]⁻ 529, 531 |
| 290 | | 1H NMR (CD3OD) δ: 7.73 (1H, d, J = 8.1 Hz), 7.16-7.15 (1H, m), 7.06-7.01 (2H, m), 6.71 (1H, dd, J = 10.6, 8.4 Hz), 5.38 (1H, d, J = 9.5 Hz), 4.68 (1H, d, J = 9.5 Hz), 3.96 (3H, s), 3.33 (1H, s), 2.25 (3H, s), 2.16 (3H, s); LC/MS RT 1.53 min, m/z [M − H]⁻ 470, 472 |

TABLE 18-62

| Example | Structural Formula | Physical Property Value |
|---|---|---|
| 291 | | LC/MS RT 1.75, 1.76 min, m/z [M − H]⁻ 472, 474 |
| 292 | | 1H-NMR (CDCl3) δ: 7.98 (1H, d, J = 8.8 Hz), 7.94 (1H, s), 7.86-7.84 (1H, m), 7.78 (1H, d, J = 8.1 Hz), 7.72-7.70 (1H, m), 7.55 (1H, t, J = 7.7 Hz), 7.42 (1H, t, J = 7.3 Hz), 7.17-7.12 (1H, m), 7.08 (1H, d, J = 8.4 Hz), 5.79-5.67 (1H, m), 5.62 (1H, d, J = 10.4 Hz), 4.94 (1H, t, J = 10.4 Hz), 4.60-4.56 (1H, m), 4.23-4.20 (1H, m), 3.99 (1H, s), 3.67-3.51 (1H, m), 2.38-2.35 (1H, m), 1.69 (3H, d, J = 5.9 Hz).; LC/MS RT 1.8 min, m/z [M − H]⁻ 534, 536 |

TABLE 18-62-continued

| Example | Structural Formula | Physical Property Value |
|---|---|---|
| 293 | | 1H-NMR (CDCl3) δ: 8.56-8.54 (1H, m), 8.37-8.35 (1H, m), 8.10 (1H, s), 6.97-6.90 (1H, m), 6.71-6.64 (1H, m), 5.82 (1H, br s), 5.03-4.97 (1H, m), 3.54-3.52 (1H, m), 2.19-2.17 (6H, m), 1.53-1.44 (3H, m).; LC/MS RT 1.64 min, m/z [M − H]⁻ 535, 537 |
| 294 | | LC/MS RT 1.83 min, m/z [M − H]⁻ 510, 512 |
| 295 | | 1H NMR (CD3OD) δ: 7.48 (d, J = 8.8 Hz, 1H), 6.91-7.03 (m, 4H), 6.70 (dt, J = 10.3, 2.0 Hz, 1H), 6.01 (dt, J = 10.3, 3.7 Hz, 1H), 4.98-5.04 (m, 2H), 4.33 (d, J = 10.6 Hz, 1H), 3.60-3.68 (m, 1H), 2.20 (s, 3H), 2.19 (s, 3H), 1.42 (d, J = 6.6 Hz, 3H); LC/MS RT 1.82 min, m/z [M − H]⁻ 474, 476 |

TABLE 18-63

| Example | Structural Formula | Physical Property Value |
|---|---|---|
| 296 | | LC/MS RT 1.73 min, m/z [M − H]⁻ 462, 464 |

TABLE 18-63-continued

| Example | Structural Formula | Physical Property Value |
|---|---|---|
| 297 | | 1H NMR (CD3OD) δ: 7.69-7.80 (m, 1H), 7.30-7.40 (m, 1H), 6.93-7.06 (m, 1H), 6.69-6.82 (m, 1H), 5.38-5.49 (m, 1H), 4.77 (d, J = 11.2 Hz, 1H), 4.66 (d, J = 11.7 Hz, 1H), 4.50 (d, J = 11.7 Hz, 1H), 4.02 (s, 3H), 3.68-3.75 (m, 1H), 2.86 (s, 3H), 2.24 (s, 3H), 2.18 (s, 3H), 1.64 (d, J = 6.6 Hz, 3H), 1.48 (d, J = 7.1 Hz, 3H); LC/MS RT 1.92 min, m/z [M − H]⁻ 556, 558 |
| 298 | | 1H-NMR (CDCl3) δ: 7.81 (1H, d, J = 8.4 Hz), 7.06-6.88 (7H, m), 6.82 (1H, dd, J = 11.4, 8.4 Hz), 5.40 (1H, d, J = 10.4 Hz), 4.86 (1H, t, J = 10.4 Hz), 3.96 (3H, s), 3.83 (3H, s), 3.42 (1H, br s), 2.16 (3H, s), 1.59 (3H, d, J = 7.0 Hz); LC/MS RT 1.93 min, m/z [M − H]⁻ 560, 562 |
| 299 | | 1H-NMR (CDCl3) δ: 7.89 (1H, br s), 7.81 (1H, d, J = 8.4 Hz), 7.04-6.98 (2H, m), 6.93 (1H, s), 6.88-6.75 (2H, m), 6.68-6.66 (2H, m), 5.44 (1H, d, J = 10.7 Hz), 4.85 (1H, t, J = 10.7 Hz), 3.96 (3H, s), 3.41 (1H, br s), 2.16 (3H, s), 1.59-1.57 (3H, m).; LC/MS RT 1.96 min, m/z [M − H]⁻ 566, 568 |
| 300 | | 1H-NMR (CDCl3) δ: 8.57-8.55 (1H, m), 8.45-8.43 (1H, m), 7.82 (1H, d, J = 8.4 Hz), 7.64-7.61 (1H, m), 7.44-7.41 (1H, m), 7.05-7.00 (2H, m), 6.94-6.88 (2H, m), 5.60-5.57 (1H, m), 4.82 (1H, t, J = 10.4 Hz), 3.96 (3H, s), 3.92 (1H, s), 3.46 (1H, s), 2.15 (3H, s), 1.61 (3H, d, J = 6.6 Hz).; LC/MS RT 1.4 min, m/z [M − H]⁻ 531, 533 |

TABLE 18-64

| Example | Structural Formula | Physical Property Value |
|---|---|---|
| 301 | | 1H-NMR (CDCl3) δ: 7.82 (1H, d, J = 8.1 Hz), 7.59 (1H, s), 7.19-7.16 (1H, m), 7.02 (1H, d, J = 8.8 Hz), 6.92 (1H, s), 6.87-6.82 (1H, m), 6.28 (1H, s), 5.85 (1H, br s), 4.84 (1H, t, J = 10.1 Hz), 3.90 (3H, s), 3.45 (1H, br s), 2.24 (3H, s), 1.56 (3H, d, J = 6.6 Hz); LC/MS RT 1.56 min, m/z [M − H]⁻ 520, 522 |

TABLE 18-64-continued

| Example | Structural Formula | Physical Property Value |
|---|---|---|
| 302 | | 1H-NMR (CDCl3) δ: 7.91 (1H, br s), 7.81 (1H, d, J = 8.4 Hz), 7.34 (2H, d, J = 8.4 Hz), 7.07-6.97 (4H, m), 6.86-6.81 (1H, m), 6.84 (1H, t, J = 9.9 Hz), 5.44 (1H, d, J = 10.6 Hz), 4.86 (1H, t, J = 10.6 Hz), 3.96 (3H, s), 3.41 (1H, br s), 2.14 (3H, s), 1.58 (3H, d, J = 7.0 Hz).; LC/MS RT 2.05 min, m/z [M − H]⁻ 564, 566 |
| 303 | | 1H-NMR (CDCl3) δ: 7.81 (1H, d, J = 8.4 Hz), 7.52-7.51 (2H, m), 7.09-6.99 (4H, m), 6.93-6.93 (1H, m), 6.85-6.80 (1H, m), 5.49-5.46 (1H, m), 4.88-4.83 (1H, m), 3.96 (3H, s), 3.43 (1H, br s), 2.27 (3H, s), 1.58 (3H, d, J = 7.0 Hz).; LC/MS RT 1.54 min, m/z [M − H]⁻ 520, 522 |
| 304 | | 1H-NMR (CDCl3) δ: 8.06 (1H, br s), 7.81 (1H, d, J = 8.4 Hz), 7.73 (1H, s), 7.59 (1H, s), 7.57-7.54 (1H, m), 7.41-7.36 (1H, m), 7.03-7.00 (1H, m), 6.93-6.92 (1H, m), 6.84 (1H, dd, J = 11.0, 8.4 Hz), 5.45 (1H, d, J = 10.4 Hz), 4.86 (1H, t, J = 10.4 Hz), 3.96 (3H, s), 3.44 (1H, br s), 2.27 (3H, s), 1.58 (3H, d, J = 9.5 Hz).; LC/MS RT 1.75 min, m/z [M − H]⁻ 570, 572 |
| 305 | | 1H-NMR (CDCl3) δ: 8.81 (1H, br s), 7.80 (1H, d, J = 8.8 Hz), 7.36 (1H, s), 7.23-7.20 (1H, m), 7.01 (1H, d, J = 8.4 Hz), 6.93 (1H, s), 6.82 (1H, t, J = 9.7 Hz), 6.19 (1H, s), 5.50 (1H, d, J = 10.4 Hz), 4.86 (1H, t, J = 10.4 Hz), 3.95 (3H, s), 3.90 (3H, s), 3.45 (1H, br s), 2.30 (3H, s), 1.56 (3H, d, J = 6.6 Hz).; LC/MS RT 1.64 min, m/z [M − H]⁻ 534, 536 |

TABLE 18-65

| Example | Structural Formula | Physical Property Value |
|---|---|---|
| 306 | | 1H-NMR (CDCl3) δ: 8.48 (1H, s), 7.80 (1H, d, J = 8.4 Hz), 7.39 (1H, s), 7.28 (1H, s), 7.06-6.99 (2H, m), 6.92-6.92 (1H, m), 6.80 (1H, dd, J = 11.2, 8.6 Hz), 5.56 (1H, d, J = 10.6 Hz), 4.84 (1H, t, J = 10.6 Hz), 3.94 (3H, s), 3.91 (3H, s), 3.44 (1H, s), 2.27 (3H, s), 1.57 (3H, d, J = 7.0 Hz).; LC/MS RT 1.62 min, m/z [M − H]⁻ 534, 536 |

TABLE 18-65-continued

| Example | Structural Formula | Physical Property Value |
|---|---|---|
| 307 | | LC/MS RT 1.65 min, m/z [M – H]⁻ 534, 536 |
| 308 | | LC/MS RT 1.82 min, m/z [M – H]⁻ 534, 536 |
| 309 | | LC/MS RT 1.94 min, m/z [M – H]⁻ 534, 536 |
| 310 | | 1H-NMR (CDCl3) δ: 8.50 (1H, s), 7.80 (1H, d, J = 8.4 Hz), 7.40 (1H, s), 7.32 (1H, s), 7.05 (1H, dd, J = 8.5, 5.9 Hz), 7.01 (1H, dd, J = 8.4, 1.5 Hz), 6.92 (1H, d, J = 1.8 Hz), 6.80 (1H, dd, J = 11.2, 8.5 Hz), 5.56 (1H, d, J = 10.3 Hz), 4.85 (1H, t, J = 10.8 Hz), 4.18 (2H, q, J = 7.3 Hz), 3.94 (3H, s), 3.44 (1H, br s), 2.28 (3H, s), 1.57 (3H, d, J = 7.0 Hz), 1.50 (3H, t, J = 7.3 Hz).; LC/MS RT 1.68 min, m/z [M – H]⁻ 548, 550 |

TABLE 18-66

| Example | Structural Formula | Physical Property Value |
|---|---|---|
| 311 | | LC/MS RT 1.71 min, m/z [M – H]⁻ 560, 562 |

TABLE 18-66-continued

| Example | Structural Formula | Physical Property Value |
|---|---|---|
| 312 | | 1H-NMR (CDCl3) δ: 7.80 (1H, d, J = 8.4 Hz), 7.42 (1H, s), 7.36 (1H, s), 7.06-6.99 (2H, m), 6.92 (1H, s), 6.82-6.77 (1H, m), 5.53 (1H, d, J = 10.7 Hz), 4.85 (1H, t, J = 10.7 Hz), 4.75 (1H, t, J = 8.4 Hz), 3.94 (3H, s), 3.44 (1H, br s), 2.55-2.46 (4H, m), 2.28 (3H, s), 1.89-1.82 (2H, m), 1.56 (3H, d, J = 7.0 Hz); LC/MS RT 1.8 min, m/z [M − H]⁻ 574, 576 |
| 313 | | 1H-NMR (CDCl3) δ: 8.20 (1H, d, J = 2.0 Hz), 7.81 (1H, d, J = 8.4 Hz), 7.47-7.44 (1H, m), 7.35 (1H, d, J = 8.4 Hz), 7.05-7.02 (1H, m), 7.01-6.99 (1H, m), 6.94 (1H, d, J = 2.0 Hz), 6.92-6.87 (1H, m), 5.43 (1H, d, J = 10.6 Hz), 4.86 (1H, t, J = 10.6 Hz), 3.96 (3H, s), 3.42 (1H, br s), 2.16 (3H, s), 1.59 (3H, d, J = 7.0 Hz); LC/MS RT 1.82 min, m/z [M − H]⁻ 565, 567 |
| 314 | | 1H-NMR (CDCl3) δ: 8.94 (1H, br s), 7.91 (1H, d, J = 2.0 Hz), 7.80 (1H, d, J = 8.4 Hz), 7.39-7.36 (1H, m), 7.01-6.97 (2H, m), 6.93 (1H, d, J = 1.0 Hz), 6.85 (1H, dd, J = 11.4, 8.4 Hz), 6.76 (1H, d, J = 8.4 Hz), 5.60 (1H, d, J = 10.4 Hz), 4.84 (1H, t, J = 10.4 Hz), 3.94 (3H, s), 3.93 (3H, s), 3.44 (1H, br s), 2.16 (3H, s), 1.58 (3H, d, J = 7.0 Hz).; LC/MS RT 1.82 min, m/z [M − H]⁻ 561, 563 |
| 315 | | 1H-NMR (CDCl3) δ: 7.95 (1H, d, J = 2.0 Hz), 7.79 (1H, d, J = 8.5 Hz), 7.32 (1H, dd, J = 8.5, 2.4 Hz), 7.00-6.95 (2H, m), 6.92 (1H, d, J = 2.0 Hz), 6.83 (1H, dd, J = 11.2, 8.7 Hz), 6.65 (1H, d, J = 8.7 Hz), 5.61 (1H, d, J = 10.5 Hz), 4.84 (1H, t, J = 10.5 Hz), 3.93 (3H, s), 3.84-3.80 (4H, m), 3.51-3.44 (5H, m), 2.17 (3H, s), 1.57 (3H, d, J = 7.0 Hz); LC/MS RT 1.48 min, m/z [M − H]⁻ 616, 618 |

TABLE 18-67

| Example | Structural Formula | Physical Property Value |
|---|---|---|
| 316 | | 1H NMR (CD3OD) δ: 8.53 (1H, s), 7.74 (1H, d, J = 8.4 Hz), 7.61 (1H, s), 7.12-7.09 (1H, m), 7.05-6.98 (2H, m), 6.88-6.83 (1H, m), 4.70-4.60 (2H, m), 3.94 (3H, s), 2.08 (3H, s), 1.52 (3H, d, J = 7.0 Hz); LC/MS RT 1.68 min, m/z [M − H]⁻ 588, 590 |

TABLE 18-67-continued

| Example | Structural Formula | Physical Property Value |
|---|---|---|
| 317 | 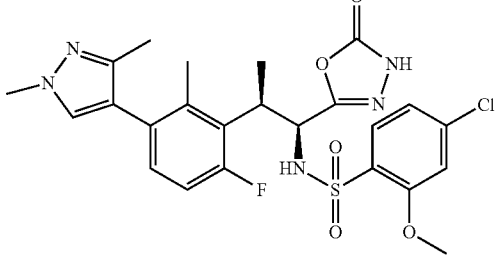 | 1H NMR (CD3OD) δ: 8.27 (1H, br s), 7.75 (1H, d, J = 8.4 Hz), 7.34 (1H, s), 7.12 (1H, d, J = 1.8 Hz), 7.04 (1H, dd, J = 8.4, 1.8 Hz), 6.96 (1H, dd, J = 8.4, 5.9 Hz), 6.84 (1H, dd, J = 11.4, 8.4 Hz), 4.68 (1H, d, J = 11.4 Hz), 3.94 (3H, s), 3.82 (3H, s), 3.67-3.62 (1H, m), 2.13 (3H, s), 1.88 (3H, s), 1.52 (3H, d, J = 7.0 Hz); LC/MS RT 1.63 min, m/z [M − H]⁻ 548, 550 |
| 318 | 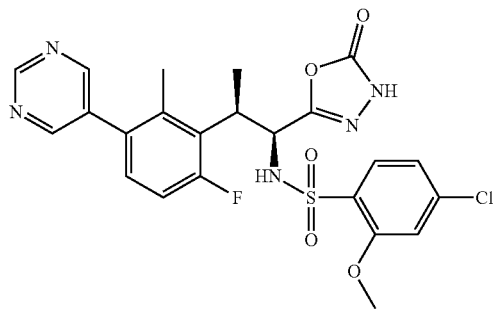 [SMILES: COc1cc(Cl)ccc1S(=O)(=O)N[C@H](c1n[nH]c(=O)o1)[C@H](C)c1c(F)ccc(-c2cncnc2)c1C] | 1H-NMR (CDCl3) δ: 9.20 (1H, s), 8.60 (2H, s), 8.02 (1H, br s), 7.82 (1H, d, J = 8.1 Hz), 7.05-7.03 (2H, m), 6.97-6.92 (2H, m), 5.53 (1H, d, J = 11.1 Hz), 4.87 (1H, t, J = 11.1 Hz), 3.96 (3H, s), 3.45 (1H, br s), 2.20 (3H, s), 1.61 (3H, d, J = 7.0 Hz).; LC/MS RT 1.55 min, m/z [M − H]⁻ 532, 534 |
| 319 | 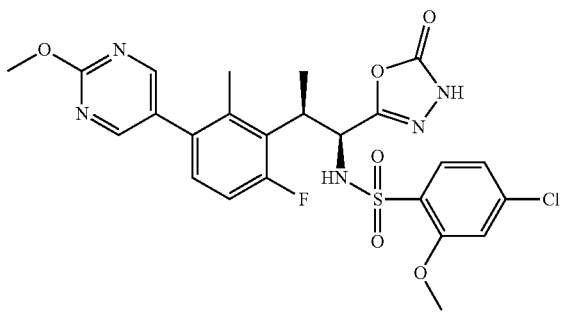 [SMILES: COc1ncc(-c2ccc(F)c([C@@H](C)[C@H](NS(=O)(=O)c3ccc(Cl)cc3OC)c3n[nH]c(=O)o3)c2C)cn1] | 1H-NMR (CDCl3) δ: 8.34 (2H, s), 7.81 (1H, d, J = 8.4 Hz), 7.03-6.88 (4H, m), 5.57 (1H, d, J = 10.6 Hz), 4.85 (1H, t, J = 10.6 Hz), 4.04 (3H, s), 3.95 (3H, s), 3.44 (1H, br s), 2.18 (3H, s), 1.59 (3H, d, J = 7.0 Hz); LC/MS RT 1.66 min, m/z [M − H]⁻ 562, 564 |
| 320 | 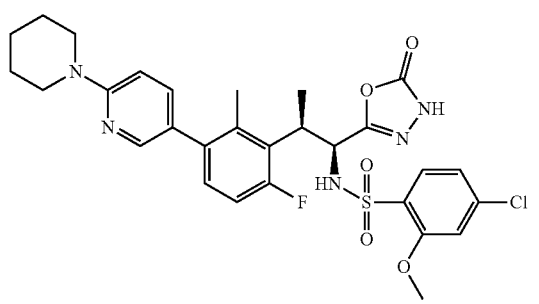 [SMILES: COc1cc(Cl)ccc1S(=O)(=O)N[C@H](c1n[nH]c(=O)o1)[C@H](C)c1c(F)ccc(-c2ccc(N3CCCCC3)nc2)c1C] | 1H-NMR (CDCl3) δ: 8.12 (1H, br s), 7.99 (1H, s), 7.80 (1H, d, J = 7.7 Hz), 7.35 (1H, d, J = 8.8 Hz), 7.03-6.93 (3H, m), 6.87-6.81 (1H, m), 6.72 (1H, d, J = 8.4 Hz), 5.52 (1H, d, J = 10.6 Hz), 4.79 (1H, t, J = 10.6 Hz), 3.94 (3H, s), 3.57-3.55 (4H, m), 3.45 (1H, br s), 2.17 (3H, s), 1.69-1.66 (6H, m), 1.59 (3H, d, J = 6.6 Hz).; LC/MS RT 1.49 min, m/z [M − H]⁻ 614, 616 |

TABLE 18-68

| Example | Structural Formula | Physical Property Value |
|---|---|---|
| 321 | 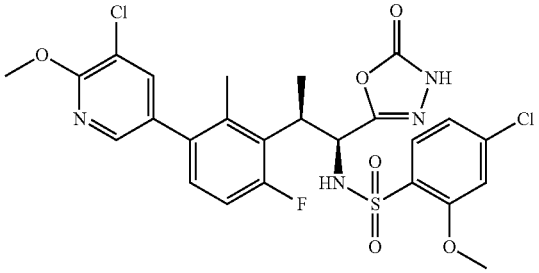 [SMILES: COc1cc(Cl)ccc1S(=O)(=O)N[C@H](c1n[nH]c(=O)o1)[C@H](C)c1c(F)ccc(-c2cnc(OC)c(Cl)c2)c1C] | 1H-NMR (CDCl3) δ: 8.19-8.08 (2H, m), 7.80 (1H, d, J = 8.4 Hz), 7.37-7.27 (1H, m), 7.02 (1H, d, J = 8.4 Hz), 6.95-6.92 (2H, m), 6.88-6.83 (1H, m), 5.50 (1H, d, J = 10.3 Hz), 4.83 (1H, t, J = 11.0 Hz), 3.95-3.94 (3H, m), 3.77 (3H, s), 3.42 (1H, br s), 2.04-2.03 (3H, m), 1.58 (3H, d, J = 6.6 Hz).; LC/MS RT 1.96 min, m/z [M − H]⁻ 595, 597 |
| 322 | 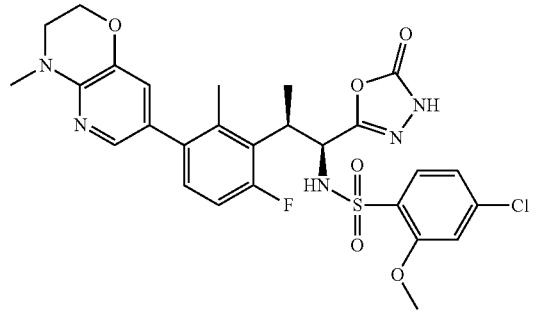 [SMILES: COc1cc(Cl)ccc1S(=O)(=O)N[C@H](c1n[nH]c(=O)o1)[C@H](C)c1c(F)ccc(-c2cnc3c(c2)OCCN3C)c1C] | 1H-NMR (CDCl3) δ: 8.08-8.05 (2H, m), 7.80 (1H, d, J = 8.1 Hz), 7.53 (1H, s), 7.02-6.93 (2H, m), 6.85-6.81 (2H, m), 5.55 (1H, d, J = 10.9 Hz), 4.80 (1H, t, J = 10.9 Hz), 4.28-4.25 (2H, m), 3.94 (3H, s), 3.51 (2H, s), 3.44 (1H, br s), 3.14 (3H, s), 2.17 (3H, s), 1.59 (3H, d, J = 6.2 Hz).; LC/MS RT 1.44 min, m/z [M − H]⁻ 602, 604 |
| 323 | 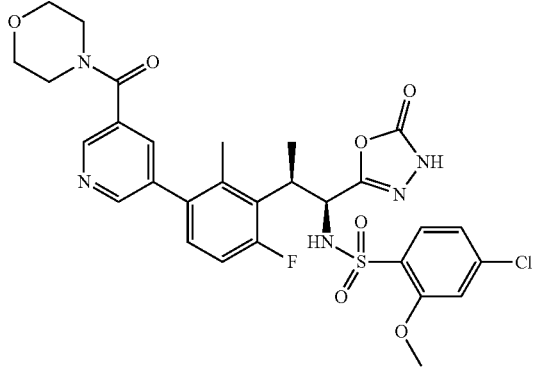 [SMILES: COc1cc(Cl)ccc1S(=O)(=O)N[C@H](c1n[nH]c(=O)o1)[C@H](C)c1c(F)ccc(-c2cncc(C(=O)N3CCOCC3)c2)c1C] | 1H NMR (CD3OD) δ: 8.60 (1H, s), 8.45 (1H, s), 7.76 (1H, d, J = 8.4 Hz), 7.68 (1H, s), 7.14-7.10 (2H, m), 7.05 (1H, dd, J = 8.4, 1.8 Hz), 6.97 (1H, dd, J = 11.2, 8.4 Hz), 4.70 (1H, d, J = 11.2 Hz), 3.94 (3H, s), 3.77-3.74 (4H, m), 3.69-3.63 (4H, m), 3.48-3.46 (1H, m), 2.20 (3H, s), 1.55 (3H, d, J = 7.0 Hz); LC/MS RT 1.52 min, m/z [M − H]⁻ 644, 646 |
| 324 | 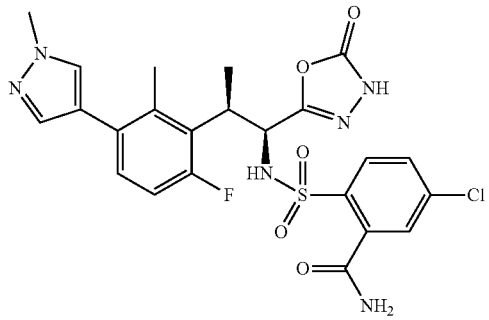 [SMILES: Cc1c(-c2cnn(C)c2)ccc(F)c1[C@@H](C)[C@H](NS(=O)(=O)c1ccc(Cl)cc1C(N)=O)c1n[nH]c(=O)o1] | 1H-NMR (CDCl3) δ: 7.96 (1H, d, J = 8.1 Hz), 7.55-7.51 (2H, m), 7.40 (1H, s), 7.28 (1H, s), 7.04 (1H, dd, J = 8.4, 5.9 Hz), 6.84-6.79 (2H, m), 6.05-6.03 (1H, m), 5.98-5.96 (1H, m), 4.95-4.90 (1H, m), 3.92 (3H, s), 3.50 (1H, br s), 2.28 (3H, s), 1.49 (3H, d, J = 7.3 Hz); LC/MS RT 1.46 min, m/z [M − H]⁻ 547, 549 |

TABLE 18-68-continued

| Example | Structural Formula | Physical Property Value |
| --- | --- | --- |
| 325 | | 1H-NMR (CDCl3) δ: 9.65 (1H, br s), 7.81-7.79 (2H, m), 7.74 (1H, s), 7.60-7.59 (1H, m), 7.50-7.48 (1H, m), 6.95-6.91 (1H, m), 6.73-6.68 (1H, m), 6.20 (1H, d, J = 10.0 Hz), 4.90 (1H, t, J = 10.0 Hz), 3.92 (3H, s), 3.47 (1H, br s), 2.15 (3H, s), 2.13 (3H, s), 1.50 (3H, d, J = 6.6 Hz).; LC/MS RT 1.69 min, m/z [M − H]⁻ 518, 520 |

TABLE 18-69

| Example | Structural Formula | Physical Property Value |
| --- | --- | --- |
| 326 | | 1H-NMR (CDCl3) δ: 7.81-7.79 (2H, m), 7.76 (1H, dd, J = 8.5, 2.2 Hz), 7.58 (1H, d, J = 8.3 Hz), 7.46-7.42 (1H, m), 7.31-7.28 (2H, m), 7.17 (1H, t, J = 8.8 Hz), 6.97-6.93 (1H, m), 6.71 (1H, dd, J = 11.7, 8.3 Hz), 5.05 (1H, d, J = 10.0 Hz), 4.85 (1H, t, J = 10.0 Hz), 3.43 (1H, br s), 2.18 (3H, s), 2.16 (3H, s), 1.47 (3H, d, J = 5.9 Hz).; LC/MS RT 1.96 min, m/z [M − H]⁻ 532, 534 |
| 327 | | 1H-NMR (CDCl3) δ: 7.80 (1H, d, J = 8.1 Hz), 7.50-7.47 (2H, m), 7.36-7.33 (5H, m), 7.02 (1H, dd, J = 8.4, 1.8 Hz), 6.93 (1H, d, J = 1.5 Hz), 6.81 (1H, dd, J = 11.4, 8.4 Hz), 5.41 (1H, d, J = 10.5 Hz), 4.82 (1H, t, J = 10.5 Hz), 3.97 (3H, s), 3.42 (1H, br s), 2.51 (3H, s), 1.57-1.54 (3H, m).; LC/MS RT 2.06 min, m/z [M − H]⁻ 554, 556 |
| 328 | | 1H NMR (CD3OD) δ: 8.34 (1H, br s), 7.76-7.65 (1H, m), 7.25-7.22 (1H, m), 7.17-7.09 (1H, m), 6.90-6.85 (1H, m), 4.79-4.70 (2H, m), 4.59-4.51 (2H, m), 4.41-4.26 (2H, m), 3.72-3.66 (1H, m), 2.38-2.37 (6H, m), 2.33-2.23 (2H, m), 1.86 (3H, d, J = 28.2 Hz).; LC/MS RT 1.39 min, m/z [M − H]⁻ 543, 545 |

TABLE 18-69-continued

| Example | Structural Formula | Physical Property Value |
|---|---|---|
| 329 | | 1H NMR (CD3OD) δ: 7.68-7.79 (m, 1H), 7.42-7.46 (m, 1H), 7.12-7.20 (m, 1H), 6.79-6.88 (m, 1H), 4.71-4.82 (m, 1H), 4.54-4.65 (m, 1H), 4.25-4.46 (m, 1H), 3.63-3.77 (m, 1H), 2.44 (s, 3H), 2.32-2.38 (m, 2H), 1.89-1.94 (m, 3H), 1.51-1.56 (m, 3H); LC/MS RT 1.39 min, m/z [M − H]⁻ 587, 589 |
| 330A | | LC/MS RT 1.37 min, m/z [M − H]⁻ 543, 545 |

TABLE 18-70

| Example | Structural Formula | Physical Property Value |
|---|---|---|
| 330B | | LC/MS RT 1.37 min, m/z [M − H]⁻ 543, 545 |
| 331 | | 1H-NMR (CDCl3) δ: 8.54 (2H, s), 8.42 (1H, s), 8.32-8.30 (1H, m), 7.75 (1H, d, J = 8.1 Hz), 6.96-6.88 (2H, m), 6.67 (1H, dd, J = 11.4, 8.4 Hz), 6.30 (1H, s), 6.10 (1H, s), 4.97 (1H, t, J = 10.3 Hz), 3.48 (1H, s), 2.16 (3H, s), 2.15 (3H, s), 1.48 (3H, d, J = 7.0 Hz).; LC/MS RT 1.5 min, m/z [M − H]⁻ 515 |

TABLE 18-70-continued

| Example | Structural Formula | Physical Property Value |
|---|---|---|
| 332 | | 1H NMR (CD3OD) δ: 7.68-7.79 (m, 3H), 6.97 (dd, J = 8.5, 5.7 Hz, 1H), 6.71 (dd, J = 11.7, 8.5 Hz, 1H), 4.89-5.02 (m, 1H), 3.58-3.65 (m, 1H), 2.20 (s, 3H), 2.15 (s, 3H), 1.47 (d, J = 7.3 Hz, 3H); LC/MS RT 1.75 min, m/z [M − H]⁻ 541, 543 |
| 333 | | 1H NMR (CD3OD) δ: 7.73 (d, J = 8.8 Hz, 1H), 7.39 (d, J = 8.6 Hz, 1H), 6.81-6.99 (m, 3H), 4.15 (d, J = 6.2 Hz, 1H), 3.98 (s, 3H), 3.38-3.43 (m, 1H), 2.75-2.92 (m, 4H), 1.92-2.13 (m, 2H), 1.27 (d, J = 7.0 Hz, 3H); LC/MS RT 1.95 min, m/z [M − H]⁻ 540, 542 |
| 334 | | LC/MS RT 1.89 min, m/z [M − H]⁻ 506, 508 |

TABLE 18-71

| Example | Structural Formula | Physical Property Value |
|---|---|---|
| 335 | | 1H NMR (CD3OD) δ: 7.65-7.74 (m, 2H), 7.57-7.64 (m, 1H), 7.50 (d, J = 3.3 Hz, 1H), 6.98-7.18 (m, 2H), 6.79-6.84 (m, 1H), 3.99 (d, J = 9.9 Hz, 1H), 3.40-3.50 (m 1H), 2.70-2.86 (m, 1H), 2.57-2.66 (m, 1H), 2.32-2.51 (m, 2H), 1.82 (s, 3H), 1.45-1.54 (m, 2H), 1.44 (s, 3H), 1.26 (d, J = 7.0 Hz, 3H); LC/MS RT 2.11 min, m/z [M − H]⁻ 534,536 |

TABLE 18-71-continued

| Example | Structural Formula | Physical Property Value |
|---------|-------------------|------------------------|
| 336 | | 1H NMR (CD3OD) δ: 8.02 (d, J = 8.4 Hz, 1H), 7.56 (d, J = 8.8 Hz, 1H), 6.97-6.99 (m, 3H), 6.88-6.90 (m, 1H), 4.31 (d, J = 10.3 Hz, 1H), 3.34-3.46 (m, 1H), 2.71-2.97 (m, 4H), 2.14 (s, 6H), 1.93-2.02 (m, 2H), 1.40 (d, J = 7.0 Hz, 3H); LC/MS RT 1.87 min, m/z [M − H]⁻ 506, 508 |
| 337 | | 1H NMR (CD3OD): 7.93 (d, J = 8.8 Hz, 1H), 7.62 (dd, J = 8.8, 2.2 Hz, 1H), 7.51 (d, J = 2.2 Hz, 1H), 7.01 (dd, J = 8.1, 5.9 Hz, 1H), 6.76 (dd, J = 11.9, 8.6 Hz, 1H), 5.58 (dd, J = 11.7, 1.8 Hz, 1H), 3.76-3.90 (m, 1H), 3.06 (s, 3H), 2.27 (s, 3H), 2.20 (s, 3H), 1.33 (d, J = 7.0 Hz, 3H); LC/MS RT 1.64 min, m/z [M − H]⁻ 495, 497 |
| 338 | | 1H-NMR (CDCl3) δ: 8.15 (1H, s), 7.86 (1H, d, J = 8.4 Hz), 7.52 (1H, dd, J = 8.4, 1.5 Hz), 7.48-7.47 (1H, m), 6.94 (1H, dd, J = 8.2, 5.7 Hz), 6.69 (1H, dd, J = 11.7, 8.4 Hz), 5.33 (1H, d, J = 9.9 Hz), 4.85 (1H, t, J = 10.3 Hz), 3.50-3.45 (1H, m), 2.18 (6H, s), 1.47 (3H, d, J = 7.0 Hz).; LC/MS RT 1.95 min, m/ [M − H]− 566, 568 |
| 339 | | 1H-NMR (CDCl3) δ: 7.97 (1H, s), 7.64-7.61 (1H, m), 7.40 (1H, dd, J = 8.8, 5.1 Hz), 6.96 (1H, dd, J = 8.1, 5.9 Hz), 6.70 (1H, dd, J = 11.4, 8.4 Hz), 5.40 (1H, d, J = 9.2 Hz), 4.89 (1H, t, J = 9.3 Hz), 3.52-3.47 (1H, m), 2.19 (6H, s), 1.48 (3H, d, J = 7.3 Hz).; LC/MS RT 1.86 min, m/ [M − H]− 519, 521 |

TABLE 18-72

| Example | Structural Formula | Physical Property Value |
|---|---|---|
| 340 | | 1H-NMR (CDCl3) δ: 8.31-8.28 (2H, m), 8.13 (1H, s), 8.02-7.98 (2H, m), 6.95 (1H, dd, J = 8.4, 5.9 Hz), 6.70 (1H, dd, J = 11.7, 8.4 Hz), 5.32-5.29 (1H, m), 4.87 (1H, t, J = 9.9 Hz), 3.48-3.44 (1H, m), 2.17 (3H, s), 2.16 (3H, s), 1.43 (3H, d, J = 7.0 Hz).; LC/MS RT 1.73 min, m/ [M − H]− 449 |
| 341 | | 1H-NMR (CDCl3) δ: 8.42 (1H, s), 7.94-7.92 (2H, m), 7.77-7.75 (2H, m), 6.95 (1H, dd, J = 8.4, 5.9 Hz), 6.70 (1H, dd, J = 11.7, 8.4 Hz), 5.45 (1H, d, J = 9.5 Hz), 4.84 (1H, t, J = 9.7 Hz), 3.48-3.42 (1H, m), 2.18 (3H, s), 2.15 (3H, s), 1.42 (3H, d, J = 7.0 Hz).; LC/MS RT 1.67 min, m/ [M − H]− 429 |
| 342 | | 1H-NMR (CDCl3) δ: 8.62 (1H, br s), 7.98 (1H, d, J = 8.1 Hz), 7.33 (1H, dd, J = 8.1, 1.1 Hz), 7.20 (1H, d, J = 1.1 Hz), 6.93 (1H, dd, J = 8.4, 5.9 Hz), 6.68 (1H, dd, J = 11.7, 8.4 Hz), 5.55 (1H, d, J = 10.3 Hz), 4.84 (1H, t, J = 10.6 Hz), 4.01 (3H, s), 3.43 (1H, br s), 2.17 (6H, s), 1.52 (3H, d, J = 7.0 Hz).; LC/MS RT 1.71 min, m/ [M − H]− 459, 461 |
| 343 | | 1H-NMR (CD3OD) δ: 8.25 (1H, s), 8.09 (1H, d, J = 2.2 Hz), 7.95-7.86 (2H, m), 7.00-6.96 (1H, m), 6.72 (1H, dd, J = 11.5, 8.2 Hz), 4.74 (1H, d, J = 11.4 Hz), 3.57-3.54 (1H, m), 2.18 (3H, s), 2.17 (3H, s), 1.45 (3H, d, J = 7.0 Hz).; LC/MS RT 1.78 min, m/ [M − H]− 507, 509 |

TABLE 18-73

| Example | Structural Formula | Physical Property Value |
|---|---|---|
| 344 | | 1H-NMR (CDCl3) δ: 7.98 (1H, s), 7.77 (1H, d, J = 2.6 Hz), 7.65 (1H, dd, J = 8.4, 2.6 Hz), 7.52 (1H, d, J = 8.4 Hz), 7.36-7.34 (2H, m), 6.99-6.92 (4H, m), 6.70 (1H, dd, J = 11.7, 8.4 Hz), 5.11 (1H, d, J = 10.0 Hz), 4.85 (1H, t, J = 10.1 Hz), 3.85 (3H, s), 3.43-3.41 (1H, m), 2.17 (3H, s), 2.15 (3H, s), 1.45 (3H, d, J = 6.2 Hz).; LC/MS RT 1.97 min, m/ [M − H]− 544, 546 |
| 345 | | 1H-NMR (CDCl3) δ: 8.08 (1H, d, J = 1.8 Hz), 7.71 (2H, dd, J = 7.9, 1.6 Hz), 7.60 (1H, d, J = 8.1 Hz), 7.39-7.35 (1H, m), 7.28-7.26 (2H, m), 7.19 (1H, d, J = 10.3 Hz), 7.07-7.03 (1H, m), 7.00-6.98 (1H, m), 6.89 (1H, dd, J = 8.4, 5.9 Hz), 6.67 (1H, dd, J = 11.4, 8.4 Hz), 6.06 (1H, s), 5.90 (1H, s), 4.95 (1H, t, J = 10.6 Hz), 3.85 (3H, s), 3.46-3.44 (1H, m), 2.16 (3H, s), 2.15 (3H, s), 1.50 (3H, d, J = 7.0 Hz).; LC/MS RT 1.8 min, m/ [M − H]− 553, 555 |
| 346 | | 1H-NMR (CDCl3) δ: 10.58 (1H, s), 7.93 (1H, d, J = 8.4 Hz), 7.36-7.34 (2H, m), 6.91 (1H, dd, J = 8.2, 5.7 Hz), 6.68 (1H, dd, J = 11.7, 8.4 Hz), 6.44 (2H, s), 5.56 (1H, d, J = 10.3 Hz), 4.84 (1H, t, J = 11.0 Hz), 4.02 (3H, s), 3.42 (1H, br s), 2.17-2.16 (6H, m), 1.56 (3H, d, J = 7.0 Hz).; LC/MS RT 1.51 min, m/ [M − H]− 477 |
| 347 | | 1H-NMR (CD3OD) δ: 7.96-7.93 (2H, m), 7.86-7.83 (2H, m), 6.96 (1H, dd, J = 8.4, 5.9 Hz), 6.71 (1H, dd, J = 11.7, 8.4 Hz), 4.74 (1H, d, J = 11.0 Hz), 3.57-3.53 (1H, m), 2.17 (3H, s), 2.15 (3H, s), 1.42 (3H, d, J = 7.0 Hz).; LC/MS RT 1.46 min, m/ [M − H]− 447 |

TABLE 18-74

| Example | Structural Formula | Physical Property Value |
|---|---|---|
| 348 | | LC/MS RT min, m/ [M − H]− 486, 488 |
| 349 | | 1H-NMR (CDCl3) δ: 7.80 (1H, d, J = 8.4 Hz), 7.05 (1H, dd, J = 8.4, 1.8 Hz), 6.96-6.93 (2H, m), 6.68 (1H, dd, J = 11.7, 8.4 Hz), 5.96 (1H, d, J = 9.9 Hz), 4.78 (1H, t, J = 9.7 Hz), 3.91 (3H, s), 3.54-3.49 (1H, m), 2.17 (3H, s), 2.13 (3H, s), 2.49 (3H, d, J = 7.0 Hz).; LC/MS RT 1.77 min, m/ [M − H]− 468, 470 |
| 350 | | 1H-NMR (CDCl3) δ: 11.70 (1H, s), 11.48 (1H, s), 7.75 (1H, d, J = 8.4 Hz), 6.92-6.89 (2H, m), 6.73-6.68 (1H, m), 6.62 (1H, d, J = 8.4 Hz), 6.16 (1H, d, J = 9.2 Hz), 4.89 (1H, t, J = 10.3 Hz), 3.85 (3H, s), 3.60-3.58 (1H, m), 2.16 (3H, s), 2.13 (3H, s), 1.47 (3H, d, J = 6.6 Hz).; LC/MS RT 1.6 min, m/ [M − H]− 483, 485 |

TEST EXAMPLE

The compound according to the present invention was evaluated using the following test method.

Test Example 1 Human RNR Inhibition Effect

The inhibitory activity against the ribonucleotide reduction reaction (hereinafter referred to as RNR reaction) of the test compound was determined by measuring the formation of deoxycytidine diphosphate (hereinafter referred to as dCDP) from cytidine diphosphate (hereinafter referred to as CDP) by the following method.

Human M1 subunit and human M2 subunit (mutant lacking amino terminal 59 amino acids), which are fused a histidine tag at the amino terminus, are overexpressed in Escherichia coli and are solubilized after collection, and histidine tagged human M1 and M2 proteins were purified on a nickel chelate column.

For measuring the inhibitory activity of the test compound against the RNR reaction, the method described in the document [CANCER RESEARCH 64, 1-6, 2004] was referred to.

First, test compounds were serially diluted with DMSO. Next, human M1 protein and human M2 protein were added to an aqueous albumin solution derived from 0.02% fetal bovine serum, a DMSO solution of the compound of the present invention or the control DMSO solution (final concentration of DMSO was 1%) was added, and the mixture was allowed to stand for 20 minutes. Thereafter, the reaction buffer [50 mM HEPES buffer (pH 7.2) at the final concentration, 4 mM magnesium acetate at the final concentration, 100 mM potassium chloride at the final concentration, 6 mM dithiothreitol at the final concentration, 2 mM adenosine triphosphate at the final concentration, 0.24 mM nicotinamide adenine dinucleotide phosphate at final concentration] and 10 μM CDP at the final concentration were added and incubated at 37° C. for 30 minutes to perform RNR reaction. Immediately after the reaction, the reaction was stopped by heating at 100° C. for 15 minutes, followed by centrifugation at 10,000 rpm for 10 minutes. After the centrifugation, a portion (5 μL) of the resulting supernatant was analyzed with a high performance liquid chromatography (Shimadzu Corporation, Prominence) using Shim-pack XR-ODS (manufactured by Shimadzu GLC Co., 3.0×100 mm). Elution was carried out at a measurement wavelength of 265 nm at a flow rate of 0.5 mL/min by a 9-minute concentration gradient from the 12:13 mixture of mobile phase A (10 mM potassium dihydrogen phosphate (pH 6.7), 10 mM tetrabutylammonium, 0.25% methanol) and mobile phase B (50 mM potassium dihydrogen phosphate (pH 6.7), 5.6 mM tetrabutylammonium, 30% methanol) to the same 2:3 mixture to measure the substrate CDP (RT 5.9 min) and the reaction product dCDP (RT 6.2 min).

The inhibitory activity of the test compound was determined by the following equation, and the concentrations of test compounds inhibiting the RNR reaction by 50% are shown as IC$_{50}$ (μM) in Tables 19-1 to 19-3.

[Mathematical Formula 1]
$$\text{Inhibition rate (\%)} = \left(1 - \frac{\text{Amount of produced } dCDP \text{ where test compound added (pmol)}}{\text{Amount of produced } dCDP \text{ of control (pmol)}}\right) \times 100$$

As a result, it is apparent from the following table that the compound of the present invention has an excellent RNR inhibitory action. In contrast, the compound of Comparative Example 1 had an IC$_{50}$ of 43 μM, and showed no inhibitory activity against RNR as found in the example compounds of the present invention.

TABLE 19-1

| Example Number | RNR Enzyme inhibitory activity IC$_{50}$ (μM) |
|---|---|
| 1 | 0.06 |
| 3 | 0.30 |
| 4 | 0.38 |
| 5 | 0.14 |
| 6 | 0.11 |
| 7 | 0.45 |
| 9 | 0.60 |
| 10 | 0.14 |
| 11 | 0.18 |
| 12 | 0.17 |
| 13 | 0.14 |
| 14 | 0.25 |
| 15 | 0.10 |
| 16 | 0.13 |
| 17 | 0.50 |
| 18 | 0.13 |
| 19 | 0.19 |
| 20 | 0.26 |
| 21 | 0.24 |
| 22 | 0.34 |
| 23 | 0.74 |
| 25 | 0.15 |
| 26 | 0.16 |
| 27 | 0.55 |
| 28 | 0.50 |
| 30 | 0.15 |
| 31 | 0.10 |
| 32 | 0.79 |
| 35 | 0.13 |
| 36 | 0.11 |
| 37 | 0.14 |
| 38 | 0.19 |
| 39 | 0.04 |
| 40 | 0.13 |
| 41 | 0.10 |
| 42 | 0.20 |
| 43 | 0.08 |
| 46 | 0.84 |
| 48 | 0.60 |
| 49 | 0.80 |
| 50 | 0.85 |
| 52 | 0.77 |
| 60 | 0.99 |
| 67 | 0.70 |
| 71 | 0.24 |
| 76 | 0.20 |
| 81 | 0.28 |
| 83 | 0.14 |
| 84 | 0.36 |
| 85 | 0.84 |
| 86 | 0.40 |
| 87 | 0.84 |
| 88 | 0.15 |
| 89 | 0.42 |
| 90 | 0.16 |
| 91 | 0.23 |
| 92 | 0.20 |
| 93 | 0.10 |
| 94 | 0.11 |
| 95 | 0.14 |
| 96 | 0.10 |
| 97 | 0.24 |
| 98 | 0.64 |
| 99 | 0.29 |
| 100 | 0.30 |
| 101 | 0.13 |
| 102 | 0.14 |
| 103 | 0.41 |
| 104 | 0.84 |
| 105 | 0.16 |
| 106 | 0.27 |
| 107 | 0.24 |
| 108 | 0.43 |
| 109 | 0.06 |
| 110 | 0.96 |
| 111 | 0.27 |
| 112 | 0.15 |
| 113 | 0.06 |
| 114 | 0.06 |
| 115 | 0.18 |
| 116 | 0.07 |
| 117 | 0.03 |
| 118 | 0.34 |
| 119 | 0.45 |
| 120 | 0.43 |

TABLE 19-1-continued

| Example Number | RNR Enzyme inhibitory activity IC$_{50}$ (μM) |
|---|---|
| 123 | 0.11 |
| 124 | 0.09 |
| 129 | 0.10 |
| 137 | 0.59 |
| 142 | 0.21 |
| 144 | 0.17 |
| 145 | 0.44 |
| 146 | 0.26 |
| 147 | 0.27 |
| 148 | 0.10 |
| 151 | 0.41 |
| 152 | 0.71 |
| 153 | 0.11 |
| 155 | 0.13 |
| 156 | 0.08 |
| 157 | 0.10 |
| 158 | 0.45 |
| 159 | 0.16 |
| 161 | 0.28 |
| 162 | 0.74 |
| 164 | 0.33 |
| 165 | 0.83 |
| 167 | 0.08 |
| 169 | 0.19 |
| 171 | 0.47 |
| 172 | 0.82 |
| 173 | 0.13 |
| 174 | 0.35 |
| 176 | 0.81 |
| 178 | 0.17 |
| 179 | 0.28 |
| 181 | 0.66 |
| 182 | 0.41 |
| 183 | 0.32 |
| 184 | 0.22 |
| 185 | 0.60 |
| 186 | 0.09 |
| 188 | 0.64 |
| 189 | 0.55 |
| 192 | 0.44 |
| 193 | 0.09 |
| 194 | 0.36 |
| 195 | 0.18 |

TABLE 19-2

| Example Number | RNR Enzyme inhibitory activity IC$_{50}$ (μM) |
|---|---|
| 196 | 0.08 |
| 197 | 0.06 |
| 198 | 0.06 |
| 199 | 0.35 |
| 200A | 0.03 |
| 200B | 0.08 |
| 201 | 0.17 |
| 202 | 0.40 |
| 203 | 0.18 |
| 204 | 0.15 |
| 205 | 0.08 |
| 206A | 0.15 |
| 207A | 0.13 |
| 207B | 0.09 |
| 208A | 0.10 |
| 208B | 0.06 |
| 209A | 0.10 |
| 209B | 0.18 |
| 210 | 0.18 |

TABLE 19-2-continued

| Example Number | RNR Enzyme inhibitory activity IC$_{50}$ (μM) |
|---|---|
| 211A | 0.12 |
| 212 | 0.11 |
| 213 | 0.50 |
| 214 | 0.99 |
| 215 | 0.19 |
| 216 | 0.20 |
| 217 | 0.96 |
| 219 | 0.27 |
| 220A | 0.06 |
| 220B | 0.08 |
| 222A | 0.08 |
| 222B | 0.06 |
| 223 | 0.79 |
| 224A | 0.09 |
| 224B | 0.10 |
| 225A | 0.12 |
| 226A | 0.05 |
| 226B | 0.07 |
| 227A | 0.05 |
| 227B | 0.09 |
| 228A | 0.08 |
| 228B | 0.14 |
| 229A | 0.06 |
| 229B | 0.11 |
| 230A | 0.12 |
| 230B | 0.05 |
| 231 | 0.65 |
| 232 | 0.23 |
| 233 | 0.13 |
| 234A | 0.31 |
| 235A | 0.08 |
| 235B | 0.07 |
| 236 | 0.38 |
| 237A | 0.29 |
| 238A | 0.11 |
| 239A | 0.20 |
| 240 | 0.91 |
| 241 | 0.14 |
| 242 | 0.23 |
| 243A | 0.07 |
| 243B | 0.10 |
| 244A | 0.09 |
| 244B | 0.22 |
| 245 | 0.04 |
| 246 | 0.50 |
| 247 | 0.41 |
| 248 | 0.27 |
| 249 | 0.10 |
| 250 | 0.02 |
| 251 | 0.25 |
| 252 | 0.06 |
| 253 | 0.08 |
| 254 | 0.07 |
| 255 | 0.12 |
| 256 | 0.42 |
| 257 | 0.10 |
| 258 | 0.14 |
| 259 | 0.10 |
| 260 | 0.36 |
| 261 | 0.09 |
| 262 | 0.13 |
| 263 | 0.07 |
| 264 | 0.06 |
| 265 | 0.26 |
| 266 | 0.85 |
| 269 | 0.51 |
| 270 | 0.73 |
| 271 | 0.23 |
| 272 | 0.66 |
| 273 | 0.13 |
| 274 | 0.44 |
| 275 | 0.10 |
| 277 | 0.37 |
| 278 | 0.13 |

TABLE 19-2-continued

| Example Number | RNR Enzyme inhibitory activity IC$_{50}$ (μM) |
|---|---|
| 280 | 0.42 |
| 281 | 0.76 |
| 282 | 0.91 |
| 283 | 0.15 |
| 284 | 0.56 |
| 285 | 0.31 |
| 286 | 0.07 |
| 287 | 0.05 |
| 288 | 0.06 |
| 289 | 0.13 |
| 290 | 0.84 |
| 292 | 0.16 |
| 294 | 0.11 |
| 295 | 0.79 |
| 298 | 0.30 |
| 299 | 0.94 |
| 300 | 0.34 |
| 301 | 0.29 |
| 302 | 0.49 |
| 303 | 0.16 |
| 304 | 0.16 |
| 305 | 0.24 |
| 306 | 0.09 |
| 308 | 0.18 |
| 310 | 0.17 |
| 311 | 0.22 |
| 312 | 0.22 |
| 313 | 0.34 |
| 314 | 0.26 |
| 315 | 0.19 |
| 317 | 0.28 |
| 318 | 0.54 |
| 319 | 0.28 |
| 320 | 0.60 |
| 322 | 0.22 |

TABLE 19-3

| Example Number | RNR Enzyme inhibitory activity IC$_{50}$ (μM) |
|---|---|
| 323 | 0.42 |
| 324 | 0.17 |
| 325 | 0.22 |
| 328 | 0.11 |
| 329 | 0.06 |
| 330A | 0.12 |
| 330B | 0.46 |
| 331 | 0.09 |
| 332 | 0.13 |
| 333 | 0.31 |
| 334 | 0.83 |
| 337 | 0.08 |
| 338 | 0.10 |
| 339 | 0.51 |
| 340 | 0.27 |
| 341 | 0.41 |
| 342 | 0.09 |
| 343 | 0.64 |
| 344 | 0.72 |
| 345 | 0.25 |
| 346 | 0.42 |
| 349 | 0.25 |
| 350 | 0.46 |

Test Example 2 Cell Proliferation Inhibitory Effect on Human Breast Cancer Cell Line Human derived breast cancer cell line HCC 1806 cells were daily passaged at a cell density not exceeding 80% in ATCC recommended Roswell Park Memorial Institute medium (RPMI-1640) containing 10% fetal bovine serum (FBS). In order to start the test of cell proliferation inhibitory activity, HCC 1806 cells were suspended in the above medium, after seeing at 180 μl in each well of a 96-well flat bottom plate so that the number of cells per well was 2,000, the cells were cultured at 37° C. for 1 day in an incubator containing 5% carbon dioxide gas. On the next day, the test compound was dissolved in DMSO, and 20 μl of a drug additive solution diluted serially with distilled water to 10 times of the final concentration was added to each well of the culture plate of the cells, and the cells were cultured at 37° C. for 72 hours in an incubator containing 5% carbon dioxide gas. After culturing for 72 hours, 20 μl of glutaraldehyde was added to each well and allowed to stand for 30 minutes, then the plate was washed 10 times with water and was dried. 100 μl of a stain solution (0.05% crystal violet in a 20% methanol solution) was added to each well and allowed to stand for 30 minutes, then the plate was washed 10 times with water and was dried. 100 μL of an extract solution (0.1 N NaH$_2$PO$_4$: 100% ethanol=1:1) was added to each well and mixed, and the mixture was measured at a wavelength of 540 nm using a plate reader (MTP-450 manufactured by Corona Electric Co., Ltd.). The growth inhibition rate was calculated from the following formula, and the concentration (IC$_{50}$ (μM)) of a test compound inhibiting 50% was determined. The results are shown in Table 20.

Growth inhibition rate (%)={(C-B)-(T-B)}/(C-B)×100

T: Absorbance of well to which test compound was added
C: Absorbance of wells to which no test compound was added
B: Absorbance of wells to which no cell suspension was added As a result, as is clear from the following table, it was revealed that the compounds of the present invention have growth inhibitory activity against cancer cells.

TABLE 20

| Example Number | Cell growth suppression IC$_{50}$ (μM) |
|---|---|
| 1 | 0.16 |
| 5 | 0.20 |
| 6 | 0.29 |
| 10 | 0.56 |
| 11 | 0.64 |
| 12 | 0.50 |
| 13 | 0.31 |
| 14 | 0.56 |
| 15 | 0.40 |
| 18 | 0.58 |
| 19 | 0.94 |
| 25 | 0.59 |
| 26 | 0.98 |
| 30 | 0.80 |
| 35 | 0.67 |
| 37 | 0.82 |
| 39 | 0.23 |
| 40 | 0.59 |
| 41 | 0.40 |
| 43 | 0.28 |

TABLE 20-continued

| Example Number | Cell growth suppression IC$_{50}$ (μM) |
|---|---|
| 71 | 0.79 |
| 76 | 0.44 |
| 83 | 0.50 |
| 91 | 0.98 |
| 93 | 0.28 |
| 94 | 0.48 |
| 95 | 0.14 |
| 96 | 0.95 |
| 100 | 0.39 |
| 101 | 0.81 |
| 102 | 0.66 |
| 106 | 0.38 |
| 109 | 0.40 |
| 113 | 0.60 |
| 114 | 0.37 |
| 116 | 0.32 |
| 117 | 0.31 |
| 123 | 0.17 |
| 129 | 0.08 |
| 144 | 0.96 |
| 146 | 0.83 |
| 147 | 0.65 |
| 148 | 0.40 |
| 153 | 0.91 |
| 156 | 0.87 |
| 157 | 0.37 |
| 167 | 0.14 |
| 186 | 0.64 |
| 193 | 0.11 |
| 196 | 0.32 |
| 197 | 0.41 |
| 198 | 0.05 |
| 200A | 0.05 |
| 200B | 0.46 |
| 203 | 0.81 |
| 204 | 0.15 |
| 205 | 0.25 |
| 206A | 0.57 |
| 207A | 0.07 |
| 207B | 0.25 |
| 208A | 0.33 |
| 208B | 0.05 |
| 209A | 0.06 |
| 209B | 0.82 |
| 211A | 0.85 |
| 212 | 0.26 |
| 216 | 0.67 |
| 220A | 0.37 |
| 220B | 0.50 |
| 222A | 0.06 |
| 222B | 0.67 |
| 224A | 0.10 |
| 224B | 0.77 |
| 225A | 0.60 |
| 226A | 0.08 |
| 226B | 0.30 |
| 227A | 0.19 |
| 228A | 0.14 |
| 229A | 0.31 |
| 230A | 0.29 |
| 230B | 0.78 |
| 232 | 0.33 |
| 233 | 0.28 |
| 234A | 0.57 |
| 235A | 0.13 |
| 235B | 0.40 |
| 238A | 0.44 |
| 239A | 0.72 |
| 241 | 0.49 |
| 243A | 0.29 |
| 243B | 0.70 |
| 244A | 0.72 |
| 245 | 0.15 |
| 249 | 0.14 |
| 250 | 0.12 |
| 252 | 0.74 |
| 253 | 0.23 |
| 254 | 0.25 |
| 255 | 0.48 |
| 257 | 0.20 |
| 258 | 0.58 |
| 259 | 0.35 |
| 261 | 0.72 |
| 262 | 0.17 |
| 264 | 0.76 |
| 273 | 0.81 |
| 275 | 0.37 |
| 278 | 0.59 |
| 288 | 0.15 |
| 289 | 0.60 |
| 292 | 0.75 |
| 294 | 0.39 |
| 303 | 0.99 |
| 304 | 0.94 |
| 308 | 0.87 |
| 310 | 0.35 |
| 311 | 0.52 |
| 312 | 0.87 |
| 315 | 0.93 |
| 328 | 0.41 |
| 329 | 0.24 |
| 330A | 0.24 |
| 337 | 0.30 |

Test Example 3 Cell Proliferation Inhibitory Effect on Human Cancer-Derived Cancer Cell Lines According to the method of Test Example 2, the cell proliferation inhibitory effect on various cancer cell lines as described in Table 21 was evaluated.

As a result, as is clear from the following table, it was revealed that the compounds of the present invention have growth inhibitory activity against various types of cancer cells derived from humans.

TABLE 21

| cell line | NUGC-3 | NCI-H460 | CFPAC-1 | A673 | GB-1 | HLE | MSTO-211H | DU145 |
|---|---|---|---|---|---|---|---|---|
| Carcinoma type | Stomach Cancer | Lung Cancer | Pancreatic Cancer | Ewing's sarcoma | Glioblastoma | Liver Cancer | Mesothelioma | Prostate Cancer |
| Culture medium | RPMI-1640 + 10% FBS | ATCC recommended RPMI-1640 + 10% FBS | IMDM + 10% FBS | DMEM + 10% FBS | DMEM + 10% FBS | DMEM + 10% FBS | ATCC recommended RPMI-1640 + 10% FBS | EMEM + 0.1 mM non-essential amino acid + 1 mM sodium pyruvate + 10% FBS |

TABLE 21-continued

| cell line | A2780 | ACHN | HCT116 | RPMI7932 | NCI-H2228 | NCI-H2170 | | |
|---|---|---|---|---|---|---|---|---|
| Carcinoma type | Ovarian Cancer | Kidney Cancer | Colorectal Cancer | Melanoma | Lung Cancer | Lung Cancer | | |
| Culture medium | RPMI-1640 + 10% FBS | EMEM + 10% FBS | McCoy's 5A + 10% FBS | RPMI-1640 + 10% FBS | ATCC recommended RPMI-1640 + 10% FBS | ATCC recommended RPMI-1640 + 10% FBS | | |
| cell number (cell/well) | 2000 | 1000 | 2000 | 2000 | 3000 | 3000 | 6000 | 5000 |
| Example 5 | 1.22 | 0.73 | 0.94 | 1.09 | 1.57 | 0.79 | 0.70 | 1.04 |
| Example 235A | 0.71 | 0.35 | 0.35 | 0.61 | 1.12 | 0.42 | 0.39 | 0.53 |
| Example 11 | 3.11 | 1.50 | 1.71 | 2.56 | 5.22 | 1.74 | 1.54 | 1.84 |
| Example 1 | 1.12 | 0.57 | 0.54 | 0.92 | 1.56 | 0.56 | 0.65 | 0.73 |
| Example 14 | 2.83 | 1.35 | 1.42 | 1.85 | 4.60 | 1.30 | 1.58 | 2.22 |
| Example 209A | 0.40 | 0.25 | 0.33 | 0.32 | 0.64 | 0.26 | 0.32 | 0.31 |
| Example 222A | 0.36 | 0.18 | 0.23 | 0.25 | 0.46 | 0.20 | 0.27 | 0.26 |
| Example 200A | 0.27 | 0.13 | 0.17 | 0.18 | 0.37 | 0.14 | 0.17 | 0.17 |
| Example 228A | 0.51 | 0.31 | 0.36 | 0.40 | 0.85 | 0.29 | 0.37 | 0.34 |

| cell line | A2780 | ACHN | HCT116 | RPMI7932 | NCI-H2228 | NCI-H2170 |
|---|---|---|---|---|---|---|
| Carcinoma type | Ovarian Cancer | Kidney Cancer | Colorectal Cancer | Melanoma | Lung Cancer | Lung Cancer |
| Culture medium | RPMI-1640 + 10% FBS | EMEM + 10% FBS | McCoy's 5A + 10% FBS | RPMI-1640 + 10% FBS | ATCC recommended RPMI-1640 + 10% FBS | ATCC recommended RPMI-1640 + 10% FBS |
| cell number (cell/well) | 2000 | 2000 | 1000 | 4000 | 5000 | 5000 |
| Example 5 | 0.83 | 0.75 | 0.91 | 2.67 | 1.27 | 1.89 |
| Example 235A | 0.40 | 0.38 | 0.48 | 1.23 | 0.88 | 1.10 |
| Example 11 | 2.08 | 1.50 | 2.30 | 4.74 | 3.21 | 3.90 |
| Example 1 | 0.63 | 0.68 | 0.75 | 1.74 | 1.35 | 1.41 |
| Example 14 | 1.71 | 0.98 | 2.20 | 3.21 | 3.53 | 4.18 |
| Example 209A | 0.30 | 0.22 | 0.28 | 0.72 | 0.73 | 0.57 |
| Example 222A | 0.19 | 0.17 | 0.27 | 0.51 | 0.48 | 0.52 |
| Example 200A | 0.13 | 0.13 | 0.22 | 0.43 | 0.50 | 0.49 |
| Example 228A | 0.38 | 0.32 | 0.38 | 0.65 | 0.74 | 0.88 |

Test Example 4 Evaluation of Antitumor Effect Using Human-Derived Blood Cancer Cell Line (MV-4-11) Subcutaneous Transplantation Model (In Vivo)

A human-derived blood cancer cell line MV-4-11 was transplanted subcutaneously into a nude mouse, and at the time when the tumor volume of the nude mouse on which the engrafted tumor reached about 100 to 300 mm³, five mice were assigned to each group by random stratification so that the average of the tumor volumes of each group was uniform (day 0), and the compound of the present invention was orally administered daily at 100 mg/kg/day once per day for 14 days. Mouse were killed during the experiments when they lost more than 20% weight based on ethical guidelines, and the final results are calculated based on each group consisting of four mice.

In order to compare the chronological transition of proliferation of tumor for the administration of each test compound, relative tumor volume (RTV) setting the tumor volume at the time of grouping as 1 as the tumor proliferation rate was calculated according to the following formula, and the transition of the average value of RTV of each individual are shown in FIGS. 1 to 4.

RTV=(tumor volume at the day of tumor volume measurement)/(tumor volume at the time of the grouping)

The average RTV value of the compound-administered group of the present invention on the final evaluation day is smaller than the average RTV value of the control group, and when a statistically significant difference (Student-t test) is shown, the compound of the present invention was determined to be significantly effective, and the statically significant difference is marked with * in the figure (*: $p<0.05$).

As a result, it was revealed that the compound of the present invention shows a significant antitumor effect.

The invention claimed is:

1. A method of treating tumor by inhibiting ribonucleotide reductase in a subject in need thereof, the method comprising administering an effective amount of a compound represented by the following formula (I) or a salt thereof to the subject:

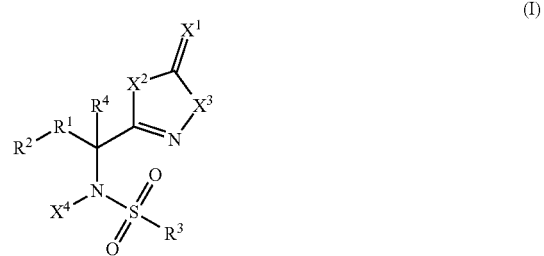

(I)

wherein $X^1$ represents an oxygen atom or a sulfur atom; $X^2$ and $X^3$ represent oxygen atoms; $X^2$ represents an oxygen atom, and $X^3$ represents —NH—; or $X^2$ represents —NH—, and $X^3$ represents an oxygen atom;

$X^4$ represents a hydrogen atom or a C1-C6 alkyl group;

$R^1$ represents —C($R^{11}$)(or C(=CH$_2$)—;

$R^{11}$ and $R^{12}$ are the same or different and represent a hydrogen atom, a halogen atom, or a hydroxy group, or a C1-C6 alkyl group, alternatively may be taken together with the carbon atoms to which $R^{11}$ and $R^{12}$ are attached to form a saturated hydrocarbon ring having 3 to 8 carbon atoms;

$R^2$ represents a C6-C14 aromatic hydrocarbon group or a 9 or 10 membered fully unsaturated heterocyclic group, wherein $R^2$ may have substituents, and when $R^2$ has two substituents on carbon atoms which are adjacent to each other on the aromatic hydrocarbon ring, the substituents may be fused together with carbon atoms to which the substituents bind to form a saturated or partially unsaturated 4-8 membered hydrocarbon ring or heterocyclic ring, either of which may have substituents, $R^3$ represents a C6-C14 aromatic hydrocarbon group or a 5-10 membered fully unsaturated heterocyclic group, wherein $R^3$ may have substituents, and when $R^3$ has two substituents on the carbon atoms which are adjacent to each other on the aromatic hydrocarbon ring, the substituents may be fused together with carbon atoms to which the substituents bind to form a saturated or partially unsaturated 4-8 membered hydrocarbon ring or heterocyclic ring, either of which may have substituents; and $R^4$ represents a hydrogen atom or a C1-C6 alkyl group; with the proviso that $X^1$ is an oxygen atom when $X^2$ represents an oxygen atom, $X^3$ represents —NH—, $X^4$ represents a hydrogen atom, $R^1$ represents —CH$_2$—, $R^2$ represents a phenyl group, $R^3$ represents 4-methylphenyl group, and $R^4$ represents a hydrogen atom.

2. The method according to claim 1, comprising orally administering the effective amount of the compound or a salt thereof to the subject in need thereof.

3. The method according to claim 1, wherein the tumor is selected from the group consisting of head and neck cancer, gastrointestinal cancer, liver cancer, biliary tract cancer, pancreatic cancer, colorectal cancer, lung cancer, breast cancer, genital cancer, ovarian cancer, uterine cancer, urinary cancer, hematopoietic tumors, bone and soft tissue tumors, skin cancer, and brain tumor.

4. The method according to claim 1, wherein in formula (I):
$R^{11}$ represents a halogen atom, a hydroxy group, or a C1-C6 alkyl group;
$R^{12}$ represents a hydrogen atom, a halogen atom, a hydroxy group, or a C1-C6 alkyl group; or
$R^{11}$ and $R^{12}$ may be taken together with carbon atoms to which $R^{11}$ and $R^{12}$ bind to form a saturated hydrocarbon ring having 3 to 8 carbon atoms.

5. The method according to claim 1, wherein in formula (I), $X^1$ represents an oxygen atom.

6. The method according to claim 1, wherein in formula (I), $X^2$ represents an oxygen atom.

7. The method according to claim 1, wherein in formula (I), $X^3$ represents —NH—.

8. The method according to claim 1, wherein in formula (I), $X^4$ represents a hydrogen atom.

9. The method according to claim 1, wherein in formula (I), $R^1$ represents —C($R^{11}$)($R^{12}$), wherein $R^{11}$ represents a C1-C6 alkyl group, and $R^{12}$ represents a hydrogen atom.

10. The method according to claim 1, wherein in formula (I):
$R^2$ represents a C6-C14 aromatic hydrocarbon group or a 9-10 membered fully unsaturated heterocyclic group, wherein $R^2$ may be substituted with $R^{21}$, and when $R^2$ has two substituents on the carbon atoms which are adjacent to each other on the aromatic hydrocarbon ring, the substituents may be fused together with carbon atoms to which the substituents bind to form a saturated or partially unsaturated 4-8 membered hydrocarbon ring or heterocyclic ring, either of which may be substituted with Rz;
$R^{21}$ represents: a halogen atom; an amino carbonyl group; a cyano group; a C1-C6 alkyl group optionally substituted with Rx; a C3-C6 cycloalkyl group optionally substituted with Rx; a C2-C6 alkynyl group optionally substituted with Rx; a C6-C14 aromatic hydrocarbon group optionally substituted with Ry; or a 5-10 membered unsaturated heterocyclic group optionally substituted with Rz;
Rx represents a halogen atom or a C6-C14 aromatic hydrocarbon group;
Ry represents a halogen atom or a C1-C6 alkoxy group;
Rz represents a halogen atom, a C1-C6 alkyl group, a halogeno C1-C6 alkyl group, a C3-C6 cycloalkyl group, a C1-C6 alkoxy group, a C6-C14 aromatic hydrocarbon group, a nitrogen-containing saturated heterocyclic group, or a nitrogen-containing saturated heterocyclic carbonyl group.

11. The method according to claim 1, wherein in formula (I):
$R^3$ represents a C6-C14 aromatic hydrocarbon group or a 5-10 membered fully unsaturated heterocyclic group, wherein $R^3$ may be substituted with $R^{31}$, and when $R^3$ has two substituents on the carbon atoms which are adjacent to each other on the aromatic hydrocarbon ring, the substituent may be fused together with carbon atoms to which the substituents bind to form a saturated or partially unsaturated 4-8 membered hydrocarbon ring or heterocyclic ring, either of which may be substituted with Rc;
$R^{31}$ represents: a halogen atom; a cyano group; a nitro group; a carboxyl group; a thioamide group; a C1-C6 alkyl group optionally substituted with Ra; an amino group optionally substituted with Ra; a C3-C6 cycloalkyl group optionally substituted with Rb; a C1-C6 alkoxy group optionally substituted with Rb; a C2-C7 alkoxycarbonyl group; a C1-C14 acyl group optionally substituted with Rb; a C6-C14 aromatic hydrocarbon group optionally substituted with Rb; a 5-10 membered unsaturated heterocyclic group optionally substituted with Rc; an amino carbonyl group optionally substituted with Rd and Re; or —S(═O)$_2$Rf;
Ra represents a halogen atom, a hydroxy group, a C1-C14 acyl group, a C1-C14 acyloxy group, a C2-C6 alkynyl group, or a C1-C6 alkoxy C1-C6 alkoxy group;
Rb represents a halogen atom, an amino group, or a C1-C6 alkoxy group;
Rc represents: a halogen atom; a hydroxy group; an amino group; an oxo group; a C1-C6 alkyl group optionally substituted with a hydroxy group; a halogeno C1-C6 alkyl groups; a C1-C14 acyl groups; a C1-C14 acylamino group; a C1-C14 acyloxy group; or a C7-C13 aralkyloxy group;
Rd and Re are the same or different and represents: a hydrogen atom; a hydroxy group; a C7-C13 aralkyloxy group; or a C1-C6 alkyl group optionally substituted with a hydroxy group; alternatively combine with nitrogen atom which is adjacent to Rd and Re to form a saturated or unsaturated 4-10 membered heterocyclic ring group optionally substituted with an amino group, a spiro heterocyclic ring group, or a bridged heterocyclic ring group; and
Rf represents an amino group, a C1-C6 alkyl group, or a 4-10 membered saturated heterocyclic group.

12. The method according to claim 1, wherein in formula (I):
$R^2$ represents a C6-C14 aromatic hydrocarbon group or a bicyclic 9-10 membered fully unsaturated heterocyclic ring group having 1-3 heteroatoms selected from the group consisting of a nitrogen atom, a sulfur atom, and an oxygen atom, wherein $R^2$ may be substituted with $R^{21}$, and when $R^2$ has two substituents on the carbon atoms which are adjacent to each other on the aromatic hydrocarbon ring, the substituents may be fused together with carbon atoms to which the substituents bind to form a saturated or partially unsaturated monocyclic hydrocarbon ring having 4-8 carbon atoms optionally substituted with a C1-C6 alkyl group, or a saturated or partially unsaturated monocyclic 4-8 membered heterocyclic ring having 1-3 heteroatoms selected from a nitrogen atom, a sulfur atom and an oxygen atom optionally substituted with a C1-C6 alkyl group;

$R^{21}$ represents a halogen atom, an amino carbonyl group, a cyano group, a C1-C6 alkyl group optionally substituted with a halogen atom, a C3-C6 cycloalkyl group, a C2-C6 alkynyl group optionally substituted with a C6-C14 aromatic hydrocarbons group, a C6-C14 aromatic hydrocarbon group optionally substituted with a group selected from a halogen atom and a C1-C6 alkoxy group, or an unsaturated monocyclic or bicyclic 5-10 membered heterocyclic group having 1-3 hetero atoms selected from the group consisting of a nitrogen atom, a sulfur atom, and an oxygen atom optionally substituted with a group selected from the group consisting of a halogen atom, a C1-C6 alkyl group, a halogeno C1-C6 alkyl group, a C3-C6 cycloalkyl group, a C1-C6 alkoxy group, a C6-C14 aromatic hydrocarbon group, a nitrogen-containing saturated heterocyclic group, and nitrogen-containing saturated heterocyclic carbonyl group.

13. The method according to claim 1, wherein in formula (I):

$R^2$ represents a C6-C14 aromatic hydrocarbon group, wherein $R^2$ may be substituted with $R^{21}$, and when $R^2$ has two substituents on the carbon atoms which are adjacent to each other on the aromatic hydrocarbon ring, the substituents may be fused together with carbon atoms to which the substituents bind to form a saturated or partially unsaturated monocyclic hydrocarbon ring having 4-8 carbon atoms optionally substituted with a C1-C6 alkyl group;

$R^{21}$ represents a halogen atom, a cyano group, a C1-C6 alkyl group optionally substituted with a halogen atom, a C3-C6 cycloalkyl group, a phenyl group optionally substituted with a group selected from the group consisting of a halogen atom and a C1-C6 alkoxy group, or an unsaturated monocyclic or bicyclic 5-10 membered heterocyclic group having 1-3 hetero atoms selected from the group consisting of a nitrogen atom, a sulfur atom, and an oxygen atom optionally substituted with a group selected from the group consisting of a halogen atom, a C1-C6 alkyl group, a halogeno C1-C6 alkyl group, a C3-C6 cycloalkyl group, a C1-C6 alkoxy group, a morpholino group, a piperidinyl group and a morpholinocarbonyl group.

14. The method according to claim 1, wherein in formula (I):

$R^2$ represents a C6-C10 aromatic hydrocarbon group, wherein $R^2$ may be substituted with $R^{21}$, and when $R^2$ has two substituents on the carbon atoms which are adjacent to each other on the aromatic hydrocarbon ring, the substituents may be fused together with carbon atoms to which the substituents bind to form a saturated or partially unsaturated monocyclic hydrocarbon ring having 5 or 6 carbon atoms optionally substituted with a C1-C6 alkyl group;

$R^{21}$ represents a halogen atom, a C1-C6 alkyl group, or a monocyclic 5 or 6 membered unsaturated heterocyclic group having 1-3 nitrogen atom(s) optionally substituted with a C1-C6 alkyl group.

15. The method according to claim 1, wherein in formula (I):

$R^3$ represents a C6-C14 aromatic hydrocarbon group, or a monocyclic or bicyclic 5-10 membered fully unsaturated heterocyclic group having 1-3 hetero atoms selected from a nitrogen atom, a sulfur atom and an oxygen atom, wherein $R^3$ may be substituted with $R^{31}$, and when $R^3$ has two substituents on the carbon atoms which are adjacent to each other on the aromatic hydrocarbon ring, the substituents may be fused together with carbon atoms to form a saturated or partially unsaturated monocyclic hydrocarbon ring having 4-8 carbon atoms optionally substituted with a group selected from the group consisting of: a halogen atom; a hydroxyl group; an amino group; an oxo group; a C1-C6 alkyl group optionally substituted with a hydroxy group; a halogeno C1-C6 alkyl group; a C1-C14 acyl group; a C1-C14 acylamino group; a C1-C14 acyloxyl group; and a C7-C13 aralkyloxy group, or a saturated or partially unsaturated monocyclic 4-8 membered heterocyclic ring having 1-4 heteroatoms selected from a nitrogen atom, a sulfur atom and an oxygen atom optionally substituted with a group selected from the group consisting of a halogen atom, a hydroxy group, an amino group, an oxo group, a C1-C6 alkyl group optionally substituted with a hydroxy group; a halogeno C1-C6 alkyl group; a C1-C14 acyl group; a C1-C14 acylamino group; a C1-C14 acyloxy group and a C7-C13 aralkyloxy group;

$R^{31}$ represents a halogen atom, a cyano group, a nitro group, a carboxyl group, thioamide group, C1-C6 alkyl group optionally substituted with a group selected from the group consisting of a halogen atom, a hydroxy group, a C1-C14 acyl group, C1-C14 acyloxy group, C2-C6 alkynyl group, and C1-C6 alkoxy C1-C6 alkoxy group, an amino group optionally substituted with a C1-C14 acyl group, a C3-C6 cycloalkyl group optionally substituted with an amino group, a C1-C6 alkoxy group optionally substituted with a halogen atom, a C2-C7 alkoxycarbonyl group, a C1-C14 acyl group optionally substituted with a halogen atom, a C6-C14 aromatic hydrocarbon group optionally substituted with a group selected from the group consisting of a halogen atom, an amino group and a C1-C6 alkoxy group, a monocyclic or bicyclic 5-10 membered unsaturated heterocyclic group having 1-4 heteroatoms selected from a nitrogen atom, a sulfur atom and an oxygen atom optionally substituted with a group selected from the group consisting of a halogen atom, an oxo group and a C1-C6 alkyl group, an amino carbonyl group optionally substituted with Rd and Re wherein Rd and Re are the same or different, and present a hydrogen atom, a hydroxy group, a C7-C13 aralkyloxy group, or a C1-C6 alkyl group optionally substituted with a hydroxy group, alternatively combine with the adjacent nitrogen atom to form: a saturated or unsaturated monocyclic or bicyclic 4-10 membered heterocyclic group, optionally substituted with an amino group, having 1-3 hetero atoms selected from a nitrogen atom, a sulfur atom, and an oxygen atom; a spiroheterocyclic group; or a bridged heterocyclic group, or —S(=O)$_2$Rf, wherein Rf represents an amino group, a C1-C6 alkyl group, or a 4-10 membered saturated heterocyclic group.

16. The method according to claim 1, wherein in formula (I):
- $R^3$ represents a C6-C10 aromatic hydrocarbon group or a monocyclic or bicyclic 5-10 membered fully unsaturated heterocyclic group having 1-3 heteroatoms selected from a nitrogen atom, a sulfur atom and an oxygen atom, wherein $R^3$ may be substituted with $R^{31}$, when $R^3$ has two substituents on the carbon atoms which are adjacent to each other on the aromatic hydrocarbon ring, $R^3$ may be fused together with carbon atoms to which the substituents bind to form a saturated or partially unsaturated monocyclic hydrocarbon having 4-8 carbon atoms optionally substituted with a group selected from the group consisting of a halogen atom, a hydroxy group, an amino group, an oxo group, C1-C6 alkyl groups (which are optionally substituted with a hydroxy group), a halogeno C1-C6 alkyl group, a C1-C14 acyl group, a C1-C14 acylamino group, and a C1-C14 acyloxy group, or a saturated or partially unsaturated monocyclic 4-8 membered heterocyclic ring having 1-3 heteroatoms selected from the group consisting of a nitrogen atom, a sulfur atom and an oxygen atom optionally substituted with a group selected from the group consisting of a halogen atom; a hydroxy group; an amino group; an oxo group; and a C1-C6 alkyl group which is optionally substituted with a hydroxy group; a halogeno C1-C6 alkyl group; a C1-C14 acyl group; a C1-C14 acylamino group; a C1-C14 acyloxy group;
- $R^{31}$ represents a halogen atom, a cyano group, a nitro group, a carboxyl group, thioamide group, C1-C6 alkyl group optionally substituted with a group selected from the group consisting of a halogen atom, a hydroxy group, a C1-C14 acyl group, a C1-C14 acyloxy group, a C2-C6 alkynyl group, and a C1-C6 alkoxy C1-C6 alkoxy group, an amino group optionally substituted with a C1-C14 acyl group, a C3-C6 cycloalkyl group optionally substituted with an amino group, a C1-C6 alkoxy group optionally substituted with a halogen atom, a C2-C7 alkoxycarbonyl group, a C1-C14 acyl group optionally substituted with a halogen atom, a C6-C10 aromatic hydrocarbon group optionally substituted with a group selected from the group consisting of an amino group and a halogen atom, an unsaturated monocyclic or bicyclic 5-10 membered heterocyclic group having 1 to 4 hetero atoms selected from a nitrogen atom, a sulfur atom and an oxygen atom optionally substituted with a group selected from the group consisting of a C1-C6 alkyl group and an oxo group, a —CONH$_2$ group, a (mono- or di-C1-C6 alkyl) aminocarbonyl group, a hydroxyamino carbonyl group, (C7-C13 aralkyl)oxyaminocarbonyl group, a cyclic aminocarbonyl group, an aminosulfonyl group, a C1-C6 alkylsulfonyl group, or a piperidinosulfonyl group.

17. The method as in claim 1, wherein in formula (I):
- $R^3$ represents a C6-C10 aromatic hydrocarbon group wherein the C6-C10 aromatic hydrocarbon group may be substituted with $R^{31}$, and when a C6-C10 aromatic hydrocarbon group has two substituents on the carbon atoms which are adjacent to each other on the aromatic hydrocarbon ring, the substituents may be fused together with carbon atoms to which the substituents bind to form a saturated or partially unsaturated monocyclic 4-6 membered heterocyclic ring having 1-3 heteroatoms selected from the group consisting of a nitrogen atom, a sulfur atom and an oxygen atom optionally substituted with a group selected from the group consisting of a hydroxy group, an amino group, an oxo group, a C1-C6 alkyl group, a halogeno C1-C6 alkyl group, a C1-C14 acyl amino group and a C1-C14 acyloxy group, alternatively presents a fully unsaturated monocyclic 5 or 6 membered heterocyclic ring having 1-3 heteroatoms selected from a nitrogen atom, a sulfur atom and an oxygen atom optionally substituted with a group selected from the group consisting of a halogen atom, a C1-C6 alkyl group optionally substituted with a hydroxy group, a C1-C6 alkoxy group, a C2-C7 alkoxycarbonyl group, a —CONH$_2$ group, a (mono- or di-C1-C6 alkyl)aminocarbonyl group, a pyrrolidin-1-ylcarbonyl group, a morpholin-4-ylcarbonyl group, a 2-oxa-7-azaspiro[3.5]nonane-7-carbonyl group, a 3-oxa-8-azabicyclo[3.2.1]octane-8-carbonyl group and an 8-oxa-3-azabicyclo[3.2.1]octane-3-carbonyl group,
- $R^{31}$ represents a halogen atom, an amino group, a C1-C6 alkyl group optionally substituted with a group selected from the group consisting of a halogen atom and a hydroxy group, C1-C6 alkoxy group optionally substituted with a halogen atom, a monocyclic 5 or 6 membered unsaturated heterocyclic group having 1 to 4 hetero atoms selected from a nitrogen atom, a sulfur atom and an oxygen atom, a —CONH$_2$ group, a (mono- or di-C1-C6 alkyl) aminocarbonyl group, or a hydroxyamino carbonyl group.

18. The method compound or a salt thereof according to claim 1, wherein in formula (I):
- $X^1$ represents an oxygen atom,
- $X^2$ represents an oxygen atom,
- $X^3$ represents —NH—,
- $X^4$ represents a hydrogen atom,
- $R^1$ represents —C($R^{11}$)($R^{12}$)— wherein $R^{11}$ represents a C1-C6 alkyl group, and $R^{12}$ represents a hydrogen atom, and
- $R^2$ represents a C6-C10 aromatic hydrocarbon group, wherein $R^2$ may be substituted with $R^{21}$, and when $R^2$ has two substituents on the carbon atoms which are adjacent to each other on the aromatic hydrocarbon ring, the substituent may be fused together with carbon atoms to which the substituents bind to form a saturated or partially unsaturated monocyclic hydrocarbon ring having 5 or 6 carbon atoms optionally substituted with a C1-C6 alkyl group; and
- $R^{21}$ represents a halogen atom, a C1-C6 alkyl group, or a monocyclic 5 or 6 membered unsaturated heterocyclic group having 1-3 nitrogen atom(s) optionally substituted with a C1-C6 alkyl group;
- $R^3$ represents a C6-C10 aromatic hydrocarbon group wherein the C6-C10 aromatic hydrocarbon group may be substituted with $R^{31}$, and when a C6-C10 aromatic hydrocarbon group has two substituents on the carbon atoms which are adjacent to each other on the aromatic hydrocarbon ring, the substitutes may be fused together with carbon atoms to which the substituents bind to form a saturated or partially unsaturated monocyclic 4-6 membered heterocyclic ring having 1-3 heteroatoms selected from a nitrogen atom, a sulfur atom and an oxygen atom optionally substituted with a group selected from the group consisting of a hydroxy group, an amino group, an oxo group, a C1-C6 alkyl group, a halogeno C1-C6 alkyl group; a C1-C14 acyl amino group and a C1-C14 acyloxy group, alternatively presents a fully unsaturated monocyclic 5 or 6 membered heterocyclic ring having 1-3 heteroatoms selected from a nitrogen atom, a sulfur atom and an oxygen atom optionally substituted with a group selected from the group consisting of a halogen atom, a C1-C6 alkyl group optionally substituted with a hydroxy group, a C1-C6 alkoxy group, a C2-C7 alkoxycarbonyl group, a —CONH$_2$ group, a (mono- or di-C1-C6 alkyl)aminocarbonyl group, a pyrrolidin-1-ylcarbonyl group, a morpholin-4-ylcarbonyl group, a 2-oxa-7-azaspiro[3.5]nonane-7-carbonyl group, a 3-oxa-8-azabicyclo[3.2.1]octane-8-carbonyl group and an 8-oxa-3-azabicyclo[3.2.1]octane-3-carbonyl group, $R^{31}$ represents a halogen atom, an amino group, a C1-C6 alkyl group optionally substituted with a group selected from the group consisting of a halogen atom and a hydroxy group, a C1-C6 alkoxy group optionally substituted with a halogen atom, a monocyclic 5 or 6 membered unsaturated heterocyclic group having 1 to 4 hetero atoms selected from a nitrogen atom, a sulfur atom and an oxygen atom, a —CONH$_2$ group, a (mono- or di-C1-C6 alkyl) aminocarbonyl group, or a hydroxyamino carbonyl group, $R^4$ represents a hydrogen atom.

19. The method according to claim 1, wherein in formula (I):

$X^1$ represents an oxygen atom,
$X^2$ represents an oxygen atom,
$X^3$ represents —NH—,
$X^4$ represents a hydrogen atom,
$R^1$ represents —C($R^{11}$)($R^{12}$)-wherein $R^{11}$ represents a methyl group, and $R^{12}$ represents a hydrogen atom, and
$R^2$ represents a phenyl group, or a naphthyl group, wherein $R^2$ may be substituted with $R^{21}$, and when $R^2$ has two substituents on the carbon atoms which are adjacent to each other on the aromatic hydrocarbon ring, the substituents may be fused together with carbon atoms to which the substituents bind, to form a saturated or partially unsaturated monocyclic hydrocarbon ring having 5 or 6 carbon atoms optionally substituted with a C1-C6 alkyl group; and
$R^{21}$ represents a halogen atom or a C1-C6 alkyl group;
$R^3$ represents
a phenyl group, wherein the phenyl group may be substituted with $R^{31}$, and when a phenyl group has two substituents on the carbon atoms which are adjacent to each other on a benzene ring, the substitutes may be fused together with carbon atoms to which the substituents bind, to form a saturated or partially unsaturated monocyclic 6 membered heterocyclic ring having 1 or 2 oxygen atom(s) optionally substituted with a group selected from the group consisting of a hydroxy group and a C1-C6 alkyl group, or a pyridyl group optionally substituted with a —CONH$_2$ group, a (mono- or di-C1-C6 alkyl) aminocarbonyl group, or a pyrrolidin-1-ylcarbonyl group;
$R^{31}$ represents a halogen atom, an amino group, a C1-C6 alkyl group or a —CONH$_2$ group;
$R^4$ represent a hydrogen atom.

20. The method compound or 3 silt thereof according to claim 1, wherein the compound is selected from the following compounds (1)-(19):

(1) 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide, (2) 5-chloro-2(N-((1S,2R)-2-(2,3-dimethylphenyl)-1-(5-oxo-4,5-dihydro-1,3,4-oxadiazol-2-yl)propyl)sulfamoyl)benzamide, (3) 5-bromo-2-(N-((1S,2R)-2-(2,3-dimethylphenyl)-1-(5-oxo-4,5-dihydro-1,3,4-oxadiazol-2-yl)propyl)sulfamoyl)benzamide, (4) 5-chloro-2(N-((1S,2R)-2-(6-fluoro-2,3-dimethylphenyl)-1-(5-oxo-4,5-dihydro-1,3,4-oxadiazol-2-yl)propyl)sulfamoyl)benzamide, (5) 5-chloro-2(N-((1S,2R)-2-(2-fluoronaphtalen-1-yl)-1-(5-oxo-4,5-dihydro-1,3,4-oxadiazol-2-yl)propyl)sulfamoyl)benzamide, (6) 5-chloro-2(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide, (7) 5-chloro-2(N-((1S,2R)-2-(3-chloro-6-fluoro-2-methylphenyl)-1-(5-oxo-4,5-dihydro-1,3,4-oxadiazol-2-yl)propyl)sulfamoyl)benzamide, (8) 5-bromo-2-(N-((1S,2R)-2-(3-chloro-6-fluoro-2-methylphenyl)-1-(5-oxo-4,5-dihydro-1,3,4-oxadiazol-2-yl)propyl)sulfamoyl)benzamide, (9) 2-(N-((1S,2R)-2-(3-bromo-6-fluoro-2-methylphenyl)-1-(5-oxo-4,5-dihydro-1,3,4-oxadiazol-2-yl)propyl)sulfamoyl)-5-chloro-benzamide,

(10) 5-chloro-(N-((1S,2R)-2-(6-fluoro-2,3-dimethylphenyl)-1-(5-oxo-4,5-dihydro-1,3,4-oxadiazol-2-yl)propyl)-6-(pyrrolidine-1-carbonyl)pyridine-2-sulfonamide,

(11) 5-chloro-(N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide,

(12) 5-chloro-(N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-chroman-8-sulfonamide,

(13) N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methyl-chroman-8-sulfonamide,

(14) 5-chloro-(N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-d3-chroman-8-sulfonamide,

(15) 5-chloro-(N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide,

(16) 3-chloro-6-(N-((1S,2R)-2-(6-fluoro-2,3-dimethylphenyl)-1-(5-oxo-4,5-dihydro-1,3,4-oxadiazol-2-yl)propyl)sulfamoyl)-N,N-dimethylpicolinamide,

(17) 4-amino-2-methoxy-(N-((1S,2R)-2-(8-methylnaphthalen-1-yl)-1-(5-oxo-4,5-dihydro-1,3,4-oxadiazol-2-yl)propyl)benzenesulfonamide,

(18) 4-amino-(N-((1S,2R)-2-(2,3-dihydro-1H-inden-4-yl)-1-(5-oxo-4,5-dihydro-1,3,4-oxadiazol-2-yl)propyl)-2-methoxybenzenesulfonamide, and

(19) 5-chloro-2-[[(1S,2R)-3,3,3-trideuterio-2-(6-fluoro-2,3-dimethylphenyl)-1-(2-oxo-3H-1,3,4-oxadiazol-5-yl)propyl]sulfamoyl]benzamide.

21. A method of treating tumor comprising administering an effective amount of a compound represented by the following formula (I) or a salt thereof to a subject in need thereof:

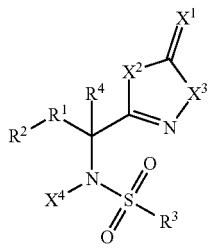

(I)

wherein X¹ represents an oxygen atom or a sulfur atom;
X² and X³ represent oxygen atoms; X² represents an oxygen atom, and X³ represents —NH—; or X² represents —NH—, and X³ represents an oxygen atom;
X⁴ represents a hydrogen atom or a C1-C6 alkyl group;
R¹ represents —C(R¹¹)(R¹²)- or —C(=CH₂)—;
R¹¹ and R¹² are the same or different and represent a hydrogen atom, a halogen atom, or a hydroxy group, or a C1-C6 alkyl group, alternatively may be taken together with the carbon atoms to which R¹¹ and R¹² are attached to form a saturated hydrocarbon ring having 3 to 8 carbon atoms;
R² represents a C6-C14 aromatic hydrocarbon group or a 9 or 10 membered fully unsaturated heterocyclic group, wherein R² may have substituents, and when R² has two substituents on carbon atoms which are adjacent to each other on the aromatic hydrocarbon ring, the substituents may be fused together with carbon atoms to which the substituents bind to form a saturated or partially unsaturated 4-8 membered hydrocarbon ring or heterocyclic ring, either of which may have substituents,
R³ represents a C6-C14 aromatic hydrocarbon group or a 5-10 membered fully unsaturated heterocyclic group, wherein R³ may have substituents, and when R³ has two substituents on the carbon atoms which are adjacent to each other on the aromatic hydrocarbon ring, the substituents may be fused together with carbon atoms to which the substituents bind to form a saturated or partially unsaturated 4-8 membered hydrocarbon ring or heterocyclic ring, either of which may have substituents; and
R⁴ represents a hydrogen atom or a C1-C6 alkyl group;
with the proviso that X¹ is an oxygen atom when X² represents an oxygen atom, X³ represents —NH—, X⁴ represents a hydrogen atom, R¹ represents —CH₂—, R² represents a phenyl group, R³ represents 4-methylphenyl group, and R⁴ represents a hydrogen atom,
wherein the tumor is selected from the group consisting of head and neck cancer, gastrointestinal cancer, liver cancer, biliary tract cancer, pancreatic cancer, colorectal cancer, lung cancer, breast cancer, genital cancer, ovarian cancer, uterine cancer, urinary cancer, hematopoietic tumors, bone and soft tissue tumors, skin cancer, and brain tumor.

22. The method according to claim 21, comprising orally administering the effective amount of the compound or a salt thereof to the subject in need thereof.

23. The method according to claim 21, wherein the tumor comprises at least one cancer cell selected from the group consisting of breast cancer, stomach cancer, lung cancer, pancreatic cancer, Ewing's sarcoma, Glioblastoma, liver cancer, mesothelioma, prostate cancer, ovarian cancer, kidney cancer, colorectal cancer, melanoma, and blood cancer.

24. The method according to claim 21, wherein in formula (I):
R¹¹ represents a halogen atom, a hydroxy group, or a C1-C6 alkyl group;
R¹² represents a hydrogen atom, a halogen atom, a hydroxy group, or a C1-C6 alkyl group; or
R¹¹ and R¹² may be taken together with carbon atoms to which R¹¹ and R¹² bind to form a saturated hydrocarbon ring having 3 to 8 carbon atoms.

25. The method according to claim 21, wherein in formula (I), X¹ represents an oxygen atom.

26. The method according to claim 21, wherein in formula (I), X² represents an oxygen atom.

27. The method according to claim 21, wherein in formula (I), X³ represents —NH—.

28. The method according to claim 21, wherein in formula (I), X⁴ represents a hydrogen atom.

29. The method according to claim 21, wherein in formula (I), R¹ represents —C(R¹¹)(R¹²), wherein R¹¹ represents a C1-C6 alkyl group, and R¹² represents a hydrogen atom.

30. The method according to claim 21, wherein in formula (I):
R² represents a C6-C14 aromatic hydrocarbon group or a 9-10 membered fully unsaturated heterocyclic group, wherein R² may be substituted with R²¹, and when R² has two substituents on the carbon atoms which are adjacent to each other on the aromatic hydrocarbon ring, the substituents may be fused together with carbon atoms to which the substituents bind to form a saturated or partially unsaturated 4-8 membered hydrocarbon ring or heterocyclic ring, either of which may be substituted with Rz;
R²¹ represents: a halogen atom; an amino carbonyl group; a cyano group; a C1-C6 alkyl group optionally substituted with Rx; a C3-C6 cycloalkyl group optionally substituted with Rx; a C2-C6 alkynyl group optionally substituted with Rx; a C6-C14 aromatic hydrocarbon group optionally substituted with Ry; or a 5-10 membered unsaturated heterocyclic group optionally substituted with Rz;
Rx represents a halogen atom or a C6-C14 aromatic hydrocarbon group;
Ry represents a halogen atom or a C1-C6 alkoxy group;
Rz represents a halogen atom, a C1-C6 alkyl group, a halogeno C1-C6 alkyl group, a C3-C6 cycloalkyl group, a C1-C6 alkoxy group, a C6-C14 aromatic hydrocarbon group, a nitrogen-containing saturated heterocyclic group, or a nitrogen-containing saturated heterocyclic carbonyl group.

31. The method according to claim 21, wherein in formula (I):
R³ represents a C6-C14 aromatic hydrocarbon group or a 5-10 membered fully unsaturated heterocyclic group, wherein R³ may be substituted with R³¹, and when R³ has two substituents on the carbon atoms which are adjacent to each other on the aromatic hydrocarbon ring, the substituent may be fused together with carbon atoms to which the substituents bind to form a saturated or partially unsaturated 4-8 membered hydrocarbon ring or heterocyclic ring, either of which may be substituted with Rc;
R³¹ represents: a halogen atom; a cyano group; a nitro group; a carboxyl group; a thioamide group; a C1-C6 alkyl group optionally substituted with Ra; an amino group optionally substituted with Ra; a C3-C6 cycloalkyl group optionally substituted with Rb; a C1-C6 alkoxy group optionally substituted with Rb; a C2-C7 alkoxycarbonyl group; a C1-C14 acyl group optionally substituted with Rb; a C6-C14 aromatic hydrocarbon group optionally substituted with Rb; a 5-10 membered unsaturated heterocyclic group optionally substituted with Rc; an amino carbonyl group optionally substituted with Rd and Re; or —S(=O)$_2$Rf;

Ra represents a halogen atom, a hydroxy group, a C1-C14 acyl group, a C1-C14 acyloxy group, a C2-C6 alkynyl group, or a C1-C6 alkoxy C1-C6 alkoxy group;

Rb represents a halogen atom, an amino group, or a C1-C6 alkoxy group;

Rc represents: a halogen atom; a hydroxy group; an amino group; an oxo group; a C1-C6 alkyl group optionally substituted with a hydroxy group; a halogeno C1-C6 alkyl groups; a C1-C14 acyl groups; a C1-C14 acylamino group; a C1-C14 acyloxy group; or a C7-C13 aralkyloxy group;

Rd and Re are the same or different and represents: a hydrogen atom; a hydroxy group; a C7-C13 aralkyloxy group; or a C1-C6 alkyl group optionally substituted with a hydroxy group; alternatively combine with nitrogen atom which is adjacent to Rd and Re to form a saturated or unsaturated 4-10 membered heterocyclic ring group optionally substituted with an amino group, a spiro heterocyclic ring group, or a bridged heterocyclic ring group; and Rf represents an amino group, a C1-C6 alkyl group, or a 4-10 membered saturated heterocyclic group.

32. The method according to claim 21, wherein in formula (I):

$R^2$ represents a C6-C14 aromatic hydrocarbon group or a bicyclic 9-10 membered fully unsaturated heterocyclic ring group having 1-3 heteroatoms selected from the group consisting of a nitrogen atom, a sulfur atom, and an oxygen atom, wherein $R^2$ may be substituted with $R^{21}$, and when $R^2$ has two substituents on the carbon atoms which are adjacent to each other on the aromatic hydrocarbon ring, the substituents may be fused together with carbon atoms to which the substituents bind to form a saturated or partially unsaturated monocyclic hydrocarbon ring having 4-8 carbon atoms optionally substituted with a C1-C6 alkyl group, or a saturated or partially unsaturated monocyclic 4-8 membered heterocyclic ring having 1-3 heteroatoms selected from a nitrogen atom, a sulfur atom and an oxygen atom optionally substituted with a C1-C6 alkyl group;

$R^{21}$ represents a halogen atom, an amino carbonyl group, a cyano group, a C1-C6 alkyl group optionally substituted with a halogen atom, a C3-C6 cycloalkyl group, a C2-C6 alkynyl group optionally substituted with a C6-C14 aromatic hydrocarbons group, a C6-C14 aromatic hydrocarbon group optionally substituted with a group selected from a halogen atom and a C1-C6 alkoxy group, or an unsaturated monocyclic or bicyclic 5-10 membered heterocyclic group having 1-3 hetero atoms selected from the group consisting of a nitrogen atom, a sulfur atom, and an oxygen atom optionally substituted with a group selected from the group consisting of a halogen atom, a C1-C6 alkyl group, a halogeno C1-C6 alkyl group, a C3-C6 cycloalkyl group, a C1-C6 alkoxy group, a C6-C14 aromatic hydrocarbon group, a nitrogen-containing saturated heterocyclic group, and nitrogen-containing saturated heterocyclic carbonyl group.

33. The method according to claim 21, wherein in formula (I):

$R^2$ represents a C6-C14 aromatic hydrocarbon group, wherein $R^2$ may be substituted with $R^{21}$, and when $R^2$ has two substituents on the carbon atoms which are adjacent to each other on the aromatic hydrocarbon ring, the substituents may be fused together with carbon atoms to which the substituents bind to form a saturated or partially unsaturated monocyclic hydrocarbon ring having 4-8 carbon atoms optionally substituted with a C1-C6 alkyl group;

$R^{21}$ represents a halogen atom, a cyano group, a C1-C6 alkyl group optionally substituted with a halogen atom, a C3-C6 cycloalkyl group, a phenyl group optionally substituted with a group selected from the group consisting of a halogen atom and a C1-C6 alkoxy group, or an unsaturated monocyclic or bicyclic 5-10 membered heterocyclic group having 1-3 hetero atoms selected from the group consisting of a nitrogen atom, a sulfur atom, and an oxygen atom optionally substituted with a group selected from the group consisting of a halogen atom, a C1-C6 alkyl group, a halogeno C1-C6 alkyl group, a C3-C6 cycloalkyl group, a C1-C6 alkoxy group, a morpholino group, a piperidinyl group and a morpholinocarbonyl group.

34. The method according to claim 21, wherein in formula (I):

$R^2$ represents a C6-C10 aromatic hydrocarbon group, wherein $R^2$ may be substituted with $R^{21}$, and when $R^2$ has two substituents on the carbon atoms which are adjacent to each other on the aromatic hydrocarbon ring, the substituents may be fused together with carbon atoms to which the substituents bind to form a saturated or partially unsaturated monocyclic hydrocarbon ring having 5 or 6 carbon atoms optionally substituted with a C1-C6 alkyl group;

$R^{21}$ represents a halogen atom, a C1-C6 alkyl group, or a monocyclic 5 or 6 membered unsaturated heterocyclic group having 1-3 nitrogen atom(s) optionally substituted with a C1-C6 alkyl group.

35. The method according to claim 21, wherein in formula (I):

$R^3$ represents a C6-C14 aromatic hydrocarbon group, or a monocyclic or bicyclic 5-10 membered fully unsaturated heterocyclic group having 1-3 hetero atoms selected from a nitrogen atom, a sulfur atom and an oxygen atom, wherein $R^3$ may be substituted with $R^{31}$, and when $R^3$ has two substituents on the carbon atoms which are adjacent to each other on the aromatic hydrocarbon ring, the substituents may be fused together with carbon atoms to form a saturated or partially unsaturated monocyclic hydrocarbon ring having 4-8 carbon atoms optionally substituted with a group selected from the group consisting of: a halogen atom; a hydroxyl group; an amino group; an oxo group; a C1-C6 alkyl group optionally substituted with a hydroxy group; a halogeno C1-C6 alkyl group; a C1-C14 acyl group; a C1-C14 acylamino group; a C1-C14 acyloxyl group; and a C7-C13 aralkyloxy group, or a saturated or partially unsaturated monocyclic 4-8 membered heterocyclic ring having 1-4 heteroatoms selected from a nitrogen atom, a sulfur atom and an oxygen atom optionally substituted with a group selected from the group consisting of a halogen atom, a hydroxy group, an amino group, an oxo group, a C1-C6 alkyl group optionally substituted with a hydroxy group; a halogeno C1-C6 alkyl group; a C1-C14 acyl group; a C1-C14 acylamino group; a C1-C14 acyloxy group and a C7-C13 aralkyloxy group;

$R^{31}$ represents a halogen atom, a cyano group, a nitro group, a carboxyl group, thioamide group, C1-C6 alkyl group optionally substituted with a group selected from the group consisting of a halogen atom, a hydroxy group, a C1-C14 acyl group, C1-C14 acyloxy group, C2-C6 alkynyl group, and C1-C6 alkoxy C1-C6 alkoxy group, an amino group optionally substituted with a C1-C14 acyl group, a C3-C6 cycloalkyl group optionally substituted with an amino group, a C1-C6 alkoxy group optionally substituted with a halogen atom, a C2-C7 alkoxycarbonyl group, a C1-C14 acyl group optionally substituted with a halogen atom, a C6-C14 aromatic hydrocarbon group optionally substituted with a group selected from the group consisting of a halogen atom, an amino group and a C1-C6 alkoxy group, a monocyclic or bicyclic 5-10 membered unsaturated heterocyclic group having 1-4 heteroatoms selected from a nitrogen atom, a sulfur atom and an oxygen atom optionally substituted with a group selected from the group consisting of a halogen atom, an oxo group and a C1-C6 alkyl group, an amino carbonyl group optionally substituted with Rd and Re wherein Rd and Re are the same or different, and present a hydrogen atom, a hydroxy group, a C7-C13 aralkyloxy group, or a C1-C6 alkyl group optionally substituted with a hydroxy group, alternatively combine with the adjacent nitrogen atom to form: a saturated or unsaturated monocyclic or bicyclic 4-10 membered heterocyclic group, optionally substituted with an amino group, having 1-3 hetero atoms selected from a nitrogen atom, a sulfur atom, and an oxygen atom; a spiroheterocyclic group; or a bridged heterocyclic group, or —S(=O)$_2$Rf, wherein Rf represents an amino group, a C1-C6 alkyl group, or a 4-10 membered saturated heterocyclic group.

36. The method according to claim 21, wherein in formula (I):

$R^3$ represents a C6-C10 aromatic hydrocarbon group or a monocyclic or bicyclic 5-10 membered fully unsaturated heterocyclic group having 1-3 heteroatoms selected from a nitrogen atom, a sulfur atom and an oxygen atom, wherein $R^3$ may be substituted with $R^{31}$, when $R^3$ has two substituents on the carbon atoms which are adjacent to each other on the aromatic hydrocarbon ring, $R^3$ may be fused together with carbon atoms to which the substituents bind to form a saturated or partially unsaturated monocyclic hydrocarbon having 4-8 carbon atoms optionally substituted with a group selected from the group consisting of a halogen atom, a hydroxy group, an amino group, an oxo group, C1-C6 alkyl groups (which are optionally substituted with a hydroxy group), a halogeno C1-C6 alkyl group, a C1-C14 acyl group, a C1-C14 acylamino group, and a C1-C14 acyloxy group, or a saturated or partially unsaturated monocyclic 4-8 membered heterocyclic ring having 1-3 heteroatoms selected from the group consisting of a nitrogen atom, a sulfur atom and an oxygen atom optionally substituted with a group selected from the group consisting of a halogen atom; a hydroxy group; an amino group; an oxo group; and a C1-C6 alkyl group which is optionally substituted with a hydroxy group; a halogeno C1-C6 alkyl group; a C1-C14 acyl group; a C1-C14 acylamino group; a C1-C14 acyloxy group;

$R^{31}$ represents a halogen atom, a cyano group, a nitro group, a carboxyl group, thioamide group, C1-C6 alkyl group optionally substituted with a group selected from the group consisting of a halogen atom, a hydroxy group, a C1-C14 acyl group, a C1-C14 acyloxy group, a C2-C6 alkynyl group, and a C1-C6 alkoxy C1-C6 alkoxy group, an amino group optionally substituted with a C1-C14 acyl group, a C3-C6 cycloalkyl group optionally substituted with an amino group, a C1-C6 alkoxy group optionally substituted with a halogen atom, a C2-C7 alkoxycarbonyl group, a C1-C14 acyl group optionally substituted with a halogen atom, a C6-C10 aromatic hydrocarbon group optionally substituted with a group selected from the group consisting of an amino group and a halogen atom, an unsaturated monocyclic or bicyclic 5-10 membered heterocyclic group having 1 to 4 hetero atoms selected from a nitrogen atom, a sulfur atom and an oxygen atom optionally substituted with a group selected from the group consisting of a C1-C6 alkyl group and an oxo group, a —CONH$_2$ group, a (mono- or di-C1-C6 alkyl) aminocarbonyl group, a hydroxyamino carbonyl group, (C7-C13 aralkyl)oxyaminocarbonyl group, a cyclic aminocarbonyl group, an aminosulfonyl group, a C1-C6 alkylsulfonyl group, or a piperidinosulfonyl group.

37. The compound or a salt thereof as in claim 21, wherein in formula (I):

$R^3$ represents a C6-C10 aromatic hydrocarbon group wherein the C6-C10 aromatic hydrocarbon group may be substituted with $R^{31}$, and when a C6-C10 aromatic hydrocarbon group has two substituents on the carbon atoms which are adjacent to each other on the aromatic hydrocarbon ring, the substituents may be fused together with carbon atoms to which the substituents bind to form a saturated or partially unsaturated monocyclic 4-6 membered heterocyclic ring having 1-3 heteroatoms selected from the group consisting of a nitrogen atom, a sulfur atom and an oxygen atom optionally substituted with a group selected from the group consisting of a hydroxy group, an amino group, an oxo group, a C1-C6 alkyl group, a halogeno C1-C6 alkyl group, a C1-C14 acyl amino group and a C1-C14 acyloxy group, alternatively presents a fully unsaturated monocyclic 5 or 6 membered heterocyclic ring having 1-3 heteroatoms selected from a nitrogen atom, a sulfur atom and an oxygen atom optionally substituted with a group selected from the group consisting of a halogen atom, a C1-C6 alkyl group optionally substituted with a hydroxy group, a C1-C6 alkoxy group, a C2-C7 alkoxycarbonyl group, a —CONH$_2$ group, a (mono- or di-C1-C6 alkyl)aminocarbonyl group, a pyrrolidin-1-ylcarbonyl group, a morpholin-4-ylcarbonyl group, a 2-oxa-7-azaspiro[3.5]nonane-7-carbonyl group, a 3-oxa-8-azabicyclo[3.2.1]octane-8-carbonyl group and an 8-oxa-3-azabicyclo[3.2.1]octane-3-carbonyl group, $R^{31}$ represents a halogen atom, an amino group, a C1-C6 alkyl group optionally substituted with a group selected from the group consisting of a halogen atom and a hydroxy group, C1-C6 alkoxy group optionally substituted with a halogen atom, a monocyclic 5 or 6 membered unsaturated heterocyclic group having 1 to 4 hetero atoms selected from a nitrogen atom, a sulfur atom and an oxygen atom, a —CONH$_2$ group, a (mono- or di-C1-C6 alkyl) aminocarbonyl group, or a hydroxyamino carbonyl group.

38. The method according to claim 21, wherein in formula (I):
$X^1$ represents an oxygen atom,
$X^2$ represents an oxygen atom,
$X^3$ represents —NH—,
$X^4$ represents a hydrogen atom,
$R^1$ represents —C($R^{11}$)($R^{12}$)— wherein $R^{11}$ represents a C1-C6 alkyl group, and $R^{12}$ represents a hydrogen atom, and
$R^2$ represents a C6-C10 aromatic hydrocarbon group, wherein $R^2$ may be substituted with $R^{21}$, and when $R^2$ has two substituents on the carbon atoms which are adjacent to each other on the aromatic hydrocarbon ring, the substituent may be fused together with carbon atoms to which the substituents bind to form a saturated or partially unsaturated monocyclic hydrocarbon ring having 5 or 6 carbon atoms optionally substituted with a C1-C6 alkyl group; and
$R^{21}$ represents a halogen atom, a C1-C6 alkyl group, or a monocyclic 5 or 6 membered unsaturated heterocyclic group having 1-3 nitrogen atom(s) optionally substituted with a C1-C6 alkyl group;
$R^3$ represents a C6-C10 aromatic hydrocarbon group wherein the C6-C10 aromatic hydrocarbon group may be substituted with $R^{31}$, and when a C6-C10 aromatic hydrocarbon group has two substituents on the carbon atoms which are adjacent to each other on the aromatic hydrocarbon ring, the substitutes may be fused together with carbon atoms to which the substituents bind to form a saturated or partially unsaturated monocyclic 4-6 membered heterocyclic ring having 1-3 heteroatoms selected from a nitrogen atom, a sulfur atom and an oxygen atom optionally substituted with a group selected from the group consisting of a hydroxy group, an amino group, an oxo group, a C1-C6 alkyl group, a halogeno C1-C6 alkyl group; a C1-C14 acyl amino group and a C1-C14 acyloxy group, alternatively presents a fully unsaturated monocyclic 5 or 6 membered heterocyclic ring having 1-3 heteroatoms selected from a nitrogen atom, a sulfur atom and an oxygen atom optionally substituted with a group selected from the group consisting of a halogen atom, a C1-C6 alkyl group optionally substituted with a hydroxy group, a C1-C6 alkoxy group, a C2-C7 alkoxycarbonyl group, a —$CONH_2$ group, a (mono- or di-C1-C6 alkyl)aminocarbonyl group, a pyrrolidin-1-ylcarbonyl group, a morpholin-4-ylcarbonyl group, a 2-oxa-7-azaspiro[3.5]nonane-7-carbonyl group, a 3-oxa-8-azabicyclo[3.2.1]octane-8-carbonyl group and an 8-oxa-3-a za bicyclo[3.2.1]octane-3-carbonyl group,
$R^{31}$ represents a halogen atom, an amino group, a C1-C6 alkyl group optionally substituted with a group selected from the group consisting of a halogen atom and a hydroxy group, a C1-C6 alkoxy group optionally substituted with a halogen atom, a monocyclic 5 or 6 membered unsaturated heterocyclic group having 1 to 4 hetero atoms selected from a nitrogen atom, a sulfur atom and an oxygen atom, a —$CONH_2$ group, a (mono- or di-C1-C6 alkyl) aminocarbonyl group, or a hydroxyamino carbonyl group,
$R^4$ represents a hydrogen atom.

39. The method according to claim 21, wherein in formula (I):
$X^1$ represents an oxygen atom,
$X^2$ represents an oxygen atom,
$X^3$ represents —NH—,
$X^4$ represents a hydrogen atom,
$R^1$ represents —C($R^{11}$)($R^{12}$)— wherein $R^{11}$ represents a methyl group, and $R^{12}$ represents a hydrogen atom, and
$R^2$ represents a phenyl group, or a naphthyl group, wherein $R^2$ may be substituted with $R^{21}$, and when $R^2$ has two substituents on the carbon atoms which are adjacent to each other on the aromatic hydrocarbon ring, the substituents may be fused together with carbon atoms to which the substituents bind, to form a saturated or partially unsaturated monocyclic hydrocarbon ring having 5 or 6 carbon atoms optionally substituted with a C1-C6 alkyl group; and
$R^{21}$ represents a halogen atom or a C1-C6 alkyl group;
$R^3$ represents
a phenyl group, wherein the phenyl group may be substituted with $R^{31}$, and when a phenyl group has two substituents on the carbon atoms which are adjacent to each other on a benzene ring, the substitutes may be fused together with carbon atoms to which the substituents bind, to form a saturated or partially unsaturated monocyclic 6 membered heterocyclic ring having 1 or 2 oxygen atom(s) optionally substituted with a group selected from the group consisting of a hydroxy group and a C1-C6 alkyl group, or a pyridyl group optionally substituted with a —$CONH_2$ group, a (mono- or di-C1-C6 alkyl) aminocarbonyl group, or a pyrrolidin-1-ylcarbonyl group;
$R^{31}$ represents a halogen atom, an amino group, a C1-C6 alkyl group or a —$CONH_2$ group;
$R^4$ represent a hydrogen atom.

40. The method according to claim 21, wherein the compound is selected from the following compounds (1)-(19):
(1) 5-bromo-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide,
(2) 5-chloro-2-(N-((1S,2R)-2-(2,3-dimethylphenyl)-1-(5-oxo-4,5-dihydro-1,3,4-oxadiazol-2-yl)propyl)sulfamoyl)benzamide,
(3) 5-bromo-2-(N-((1S,2R)-2-(2,3-dimethylphenyl)-1-(5-oxo-4,5-dihydro-1,3,4-oxadiazol-2-yl)propyl)sulfamoyl)benzamide,
(4) 5-chloro-2-(N-((1S,2R)-2-(6-fluoro-2,3-dimethylphenyl)-1-(5-oxo-4,5-dihydro-1,3,4-oxadiazol-2-yl)propyl)sulfamoyl)benzamide,
(5) 5-chloro-2-(N-((1S,2R)-2-(2-fluoronaphtalen-1-yl)-1-(5-oxo-4,5-dihydro-1,3,4-oxadiazol-2-yl)propyl)sulfamoyl)benzamide,
(6) 5-chloro-2-(N-((1S,2R)-2-(3-ethyl-6-fluoro-2-methylphenyl)-1-(5-oxo-4,5-dihydro-1,3,4-oxadiazol-2-yl)propyl)sulfamoyl)benzamide,
(7) 5-chloro-2-(N-((1S,2R)-2-(3-chloro-6-fluoro-2-methylphenyl)-1-(5-oxo-4,5-dihydro-1,3,4-oxadiazol-2-yl)propyl)sulfamoyl)benzamide,
(8) 5-bromo-2-(N-((1S,2R)-2-(3-chloro-6-fluoro-2-methylphenyl)-1-(5-oxo-4,5-dihydro-1,3,4-oxadiazol-2-yl)propyl)sulfamoyl)benzamide,
(9) 2-(N-((1S,2R)-2-(3-bromo-6-fluoro-2-methylphenyl)-1-(5-oxo-4,5-dihydro-1,3,4-oxadiazol-2-yl)propyl)sulfamoyl)-5-chloro-benzamide,
(10) 5-chloro-N-((1S,2R)-2-(6-fluoro-2,3-dimethylphenyl)-1-(5-oxo-4,5-dihydro-1,3,4-oxadiazol-2-yl)propyl)-6-(pyrrolidine-1-carbonyl)pyridine-2-sulfonamide,
(11) 5-chloro-N-((1S,2R)-2-(6-fluoro-2,3-dimethylphenyl)-1-(5-oxo-4,5-dihydro-1,3,4-oxadiazol-2-yl)propyl)-4-hydroxy-4-methyl-d3-chroman-8-sulfonamide,

(12) 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-chroman-8-sulfonamide,
(13) N-((1S,2R)-2-(3-bromo-6-fluoro-2-methylphenyl)-1-(5-oxo-4,5-dihydro-1,3,4-oxadiazol-2-yl)propyl)-5-chloro-4-hydroxy-4-methyl-chroman-8-sulfonamide,
(14) 5-chloro-N-((1S,2R)-2-(3-chloro-6-fluoro-2-methylphenyl)-1-(5-oxo-4,5-dihydro-1,3,4-oxadiazol-2-yl)propyl)-4-hydroxy-4-methyl-d3-chroman-8-sulfonamide,
(15) 5-chloro-N-((1S,2R)-2-(6-fluoro-2,3-dimethylphenyl)-1-(5-oxo-4,5-dihydro-1,3,4-oxadiazol-2-yl)propyl)-4-hydroxychroman-8-sulfonamide,
(16) 3-chloro-6-(N-((1S,2R)-2-(6-fluoro-2,3-dimethylphenyl)-1-(5-oxo-4,5-dihydro-1,3,4-oxadiazol-2-yl)propyl)sulfamoyl)-N,N-dimethylpicolinamide,
(17) 4-amino-2-methoxy-N-((1S,2R)-2-(8-methylnaphthalen-1-yl)-1-(5-oxo-4,5-dihydro-1,3,4-oxadiazol-2-yl)propyl)benzenesulfonamide,
(18) 4-amino-N-((1S,2R)-2-(2,3-dihydro-1H-inden-4-yl)-1-(5-oxo-4,5-dihydro-1,3,4-oxadiazol-2-yl)propyl)-2-methoxybenzenesulfonamide, and
(19) 5-chloro-2-[[(1S,2R)-3,3,3-trideuterio-2-(6-fluoro-2,3-dimethylphenyl)-1-(2-oxo-3H-1,3,4-oxadiazol-5-yl)propyl]sulfamoyl]benzamide.

* * * * *

UNITED STATES PATENT AND TRADEMARK OFFICE
CERTIFICATE OF CORRECTION

| | | |
|---|---|---|
| PATENT NO. | : 11,634,395 B2 | Page 1 of 1 |
| APPLICATION NO. | : 17/000807 | |
| DATED | : April 25, 2023 | |
| INVENTOR(S) | : Seiji Miyahara | |

It is certified that error appears in the above-identified patent and that said Letters Patent is hereby corrected as shown below:

On the Title Page

Column 1, Item (73), should read:
--(73) Assignee: Taiho Pharmaceutical Co., Ltd., Tokyo (JP)--

Signed and Sealed this
Third Day of September, 2024

Katherine Kelly Vidal
*Director of the United States Patent and Trademark Office*